(12) United States Patent
Renard et al.

(10) Patent No.: US 8,597,657 B2
(45) Date of Patent: *Dec. 3, 2013

(54) MUTATED ENV SEQUENCE INVOLVED IN THE MODULATION OF THE IMMUNOSUPPRESSIVE EFFECT OF VIRAL PROTEINS

(75) Inventors: Martial Renard, Paris (FR); Marianne Mangeney, Paris (FR); Thierry Heidmann, Paris (FR)

(73) Assignees: Institut Gustave Roussy, Villejuif (FR); Centre National de la Recherche Scientifique, Paris (FR); Universite Paris Sud XI, Orsay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/399,208

(22) Filed: Feb. 17, 2012

(65) Prior Publication Data

US 2012/0189647 A1    Jul. 26, 2012

Related U.S. Application Data

(63) Continuation of application No. 11/547,399, filed as application No. PCT/EP2005/003339 on Mar. 30, 2005, now Pat. No. 8,178,657.

(30) Foreign Application Priority Data

Mar. 30, 2004    (EP) .................................... 04290838

(51) Int. Cl.
*A61K 39/21*    (2006.01)
*A61K 38/00*    (2006.01)

(52) U.S. Cl.
USPC ..................... 424/187.1; 424/207.1; 514/1.1

(58) Field of Classification Search
None
See application file for complete search history.

(56) References Cited

U.S. PATENT DOCUMENTS

| | | | |
|---|---|---|---|
| 4,822,606 A | | 4/1989 | Snyderman et al. |
| 6,919,438 B1 * | | 7/2005 | Alliel et al. .................. 536/23.1 |

FOREIGN PATENT DOCUMENTS

| | | |
|---|---|---|
| EP | 0 377 842 | 7/1990 |
| WO | WO9967395 | * 12/1999 |
| WO | WO 01/31021 | 5/2001 |
| WO | WO 02/47720 | 6/2002 |
| WO | WO 02/094860 | 11/2002 |

OTHER PUBLICATIONS

Benit Laurence et al: "Identification, phylogeny, and evolution of retroviral elements based on their envelope genes" Journal of Virology, vol. 75, No. 23, Dec. 2001, pp. 11709-11719, XP002336696.

Delamarre Lelia et al: "A novel human T-leukemia virus type 1 cell-to-cell transmission assay permits definition of SU glycoprotein amino acids important for infectivity" Journal of Virology, vol. 71, No. 1, 1997, pp. 259-266, XP002336697.

Rosenberg Arielle R et al: "Early assembly step of a retroviral envelope glycoprotein: Analysis using a dominant negative assay" Journal of Cell Biology, vol. 145, No. 1, Apr. 5, 1999, pp. 57-68, XP002336698.

Blaise Sandra et al: "Identification of an envelope protein from the FRD family of human endogenous retroviruses (HERV-FRD) conferring infectivity and functional conservation among simians." Journal of Virology, vol. 78, No. 2, Jan. 2004, pp. 1050-1054, XP002336699.

Mangeney Marianne et al: "Tumor cells expressing a retroviral envelope escape immune rejection in vivo" Proceedings of the National Academy of Sciences of the United States of America, vol. 95, No. 25, Dec. 1998, pp. 14920-14925, XP002298109.

Mangeney Marianne et al: "The full-length envelope of an HERV-H human endogenous retrovirus has immunosuppressive properties" Journal of General Virology, vol. 82, No. 10, Oct. 2001, pp. 2515-2518, XP002298110.

Matthews et al., 1987, AIDS Research and Human Retroviruses, 3(1):197-206.

* cited by examiner

*Primary Examiner* — Nicole Kinsey White
(74) *Attorney, Agent, or Firm* — Young & Thompson

(57) ABSTRACT

Mutated viral ENV proteins having mutations in the immunosuppressive domain (ISU) of the transmembrane subunit (TM) have decreased immunosuppressive activity with respect to the wild-type ENV protein. Pharmaceutical compositions that include the protein and nucleic acids coding for the protein are also disclosed.

17 Claims, 21 Drawing Sheets

| Name | Origin | Nucleotide sequence | Accession Number |
|---|---|---|---|
| HERV-T | Human endogenous | LQNCRCLDLLFLSQGGLCAA | AC 078 899 |
| HTLV-1 | Human retrovirus | AQNRRGLDLLFWEQGGLCKA | AY 324 800 |
| STLV-1 | Simian retrovirus | AQNRRGLDLLFWEQGGLCKA | AY 324 800 |
| HERV-FRD | Human endogenous | LQNRRGLDMLTAAQGGLCLA | AL 136 139 |
| MPMV | Human retrovirus | LQNRRGLDLLTAEQGGICLA | AF 033 815 |
| Fowlpox | Poxvirus | LQNRRGLDLLTAEQGGICLA | NC 002 188 |
| MoMLV | Human retrovirus | LQNRRGLDLLFLKEGGLCAA | AF 033 811 |
| Friend | Human retrovirus | LQNRRGLDLLFLKEGGLCAA | M 90 673 |
| PyERV | python endogenous | LQNRRGLDLLFLKEGGLCVA | AF 500 297 |
| PERV | porcine endogenous | LQNRRGLDLLFLKEGGLCVA | AY 364 236 |
| FeLV | feline leukaemia virus | LQNRRGLDILFLQEGGLCAA | M 18248 |
| SSAV | Simian Sarcoma-associated virus | LQNRRGLDLLFLKEGGLCAA | J 02396 |
| GLV-X | Gibbon leukemia virus X | LQNRRGLDLLFLKEGGLCAA | U 60065 |
| EBOLA | Filovirus | ILNRKAIDFLLQRWGGTCHI | EVU 31033 |
| Marburg | Filovirus | LINRHAIDFLLTRWGGTCKV | MVVIRPR |
| HERV-W | Human endogenous | LQNRRALDLLTAERGGTCLF | AF 072 503 |
| HERV-W | Human endogenous | LQNWRALDLLTAKRGGTCLF | |
| HERV-W | Human endogenous | LQNWRALDLLIAKRGGTCVF | |
| HERV-H1 | Human endogenous | LQNRRGLDLLTAEKGGLCIF | AJ 289 709 |
| HERV-F(c)1 | Human endogenous | MQNRRALDLLTADKGGTCMF | AL 354 685 |
| HERV-F(c)2 | Human endogenous | AQNRQALDLLMAEKGRTCLF | AC 016 222 |

Figure 9

A. Nucleotide sequence encoding envMoMLV

```
ATGGCGCGTTCAACGCTCTCAAAACCCCTTAAAAATAAGGTTAACCCGCG
AGGCCCCCTAATCCCCTTAATTCTTCTGATGCTCAGAGGGGTCAGTACTG
CTTCGCCCGGCTCCAGTCCTCATCAAGTCTATAATATCACCTGGGAGGTA
ACCAATGGAGATCGGGAGACGGTATGGGCAACTTCTGGCAACCACCCTCT
GTGGACCTGGTGGCCTGACCTTACCCCAGATTTATGTATGTTAGCCCACC
ATGGACCATCTTATTGGGGCTAGAATATCAATCCCCTTTTTCTTCTCCC
CCGGGGCCCCCTTGTTGCTCAGGGGCAGCAGCCCAGGCTGTTCCAGAGA
CTGCGAAGAACCTTTAACCTCCCTCACCCCTCGGTGCAACACTGCCTGGA
ACAGACTCAAGCTAGACCAGACAACTCATAAATCAAATGAGGGATTTTAT
GTTTGCCCCGGGCCCCACCGCCCCGAGAATCCAAGTCATGTGGGGTCC
AGACTCCTTCTACTGTGCCTATTGGGGCTGTGAGACAACCGGTAGAGCTT
ACTGGAAGCCCTCCTCATCATGGGATTTCATCACAGTAAACAACAATCTC
ACCTCTGACCAGGCTGTCCAGGTATGCAAAGATAATAAGTGGTGCAACCC
CTTAGTTATTCGGTTTACAGACGCCGGGAGACGGGTTACTTCCTGGACCA
CAGGACATTACTGGGGCTTACGTTTGTATGTCTCCGGACAAGATCCAGGG
CTTACATTTGGGATCCGACTCAGATACCAAAATCTAGGACCCCGCGTCCC
AATAGGGCCAAACCCCGTTCTGGCAGACCAACAGCCACTCTCCAAGCCCA
AACCTGTTAAGTCGCCTTCAGTCACCAAACCACCCAGTGGGACTCCTCTC
TCCCCTACCCAACTTCCACCGGCGGGAACGGAAAATAGGCTGCTAAACTT
AGTAGACGGAGCCTACCAAGCCCTCAACCTCACCAGTCCTGACAAAACCC
AAGAGTGCTGGTTGTGTCTAGTAGCGGGACCCCCCTACTACGAAGGGGTT
GCCGTCCTGGGTACCTACTCCAACCATACCTCTGCTCCAGCCAACTGCTC
CGTGGCCTCCCAACACAAGTTGACCCTGTCCGAAGTGACCGGACAGGGAC
TCTGCATAGGAGCAGTTCCCAAAACACATCAGGCCCTATGTAATACCACC
CAGACAAGCAGTCGAGGGTCCTATTATCTAGTTGCCCCTACAGGTACCAT
GTGGGCTTGTAGTACCGGGCTTACTCCATGCATCTCCACCACCATACTGA
ACCTTACCACTGATTATTGTGTTCTTGTCGAACTCTGGCCAAGAGTCACC
TATCATTCCCCCAGCTATGTTTACGGCCTGTTTGAGAGATCCAACCGACA
CAAAAGAGAACCGGTGTCGTTAACCCTGGCCCTATTATTGGGTGGACTAA
CCATGGGGGGAATTGCCGCTGGAATAGGAACAGGGACTACTGCTCTAATG
GCCACTCAGCAATTCCAGCAGCTCCAAGCCGCAGTACAGGATGATCTCAG
GGAGGTTGAAAAATCAATCTCTAACCTAGAAAAGTCTCTCACTTCCCTGT
CTGAAGTTGTCCTACAGAATCGAAGGGGCCTAGACTTGTTATTTCTAAAA
GAAGGAGGGCTGTGTGCTGCTCTAAAAGAAGAATGTTGCTTCTATGCGGA
CCACACAGGACTAGTGAGAGACAGCATGGCCAAATTGAGAGAGAGGCTTA
ATCAGAGACAGAAACTGTTTGAGTCAACTCAAGGATGGTTTGAGGGACTG
TTTAACAGATCCCCTTGGTTTACCACCTTGATATCTACCATTATGGGACC
CCTCATTGTACTCCTAATGATTTTGCTCTTCGGACCCTGCATTCTTAATC
GATTAGTCCAATTTGTTAAAGACAGGATATCAGTGGTCCAGGCTCTAGTT
TTGACTCAACAATATCACCAGCTGAAGCCTATAGAGTACGAGCCATAG
```

*FIG. 10A*

B. Protein sequence of envMoMLV

MARSTLSKPLKNKVNPRGPLIPLILLMLRGVSTASPGSSPHQVYNITWEV
TNGDRETVWATSGNHPLWTWWPDLTPDLCMLAHHGPSYWGLEYQSPFSSP
PGPPCCSGGSSPGCSRDCEEPLTSLTPRCNTAWNRLKLDQTTHKSNEGFY
VCPGPHRPRESKSCGGPDSFYCAYWGCETTGRAYWKPSSSWDFITVNNNL
TSDQAVQVCKDNKWCNPLVIRFTDAGRRVTSWTTGHYWGLRLYVSGQDPG
LTFGIRLRYQNLGPRVPIGPNPVLADQQPLSKPKPVKSPSVTKPPSGTPL
SPTQLPPAGTENRLLNLVDGAYQALNLTSPDKTQECWLCLVAGPPYYEGV
AVLGTYSNHTSAPANCSVASQHKLTLSEVTGQGLCIGAVPKTHQALCNTT
QTSSRGSYYLVAPTGTMWACSTGLTPCISTTILNLTTDYCVLVELWPRVT
YHSPSYVYGLFERSNRHKREPVSLTLALLLGGLTMGGIAAGIGTGTTALM
ATQQFQQLQAAVQDDLREVEKSISNLEKSLTSLSEVVLQNRRGLDLLFLK
EGGLCAALKEECCFYADHTGLVRDSMAKLRERLNQRQKLFESTQGWFEGL
FNRSPWFTTLISTIMGPLIVLLMILLFGPCILNRLVQFVKDRISVVQALV
LTQQYHQLKPIEYEP*

*FIG. 10B*

C. Nucleotide sequence encoding envMPMV

ATGAACTTCAATTATCATTTCATCTGGAGCTTAGTGATACTATCTCAAAT
ATCTCAAGTTCAAGCCGGTTTTGGAGATCCGCGTGAAGCCCTGGCAGAAA
TACAACAAAAACATGGTAAACCTTGTGACTGTGCTGGAGGATATGTTTCC
TCCCCACCGATTAACTCTCTTACAACTGTTTCTTGCTCTACTCATACTGC
TTATTCAGTGACAAACTCCCTAAAATGGCAGTGTGTGTCAACTCCCACTA
CCCCTAGCAATACACATATAGGAAGTTGTCCGGTGAATGCAACACGATC
TCATATGATTCTGTACATGCCTCTTGCTATAACCACTATCAACAATGTAA
CATTGGTAATAAAACATATCTCACTGCCACTATAACTGGAGATAGAACTC
CTGCCATTGGTGACGGGAATGTCCTACAGTACTAGGACTAGTCACAAC
CTCATTACAGCAGGCTGTCCCAATGGTAAAAGGGCCAAGTGGTCTGTTG
GAATAGCCGACCTTCTGTTCATATATCTGATGGAGGAGGGCCTCAAGATA
AGGCCCGCGACATTATAGTAAATAAAAAGTTTGAGGAATTGCACAGGTCG
CTGTTCCCAGAACTTTCTTACCATCCTCTGGCCTTGCCCGAAGCCCGTGG
TAAAGAAAAAATTGACGCACACACTCTTGATCTCCTTGCCACTGTACATA
GTTTACTCAATGCTTCCCAACCCAGTTTAGCCGAAGATTGCTGGCTGTGC
TTACAGTCAGGAGATCCCGTTCCTCTTGCCCTGCCCTATAATGATACACT
CTGCTCTAACTTTGCCTGTTTATCTAATCACTCCTGCCCTTTAACCCCCC
CTTTTTTAGTACAGCCCTTTAACTTCACTGATTCCAATTGCCTTTACGCT
CATTATCAAAACAACTCATTTGACATAGATGTAGGTCTAGCTAGCTTTAC
TAATTGCTCTAGCTATTATAACGTTTCTACAGCCTCCAAACCCTCTAATT
CCCTATGCGCCCAAACAGCTCGGTTTTGTATGCGGTAACAATAAGGCA
TACACTTATCTACCCACAAATTGGACGGGAAGTTGTGTACTTGCTACTCT
TTTGCCCGATATAGACATCATTCCAGGTAGTGAGCCTGTCCCCATTCCAG
CTATTGATCATTTTTTAGGCAAAGCCAAAAGAGCAATCCAACTTATCCCC
CTGTTCGTAGGGTTAGGTATAACTACTGCAGTATCTACTGGGGCTGCTGG
TCTAGGGGTTTCCATCACTCAATATACAAAATTATCTCATCAACTAATAT
CAGATGTTCAAGCTATTTCTAGCACTATACAAGATCTCCAAGATCAGGTA
GACTCTCTAGCAGAAGTAGTACTGCAAAACAGAAGAGGATTAGATCTACT
TACAGCAGAGCAGGGAGGTATCTGCTTAGCCTTACAGGAAAAATGTTGTT
TCTACGCCAATAAATCTGGAATCGTCAGAGACAAGATTAAAAACCTACAA
GACGACTTAGAAAGACGCCGAAGACAACTGATCGACAACCCATTTTGGAC
CAGTTTTCATGGATTCCTCCCTTATGTTATGCCCCTATTAGGCCCTTTGC
TTTGCTTATTGCTTGTGTTATCTTTCGGTCCAATTATTTTCAACAAGCTT
ATGACCTTTATTAAACATCAAATTGAGAGCATCCAGGCCAAACCTATACA
AGTCCATTATCATCGCCTTGAACAAGAAGACAGTGGTGGCTCATATTTGA
CCTTAACATAG

*FIG. 10C*

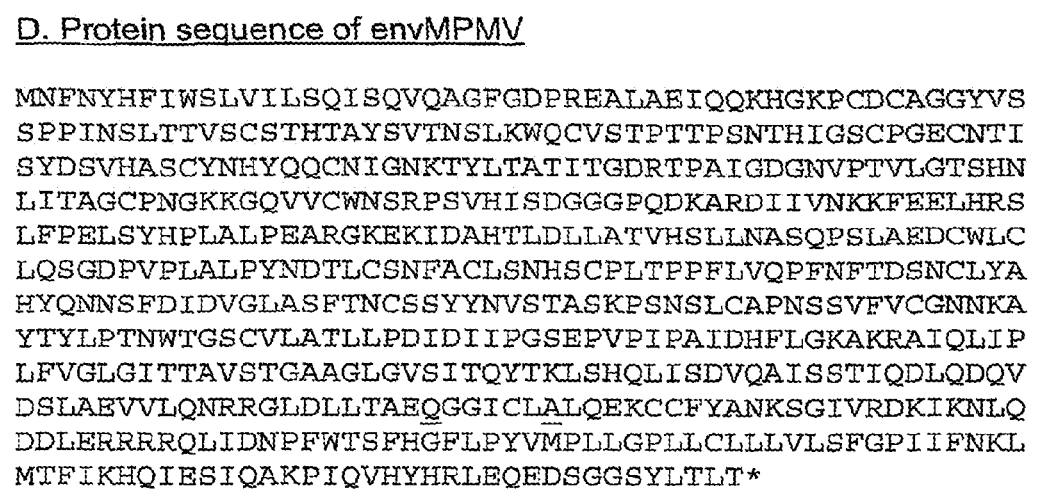

D. Protein sequence of envMPMV

MNFNYHFIWSLVILSQISQVQAGFGDPREALAEIQQKHGKPCDCAGGYVS
SPPINSLTTVSCSTHTAYSVTNSLKWQCVSTPTTPSNTHIGSCPGECNTI
SYDSVHASCYNHYQQCNIGNKTYLTATITGDRTPAIGDGNVPTVLGTSHN
LITAGCPNGKKGQVVCWNSRPSVHISDGGGPQDKARDIIVNKKFEELHRS
LFPELSYHPLALPEARGKEKIDAHTLDLLATVHSLLNASQPSLAEDCWLC
LQSGDPVPLALPYNDTLCSNFACLSNHSCPLTPPFLVQPFNFTDSNCLYA
HYQNNSFDIDVGLASFTNCSSYYNVSTASKPSNSLCAPNSSVFVCGNNKA
YTYLPTNWTGSCVLATLLPDIDIIPGSEPVPIPAIDHFLGKAKRAIQLIP
LFVGLGITTAVSTGAAGLGVSITQYTKLSHQLISDVQAISSTIQDLQDQV
DSLAEVVLQNRRGLDLLTAEQGGICLALQEKCCFYANKSGIVRDKIKNLQ
DDLERRRRQLIDNPFWTSFHGFLPYVMPLLGPLLCLLLVLSFGPIIFNKL
MTFIKHQIESIQAKPIQVHYHRLEQEDSGGSYLTLT*

FIG. 10D

E. Nucleotide sequence encoding envHERV-W (envW)

```
ATGGCCCTCCCTTATCATATTTTTCTCTTTACTGTTCTTTTACCCTCTTT
CACTCTCACTGCACCCCTCCATGCCGCTGTATGACCAGTAGCTCCCCTT
ACCAAGAGTTTCTATGGAGAATGCAGCGTCCCGGAAATATTGATGCCCCA
TCGTATAGGAGTCTTTCTAAGGGAACCCCCACCTTCACTGCCCACACCCA
TATGCCCCGCAACTGCTATCACTCTGCCACTCTTTGCATGCATGCAAATA
CTCATTATTGGACAGGAAAAATGATTAATCCTAGTTGTCCTGGAGGACTT
GGAGTCACTGTCTGTTGGACTTACTTCACCCAAACTGGTATGTCTGATGG
GGGTGGAGTTCAAGATCAGGCAAGAGAAAACATGTAAAGAAGTAATCT
CCCAACTCACCCGGGTACATGGCACCTCTAGCCCCTACAAGGACTAGAT
CTCTCAAAACTACATGAAACCCTCCGTACCCATACTCGCCTGGTAAGCCT
ATTTAATACCACCCTCACTGGGCTCCATGAGGTCTCGGCCCAAAACCCTA
CTAACTGTTGGATATGCCTCCCCTGAACTTCAGGCCATATGTTTCAATC
CCTGTACCTGAACAATGGAACAACTTCAGCACAGAAATAAACACCACTTC
CGTTTTAGTAGGACCTCTTGTTTCCAATCTGGAAATAACCCATACCTCAA
ACCTCACCTGTGTAAAATTTAGCAATACTACATACACAACCAACTCCCAA
TGCATCAGGTGGGTAACTCCTCCCACACAAATAGTCTGCCTACCCTCAGG
AATATTTTTGTCTGTGGTACCTCAGCCTATCGTTGTTTGAATGGCTCTT
CAGAATCTATGTGCTTCCTCTCATTCTTAGTGCCCCCTATGACCATCTAC
ACTGAACAAGATTTATACAGTTATGTCATATCTAAGCCCCGCAACAAAAG
AGTACCCATTCTTCCTTTTGTTATAGGAGCAGGAGTGCTAGGTGCACTAG
GTACTGGCATTGGCGGTATCACAACCTCTACTCAGTTCTACTACAAACTA
TCTCAAGAACTAAATGGGGACATGGAACGGGTCGCCGACTCCCTGGTCAC
CTTGCAAGATCAACTTAACTCCCTAGCAGCAGTAGTCCTTCAAAATCGAA
GAGCTTTAGACTTGCTAACCGCTGAAAGAGGGGGAACCTGTTTATTTTA
GGGGAAGAATGCTGTTATTATGTTAATCAATCCGGAATCGTCACTGAGAA
AGTTAAAGAAATTCGAGATCGAATACAACGTAGAGCAGAGGAGCTTCGAA
ACACTGGACCCTGGGGCCTCCTCAGCCAATGGATGCCCTGGATTCTCCCC
TTCTTAGGACCTCTAGCAGCTATAATATTGCTACTCCTCTTTGGACCCTG
TATCTTTAACCTCCTTGTTAACTTTGTCTCTTCCAGAATCGAAGCTGTAA
AACTACAAATGGAGCCCAAGATGCAGTCCAAGACTAAGATCTACCGCAGA
CCCCTGGACCGGCCTGCTAGCCCACGATCTGATGTTAATGACATCAAGG
CACCCCTCCTGAGGAAATCTCAGCTGCACAACCTCTACTACGCCCCAATT
CAGCAGGAAGCAGTTAG
```

FIG. 10E

F. Protein sequence of envHERV-W (envW)

```
MALPYHIFLFTVLLPSFTLTAPPPCRCMTSSSPYQEFLWRMQRPGNIDAP
SYRSLSKGTPTFTAHTHMPRNCYHSATLCMHANTHYWTGKMINPSCPGGL
GVTVCWTYFTQTGMSDGGGVQDQAREKHVKEVISQLTRVHGTSSPYKGLD
LSKLHETLRTHTRLVSLFNTTLTGLHEVSAQNPTNCWICLPLNFRPYVSI
PVPEQWNNFSTEINTTSVLVGPLVSNLEITHTSNLTCVKFSNTTYTTNSQ
CIRWVTPPTQIVCLPSGIFFVCGTSAYRCLNGSSESMCFLSFLVPPMTIY
TEQDLYSYVISKPRNKRVPILPFVIGAGVLGALGTGIGGITTSTQFYYKL
SQELNGDMERVADSLVTLQDQLNSLAAVVLQNRRALDLLTAERGGTCLFL
GEECCYYVNQSGIVTEKVKEIRDRIQRRAEELRNTGPWGLLSQWMPWILP
FLGPLAAIILLLLFGPCIFNLLVNFVSSRIEAVKLQMEPKMQSKTKIYRR
PLDRPASPRSDVNDIKGTPPEEISAAQPLLRPNSAGSS*
```

*FIG. 10F*

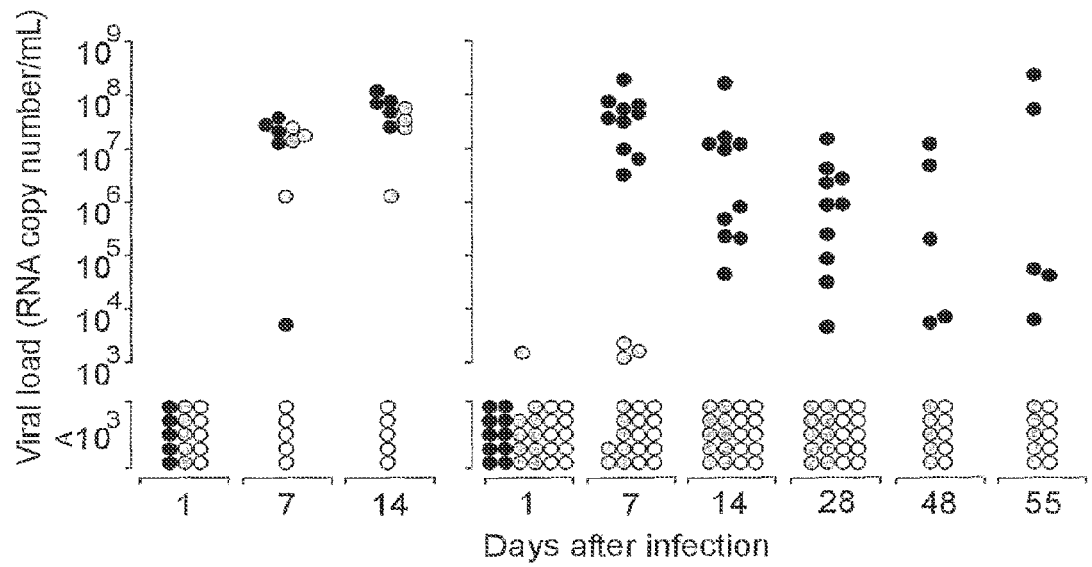
Figure 12A
Figure 12B
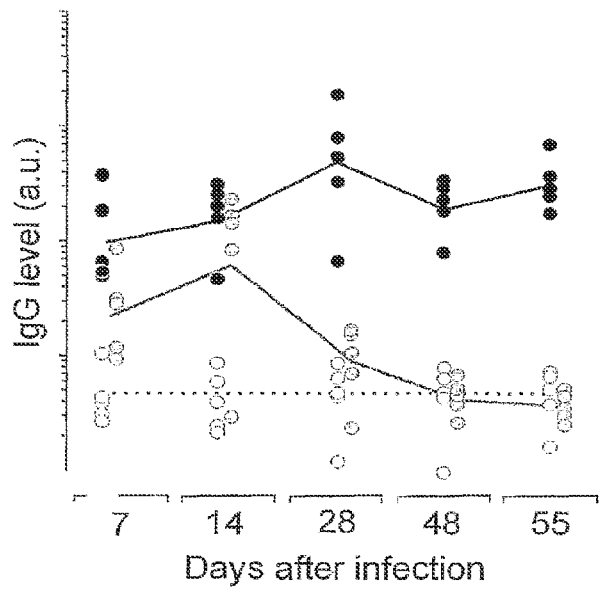
Figure 13

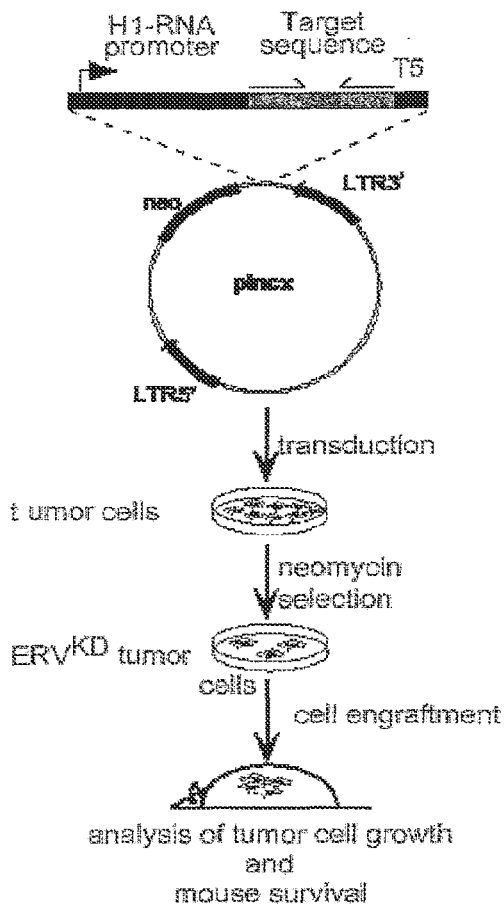
Figure 16A
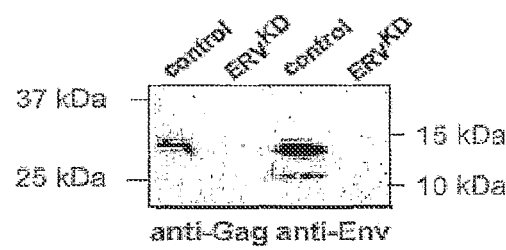
Figure 16C
predicted transcripts against ERV (1220-1238)
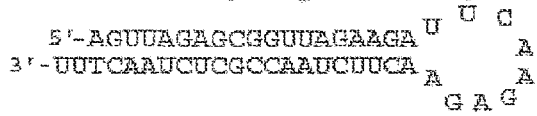
predicted control transcripts against GFP (215-233)
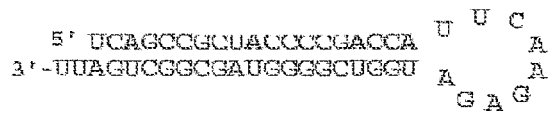
Figure 16B

MUTATED ENV SEQUENCE INVOLVED IN THE MODULATION OF THE IMMUNOSUPPRESSIVE EFFECT OF VIRAL PROTEINS

CROSS REFERENCE TO RELATED APPLICATIONS

This application is a continuation of application Ser. No. 11/547,399 filed on Aug. 20, 2007, now U.S. Pat. No. 8,178,657; which is the 35 U.S.C. 371 national stage of International application PCT/EP05/03339 filed on Mar. 30, 2005; which claims priority to European application 04290838.4 filed on Mar. 30, 2004. The entire contents of each of the above-identified applications are hereby incorporated by reference.

FIELD OF THE INVENTION

The present invention relates to an amino acid sequence capable of modulating the immunosuppressive properties of a protein, especially from antigenic proteins. The invention also provides polypeptides, derived from an antigenic and immunosuppressive protein, having acquired modulated immunosuppressive properties with respect to the protein from which it is derived, while substantially retaining its antigenic properties.

The invention especially concerns the field of viral or retroviral infections, including the field of endogenous retroviruses, and provides means for the design of agents for the prophylaxis and/or treatment of hosts susceptible to such viruses or retroviruses, including animal or human hosts.

Polypeptides of the invention can especially be used in the generation of immunogenic compositions and in the production of attenuated viruses, for use in methods for prophylaxis and/or treatment of viral infections or their detrimental consequences or for prophylaxis and/or treatment of the detrimental consequences of the induction of expression of endogenous retroviruses (ERV).

BACKGROUND OF THE INVENTION

Infectious agents, such as viruses, have evolved mechanisms and strategies to invade their hosts and to escape their immune response. Various publications have demonstrated the immunosuppressive properties of proteins encoded by viruses: the Epstein Barr human herpes virus 4 (Suzuki et al. 1995. J. Exp. Med. 182, 477-486; Qin et al. 1996 J. Immunol. 156, 2316-2323), the Mason-Pfizer monkey virus (Blaise et al. 2001 J. Gen. Virol. 82, 1597-1600), the Moloney murine leukaemia virus (Mangeney and Heidmann. 1998. Proc. Natl. Sci. USA. 95, 14920-14925) and others (see review Alcami et al. 2002 EMBO reports. 3(10), 927-932). This may be confirmed by the fact that infection by retroviruses is frequently associated with dysfunctions of the immune system of the host.

These immunosuppressive effects include the inhibition of interleukin-2-dependent lymphocyte proliferation, of the cytolytic activity of human natural killer cells, and of monocyte-medicated tumor cell killing as well as modulation of cytokine synthesis.

In vivo tests demonstrated that inactivated viruses, as well as synthetic peptides similar to retrovirus envelope proteins have immunosuppressive properties (Oostendorp et al. 1993 Crit. Rev. Oncol. Hematol. 14, 189-206; Haraguchi et al. 1997 J. Leukocyte Biol. 61, 654-666). More recently, Mangeney et al. (1998. Proc. Natl. Sci. USA. 95, 14920-14925) showed that murine tumoral cells from C57BL/6 strain, expressing a retroviral envelope protein, form tumours when injected in Balb/c mice (allograft), whereas the same cells, which do not express the retroviral envelope protein, are rejected. By carrying out different deletions in the envelope protein, a domain responsible for the immunosuppressive function that was called ISU (for "immunosuppressive") domain, was identified.

The ISU domain was first identified in the transmembrane moiety of the envelope glycoprotein. The env (envelope) gene of retroviruses encodes a precursor polypeptide which is then cleaved into two proteins: the surface glycoprotein (SU) and the transmembrane subunit (TM). The SU protein is responsible for the recognition and the binding to the cellular receptor for the virus. The TM moiety is involved in anchoring the envelope complex (SU and TM) to the target cell membrane, and is directly responsible for cell membrane fusion and virus entry.

The structure of the TM subunit has been elucidated for many viruses, especially for the Moloney murine leukaemia virus (Mo-MuLV), the human immunodeficiency virus 1 (HIV-1) and the human T-cell leukaemia virus type 1 (HTLV-1). A highly conserved organization in the envelope proteins has also been found in non-retroviral proteins, such as those of influenza virus and Ebola virus.

Immunosuppressive effects have also been discovered in another class of proteins, characterized in the ERVs, especially HERVs (Human Endogenous Retroviruses). HERVs comprise elements which are sequences of retroviral origin that have spread into the human genome, and represent proviral remnants of ancestral infections. Therefore, strong similarities can be inferred between HERVs and retroviruses. Some of these HERV elements are still functional and can encode active proteins, i.e., viral-like proteins although most of them have accumulated mutations, deletions and/or truncations.

A role for these functional HERVs has been proposed, including a protection against retrovirus infection (Best et al. 1997 Trends Microbiol. 5, 313-318) or a protection of the foetus against the maternal immune system via immunosuppressive effects (Cianciolo et al. 1985 Science 230, 453-455; Mangeney and Heidmann 1998 Proc. Natl. Sci. USA. 95, 14920-14925). An HERV encoding an envelope protein having immunosuppressive properties was identified by Mangeney et al. (2001 J. Gen. Virology 82, 2515-2518). This publication reports that the protein encoded by HERV-H allows the envelope-expressing cells to escape immune response and to proliferate, whereas the same cells transfected with empty vectors are normally rejected by engrafted mice.

Other ERVs, especially HERVs, encoding functional envelope proteins were identified, which have fusogenic properties, i.e. are able to form syncytia in vitro (multi-nucleate cells): they include HERV-FRD and HERV-W (Blond et al. 2000 J. Virol. 74, 3321-3329; Blaise et al. 2003 Proc. Natl. Acad. Sci. 22, 13013-13018). Moreover, in vivo experiments have shown that when co-expressed with MoMLV viral particles deficient for the production of their own envelope protein, the HERV-W envelope protein can form functional viral particles, capable of infecting human cells (Patience et al. 1998 J. Virol. 72, 2671-2676). In conclusion, HERV-W has conserved its fusogenic and infectiosity properties. Analog fusogenic and infectious properties have been observed for HERV-FRD.

The observed immunosuppressive effects may be related, depending on the context, on the one hand to a virulent viral infection and on the other hand to an active proliferation of tumour cells, in mammals and particularly in human. Active proliferation of tumour cells is especially a consequence of expression of ERV viral-like proteins. However, whereas more insights are needed to completely understand the mechanisms of immunosuppression, the identification of these immunosuppressive proteins opens new perspectives for therapeutic, including vaccinal, strategies against viral infections, against induction of expression of endogenous retroviruses, or against their detrimental consequences in a host.

Vaccines currently used can especially be classified as follows:

- live attenuated vaccines (bacteria or virus vaccine) consisting in an attenuated or weakened, modified pathogen. After administration to the host, the modified pathogenic organism replicates in the host and stimulates an immune response. This type of vaccine generally produces a long-lasting immunity upon single dose administration, but may cause side effects, i.e. a mild case of the illness caused by said pathogen, and thus should not be given to people with a weakened immune system.
- inactivated or killed vaccines, consisting in killed or inactivated pathogen, especially as a result of heat and/or chemical treatments (whole organism). Such treated pathogens cannot replicate, and cannot cause the disease they normally raise. Therefore, they are safe and can be administered even to hosts whose immune system is weakened. However, they are not usually as effective as live vaccines and therefore require multiple dose administration.
- vaccines consisting in antigenic fractions of a pathogen organism, including whole proteins or antigenic determinants thereof, especially obtained by recombinant technologies, as a result of the expression of genes encoding the antigen. The expressed protein can be administered to a patient, or the gene encoding the protein can be inserted into an expression vector which is administered to the host. Such vaccines however are usually not as effective as live vaccines and therefore require multiple doses.

Principles applied for the design of compounds suitable for vaccine preparations capable of eliciting an immune response in a host, in order to protect a host from infection due to pathogens, including viruses, bacteria or others, have been transposed to the design of compounds suitable for treatment of established infections, by immunotherapy. Efficiency of such compounds has however not proved to be sufficient enough, especially in the field of anti-viral or anti-viral-like prophylaxis or immunotherapy. Moreover, the use of compounds still raises many issues regarding safety.

One drawback observed in the use of some retroviral envelope proteins for immunisation, either as vaccine principles or for immunotherapy, lies in their immunosuppressive properties which can prevent or affect the efficiency of the host's immune response. Consequently these proteins cannot be administered to a patient in their native form because of their potential inhibition of the immune response. A great challenge would hence be to suppress or modulate the immunosuppression properties of these proteins, without altering their antigenic properties and/or their properties related to host cell infection. However, attempts to mutate the envelope protein complex, have led to a strong alteration of its fusion and infection functions and therefore of their interest as active principle to raise an immune response (Delamarre et al. 1997 J. Virol. 71(1), 259-266; Rosenberg et al. 1999 J. Cell Biol. 145, 57-68).

This is a purpose of the present invention to identify determinants of the immunosuppressive properties of proteins, including to identify polypeptide sequences and amino acid residues involved in the modulation of the immunosuppressive properties of proteins, particularly viral or viral-like proteins, which substantially retain their antigenic properties of said immunosuppressive proteins.

It is a further object of the invention, to identify such determinants of the immunosuppressive properties of the protein, and to use the same for the design of polypeptides having modified, i.e., modulated immunosuppressive properties.

Another object of the present invention is to provide such polypeptides, which are derived from an antigenic and immunosuppressive protein, which polypeptides are characterized by modulated immunosuppressive properties while retaining antigenic properties of the starting protein.

This is also an object of the present invention, to provide means to promote an efficient immune response against pathogen organisms, especially against viruses, i.e., a cell-mediated and/or humoral immune response which would be protective against infection by such pathogen organisms, especially viruses, or protective against their detrimental effects in the host, or protective against the detrimental consequences of expression of endogenous retroviruses in a host, with reduced risks of immune system alteration. The invention also provides means suitable for treatment by immunotherapy, of patients infected with pathogen organisms including viruses, or for treatment of their detrimental effects, including malignant effects or for the treatment of patients suffering from pathologies associated with induction of the expression of endogenous viruses which are normally silent in hosts.

SUMMARY OF THE INVENTION

In one aspect, the invention provides a polypeptide which is capable of modulating the immunosuppressive properties of a viral protein or a fragment thereof against the host in which it is expressed when it substitutes the homologous sequence of said protein or fragment, said polypeptide having the minimum following consensus amino acid sequence:

$$X1\text{-}(Y)_3\text{-}C\text{-}(Y)_1\text{-}X2$$

wherein, X1 and X2 are selected to impact on said immunosuppressive properties, Y represents variable amino acid residues, and 3 and 1 represent the number of variable amino acid residues respectively between X1 and C and between C and X2.

Said minimum consensus sequence is designated "immunosuppression-modulatory sequence".

In an embodiment, peptides replying to the above definition, comprising an immunosuppression-modulatory sequence, are derived from a viral including from a viral-like protein, especially a retroviral protein, in particular, a viral or retroviral envelope protein or an envelope protein from an endogenous retrovirus, especially from a human endogenous retrovirus (HERV).

The amino acid sequences of several envelope proteins of viruses (including ERV) have been disclosed in FIG. 3 of Benit et al (J Virol. December 2001, p. 11707-11719).

Particular pairs of amino acid residues impacting on the immunosuppressive properties in the context of a determined protein have been characterized, and accordingly sequences having the desired "immunosuppression-modulatory" properties have been identified and can be selected from the group consisting of:

a) sequences involved in the occurrence of immunosuppressive properties of a protein in which they are present comprise:

E-(Y)$_3$-C-(Y)$_1$-A

Q-(Y)$_3$-C-(Y)$_1$-A and b) sequences altering, e.g. decreasing or suppressing immunosuppressive properties of an immunosuppressive protein when they are present therein, comprise

R-(Y)$_3$-C-(Y)$_1$-F

In another aspect, the invention provides a polypeptide derived from a determined antigenic and immunosuppressive protein, said polypeptide comprising an amino acid sequence (so-called immunosuppression-modulatory sequence) represented by X1-(Y)$_3$-C-(Y)$_1$-X2 wherein in said polypeptide Y represents variable amino acid residues, 3 and 1 represent the number of variable amino acid residues Y respectively between X1 and C and between C and X2, and X1 and X2 are chosen to confer to said polypeptide altered immunosuppressive properties with respect to the immunosuppressive properties of said determined protein.

In a particular embodiment, the protein having antigenic and immunosuppressive properties is encoded by a gene derived from a virus, and especially by an env gene from a retrovirus.

Such protein comprises an immunosuppressive sequence determinant having the following consensus sequence: E/Q-G-G-L/T/I-C-A/K/L/M/V/I-A (SEQ ID NO: 153). The same protein wherein X1 (E/Q) and optionally X2 (A) residues are substituted can be devoid of immunosuppressive properties but retains its antigenic properties. An example of modified immunosuppression-modulatory sequence is R-G-G-L/T/I-C-A/K/L/M/V/I-F (SEQ ID NO: 154), which alters immunosuppressive properties and especially can give rise to a non-immunosuppressive polypeptide which contains said sequence. A particular modified immunosuppression-modulatory sequence is selected from the group of:

| | |
|---|---|
| RGGLCAF | (SEQ ID NO: 1) |
| RGGLCKF | (SEQ ID NO: 2) |
| RGGLCLF | (SEQ ID NO: 3) |
| RGGLCMF | (SEQ ID NO: 4) |
| RGGLCVF | (SEQ ID NO: 5) |
| RGGLCIF | (SEQ ID NO: 6) |
| RGGTCAF | (SEQ ID NO: 7) |
| RGGTCKF | (SEQ ID NO: 8) |
| RGGTCMF | (SEQ ID NO: 9) |
| RGGTCIF | (SEQ ID NO: 10) |
| RGGICAF | (SEQ ID NO: 11) |
| RGGICKF | (SEQ ID NO: 12) |
| RGGICLF | (SEQ ID NO: 13) |
| RGGICMF | (SEQ ID NO: 14) |
| RGGICVF | (SEQ ID NO: 15) |
| RGGICIF | (SEQ ID NO: 16) |

In a particular embodiment, the protein further has infectious and/or fusion properties. The modification of the immunosuppression-modulatory sequence, e.g. by substitution of X1 and optionally X2 amino acid residues can advantageously be carried out in a way that does not affect one of these or both supplementary properties.

In another aspect, the invention relates to compositions comprising such polypeptides or recombinant viral particles expressing these polypeptides. Such compositions or particles can be used in the prevention or treatment of a viral infection including for the prevention or treatment of its detrimental effects, or for prevention or treatment or the consequences in a host, of the expression of an endogenous virus, especially an HERV, by the elicitation of an immune response in the host in which they are injected. They can also be used in the preparation of attenuated viruses.

In another aspect, the invention relates to methods to modulate the immunosuppressive properties of a protein by modifying the amino acid composition of the immunosuppression-modulatory sequence.

BRIEF DESCRIPTION OF THE DRAWINGS

FIG. 1: schematic representation of vectors containing the env nucleic acid of MoMLV or its derived polypeptides.
Nucleic acids contained in these vectors encode the wild-type envelope protein of MoMLV (envMoMLV) or its derived polypeptides of the invention by substitutions of codons encoding X1 and/or X2.

FIG. 2: schematic representation of vectors containing the env nucleic acid of MPMV or its derived polypeptides.
Nucleic acids contained in these vectors encode the wild-type envelope protein of MPMV (envMPMV) or its derived polypeptides of the invention by substitutions of codons encoding X1 and/or X2.

FIG. 3: schematic representation of vectors containing the HERV-W nucleic acid of HERV-W or its derived polypeptides.
Nucleic acids contained in these vectors encode the wild-type envelope protein W (envW) or its derived polypeptides of the invention by substitutions of codons encoding X1 and/or X2.

and an IRES (Internal Ribosome Entry Site). White boxes represent LTRs and the arrow indicates the start of transcription.

Figure 6:
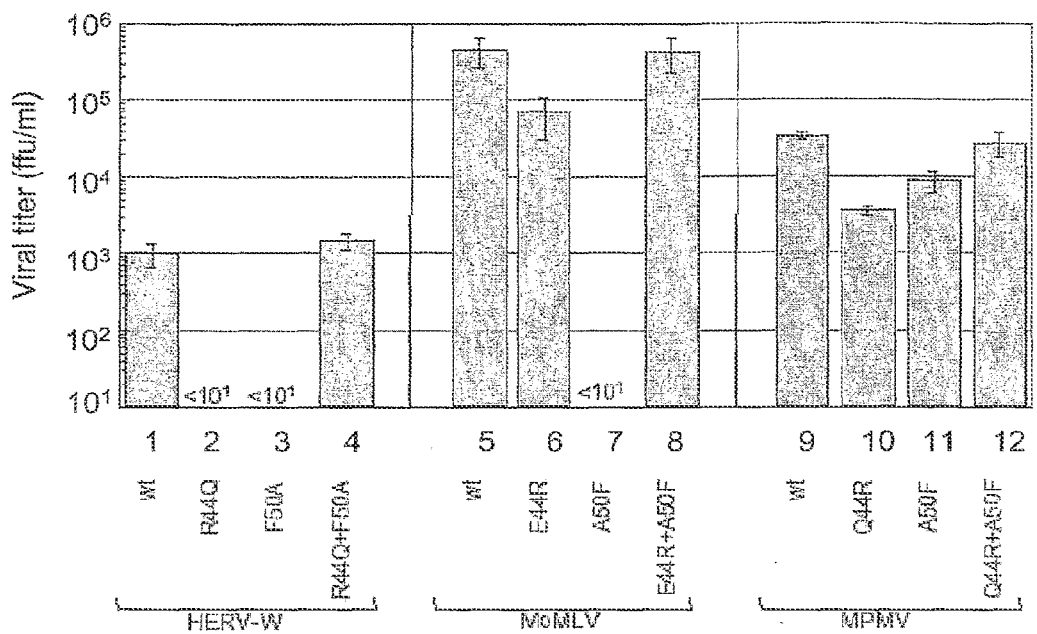

FIG. 6: Results of infectious property assay.
The numbers 1 to 12 refer to lines used in the present specification. This diagram presents the results of infection for wild-type (wt) or mutant envelope proteins according to the invention.

Figure 7:
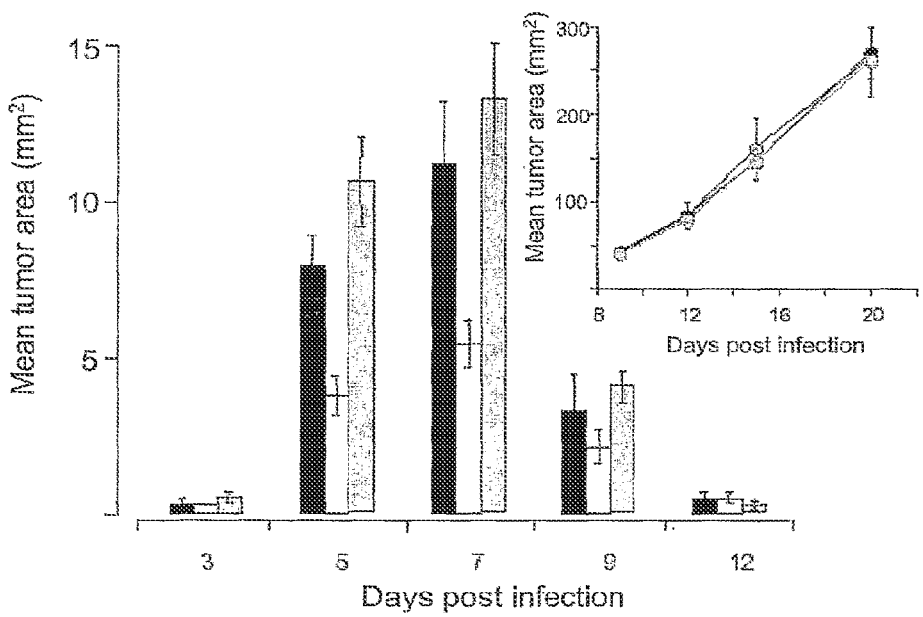

FIG. 7: Results of immunosuppressive property assay.
The diagram presents the results of immunosuppressive property assay of MCA205 cells expressing envelope when injected in allogenic balb/c mice. In insets, results of MCA205 cells expressing envelope protein injected in syngenic C57Bl/6 mice. Filled bars represent HERV-W envelope protein, white bars represent MPMV envelope protein and shaded bars represent double-mutant (R44Q+F50A) HERV-W envelope protein.

Figure 8:
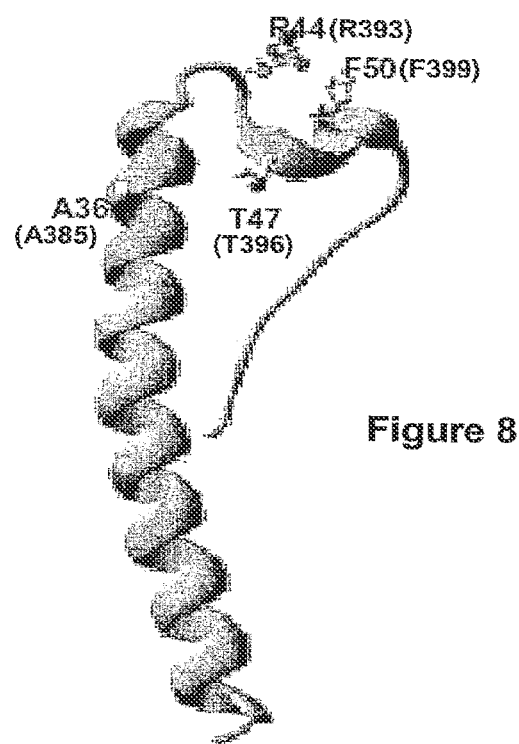

FIG. 8: Structural design of the TM subunit of the HERV-W ENV protein.
This structural design shows the position of the Arginine (X1) and Phenylalanine (X2) amino acid residues of the immunosuppression-modulatory sequence, as well as the two amino acid residues (Alanine and Threonine) not involved in such properties.

FIG. 9: Examples of immunosuppression-modulatory sequence of different viruses and HERVs.
The first column indicates the common names of viruses or HERVs, the second column indicates the origin of the viruses or HERVs, the third column indicates the nucleotide sequences of identified immunosuppression-modulatory sequences (one letter amino acid used) and the last column indicates the Accession Number of the envelope protein. The X1 and X2 amino acid residues are in bold. The following SEQ ID NOS are disclosed respectively in order of appearance: 34, 33, 80, 35, 36, 75, 38, 77, 78, 39, 37, 76, 79, 67, 68, 40-42 & 45-47.

FIGS. 10A-10F: Nucleotide and amino acid sequences of wild-type envelope proteins.
In the amino acid sequences, the X1 and X2 positions have been underlined.
FIG. 10A (SEQ ID NO: 69) and FIG. 10B (SEQ ID NO: 70) represent the nucleotide and protein sequences of the envelope protein of MoMLV, FIG. 10C (SEQ ID NO: 71) and FIG. 10D (SEQ ID NO: 72) represent the nucleotide and protein sequences of the envelope protein of MPMV and FIG. 10E (SEQ ID NO: 73) and FIG. 10F (SEQ ID NO: 74) represent the nucleotide and protein sequences of the envelope protein of HERV-W (envW).
The nucleotide sequences (A, C and E) are the coding sequences of the envelope proteins, with the first codon (ATG) being the first codon of transcription and the last codon (TAG) being the termination codon.
For the protein sequences (B, D and F), the first letter amino acid code is used. The first M represents the first methionine of the protein, and the symbol "*" represent the termination codon.

Figure 11A:
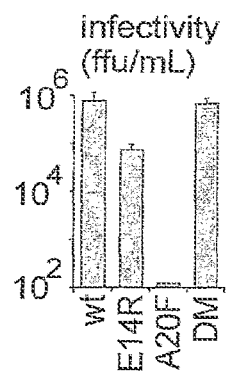
Figure 11B:
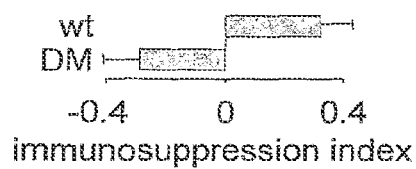
Figure 11C:
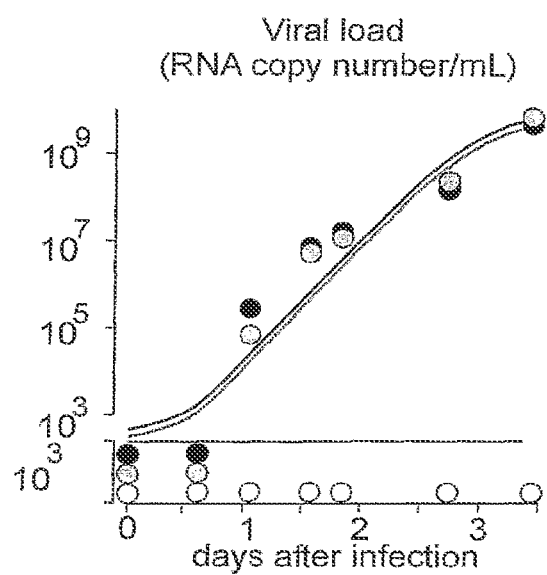

FIG. 11A, FIG. 11B and FIG. 11C: In vitro properties of the immunosuppression-defective FV envelope protein. FIG. 11A, Infectivity of FV wild type (wt) envelope protein, E14R mutant envelope protein, A20F mutant envelope protein, and E14R+A20F double mutant (DM) envelope protein as expressed on the surface of a MLV viral pseudotypes, using NIH 3T3 cells as a target. The vertical axis represents the infectivity (ffu/ml) FIG. 11B, In vivo immunosuppressive activity (horizontal axis, immunosuppression index) of the wild-type (wt) and the double-mutant (DM) FV envelope protein. FIG. 11C, Comparison of in vitro propagation rates of the wild-type (black circles) and immunosuppression-defective (gray circles) FV virions, using NIH 3T3 cells as a target. Viral load of cell supernatants (vertical axis, RNA copy number/mL) is assayed by quantitative RT-PCR. Horizontal axis represents the number of days after infection. The white circles represent a control.

FIG. 12A and FIG. 12B: In vivo effects of the loss of envelope-driven immunosuppression on FV infection. Serum viral loads (Vertical axis, RNA copy numbers/mL) of irradiated (FIG. 12A) and non-irradiated (FIG. 12B) Swiss mice after injection of the wild-type FV (black circles) or the non-immunosuppressive mutant FV (gray circles). The signal for PBS-injected mice was below detection threshold (white circles). Horizontal axis represents the days after injection.

FIG. 13: Immunological detection of FV in infected mice. IgGs directed against the SU subunit of the FV envelope protein were quantitated (vertical axis, arbitrary units) in the sera of mice injected with the wild-type FV (black circles and line), the non-immunosuppressive mutant FV (gray circles and line) or PBS (white circles and dotted lines). The lines represent the geometric means of the IgG levels. Horizontal axis represents the days after injection.

Figure 14A:
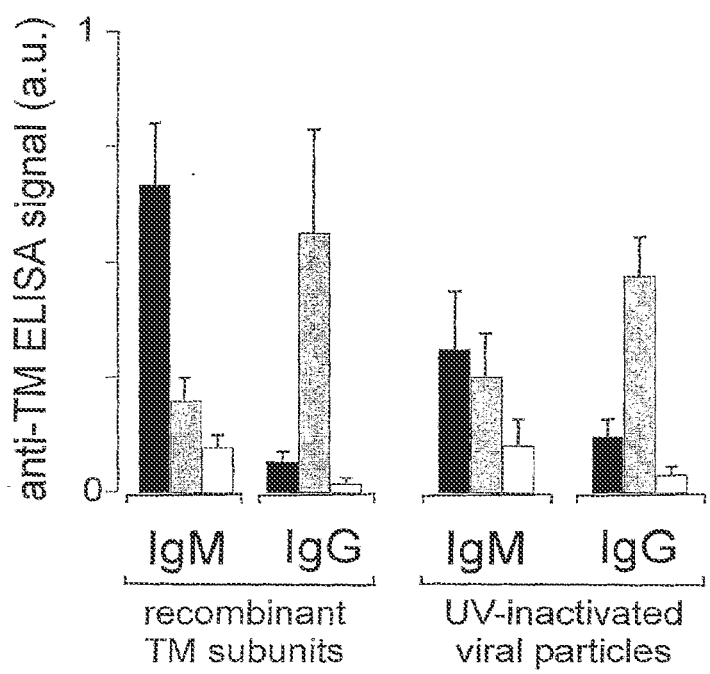
Figure 14B:
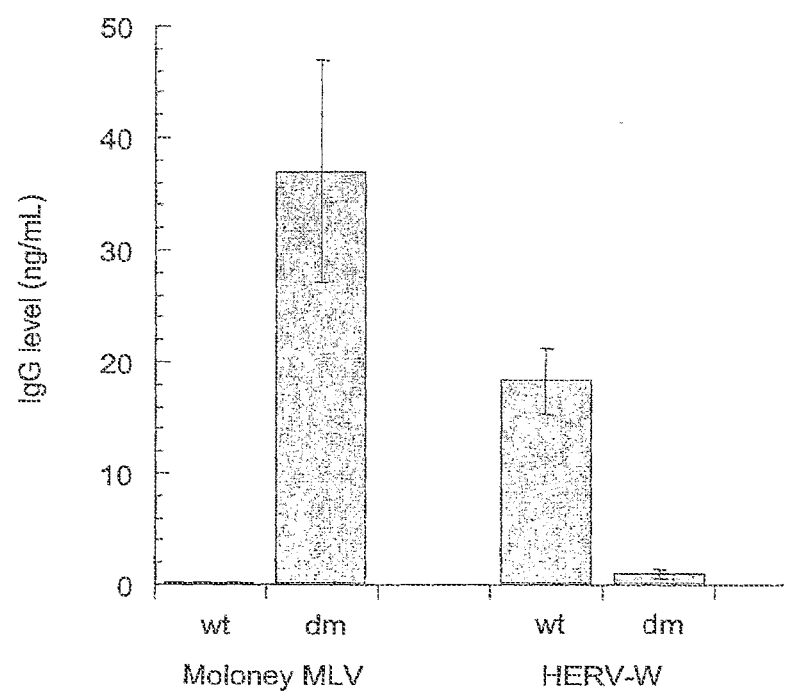

FIG. 14A and FIG. 14B: Antigenicity of the wild-type and non-immunosuppressive mutant FV envelope proteins. FIG. 14A, IgMs and IgGs directed against the TM subunit of the FV envelope protein were quantitated in the sera of mice injected with recombinant TM subunits of the FV envelope protein (left) or UV-inactivated FV viral particles (right). Black: wild-type FV; gray: non-immunosuppressive mutant FV; white: adjuvant only. Mean± standard deviation on 5 (left) or 14 (right) Swiss mice. The vertical axis represents the anti-TM ELISA signal in arbitrary units (a.u.). FIG. 14B, same as in FIG. 14A with mice injected with the wild type (wt) or double mutant (dm) recombinant TM subunits of MoMLV (left) and HERV-W ENV (right) as described in Example 1. The vertical axis represents the IgG level in ng/mL.

Figure 15:
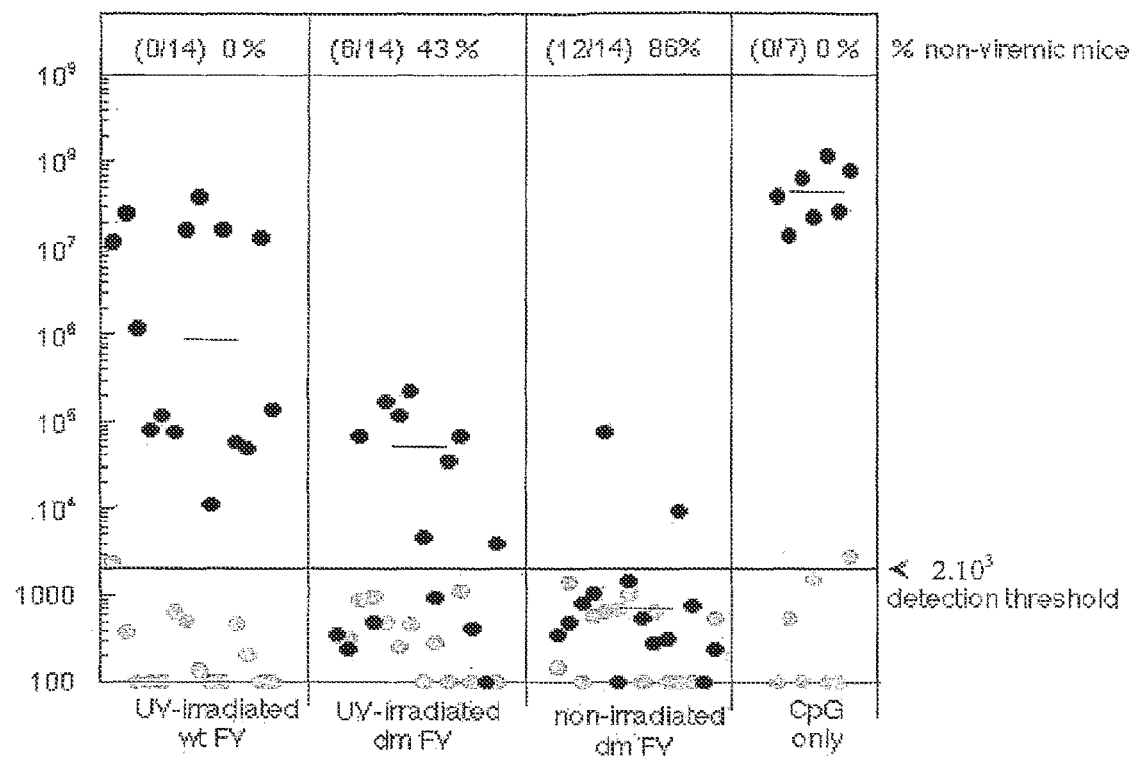

FIG. 15: Vaccination assays. FIG. 15 represents the viral load (Vertical axis, RNA copies/mL serum) of mice immunized with UV-inactivated wild-type or non-immunosuppressive double mutant Friend Virus (FV), with intact non-immunosuppressive double mutant Friend Virus (FV), or with CpG adjuvant only, and challenged with the wild-type FV. Immunization was performed on day 1, day 7 and day 14 before challenge on day 21, and the corresponding viral loads are represented as grey dots. 5 days post-challenge viral loads are represented as black dots. The detection threshold is represented as a horizontal line at $2.10^3$ RNA copies/mL. On top of the graph is indicated the number and the percentage of mice having a viral load below the detection level at 5 days post-challenge. Horizontal bars represent the geometric means of the viral loads.

FIG. 16A, FIG. 16B and FIG. 16C: Knockdown procedure and rationale of the assay. FIG. 16A represents the procedure to knock down ERV expression, a plncx-derived vector was constructed making use of the pSUPER vector to generate, under control of the H1-RNA promoter, short double-stranded transcripts for RNA interference. B16 cells were transduced with these expression vectors, submitted to G418 selection, and the resulting ERV$^{KD}$ and control B16 cells were injected subcutaneously into the flank of the mice, whose tumor growth was monitored. FIG. 16B (SEQ ID NO: 170 & 171), predicted structure of the dsRNA generated by the ERV and control (gfp) vectors; numbers refer to nt positions within the respective targeted sequences (see Methods). FIG. 16C, Western blot analysis of Gag (anti-Gag) and Env (anti-Env) expression in the supernatant of ERV-knocked down (ERV$^{KD}$) and control cells. Molecular weights are represented on both side of the Figure.

Figure 17A:
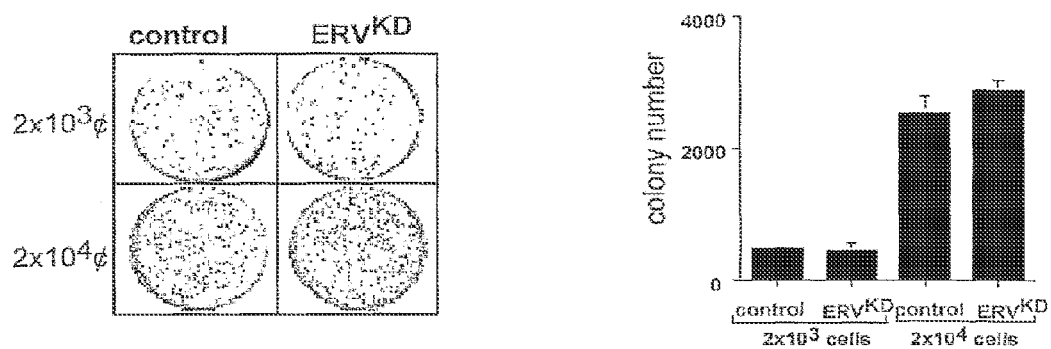
Figure 17B:
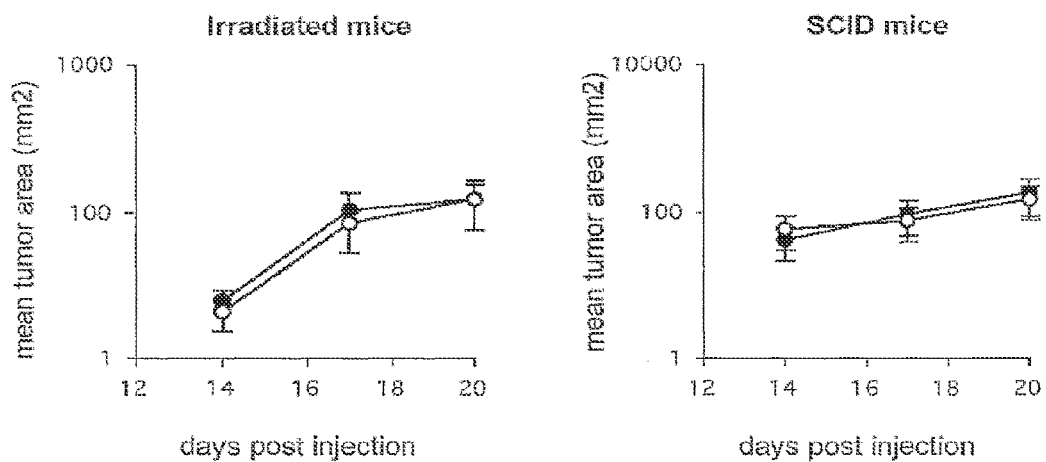

FIG. 17A and FIG. 17B: Knocked down cells have conserved a transformed phenotype. FIG. 17A, in vitro analysis of the transformed phenotype using soft agar assay. Left panel, ERV$^{KD}$ (right plates) and control B16 (left plates) cells ($2\times10^3$ or $2\times10^4$) were plated onto a semi-solid layer for 4 weeks, and then colonies were numbered (right panel). FIG. 17B, assay for the transformed phenotype in vivo using immuno-incompetent mice. ERV$^{KD}$ and control B16 cells ($2\times10^5$) were injected subcutaneously into the flank of either X-irradiated (5 Gy) C57Bl/6 (left panel) or SCID mice (right panel) (2-5 independent experiments with 5 mice per group) and tumor growth was determined by measuring tumor area (vertical axis, mm$^2$) as a function of time (horizontal axis, days post injection).

Figure 18A:
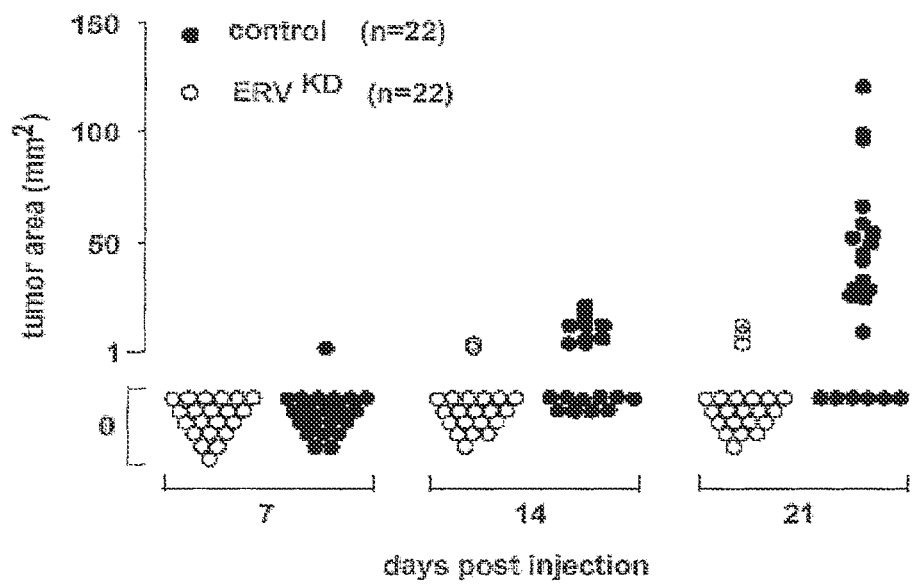
Figure 18B:
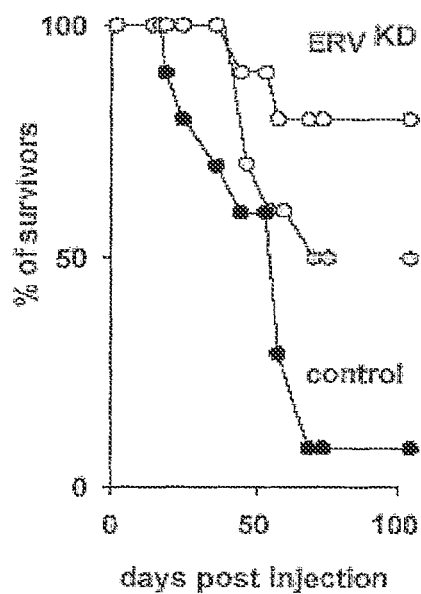
Figure 18C:
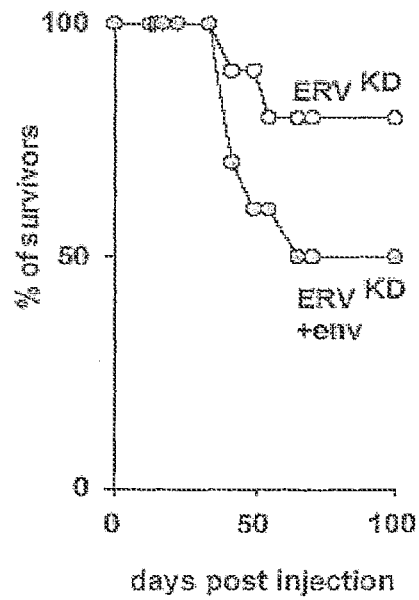

FIG. 18A, FIG. 18B and FIG. 18C: Inhibition of tumor cell growth and increased mouse survival upon ERV knockdown. FIG. 18A, tumor cell growth of control (black dots) and ERV$^{KD}$ B16 cells (white dots) engrafted into immunocompetent C57Bl/6 mice (22 mice per group; same experimental conditions as in FIG. 17B). Tumor area (vertical axis, mm$^2$) is measured as a function of time (horizontal axis, days post injection). FIG. 18B, percentage of survivors (vertical axis) among the control (black dots) and ERV$^{KD}$ B16 cells (white dots) engrafted mice (10 mice per group) as a function of time (horizontal axis, days post injection). FIG. 18C, percentage of survivors (vertical axis) (10 mice per group) among MelARV env-transduced ERV$^{KD}$ B16 cells (grey dots) and ERV$^{KD}$ B16 cells (white dots) engrafted mice as a function of time (horizontal axis, days post injection).

Figure 19:
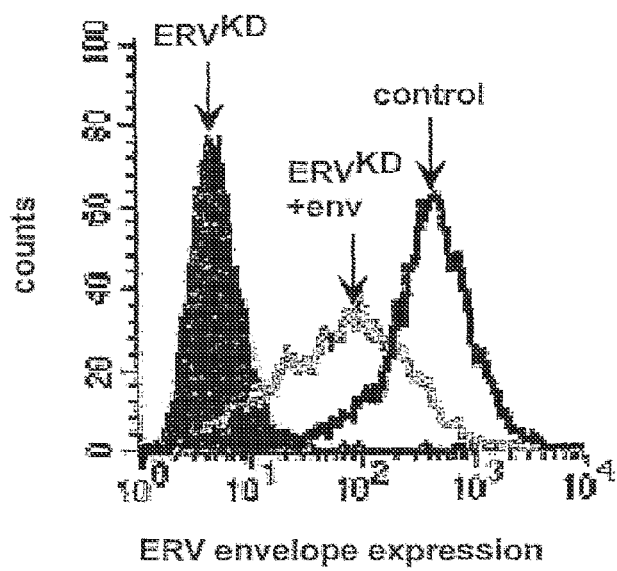

FIG. 19: Immunostaining for ERV envelope protein detection. Control, ERV$^{KD}$, and ERV$^{KD}$+env B16 cells were labelled with the 9B6 antibody (directed against the MelARV envelope protein; gift from E. Gorelik, Cancer Res 1988; 48:4954-4958) revealed by a goat anti-mouse FITC antibody (Caltag, Burlingame, USA). Flow cytometry analysis was performed using a Facscalibur cytometer. The number of counts (vertical axis) is represented as a function of ERV envelope expression (horizontal axis).

Figure 20A:
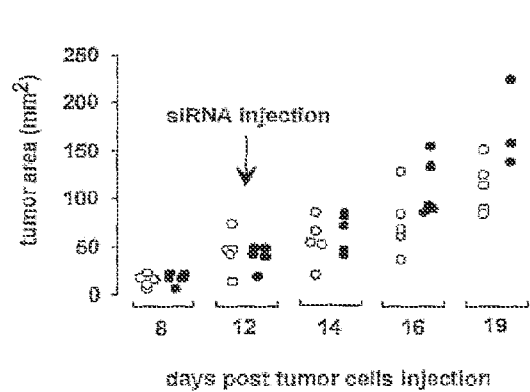
Figure 20B:
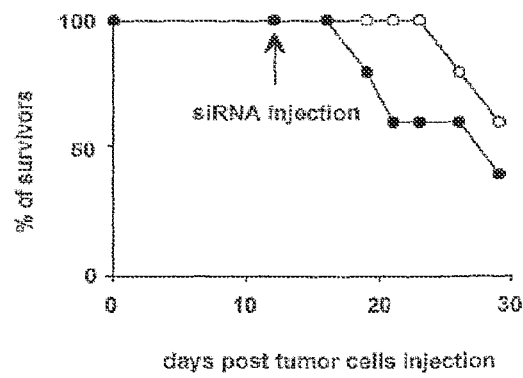

FIG. 20A and FIG. 20B: In vivo systemic administration of siRNA reduces tumor cell progression. Synthetic siRNA targeted to the 19 nt ERV (white dots) and control (gfp) (black dots) sequences referred to in FIG. 16B were purchased from MWG Biotech. They were injected intraperitoneously (3 µg of siRNA in 50 µl of PBS), at day 12 after prior engraftement of $2\times10^5$ B16 cells in the right flank of the mice. FIG. 20A, the tumor area (vertical axis, mm$^2$) is measured as a function of time (horizontal axis, days post tumour injection), siRNA injection is represented as an arrow. FIG. 20B, the percentage of survivors (vertical axis) were monitored (5 mice per group in two independent experiments) as a function of time (horizontal axis, days post tumour injection).

DETAILED DESCRIPTION

The present invention provides a polypeptide having a sequence of 7 to 20 amino acid residues, which is capable of modulating the immunosuppressive properties of a viral protein or a fragment thereof against the host in which it is expressed when it substitutes the homologous sequence of said viral protein or fragment, said polypeptide comprising the minimum following consensus amino acid sequence:

$$X1\text{-}(Y)_3\text{-}C\text{-}(Y)_1\text{-}X2$$

wherein, X1 and X2 are selected to impact on said immunosuppressive properties, Y represents variable amino acid residues, and 3 and 1 represent the number of variable amino acid residues Y, respectively between X1 and C and between C and X2.

In all the sequences of the present invention, the amino acid one-letter code is used. X and Y are used to designate variable amino acid residues, X being determined to influence the immunosuppressive properties of a determined protein.

Y represents amino acid residues that can vary for different polypeptides and within one determined polypeptide. "(Y)$_3$" indicates that 3 amino acid residues are present between the X1 residues and the cysteine residue (C). The 3 amino acid residues can be different or identical and can be selected independently of each other. The indication of a particular amino acid residue in a sequence, like the cysteine in the sequence above, means that this amino acid residue is invariant, i.e. it has a constant position in said sequence.

Optionally the consensus sequence can also be noted as follows:

$$X_1Y_9Y_{10}Y_{11}CY_{12}X_2$$

wherein $X_1$ represents X1, $X_2$ represents X2, and $Y_9$ to $Y_{12}$ represent any amino acid. As intended herein amino acids $Y_9$ to $Y_{12}$ are identical or different.

In the present invention, the expressions "virus" or "viral" apply both exogenous or endogenous viruses or their compounds, unless otherwise stated. Therefore, "viral protein" encompasses "viral-like proteins" which may also be referred to when describing the expression products of endogenous viruses, especially ERV, in particular HERV.

The above consensus sequence of the polypeptide according to the invention is called "immunosuppression-modulatory sequence" meaning that, when it is present in the polypeptide having 7 to 20 amino acid residues, the polypeptides can be used to modulate immunosuppressive properties of a protein which has been identified as harbouring such immunosuppressive properties or, as lacking such properties despite the fact that is comprises a peptidic motif having a sequence X1-(Y)$_3$-C-(Y)$_1$-X2.

More especially, X represents both amino acid residues (X1 and X2) directly involved, individually or together, in the modulation of the immunosuppressive properties of a protein comprising the above consensus sequence. They are respectively located at the N-terminal and C-terminal ends of the minimum polypeptide having 7 amino acid residues.

A protein is said to have immunosuppressive properties, when this protein, expressed in tumour cells engrafted in a host which would normally be rejected by said host, to the contrary allows these tumour cells to proliferate and to escape immune rejection by the host.

Figure 5:
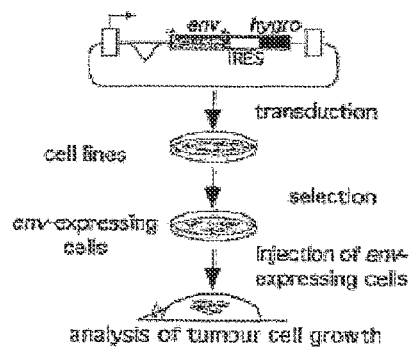
FIG. 5: Schematic representation of the establishment of Envelope Expressing tumours cells and in vivo assay.
The vector used comprises the nucleic acid encoding an envelope protein of interest (env), the hygromycin gene (hygro)

An in vivo procedure to assay the immunosuppressive activity of a protein is that used by Mangeney M. and Heidmann T., 1998 PNAS or by Blaise et al. 2001 represented in FIG. 5. A wild-type or modified nucleic acid expressing the protein to be tested is transfected in tumour cell lines such as MCA 205 or Cl8.1 cell lines by known transfection methods. The tumour cells expressing the protein to be tested are then injected especially s.c. injection to a host, generally mice. Following said injection, the establishment of tumour or, to the contrary, its rejection, is determined and the tumour area is measured. In vitro assay could be carried out, using high doses of synthetic peptides but they are indirect and less convincing, since the expression "immunosuppressive" is relevant when applied to animals possessing a complete immune system and not to cell lines.

The expression "modified nucleic acid" as used herein refers to any genetic alteration such as nucleotide substitution, deletion or insertion that change the amino acid composition of the encoded polypeptide or protein. Thus, an amino acid sequence can substitute, i.e. replace a homologous sequence present in the original protein.

The terms "homologous sequence" in the protein which is tested for modulation of its immunosuppressive properties refer to a sequence having the same amino acid sequence as that replacing (i.e. substituting) it for the assay, i.e., X1-(Y)$_3$-C-(Y)$_1$-X$_2$ except for the X1 and X2 residues; at least one of which and possibly both, are selected to be different from their corresponding amino acid residues in the original sequence. Thus, the Y amino acid residues are conserved between the homologous sequence of the protein to be modified and the sequence of the polypeptide having 7-20 amino acid residues as defined above. Such homologous sequences are disclosed in FIG. 9 for various viruses and are illustrated in the context of the TM subunit of various envelopes for several viruses in Benit L. et al. (J. Virol. Vol. 75, No. 23, December 2001, p. 11709-11719) in FIG. 3.

The X1 and X2 amino acid residues are chosen to modulate the immunosuppressive properties of the original viral protein. The term "modulate" as used herein refers to an increase or decrease of the immunosuppressive activity of the modified protein with respect to the immunosuppressive activity of the original (i.e., non modified) protein, when tested in the same conditions.

The invention especially relates to an "immunosuppression-modulatory sequence" which allows a decrease in the immunosuppressive properties of the modified protein with respect to the originally immunosuppressive protein. The modulation is preferably significant meaning that the immune response of the host becomes detectable, and advantageously becomes sufficient to eliminate the pathogen agent or becomes sufficient to stop, stabilize or reverse the detrimental consequences of infection by said pathogen in a host or of the expression of endogenous viruses, especially of normally silent ERV, especially HERV, in a host.

In a particular embodiment, modulation results in decreasing the immunosuppressive properties of the original protein.

In a particular embodiment it corresponds to at least a two-fold decrease of the immunosuppressive properties of the original protein, in the modified, i.e., derived protein.

The above defined polypeptide of the invention having 7 to 20 amino acid residues and comprising sequence X1-(Y)$_3$-C-(Y)$_1$-X2 is such that X1 and/or X2 are selected to modulate the immunosuppressive properties of a protein and accordingly:

in a particular embodiment of the invention, X1 is an alkaline amino acid residue and X2 is an aromatic residue or vice versa.

As intended herein "alkaline" relates to basic amino acids.

In another particular embodiment of the invention, X1 is an alkaline residue or X2 is an aromatic residue or vice versa.

The inventors have observed that the modulation effect of X1 and X2 on immunosuppressive proteins is lower when only one of X1 or X2 residues is modified in an original immunosuppressive protein.

Therefore, modification of both X1 and X2 in an immunosuppression-modulatory sequence may be regarded as advantageous.

In another particular embodiment of the invention, residues X1 or X2 located in amino acid sequence represented as X1-(Y)$_3$-C-(Y)$_1$-X2 are selected as follows:
where X1 is chosen among R, H and K, X2 is chosen among F, W, Y and H or where X1 is chosen among F, W, Y and H, X2 is chosen among R, H and K.

In a further embodiment of the invention, X1 is R, H or K and X2 is F, or vice versa.

In a further embodiment of the invention, X1 is R and X2 is F, W, Y or H.

In another further embodiment of the invention X1 and X2 are selected from the group consisting of:
  a. X1 is E, K or Q and X2 is A
  b. X1 is W and X2 is I or V
  c. X1 is R and X2 is F
  d. X1 is K and X2 is F.

The inventors have identified the effects of particular X1 and X2 residues, in a immunosuppression-modulatory sequence on modulation of the immunosuppressive properties of a viral envelope protein.

Their observations enable to consider that, when X1 is either glutamic acid (E) or glutamine (Q) and X2 can be alanine (A), the resulting viral envelope protein comprising the consensus sequence of the invention harbours immunosuppressive properties. To the contrary, when X1 is arginine (R) and X2 is phenylalanine (F), the resulting viral envelope protein having the consensus sequence of the invention has low or has no immunosuppressive properties. Interestingly, whereas van der Waals interactions are suspected in the pair E/A, an electrostatic interaction may occur in the pair R/F, between the positively charged side chain of Arginine and the pi-electrons (negative pole) of Phenylalanine.

Accordingly, in a particular embodiment of the invention, the polypeptide having 7 to 20 amino acid residues has an immunosuppression-modulatory sequence X1-(Y)$_3$-C-(Y)$_1$-X2 suitable to confer low or no immunosuppressive properties to a protein, wherein X1 is R and/or X2 is F.

In another embodiment, X1 is K and X2 is F to confer low or no immunosuppressive properties to a protein. In particular, such a protein has low immunosuppressive properties.

It is recalled that the immunosuppressive properties are assayed in a test as defined above and illustrated in the Examples.

The consensus sequence, X1-(Y)$_3$-C-(Y)$_1$-X2, can be identified in viral proteins and especially in viral envelope proteins. Particular envelope proteins are those of retroviruses that comprise two subunits: the SU and TM subunits. Such consensus sequences have been found in MoMLV, Friend retrovirus, FeLV, HTLV-1, HTLV-2, STLV-1, GLV-X, Pox viruses, MPMV or SSAV, or in Ebola or Marburg viruses or in endogenous retroviruses such as FRD, PyERV, PERV or HERV-T.

The Y amino acid residues thus identified in various proteins allow determining particular sequences of the invention such as E/Q-G-G-L/T/I-C-A/K/L/M/V/I-A (SEQ ID NO: 153) or R-G-G-L/T/I-C-A/K/L/M/V/I-F (SEQ ID NO: 154). The "/" indicates that this sequence position accepts several types of amino acid residues according to the indications which are provided.

Therefore, the above-defined polypeptide of the invention comprises, in a particular embodiment, a minimum sequence which can be selected from the group consisting of:
  QGGLCKA (SEQ ID NO: 17)
  QGGLCAA (SEQ ID NO: 18)
  QGGLCLA (SEQ ID NO: 19)
  QGGICLA (SEQ ID NO: 20)
  EGGLCAA (SEQ ID NO: 21)
  EGGLCVA (SEQ ID NO: 22), wherein these immunosuppression-modulatory sequences provide immunosuppressive properties to a protein comprising them, or
  RGGTCLF (SEQ ID NO: 23)
  KGGTCMF (SEQ ID NO: 24)
  KGRTCLF (SEQ ID NO: 25)
  KGGLCIF (SEQ ID NO: 26)
  RGGLCKF (SEQ ID NO: 27)

RGGLCAF (SEQ ID NO: 28)
RGGLCLF (SEQ ID NO: 29)
RGGICLF (SEQ ID NO: 30)
RGGLCVF (SEQ ID NO: 31)
RGGTCVF (SEQ ID NO: 32), these immunosuppression-modulatory sequences providing low or no immunosuppressive properties to a protein comprising them.

More particularly, the above-defined polypeptide of the invention comprises, in another embodiment, a minimum sequence which can be selected from the group consisting of:
QGGLCKA (SEQ ID NO: 17)
QGGLCAA (SEQ ID NO: 18)
QGGLCLA (SEQ ID NO: 19)
QGGICLA (SEQ ID NO: 20)
EGGLCAA (SEQ ID NO: 21)
EGGLCVA (SEQ ID NO: 22), wherein these immunosuppression-modulatory sequences provide immunosuppressive properties to a protein comprising them, or
KGGTCMF (SEQ ID NO: 24)
KGRTCLF (SEQ ID NO: 25)
KGGLCIF (SEQ ID NO: 26), wherein these immunosuppression-modulatory sequences provide low immunosuppressive properties to a protein comprising them, or
RGGTCLF (SEQ ID NO: 23)
RGGLCKF (SEQ ID NO: 27)
RGGLCAF (SEQ ID NO: 28)
RGGLCLF (SEQ ID NO: 29)
RGGICLF (SEQ ID NO: 30)
RGGLCVF (SEQ ID NO: 31)
RGGTCVF (SEQ ID NO: 32), these immunosuppression-modulatory sequences providing essentially no immunosuppressive properties to a protein comprising them.

As intended herein, "low immunosuppressive properties" relates to a polypeptide which provides lower immunosuppressive properties to a protein comprising it than polypeptides represented by SEQ ID NO: 17 to 22, but provides higher immunosuppressive properties to a protein comprising it than polypeptides represented by SEQ ID NO: 23 to and 27 to 32. In particular, a protein comprising a polypeptide which provides low immunosuppressive properties is less immunosuppressive than a HERV-W ENV R393Q F399A double mutant, such as represented by SEQ ID NO: 118. More particularly, the immunosuppressive index of a protein comprising a polypeptide which provides low immunosuppressive properties is positive but lower than the immunosuppressive index of said HERV-W ENV R393Q F399A double mutant, and preferably lower than 50% the immunosuppressive index of said HERV-W ENV R393Q F399A double mutant.

All the polypeptides of the invention are encoded by nucleic acids that can be obtained by all known methods to enable expression of the polypeptides in host cells, especially in prokaryotic or eukaryotic cells. As example, nucleic acids can be isolated from samples expressing viruses, using suitable probes and amplification technique. They can also be chemically synthesized or obtained by enzymatic digestion from existing plasmids or plasmids from the invention.

Furthermore, the polypeptides of the invention can also be chemically synthesized or semi-synthesized according to well-established procedures.

A particular 20-amino acid polypeptide has the following consensus sequence:

$$(Y)_{13}\text{-}X1\text{-}(Y)_3\text{-}C\text{-}(Y)_1\text{-}X2$$

As above explained, X1 and X2 are selected to impact on the immunosuppressive properties of a tested i.e., original viral immunosuppressive protein in which the polypeptide is inserted, including by replacement of X1 and X2 residues in an homologous sequence as defined above, wherein Y represents variable amino acid residues, 3 and 1 represent the number of variable amino acid Y residues respectively between X1 and C and between C and X2, and 13 represents the number of amino acid residues in the N-terminal part of the polypeptide. The Y residues can independently be identical or different in the sequence.

The identification of invariant amino acid residues in various protein sequences allows defining a particular sequence: $(Y)_2\text{-}N\text{-}(Y)_3\text{-}L\text{-}(Y)_2\text{-}L\text{-}(Y)_3\text{-}X1\text{-}(Y)_3\text{-}C\text{-}(Y)_1\text{-}X2$ (SEQ ID NO: 155), i.e. from the N-terminal-end to C-terminal end: two variable amino acid residues, an asparagine (N), three variable amino acid residues, a leucine (L), two variable amino acid residues, a leucine (L), three variable amino acid residues, the X1 residue, three variable amino acid residues, a cysteine (C), one variable amino acid residue and the X2 residue.

Optionally the above consensus sequence can be noted as follows:

(SEQ ID NO: 157)
$$Y_{13}Y_{14}NY_1Y_2Y_3LY_4Y_5LY_6Y_7Y_8X_1Y_9Y_{10}Y_{11}CY_{12}X_2$$

wherein $X_1$ and $X_2$ are respectively identical to X1 and X2, and $Y_1$ to $Y_{14}$ represent any aminoacid. As intended herein amino acids $Y_1$ to $Y_{14}$ can be identical or different.

Particular amino acid sequences presenting the capacity to modulate the immunosuppressive properties of a viral immunosuppressive protein in the above disclosed test, can be selected from the group consisting of:
AQNRRGLDLLFWEQGGLCKA (SEQ ID NO: 33)
LQNCRCLDLLFLSQGGLCAA (SEQ ID NO: 34)
LQNRRGLDMLTAAQGGLCLA (SEQ ID NO: 35)
LQNRRGLDLLTAEQGGICLA (SEQ ID NO: 36)
LQNRRGLDILFLQEGGLCAA (SEQ ID NO: 37)
LQNRRGLDLLFLKEGGLCAA (SEQ ID NO: 38)
LQNRRGLDLLFLKEGGLCVA (SEQ ID NO: 39), wherein these immunosuppression-modulatory sequences provide immunosuppressive properties to a protein comprising them, or
LQNRRALDLLTAERGGTCLF (SEQ ID NO: 40)
LQNWRALDLLTAKRGGTCLF (SEQ ID NO: 41)
LQNWRALDLLIAKRGGTCVF (SEQ ID NO: 42)
LQNRRGLDLLTAERGGTCLF (SEQ ID NO: 43)
LQNRRALDLLTAERGGICLF (SEQ ID NO: 44)
LQNRRGLDLLTAEKGGLCIF (SEQ ID NO: 45)
MQNRRALDLLTADKGGTCMF (SEQ ID NO: 46)
AQNRQALDLLMAEKGRTCLF (SEQ ID NO: 47)
AQNRRGLDLLFWERGGLCKF (SEQ ID NO: 48)
LQNCRCLDLLFLSRGGLCAF (SEQ ID NO: 49)
LQNRRGLDMLTAARGGLCLF (SEQ ID NO: 50)
LQNRRGLDLLTAERGGICLF (SEQ ID NO: 51)
LQNRRGLDILFLQRGGLCAF (SEQ ID NO: 52)
LQNRRGLDLLFLKRGGLCAF (SEQ ID NO: 53)
LQNRRGLDLLFLKRGGLCVF (SEQ ID NO: 54), these immunosuppression-modulatory sequences providing low or no immunosuppressive properties to a protein comprising them.

According to a preferred embodiment, particular amino acid sequences presenting the capacity to modulate the immunosuppressive properties of a viral immunosuppressive protein in the above disclosed test, can be selected from the group consisting of:
AQNRRGLDLLFWEQGGLCKA (SEQ ID NO: 33)
LQNCRCLDLLFLSQGGLCAA (SEQ ID NO: 34)
LQNRRGLDMLTAAQGGLCLA (SEQ ID NO: 35)

LQNRRGLDLLTAEQGGICLA (SEQ ID NO: 36)
LQNRRGLDILFLQEGGLCAA (SEQ ID NO: 37)
LQNRRGLDLLFLKEGGLCAA (SEQ ID NO: 38)
LQNRRGLDLLFLKEGGLCVA (SEQ ID NO: 39),
wherein these immunosuppression-modulatory sequences provide immunosuppressive properties to a protein comprising them, or
LQNRRGLDLLTAEKGGLCIF (SEQ ID NO: 45)
MQNRRALDLLTADKGGTCMF (SEQ ID NO: 46)
AQNRQALDLLMAEKGRTCLF (SEQ ID NO: 47),
wherein these immunosuppression-modulatory sequences provide low immunosuppressive properties to a protein comprising them, or
LQNRRALDLLTAERGGTCLF (SEQ ID NO: 40)
LQNWRALDLLTAKRGGTCLF (SEQ ID NO: 41)
LQNWRALDLLIAKRGGTCVF (SEQ ID NO: 42)
LQNRRGLDLLTAERGGTCLF (SEQ ID NO: 43)
LQNRRALDLLTAERGGICLF (SEQ ID NO: 44)
AQNRRGLDLLFWERGGLCKF (SEQ ID NO: 48)
LQNCRCLDLLFLSRGGLCAF (SEQ ID NO: 49)
LQNRRGLDMLTAARGGLCLF (SEQ ID NO: 50)
LQNRRGLDLLTAERGGICLF (SEQ ID NO: 51)
LQNRRGLDILFLQRGGLCAF (SEQ ID NO: 52)
LQNRRGLDLLFLKRGGLCAF (SEQ ID NO: 53)
LQNRRGLDLLFLKRGGLCVF (SEQ ID NO: 54), these immunosuppression-modulatory sequences providing essentially no immunosuppressive properties to a protein comprising them.

The present invention also relates to the use of a first mutation of a first amino acid and optionally of a second mutation of a second amino acid in a wild type viral envelope (ENV) protein essentially comprising the following sequence:

$$\mathbf{N}Y_1Y_2Y_3\mathbf{L}Y_4Y_5\mathbf{L}Y_6Y_7Y_8X_1Y_9Y_{10}Y_{11}\mathbf{C}Y_{12}X_2$$
(SEQ ID NO: 156)

wherein the first amino acid to be mutated is $X_1$ and the second amino acid to be mutated is $X_2$, and $Y_1$ to $Y_{12}$ represent any amino acid, for manufacturing a mutated ENV protein having a modified immunosuppressive activity with respect to said wild type ENV protein.

The expression "wild type viral envelope protein" relates to an envelope protein in which amino acid $X_1$ has not been mutated. In particular, it is not excluded that other mutations or modifications have been brought to the envelope protein.

The expression "essentially comprising" means that at least two of the four constant amino acids of the above sequence (represented in bold) are present in said wild type viral envelope. Two amino acids are sufficient to unambiguously determine the position of $X_1$ and $X_2$ in the envelope sequence. Advantageously, the above sequence is usually localized in the transmembrane (TM) subunit, more particularly in the ectodomain of the TM subunit.

As intended herein, amino acids $Y_1$ to $Y_{12}$, independently of each other are different or identical.

As intended herein the mutated ENV protein essentially carries the following sequence:

$$\mathbf{N}Y_1Y_2Y_3\mathbf{L}Y_4Y_5\mathbf{L}Y_6Y_7Y_8X'_1Y_9Y_{10}Y_{11}\mathbf{C}Y_{12}X'_2$$
(SEQ ID NO: 156)

wherein $X'_1$ corresponds to the mutated $X_1$ and $X'_2$ corresponds to the mutated $X_2$.

The expression "modified immunosuppressive activity" means that the mutated ENV protein has either increased or decreased immunosuppressive activity with respect to the corresponding wild-type ENV protein. In particular, the mutated ENV protein can be essentially deprived of any residual immunosuppressive activity. In another instance, the mutated ENV protein can have immunosuppressive activity whereas the corresponding wild-type ENV protein is essentially deprived of immunosuppressive activity. The immunosuppressive activity can be measured as described above and in the Examples, for instance by using the immunosuppressive index method.

Advantageously, mutated ENV proteins having a modified immunosuppressive activity have many applications, in particular therapeutic applications, which will be discussed hereafter.

In a preferred embodiment of the above-defined use, structures responsible for the antigenicity of the mutated ENV protein are essentially preserved.

As intended herein, the expression "structures responsible for antigenicity" relates to structures of the protein which are liable to interact with components of the immune system such as antibodies or membrane receptors of immune cells, in particular T cells.

According to the invention, at least one or more of these structures presents the same conformation in the mutated ENV protein with respect to the corresponding wild type ENV protein. Advantageously, this means that an immune reaction elicited against a mutated ENV protein will also be directed against the corresponding wild type ENV protein.

According to a preferred embodiment, the invention also relate to the above-defined use of a first mutation of a first amino acid and optionally of a second mutation of a second amino acid in a wild type viral envelope (ENV) protein essentially comprising the following sequence:

$$\mathbf{N}Y_1Y_2Y_3\mathbf{L}Y_4Y_5\mathbf{L}Y_6Y_7Y_8X_1Y_9Y_{10}Y_{11}\mathbf{C}Y_{12}X_2$$
(SEQ ID NO: 156)

wherein the first amino acid to be mutated is $X_1$ and the second amino acid to be mutated is $X_2$, and $Y_1$ to $Y_{12}$ represent any amino acid,
for manufacturing a mutated ENV protein having a decreased immunosuppressive activity with respect to said wild type ENV protein.

In a most preferred embodiment, the decrease in immunosuppressive activity is such that almost no residual activity is seen in the mutated ENV protein.

According to a preferred embodiment, the invention also relates to the above-defined use of a first mutation of a first amino acid and a second mutation of a second amino acid in a wild type viral envelope (ENV) protein essentially comprising the following sequence:

$$\mathbf{N}Y_1Y_2Y_3\mathbf{L}Y_4Y_5\mathbf{L}Y_6Y_7Y_8X_1Y_9Y_{10}Y_{11}\mathbf{C}Y_{12}X_2$$
(SEQ ID NO: 156)

wherein the first amino acid to be mutated is $X_1$ and the second amino acid to be mutated is $X_2$, and $Y_1$ to $Y_{12}$ represent any amino acid,
for manufacturing a mutated ENV protein having a decreased immunosuppressive activity with respect to said wild type ENV protein.

The mutation of $X_1$ alone is sufficient to modify the immunosuppressive activity of the mutated ENV protein with respect to the corresponding wild type ENV. However, it is advantageous that $X_2$ be also mutated because it ensures that the structure of the mutated ENV protein is essentially conserved with respect to the corresponding wild type ENV protein.

In a preferred embodiment of the above-defined use, the mutation is a substitution.

In another preferred embodiment of the above-defined use, $X_1$ is substituted by R or H.

In another preferred embodiment of the above-defined use, $X_2$ is substituted by F, M, Y or W.

In a further preferred embodiment of the above-defined use, $X_1$ is E, K, or Q and is substituted by R or H.

In a preferred embodiment of the above defined use, the ENV protein is HERV-H ENV and $X_1$ is K.

In a further preferred embodiment of the above-defined use, $X_2$ is A, V, L, I, or K and is substituted by F, M, Y, or W.

In a particularly preferred embodiment of the above defined use, the ENV protein is a HERV ENV, in particular selected from:
HERV-FRD ENV (SEQ ID NO: 82), wherein $X_1$ is Q427 and $X_2$ is A433, or
HERV-T ENV (SEQ ID NO: 84), wherein $X_1$ is Q516 and $X_2$ is A522, or
HERV-R ENV (SEQ ID NO: 86), wherein $X_1$ is E561 and $X_2$ is K567, or
HERV-V ENV (SEQ ID NO: 88), wherein $X_1$ is Q381 and $X_2$ is V387, or
HERV-R(b) ENV (SEQ ID NO: 90), wherein $X_1$ is E391 and $X_2$ is L397.

HERV relates to Human Endogenous RetroVirus, which have been described previously. HERV ENV proteins have been found to be expressed in cancer cells. The HERV ENV listed above present an immunosuppressive activity and can help cancer cells carrying them escape immune response. These HERV are well known to the man skilled in the art and are in particular discussed in Benit et al. J. Virol. 2001, 75:11709-11719. As will be apparent later HERV ENV proteins having decreased immunosuppressive activity are advantageous to prepare vaccines inhibiting the activity of wild type ENV proteins expressed by cancer cells.

In an advantageous embodiment of the above-defined use, the ENV protein is HERV-FRD ENV and the sequence of the mutated ENV protein is selected from:
SEQ ID NO: 120,
SEQ ID NO: 122.
SEQ ID NO: 120 carries the mutation Q427R.
SEQ ID NO: 122 carries the mutation Q427R+A433F.
The mutated HERV-FRD ENV represented by SEQ ID NO: 120 or 122 presents a decreased immunosuppressive activity with respect to the corresponding wild-type HERV-FRD ENV.

In another advantageous embodiment of the above-defined use, the ENV protein is HERV-V ENV and the sequence of the mutated ENV protein is selected from:
SEQ ID NO: 124,
SEQ ID NO: 126.
SEQ ID NO: 124 carries the mutation Q381R.
SEQ ID NO: 126 carries the mutation Q381R+V387F.
The mutated HERV-V ENV represented by SEQ ID NO: 124 or 126 presents a decreased immunosuppressive activity with respect to the corresponding wild-type HERV-V ENV.

In another advantageous embodiment of the above-defined use, the ENV protein is HERV-T ENV and the sequence of the mutated ENV protein is selected from:
SEQ ID NO: 128,
SEQ ID NO: 130.
SEQ ID NO: 128 carries the mutation Q516R.
SEQ ID NO: 130 carries the mutation Q516R+A522F.

The mutated HERV-T ENV represented by SEQ ID NO: 128 or 130 presents a decreased immunosuppressive activity with respect to the corresponding wild-type HERV-T ENV.

In another advantageous embodiment of the above-defined use, the ENV protein is HERV-R ENV and the sequence of the mutated ENV protein is selected from:
SEQ ID NO: 146,
SEQ ID NO: 148.
SEQ ID NO: 146 carries the mutation E561R.
SEQ ID NO: 148 carries the mutation E561R+K567F.
The mutated HERV-R ENV represented by SEQ ID NO: 128 or 130 presents a decreased immunosuppressive activity with respect to the corresponding wild-type HERV-R ENV.

In another particularly preferred embodiment of the above defined use, the ENV protein is selected from:
HTLV-1 ENV (SEQ ID NO: 92), wherein $X_1$ is Q389 and $X_2$ is A395, or
HTLV-2 ENV (SEQ ID NO: 94) wherein $X_1$ is Q385 and $X_2$ is A391, or
FeLV ENV (SEQ ID NO: 96), wherein $X_1$ is E527 and $X_2$ is A533, or
PERV ENV (SEQ ID NO: 98), wherein $X_1$ is E545 and $X_2$ is A551, or
STLV-1 ENV (SEQ ID NO: 100), wherein $X_1$ is Q389 and $X_2$ is A395, or
MoMLV ENV (SEQ ID NO: 70), wherein $X_1$ is E551 and $X_2$ is A557, or
MPMV ENV (SEQ ID NO: 72), wherein $X_1$ is Q471 and $X_2$ is A477, or
FV ENV (SEQ ID NO: 102), wherein $X_1$ is E561 and $X_2$ is A567.

HTLV-1 and 2 relate to Human T-cell Leukemia Virus type 1 and 2.
FeLV relates to Feline Leukemia Virus.
PERV relates to Porcine Endogenous RetroVirus.
STLV-1 relates to Simina T-cell Leukemia Virus type 1.
MoMLV relates to Moloney Murine Leukemia Virus.
MPMV relates to Mason-Pfizer Monkey Virus.
FV relates to the mouse Friend Virus.

These virus are well known to the man skilled in the art and are notably described in Benit et al. J. Virol. 2001, 75:11709-11719. The propagation of these viruses is notably favoured by the presence of an immunosuppressive ENV protein, which helps viruses escape the immune response. As will be apparent later viral ENV proteins having decreased immunosuppressive activity are advantageous to inhibit the activity of wild type ENV proteins expressed by viruses.

In an advantageous embodiment of the above-defined use, the ENV protein is FeLV ENV and the sequence of the mutated ENV protein is selected from:
SEQ ID NO: 104,
SEQ ID NO: 106.
SEQ ID NO: 104 carries the mutation E527R.
SEQ ID NO: 106 carries the mutation E527R+A533F.
The mutated FeLV ENV represented by SEQ ID NO: 104 or 106 presents a decreased immunosuppressive activity with respect to the corresponding wild-type FeLV ENV.

In another advantageous embodiment of the above-defined use, the ENV protein is HTLV-1 ENV and the sequence of the mutated ENV protein is selected from:
SEQ ID NO: 108,
SEQ ID NO: 110.
SEQ ID NO: 108 carries the mutation Q389R.
SEQ ID NO: 110 carries the mutation Q389R+A395F.
The mutated HTLV-1 ENV represented by SEQ ID NO: 108 or 110 presents a decreased immunosuppressive activity with respect to the corresponding wild-type HTLV-1 ENV.

In another advantageous embodiment of the above-defined use, the ENV protein is HTLV-2 ENV and the sequence of the mutated ENV protein is selected from:
SEQ ID NO: 112,
SEQ ID NO: 114.
SEQ ID NO: 112 carries the mutation Q385R.
SEQ ID NO: 114 carries the mutation Q385R+A391 F.

The mutated HTLV-2 ENV represented by SEQ ID NO: 112 or 114 presents a decreased immunosuppressive activity with respect to the corresponding wild-type HTLV-2 ENV.

In another advantageous embodiment of the above-defined use, the ENV protein is PERV ENV and the sequence of the mutated ENV protein is selected from:
SEQ ID NO: 150,
SEQ ID NO: 152.
SEQ ID NO: 150 carries the mutation E545R.
SEQ ID NO: 152 carries the mutation E545R+A551 F.

The mutated PERV ENV represented by SEQ ID NO: 150 or 152 presents a decreased immunosuppressive activity with respect to the corresponding wild-type PERV.

The present invention also relates to the above use of a first mutation of a first amino acid and optionally of a second mutation of a second amino acid in a wild type viral envelope (ENV) protein essentially comprising the following sequence:

$$NY_1Y_2Y_3LY_4Y_5LY_6Y_7Y_8X_1Y_9Y_{10}Y_{11}CY_{12}X_2$$
(SEQ ID NO: 156)

wherein the first amino acid to be mutated is $X_1$ and the second amino acid to be mutated is $X_2$, and $Y_1$ to $Y_{12}$ represent any amino acid, for manufacturing a mutated ENV protein having an increased immunosuppressive activity with respect to said wild type ENV protein.

The mutation of $X_1$ alone is sufficient to increase the immunosuppressive activity of the mutated ENV protein with respect to the corresponding wild type ENV. However, it is advantageous that $X_2$ be also mutated because it ensures that the structure of the mutated ENV protein is essentially conserved with respect to the corresponding wild type ENV protein.

Advantageously, it is possible according to the invention to obtain a mutated ENV protein with immunosuppressive activity whereas the corresponding wild-type ENV protein is essentially deprived of such an activity. Such mutated ENV proteins with increased immunosuppressive activity are useful to inhibit the immune system, for instance in graft rejections or autoimmune diseases.

In a preferred embodiment of the above mentioned use for manufacturing a mutated ENV protein having an increased immunosuppressive activity, the mutation is a substitution.

In another preferred embodiment of the above mentioned use for manufacturing a mutated ENV protein having an increased immunosuppressive activity, $X_1$ is substituted by E, K or Q and $X_2$ is substituted by A.

In another preferred embodiment of the above mentioned use for manufacturing a mutated ENV protein having an increased immunosuppressive activity, the ENV protein is HERV-W ENV, such as represented by SEQ ID NO: 74, and the sequence of the mutated HERV-W ENV is preferably selected from
SEQ ID NO: 116,
SEQ ID NO: 118.
SEQ ID NO: 116 carries the mutation R393E/Q.
SEQ ID NO: 118 carries the mutation R393E/Q+F399A.

The mutated HERV-W ENV represented by SEQ ID NO: 116 or 118 presents an increased immunosuppressive activity with respect to the corresponding wild-type HERV-W which is essentially deprived of such an activity.

The present invention also provides a polypeptide derived from a determined antigenic and immunosuppressive protein, said polypeptide comprising an amino acid sequence (so-called "immunosuppression-modulatory sequence") represented by $X1-(Y)_3-C-(Y)_1-X2$ wherein in said polypeptide Y represents variable amino acid residues, 3 and 1 represent the number of variable amino acid Y residues, respectively between X1 and C and between C and X2, and X1 and X2 are chosen to confer to said polypeptide, altered immunosuppressive properties with respect to the immunosuppressive properties of said determined protein.

The term "derived" as used herein indicates that the amino acid sequence, and especially the immunosuppression-modulatory sequence, in the polypeptide, is modified with respect to the sequence of the determined protein. Said "determined" protein is hence the original protein whose modification is required to modulate its immunosuppressive properties. A polypeptide according to the invention can be derived, biologically or chemically, from a determined protein by substitution, deletion, addition, recombination or insertion of one or several amino acid residues or sequences, provided the consensus sequence of the invention is such that X1 and X2 are selected to modulate the immunosuppressive properties of the starting determined protein, and therefore provided X1 and/or X2 are mutated by substitution with respect to their original corresponding residues in said determined immunosuppressive protein. In case of sequence insertion, the immunosuppression-modulatory sequence can replace a homologous sequence present in the determined protein, or can replace a sequence known or likely to be involved in the same function of modulation of the immunosuppressive properties as the inserted sequence, or can be inserted within the starting amino acid sequence. In all cases, the open reading frame of the amino acid sequence following the site of insertion (at the C-terminal part of the polypeptide) is conserved.

Obviously, the invention can be carried out with or without actually starting from said determined protein to derive the polypeptide of the invention. Hence, said determined protein is a reference for the design of the derived polypeptide rather than a necessary starting material from a biological or chemical point of view.

In a particular embodiment of the invention, the derived polypeptide has lower immunosuppressive properties than said determined starting polypeptide and advantageously has substantially lost said immunosuppressive properties, e.g. has no immunosuppressive properties.

The expressions "polypeptide" and "protein" throughout the present invention define molecules, whatever their length (except otherwise stated in the present description) comprising an amino acid sequence.

In a particular embodiment, the polypeptide or protein is multimeric, especially trimeric.

"Determined" as used herein refers to a starting protein from which the polypeptide of the invention is designed, i.e., derived to have modulated immunosuppressive properties. This protein can be a wild-type protein (for example isolated from a viral, especially retroviral, strain) or a protein previously modified (for example expressed from a vector in a host). Such protein is chosen among those having antigenic and immunosuppressive properties.

The determined protein has immunosuppressive properties has defined above: when this determined protein is expressed in tumour cells normally rejected by an engrafted host, it allows these tumour cells to proliferate and to escape immune rejection.

Second, it is an antigenic protein, i.e. it is capable of being recognized by antibodies formed in a host to whom it is administered. Advantageously it is capable of inducing an immune response, in the host to whom it is administered in appropriate known conditions, and accordingly said antigenic protein is advantageously an immunogenic protein. This involves that said host produces antibodies against epitopes of the protein.

In view of these desired property of the protein to be antigenic, especially immunogenic, and in view of the required property for the derived polypeptide to substantially retain these antigenic, especially immunogenic properties, the determined protein used to derive the polypeptide of the invention encompasses native or naturally occurring proteins or antigenic, especially immunogenic, fragments thereof, provided said fragments further have immunosuppressive properties. It also encompasses modified proteins with respect to the native or naturally occurring protein, provided the modified proteins have antigenic and immunosuppressive properties.

The determined protein used as reference to derive the polypeptide of the invention can be a viral protein, i.e. coded by nucleic acids of infectious agents like viruses, or a protein coded by nucleic acid of viral origin, such as endogenous retroviruses, especially HERV. A particular protein is a protein originating from a subclass of viruses: retroviruses. In a particular embodiment, the determined protein is an envelope protein, i.e., the expression product of the env gene.

"Nucleic acid" as used herein refers to viral nucleic acids in DNA or RNA forms, including cellular nucleic acids such as genomic DNA, complementary DNA, coding sequences. All the nucleic acid quoted in the present application can be single or double-stranded.

The X1 and X2 amino acid residues of the $X1$-$(Y)_3$-C-$(Y)_1$-X2 motif are chosen as described above.

The above defined polypeptide of the invention derived from an antigenic and immunosuppressive protein and comprising sequence $X1$-$(Y)_3$-C-$(Y)_1$-X2 can be defined as follows:

in a particular embodiment of the invention, X1 is an alkaline amino acid residue and X2 is an aromatic residue or vice versa.

In another particular embodiment of the invention, X1 is an alkaline residue or X2 is an aromatic residue or vice versa.

The inventors have observed that the modulation effect of X1 and X2 on immunosuppressive properties of proteins is usually lower when only one of X1 or X2 residues is modified in an original immunosuppressive protein.

Therefore, modification of both X1 and X2 is an immunosuppression-modulatory sequence may be regarded as advantageous.

In another particular embodiment of the invention, residues X1 or X2 located in amino acid sequence represented as $X1$-$(Y)_3$-C-$(Y)_1$-X2 are selected as follows:

where X1 is chosen among R, H and K, X2 is chosen among F, W, Y and H or where X1 is chosen among F, W, Y and H, X2 is chosen among R, H and K.

In a further embodiment of the invention, X1 is R, H or K and X2 is F, or vice versa.

In a further embodiment of the invention, X1 is R and X2 is F, W, Y or H.

The inventors have especially identified that a polypeptide, derived from an antigenic and immunosuppressive protein, has altered immunosuppressive properties compared to the immunosuppressive properties of the protein from which is derived when particular interesting X1 and X2 residues are respectively R and F or K and F.

The determined protein can advantageously be a viral protein and particularly a retroviral protein or a protein of viral origin like one of an HERV, having antigenic and immunosuppressive properties.

Known naturally occurring low or non-immunosuppressive envelope proteins of HERV-W, H1, F(c)1 or F(c)2 are not, as such, the object of the present invention.

In a particular embodiment of the present invention, the polypeptide derived from an antigenic protein has altered immunosuppressive properties and especially reduced immunosuppressive properties, while retaining its antigenic properties.

In another particular embodiment, these proteins have, further to antigenic and immunosuppressive properties, infectious and/or fusion properties.

When the determined starting protein further has fusion and infectious properties, such as those identified for viral envelope proteins, one of these or both properties can be retained, but not necessary, in the derived polypeptide.

The evaluation or measurement of fusion and/or infectious properties to determine whether these properties of the original determined protein are maintained in the derived polypeptide of the invention can provide useful indications as to whether the derived polypeptide has substantially retained the structure, especially the antigenic structure, e.g., immunogenic determinants, of the original determined protein.

A protein is said to have fusion properties when cells transfected with nucleic acids encoding said protein are able to form syncytia (multi-nucleated cells) with other cells probably not expressing the same protein. Indeed, it is suspected that a strong expression of a protein with fusion properties blocks the expression of the receptors of said protein involved in the fusion event. Therefore, the capacity of fusion can be defined by the formation of syncytia between cells expressing said protein with fusion properties and cells expressing its receptor. Cells can be transfected having recourse to various known methods such as calcium phosphate precipitation or with liposomes, such as Lipofectamine™.

A protein is said to have infectious properties when pseudotypes coated with this protein are able to infect cells. "Pseudotypes" as used herein refers to viral particles in which an ENV protein from a different strain is incorporated. MLV core particles are currently used. Pseudotypes are produced in cell lines (such as 293T cells) in which a vector encoding the infectious protein is co-transfected with one or several vector(s) encoding the GAG and POL proteins of another viral strain.

Particular polypeptides having the properties described are derived from viral envelope protein (ENV) and especially retroviral envelope proteins. Such retroviral ENV can be selected from the group of retroviruses consisting of: MoMLV, Friend retrovirus, FeLV, HTLV-1, STLV-1 and MPMV. Other interesting polypeptides are those encoded by nucleic acids of viral origin such as HERV. As far as viruses are concerned, Ebola and Marburg viruses have ENV proteins from which the polypeptides of the invention can be derived.

Said envelope protein can be all or part of the native or naturally occurring protein or from an antigenic, especially immunogenic variant thereof, including a fragment thereof, i.e., an analogue of a naturally occurring viral envelope protein as far as antigenic, especially immunogenic properties, and immunosuppressive properties are concerned.

Within the amino acid sequence of determined proteins described above, inventors have identified particular residues that are involved in the regulation of immunosuppression. Such a sequence, called immunosuppression-modulatory sequence which confers immunosuppressive properties to a protein is the following: E/Q-G-G-L/T/I-C-A/K/L/M/V/I-A (SEQ ID NO: 153), wherein "/" indicates that this sequence position accepts several types of amino acid residues. Thus, proteins comprising an immunosuppression-modulatory sequence selected from the group consisting of

| | |
|---|---|
| QGGLCKA | (SEQ ID NO: 17) |
| QGGLCAA | (SEQ ID NO: 18) |
| QGGLCLA | (SEQ ID NO: 19) |
| QGGICLA | (SEQ ID NO: 20) |
| EGGLCVA | (SEQ ID NO: 21) |
| EGGLCVA | (SEQ ID NO: 22) | are particular determined proteins having immunosuppressive properties, from which the polypeptides of the invention can be derived by modifying the terminal E/Q and or A residues figuring X1 and X2 positions of the consensus sequence of the invention.

As described above, the term "derived" as used herein indicates that the amino acid sequence, and especially the immunosuppression-modulatory sequence, of the polypeptide is modified with respect to the sequence of the determined protein in order to impact on immunosuppressive properties, especially to decrease said properties. These altered immunosuppressive properties can be the consequence of substitution of the X1 and X2 residues according to the amino acid characteristics described above.

These altered immunosuppressive properties can also be the consequence of the insertion of the polypeptide comprising X1-(Y)$_3$-C-(Y)$_1$-X2 sequence wherein X1 and X2 are selected to alter the immunosuppressive properties, in a permissive site of the chosen protein.

"Permissive site" as used herein refers to a site which does not substantially alter the antigenic properties of a protein.

The insertion can replace a homologous sequence or a sequence involved in immunosuppression. The polypeptide of 7 to 20 amino acid residues according to the invention can also be inserted without deletion of amino acid residues from the determined protein.

A polypeptide derived from a determined protein as described above, and having altered immunosuppressive properties comprises a sequence having the following sequence R-G-G-L/T/I-C-A/K/L/M/V/I-F (SEQ ID NO: 154), and particularly a sequence selected from the group consisting of:

| | |
|---|---|
| RGGLCKF | (SEQ ID NO: 27) |
| RGGLCAF | (SEQ ID NO: 28) |
| RGGLCLF | (SEQ ID NO: 29) |
| RGGICLF | (SEQ ID NO: 30) |
| RGGLCVF | (SEQ ID NO: 31) |

The sequences given above have been derived by mutation of said X1 and X2 residues in identified naturally occurring retroviral ENV proteins.

The same strategy can be applied with viruses which express proteins presenting a sequence similar to X1-(Y)$_3$-C-(Y)$_1$-X2. In particular, the Y residues can be different amino acid residues from those described above (Benit et al. 2001).

Moreover, the structure, e.g. their 3-dimensional structure of the determined ENV proteins of the present application have been shown to share similar structural features with that of other viruses and especially with other retroviruses, despite amino acid sequence diversity. Thus, a highly conserved organization of the TM structure has been found in proteins of Ebola or Marburg viruses, most probably relevant to a common mechanism for triggering the fusion process and viral entry. Consequently, a same approach can be applied to identify particular sequences, involved in the modulation of the immunosuppression in such viruses.

The present invention also relates to a mutated ENV protein resulting from the mutation of a wild type ENV protein essentially carrying the following sequence:

(SEQ ID NO: 156)
$NY_1Y_2Y_3LY_4Y_5LY_6Y_7Y_8X_1Y_9Y_{10}Y_{11}CY_{12}X_2$ wherein amino acid $X_1$ and optionally amino acid $X_2$ are mutated, and $Y_1$ to $Y_{12}$ represent any amino acid, said mutated ENV protein having a modified immunosuppressive activity with respect to the wild type ENV protein, or a fragment thereof, provided that said fragment carries the mutated amino acid $X_1$ and optionally $X_2$, that it has an immunosuppressive activity similar to that of the mutated ENV protein, and that optionally its antigenic structure is essentially similar to the structure it adopts in the context of the mutated ENV protein, or a protein derived from the mutated ENV protein, or fragments thereof, by insertion, deletion or substitution of at least one amino acid, provided that said derived protein carries the mutated amino acid $X_1$ and $X_2$, that it has an immunosuppressive activity similar to that of the mutated ENV protein, and that, optionally, its antigenic structure is essentially similar to that of the mutated ENV protein, or fragment thereof.

As intended herein the mutated ENV protein essentially carries the following sequence:

(SEQ ID NO: 156)
$NY_1Y_2Y_3LY_4Y_5LY_6Y_7Y_8X'_1Y_9Y_{10}Y_{11}CY_{12}X'_2$

Wherein $X'_1$ corresponds to the mutated $X_1$ and $X'_2$ corresponds to the mutated $X_2$.

As intended herein fragments of the mutated ENV protein according to the invention are in particular at least 7 amino acids long and comprise the mutated amino acid $X_1$. Optionally, fragments are at least 7 amino acids long and comprise both $X_1$ and $X_2$. Preferred fragments of the mutated ENV protein according to the invention are notably constituted of the TM subunit or of the ectodomain of the TM subunit.

In a preferred embodiment of the invention the above mentioned protein derived from the mutated ENV protein presents at least 80% sequence identity with said mutated ENV protein, in particular at least 90% sequence identity.

In a preferred embodiment of the above-defined mutated ENV protein, or fragment thereof, the structures responsible for the antigenicity of said mutated ENV protein, or fragment thereof, are essentially preserved with respect to the wild type ENV protein.

According to a preferred embodiment, the present invention relates to an above-defined mutated ENV protein resulting from the mutation of a wild type ENV protein essentially comprising the following sequence:

(SEQ ID NO: 156)
NY$_1$Y$_2$Y$_3$LY$_4$Y$_5$LY$_6$Y$_7$Y$_8$X$_1$Y$_9$Y$_{10}$Y$_{11}$CY$_{12}$X$_2$, wherein amino acid X$_1$ and optionally amino acid X$_2$ are mutated, and Y$_1$ to Y$_{12}$ represent any amino acid, said mutated ENV protein having a decreased immunosuppressive activity with respect to the wild type ENV protein,
or a fragment thereof, provided that said fragment carries the mutated amino acid X$_1$ and optionally X$_2$, that it has an immunosuppressive activity similar to that of the mutated ENV protein, and that optionally its antigenic structure is essentially similar to the structure it adopts in the context of the mutated ENV protein,
or a protein derived from the mutated ENV protein, or fragments thereof, by insertion, deletion or substitution of at least one amino acid, provided that said derived protein carries the mutated amino acid X$_1$ and X$_2$, that it has an immunosuppressive activity similar to that of the mutated ENV protein, and that, optionally, its antigenic structure is essentially similar to that of the mutated ENV protein, or fragment thereof.

According to a preferred embodiment, the present invention relates to an above-defined mutated ENV protein resulting from the mutation of a wild type ENV protein essentially comprising the following sequence:

(SEQ ID NO: 156)
NY$_1$Y$_2$Y$_3$LY$_4$Y$_5$LY$_6$Y$_7$Y$_8$X$_1$Y$_9$Y$_{10}$Y$_{11}$CY$_{12}$X$_2$, wherein amino acid X$_1$ and amino acid X$_2$ are mutated, and Y$_1$ to Y$_{12}$ represent any amino acid, said mutated ENV protein having a decreased immunosuppressive activity with respect to the wild type ENV protein,
or a fragment thereof, provided that said fragment carries the mutated amino acid X$_1$ and X$_2$, that it has an immunosuppressive activity similar to that of the mutated ENV protein, and that optionally its antigenic structure is essentially similar to the structure it adopts in the context of the mutated ENV protein,
or a protein derived from the mutated ENV protein, or fragments thereof, by insertion, deletion or substitution of at least one amino acid, provided that said derived protein carries the mutated amino acid X$_1$ and X$_2$, that it has an immunosuppressive activity similar to that of the mutated ENV protein, and that, optionally, its antigenic structure is essentially similar to that of the mutated ENV protein, or fragment thereof.

In a preferred embodiment of the above-defined mutated ENV protein, or fragment thereof, the mutation is a substitution.

In another preferred embodiment of the above-defined mutated ENV protein, or fragment thereof, X$_1$ is substituted by R or H.

In another preferred embodiment of the above-defined mutated ENV protein, or fragment thereof, X$_2$ is substituted by F, M, Y or W.

In another preferred embodiment of the above-defined mutated ENV protein, or fragment thereof X$_1$ is E, K, or Q and is substituted by R or H.

In a preferred embodiment, the above defined mutated ENV protein, or fragment thereof, is HERV-H ENV wherein X$_1$ is K.

In another preferred embodiment of the above-defined mutated ENV protein, or fragment thereof, X$_2$ is A, V, L, I, or K and is substituted by F, M, Y, or W.

In a particularly preferred embodiment of the above-defined mutated ENV protein, or fragment thereof, the ENV protein is a HERV ENV, in particular selected from:
HERV-FRD ENV (SEQ ID NO: 82), wherein X$_1$ is Q427 and X$_2$ is A433, or
HERV-T ENV (SEQ ID NO: 84), wherein X$_1$ is Q516 and X$_2$ is A522, or
HERV-R ENV (SEQ ID NO: 86), wherein X$_1$ is E561 and X$_2$ is K567, or
HERV-V ENV (SEQ ID NO: 88), wherein X$_1$ is Q381 and X$_2$ is V387, or
HERV-R(b) ENV (SEQ ID NO: 90), wherein X$_1$ is E391 and X$_2$ is L397.

In an advantageous embodiment of the above-defined mutated ENV protein, or fragment thereof, the ENV protein is HERV-FRD ENV and the sequence of the mutated ENV protein is selected from:
SEQ ID NO: 120
SEQ ID NO: 122

In an advantageous embodiment of the above-defined mutated ENV protein, or fragment thereof, the ENV protein is HERV-V ENV and the sequence of the mutated ENV protein is selected from:
SEQ ID NO: 124
SEQ ID NO: 126

In an advantageous embodiment of the above-defined mutated ENV protein, or fragment thereof, the ENV protein is HERV-T ENV and the sequence of the mutated ENV protein is selected from:
SEQ ID NO: 128
SEQ ID NO: 130

In an advantageous embodiment of the above-defined mutated ENV protein, or fragment thereof, the ENV protein is HERV-R ENV and the sequence of the mutated ENV protein is selected from:
SEQ ID NO: 146,
SEQ ID NO: 148.

In a particularly preferred embodiment of the above-defined mutated ENV protein, or fragment thereof, the ENV protein is selected from:
HTLV-1 ENV (SEQ ID NO: 92), wherein X$_1$ is Q389 and X$_2$ is A395, or
HTLV-2 ENV (SEQ ID NO: 94) wherein X$_1$ is Q385 and X$_2$ is A391, or
FeLV ENV (SEQ ID NO: 96), wherein X$_1$ is E527 and X$_2$ is A533, or
PERV ENV (SEQ ID NO: 98), wherein X$_1$ is E545 and X$_2$ is A551, or
STLV-1 ENV (SEQ ID NO: 100), wherein X$_1$ is Q389 and X$_2$ is A395, or
MoMLV ENV (SEQ ID NO: 70), wherein X$_1$ is E551 and X$_2$ is A557, or
MPMV ENV (SEQ ID NO: 72), wherein X$_1$ is Q471 and X$_2$ is A477, or
FV ENV (SEQ ID NO: 102), wherein X$_1$ is E561 and X$_2$ is A567.

In an advantageous embodiment of the above-defined mutated ENV protein, or fragment thereof, the ENV protein is FeLV ENV and the sequence of the mutated ENV protein is selected from:
SEQ ID NO: 104
SEQ ID NO: 106

In an advantageous embodiment of the above-defined mutated ENV protein, or fragment thereof, the ENV protein is HTLV-1 ENV and the sequence of the mutated ENV protein is selected from:
SEQ ID NO: 108
SEQ ID NO: 110

In an advantageous embodiment of the above-defined mutated ENV protein, or fragment thereof, the ENV protein is HTLV-2 ENV and the sequence of the mutated ENV protein is selected from:
SEQ ID NO: 112
SEQ ID NO: 114

In an advantageous embodiment of the above-defined mutated ENV protein, or fragment thereof, the ENV protein is PERV ENV and the sequence of the mutated ENV protein is selected from:
SEQ ID NO: 150,
SEQ ID NO: 152.

According to a preferred embodiment, the present invention relates a mutated ENV protein as defined above resulting from the mutation of a wild type ENV protein essentially comprising the following sequence:
$NY_1Y_2Y_3LY_4Y_5LY_6Y_7Y_8X_1Y_9Y_{10}Y_{11}CY_{12}X_2$ (SEQ ID NO: 156),
wherein amino acid $X_1$ and optionally amino acid $X_2$ are mutated, and $Y_1$ to $Y_{12}$ represent any amino acid, said mutated ENV protein having an increased immunosuppressive activity with respect to the wild type ENV protein,
or a fragment thereof, provided that said fragment carries the mutated amino acid $X_1$ and $X_2$, that it has an immunosuppressive activity similar to that of the mutated ENV protein, and that optionally its antigenic structure is essentially similar to the structure it adopts in the context of the mutated ENV protein, or a protein derived from the mutated ENV protein, or fragments thereof, by insertion, deletion or substitution of at least one amino acid, provided that said derived protein carries the mutated amino acid $X_1$ and $X_2$, that it has an immunosuppressive activity similar to that of the mutated ENV protein, and that, optionally, its antigenic structure is essentially similar to that of the mutated ENV protein, or fragment thereof.

In a preferred embodiment of the above-defined mutated ENV protein having increased immunosuppressive activity, or fragment thereof, the mutation is a substitution.

In a preferred embodiment of the above-defined mutated ENV protein having increased immunosuppressive activity, or fragment thereof, $X_1$ is substituted by E, K, or Q and $X_2$ is substituted by A.

In a preferred embodiment of the above-defined mutated ENV protein having increased immunosuppressive activity, or fragment thereof, the ENV protein is HERV-W ENV, such as represented by SEQ ID NO: 74, and the sequence of the mutated HERV-W ENV is selected from:
SEQ ID NO: 116
SEQ ID NO: 118

The present invention also relates to a protein, characterized in that it comprises at least one polypeptide as defined above, or at least one mutated ENV protein, or a fragment thereof, as defined above, provided that when said polypeptide originates from a wild type ENV protein then said protein comprising said polypeptide is different from said wild type ENV protein.

The present invention also relates to nucleic acids, and especially polynucleotides, encoding polypeptides of the invention. In a particular embodiment, these nucleic acids are inserted in a vector. The recombinant vector can be a plasmid, a phage for bacterium introduction or a YAC able to transform yeast, or any expression vector.

In addition, the recombinant vector comprises transcription regulation regions (including promoter) allowing either inducible expression or conditional expression of the nucleic acid under control or if appropriate, constitutive expression. A tissue specific transcription region can also be used. Moreover, the recombinant vector comprises an origin of replication and/or marker genes.

In a particular embodiment of the invention, the vector comprises also nucleic acid encoding viral GAG and/or POL proteins or sufficient fragments thereof to express functional viral proteins. Optionally, the vector can comprises nucleic acids encoding viral accessory proteins, like NEF, TAT or fragments thereof.

Alternatively, GAG and POL coding sequences can be inserted in separate vectors, including in vector(s) different from the ENV expressing vector.

In a particular embodiment of the invention, a provirus genome is modified with a nucleic acid encoding a polypeptide of the invention having antigenic properties but altered immunosuppressive properties with respect to a determined protein or a nucleic acid encoding a polypeptide of the invention having infectious, fusion and antigenic properties, but altered immunosuppressive properties with respect to a determined protein.

The present invention also relates to cells comprising nucleic acids encoding polypeptides of the invention.

In a particular embodiment, a cell is transformed with a polynucleotide of the invention, in a way that the polynucleotide is integrated in the cell genome either by a recombination with the homologous cellular sequence or by insertion in the cellular genome. The cell can also be transfected with a vector of the invention, by methods well known to the man skilled in the art. The transfection or infection can occurred ex vivo, i.e. in an artificial environment outside the living organism.

In another embodiment, a vector containing a nucleic acid encoding a polypeptide according to the invention cells is complemented with the introduction of other nucleic acids, contained in additional vectors, especially encoding viral GAG protein and/or POL protein.

These cell lines are useful to the production of recombinant viral particles. In a particular embodiment, the GAG and POL polypeptides originate from the same virus strain as the ENV protein. In another embodiment, the GAG and POL polypeptides originate from a different strain from the ENV protein.

The recombinant viral particles produced comprise a nucleic acid encoding a functional POL protein, a nucleic acid encoding a functional GAG protein and a nucleic acid encoding the polypeptide of the invention.

Moreover, the ENV protein can be chosen among viral amphotropic ENV protein according to the host, i.e. able to infect cells of a species from which the virus is not originated, or viral ecotropic ENV proteins according to the host, i.e. able to replicate only in the cells of the species from which the virus is originated.

To ensure that the recombinant viral particles be infectious and replicative, the vector comprises various nucleic sequences chosen among transcription, expression and encapsidation signals, such as LTRs, cPPT, PPT3', CTS, SA, SD, psi sequence and RRE. However, such elements can be deleted to produce non-replicative viral particles. Moreover, the proviral genome comprises nucleic acids encoding accessory proteins.

Optionally the particles can be prepared to express additional compounds useful for medical application in a host.

The present invention also relates to a nucleic acid coding for a polypeptide as defined above, for a mutated ENV protein according as defined above or for a protein as defined above.

In a preferred embodiment the above-defined nucleic acid is characterized in that it is represented by a sequence selected from the list comprising:
SEQ ID NO: 103,
SEQ ID NO: 105,
SEQ ID NO: 107,
SEQ ID NO: 109,
SEQ ID NO: 111,
SEQ ID NO: 113,
SEQ ID NO: 115,
SEQ ID NO: 117.
SEQ ID NO: 119,
SEQ ID NO: 121,
SEQ ID NO: 123,
SEQ ID NO: 125,
SEQ ID NO: 127,
SEQ ID NO: 129,
SEQ ID NO: 145,
SEQ ID NO: 147,
SEQ ID NO: 149, and
SEQ ID NO: 151.

The above mentioned SEQ ID NO: 103 to 129 and SEQ ID NO: 147 to 151 (odd numbers) respectively encode SEQ ID NO: 104 to 130 and SEQ ID NO: 146 to 152 (even numbers).

The present invention also relates to an eukaryotic or prokaryotic expression vector, characterized in that it comprises a nucleic acid as defined above as well as the elements necessary for the expression of said nucleic acid.

In a preferred embodiment, the above-defined eukaryotic or prokaryotic expression vector is a viral vector, in particular a pox vector, such as a fowlpox, a canarypox, or a MVA (modified vaccinia virus Ankara) vector, an adenoviral vector, a measles vector, or a CMV (cytomegalovirus) vector.

In a further preferred embodiment, the above-defined eukaryotic or prokaryotic expression vector is a viral vector, in particular a canarypox vector, comprising a nucleic acid sequence coding for an as above defined mutated ENV protein, or a fragment thereof, in particular a mutated FeLV ENV, such as represented by SEQ ID NO: 103 or SEQ ID NO: 105, as well as optionally a nucleic acid coding for a GAG protein originating from the same virus as said mutated ENV.

The present invention also relates to a recombinant cell, characterized in that it comprises a nucleic acid as defined above, or an eukaryotic or prokaryotic expression vector as defined above.

The present invention also relates to a composition comprising a polypeptide of the invention having altered immunosuppressive properties with respect to a determined protein and particularly a polypeptide substantially retaining antigenic properties, especially immunogenic properties of the protein from which they derive.

A particular composition of the invention has lower immunosuppressive properties with respect to the starting determined protein, or even has substantially no immunosuppressive properties.

Other compositions comprise polynucleotides or vectors comprising nucleic acid encoding polypeptides of the invention. In this case, tissue specific promoters can be chosen depending upon the organ in which the composition is administered, for example injected and depending upon the expression intensity required.

Other compositions of the invention comprise recombinant viral particles or viruses harbouring the polypeptides of the invention and optionally expressing further compounds having a medical interest in a host.

The polypeptides and compositions of the invention are useful for the design of active principle for drugs and have accordingly interesting properties for the prophylaxis and or treatment of infections especially viral infections or for the treatment of detrimental consequences, especially malignant states, including tumors, resulting from the viral infection or also for the prophylaxis and/or for the treatment of detrimental consequences, in particular malignant states, including tumors associated with the expression of endogenous viruses, especially HERV, which are normally silent in a host. The expression “treatment” encompasses the curative effect achieved with the polypeptides and compositions of the invention and also the alleviation of the symptoms observed in a patient or the improvement of the patient’s condition.

In a particular embodiment, the composition of the invention further comprises additional active compounds useful for the prophylaxis or the treatment of infections, especially viral infections, in particular retroviral infections, including cytokines or useful for the treatment of consequences resulting from the expression of normally silent ERV.

When used for administration either for systemic or local administration, especially by injection, the composition further comprises a pharmaceutically suitable excipient or carrier and/or vehicle.

Several types of compositions can be used to elicit an immune response against an antigenic polypeptide of the invention.

First, a composition comprising a nucleic acid is administered to a host, for instance injected (known as DNA vaccination) and said nucleic acid expresses in vivo a polypeptide according to the invention. DNA vaccines usually consist of plasmid vectors comprising eukaryotic promoter, cloning site, a polyadenylation sequence, a selectable marker and a bacterial origin of replication. All these elements are well known to the man skilled in the art. The delivery of naked DNA has shown to be poorly efficient, and some carriers are needed to improve the delivery of DNA into cells. Two types of carriers have been developed: viral carriers (adenoviruses, lentiviruses) or non-viral carriers such as polymers (and especially cationic polymers), encapsulated-DNA (liposomes) or DNA linked to gold microparticles.

Another type of composition comprises a polypeptide of the invention having altered immunosuppressive properties with respect to a determined protein and having antigenic properties. Such a composition may be immunogenic, i.e. it is capable of elicit an immune response in a host in which it is administered. However, since proteins are sometimes non-immunogenic or poorly immunogenic, an adjuvant can be administered with the polypeptide, to elicit or improve the immune response. An adjuvant is defined as any substance that enhances the immunogenicity of an antigen mixed with said adjuvant. Some adjuvants convert soluble antigens into small particles, such as aluminium hydroxide gel, oil in water emulsion or immune stimulatory complexes (ISCOMs). Another class of adjuvants comprises sterile constituents of bacteria such as cell wall or polysaccharides, Freund adjuvant.

Therefore, a composition comprising a polypeptide having antigenic properties but altered immunosuppressive properties with respect to a determined protein is interesting in the elicitation of an immune response in a host in which it is administered and in the production of a humoral and/or cell-mediated immune response.

Indeed, the administration, e.g., the injection, of a polypeptide having non-immunosuppressive properties provides a more efficient immune reaction than the administration of the determined protein (having immunosuppressive properties), because the immune system of the host is fully functional.

In a particular embodiment, a polypeptide according to the invention has antigenic, fusion and infectious properties but has altered immunosuppressive properties with respect to a determined immunosuppressive protein.

Altered immunosuppressive properties according to the invention advantageously correspond to decreased immunosuppressive properties with respect to the original starting protein.

Viral particles coated with a polypeptide having said properties described above can be constructed in recombinant cell lines transfected with gag-pol vectors and vector comprising a nucleic acid encoding said polypeptide.

Optionally, these viral particles also express other compounds of therapeutic or prophylactic interest.

Interestingly, such viral particles are able to infect and to fuse with the cells of a host, and incorporate a non-immunosuppressive envelope protein. A composition comprising such viral particles elicits an efficient immune reaction, better than viral particle incorporating the determined protein having immunosuppressive properties. Indeed, the envelope protein is not able to immunosuppress its host, resulting in an optimal immune reaction. Another consequence is that viral particles that would have the capacity to replicate, due to recombination events which do not involve the ENV gene, would have their propagation in the host limited, since recombinant viral particle cannot evade the immune response.

A composition comprising viral particles coated with an antigenic envelope protein with fusion and infectious properties appears to be an efficient and safe vaccine.

Interestingly, such viral particles can be either replicative (functional) or non-replicative. This can have consequences on the time of residence of the particles once administered in the host and on the quality of the immune response.

All compositions quoted above can be injected in a host via different routes: subcutaneous (s.c.), intradermal (i.d.), intramuscular (i.m.) or intravenous (i.v.) injection, oral administration and intranasal administration or inhalation.

The present invention also relates to a pharmaceutical or a vaccine composition comprising as active substance:
at least one polypeptide as defined above, or
at least one mutated ENV protein, or fragments thereof, as defined above, or
at least one nucleic acid as defined above, or
at least one prokaryotic or eukaryotic expression vector as defined above, or
at least one recombinant cell as defined above,
in association with a pharmaceutically acceptable carrier.

As will be described hereafter these pharmaceutical compositions are particularly useful for treating cancers, immune disorders or viral diseases.

The present invention also relates to the use of at least one protein comprising or constituted of a mutated ENV protein, or fragments thereof, having decreased immunosuppressive activity as defined above, or of a nucleic acid coding for said protein, for the manufacture of a medicament or a vaccine intended for the prevention and/or the treatment of viral diseases, such as HTLV or FeLV infections.

The administration to an individual of mutated ENV protein having decreased immunosuppressive activity is liable to protect said individual from infection by the corresponding virus. Indeed, the immune response elicited against the mutated ENV protein is also directed against the corresponding wild type ENV protein. As demonstrated herein, this immune response effectively blocks the immunosuppressive activity of the wild type ENV protein and prevents the immune escape of the virus.

Furthermore, the mutated ENV protein is also liable to act as a molecular decoy which competes with the viral wild-type ENV for binding to its natural receptor, thus inhibiting the activity of said wild-type ENV.

The present invention also relates to the use of at least one protein comprising or constituted of a mutated HERV ENV protein, or fragments thereof, as defined above, or of a nucleic acid coding for said protein, for the manufacture of a medicament or a vaccine intended for the prevention and/or the treatment of cancer.

As demonstrated herein, blocking the activity of HERV ENV proteins expressed by cancer cells prevents immune escape of these cells. As such, the immune response effectively elicited against mutated HERV ENV proteins having decreased immunosuppressive activity would also be directed against wild-type HERV ENV expressed by cancer cells and thus prevent them from enabling immune escape of these cancer cells.

Furthermore, the mutated ENV protein is also liable to act as a molecular decoy which competes with the wild-type ENV expressed by cancer cells for binding to its natural receptor, thus inhibiting the activity of said wild-type ENV.

The present invention also relates to the use of at least one protein comprising or constituted of a mutated ENV protein having increased immunosuppressive activity, or fragments thereof, as defined above, or of a nucleic acid coding for said protein, for the manufacture of a medicament or a vaccine intended for the prevention and/or the treatment of pathologies requiring an inhibition of the immune system, such as autoimmune diseases, allergies or graft rejections.

As intended herein graft rejections also encompass Graft Versus Host Disease (GVHD).

The present invention also relates to the use of at least one polypeptide as defined above, or of a protein comprising said polypeptide as defined above, or of a nucleic acid coding for said polypeptide or said protein, for the manufacture of a medicament intended for the prevention and/or the treatment of cancer, of viral diseases, or of pathologies requiring an inhibition of the immune system, such as autoimmune diseases, allergies or graft rejections.

Polypeptides as defined above, and proteins comprising them, can have several applications. When originating from wild type immunosuppressive ENV protein they can be used directly to inhibit the immune system. Otherwise, whether originating from an immunosuppressive or non-immunosuppressive ENV protein they can be used as decoys intended to bind to the natural receptors of the corresponding wild type ENV proteins expressed by cancer cells or viruses, which prevents the activity of said wild type ENV proteins.

The present invention also relates to the use of at least one protein or of a nucleic acid coding for said protein, said protein comprising or being constituted of:
an immunosuppressive ENV protein essentially comprising the following sequence:

(SEQ ID NO: 156)
$NY_1Y_2Y_3LY_4Y_5LY_6Y_7Y_8X_1Y_9Y_{10}Y_{11}CY_{12}X_2$, wherein amino acids $Y_1$ to $Y_{12}$ represent any amino acid, amino acid $X_1$ represents E, K or Q, and optionally amino acid $X_2$ represents A, or a fragment thereof, provided that said fragment carries amino acid $X_1$ and optionally $X_2$, and that it has an immunosuppressive activity similar to that of said ENV protein, or a protein derived from said ENV protein, or fragments thereof, by insertion, deletion or substitution of at least one amino acid, provided that said derived protein carries amino acid $X_1$ and optionally $X_2$, and that it has an immunosuppressive activity similar to that of the mutated ENV protein, for the manufacture of a medicament or a vaccine intended for the prevention and/or the treatment of cancers, of viral diseases, or of pathologies requiring an inhibition of the immune system, such as autoimmune diseases, allergies or graft rejections.

In a preferred embodiment of the above-defined use at least one protein comprising or constituted of an immunosuppressive ENV protein essentially comprising the following sequence:

$$NY_1Y_2Y_3LY_4Y_5LY_6Y_7Y_8X_1Y_9Y_{10}Y_{11}CY_{12}X_2,$$ (SEQ ID NO: 156)

for the manufacture of a medicament or a vaccine intended for the prevention and/or the treatment of cancers, of viral diseases, or of pathologies requiring an inhibition of the immune system, such as autoimmune diseases, allergies or graft rejections, the ENV protein is selected from:
HERV-T ENV, such as represented by SEQ ID NO: 84, or
HERV-R ENV, such as represented by SEQ ID NO: 86, or
HERV-V ENV, such as represented by SEQ ID NO: 88, or
HERV-R(b) ENV, such as represented by SEQ ID NO: 90, or
HTLV-1 ENV, such as represented by SEQ ID NO: 92, or
HTLV-2 ENV, such as represented by SEQ ID NO: 94, or
FeLV ENV, such as represented by SEQ ID NO: 96, or
PERV ENV, such as represented by SEQ ID NO: 98, or
STLV-1 ENV, such as represented by SEQ ID NO: 100, or
FV ENV, such as represented by SEQ ID NO: 102.

As for the above-mentioned polypeptides, these proteins, and fragments thereof, can have several application. They can be used either directly to inhibit the immune system or as decoys intended to bind to the natural receptors of the corresponding wild type ENV proteins expressed by cancer cells or viruses.

The invention also relates to a method for producing antibodies comprising:
a. modifying the nucleotide immunosuppression-modulatory sequence in a way to modulate the immunosuppression effect, but to retain the fusion, infectious and immunosuppressive properties,
b. expressing the modified gene,
c. purifying the modified polypeptide,
d. injecting the modified polypeptide in an animal to induce a immune response,
e. purifying the produced antibodies reacting against the modified polypeptide.

The invention also provides a method to modulate the immunosuppressive properties of a antigenic and immunosuppressive protein while retaining its antigenic properties comprising:
a. identifying the nucleic acid sequence encoding an immunosuppression-modulatory sequence encoding a consensus amino acid sequence as defined above in a nucleic acid sequence encoding said antigenic and immunosuppressive properties,
b. identifying the codons encoding amino acids X1 and X2 impacting on the immunosuppressive properties in sequence $X1-(Y)_3-C(Y)_1-X2$ as defined above,
c. modifying the codons encoding said both amino acids in such a way that the resulting protein retains its antigenic properties but has modified immunosuppressive properties,
d. expressing the obtained modified nucleic acid sequence encoding said antigenic protein having modified immunosuppressive properties.

A particular method to modulate the immunosuppressive properties of an antigenic and immunosuppressive protein having further infectious and fusion properties while retaining its fusion, infectious and antigenic properties comprises:
a. identifying the immunosuppression-modulatory sequence of an env gene encoding an amino acid sequence similar to that defined above,
b. modifying the codons coding amino acids impacting on the immunosuppressive properties in such a way that the resulting protein retains its fusion, infectious and antigenic properties but has modified its immunosuppressive properties.

The invention also provides a method to prepare attenuated virus comprising:
a. modifying the gene coding for an antigenic and immunosuppressive protein of a virus in a way to modulate its immunosuppressive properties, but to retain its antigenic properties,
b. expressing the modified gene in a recombinant cell lines, to produce attenuated recombinant viral particles integrating a modified proviral genome.

The invention also concerns a method to prepare attenuated virus comprising:
a. modifying the gene coding for an antigenic and immunosuppressive ENV protein of a virus having further fusion and infectious properties in a way to modulate its immunosuppressive properties but to retain its fusion, infectious and antigenic properties,
b. expressing the modified gene in a recombinant cell lines, to produce attenuated recombinant viral particles integrating a modified proviral genome.

The invention also more generally relates to the use non-immunosuppressive or low-immunosuppressive polypeptides for the preparation of an immunogenic composition suitable for prophylaxis, or treatment of a viral disease or of a malignant state, or a tumor disease.

Naturally occurring proteins which have no immunosuppressive or low-immunosuppressive properties can be used accordingly; they encompass HERV-W or HERV-H.

The present invention relates to the use of a polypeptide as defined above, or of a mutated protein or a protein as defined above, for the preparation of ligands of ENV proteins selected from:
polyclonal or monoclonal antibodies, or fragments thereof, such as Fab or F(ab)'$_2$ fragments,
scFv polypeptides,
aptamers,
binding peptides.

Such ligands and methods for preparing them are well known to man skilled in the art.

The present invention also relates to antibodies or fragments thereof, scFv polypeptides, aptamers, or binding peptides, directed against mutated ENV proteins as defined above, or proteins or polypeptides comprising them as defined above, provided that said antibodies or fragments thereof, scFv polypeptides, aptamers, or binding peptides do not bind to the corresponding wild type ENV proteins.

The present invention also relates to the use of polypeptides as defined above, or of proteins as defined above, for screening compounds liable to modulate the immunosuppressive activity of viruses or tumor cells.

The present invention also relates to the use of antibodies or fragments thereof, scFv polypeptides, aptamers, or binding peptides as defined above, for screening compounds liable to modulate the immunosuppressive activity of viruses or tumor cells.

In a preferred embodiment of the above defined uses of polypeptides as defined above, of proteins as defined above, or of antibodies or fragments thereof, scFv polypeptides, aptamers, or binding peptides as defined above, the compounds to screen are peptides, in particular peptides comprising from 5 to 30 amino acids, such as peptides originating from combinatorial peptide libraries.

EXAMPLES

Example 1

Methods

Mice and Cell Lines.
The cell lines used in these tests were:
 293T, embryonal kidney cells (ATCC CRL11268),
 HeLa, human epithelioid carcinoma cells (ATCC CCL2)
 MCA205, methylcholanthrene-induced murine fibrosarcoma cells (Shu and Rosenberg, 1985)
 NIH 3T3, mouse fibroblasts
Cells were cultured in DMEM supplemented with 10% fetal calf serum, streptomycin (100 µg/ml) and penicillin (100 units/ml).

In order to test the immunosuppressive effect of the modified protein, C57BL/6 and BALB/c mice, 8- to 12-wk-old, obtained from Janvier (Laval, France), were used.
Constructions.

Figure 3A:
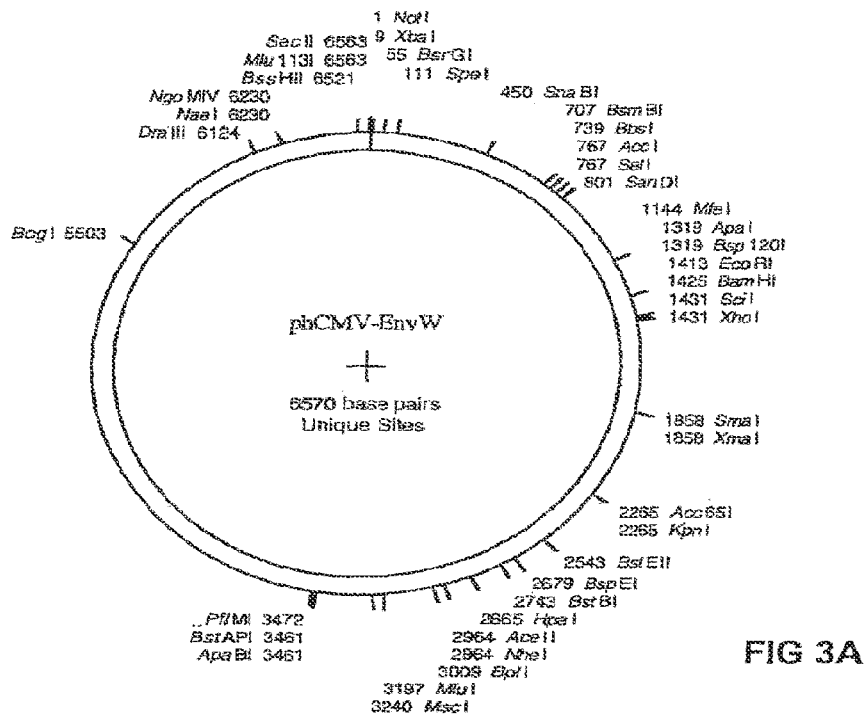
FIG. 3A represents the phCMV-envW vector (SEQ ID NO: 166 & 167 are disclosed respectively in order of appearance).
Figure 3B:
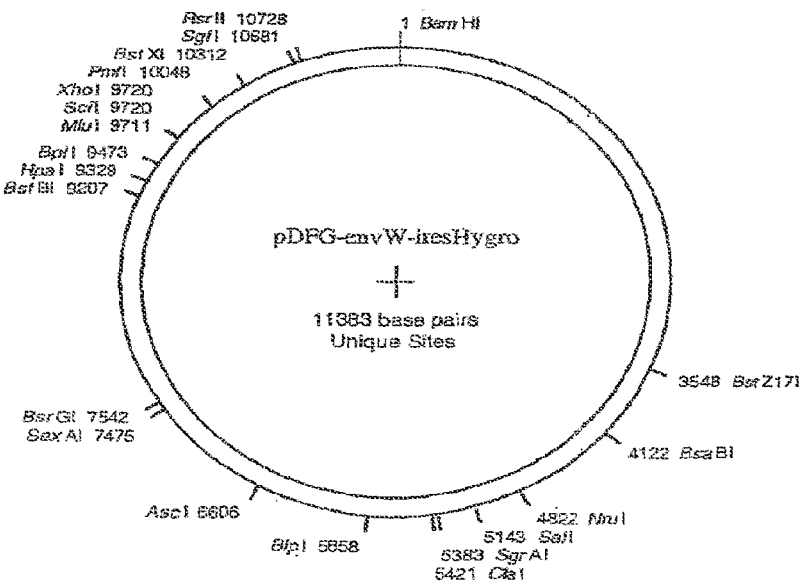
FIG. 3B represents the pDFG-envW-iresHygro vector (SEQ ID NO: 168 & 169 are disclosed respectively in order of appearance).

The vectors expressing the envelope of HERV-W and HERV-T (phCMV-envW and phCMV-envT) have been previously described (Blaise et al., 2003). In brief, they comprise a promoter (human cytomegalovirus early promoter), the rabbit β-globin intron and polyadenylation sequences. The cDNA of HERV-W env was inserted between the EcoRI sites of the vector (FIG. 3A).

Figure 1A:
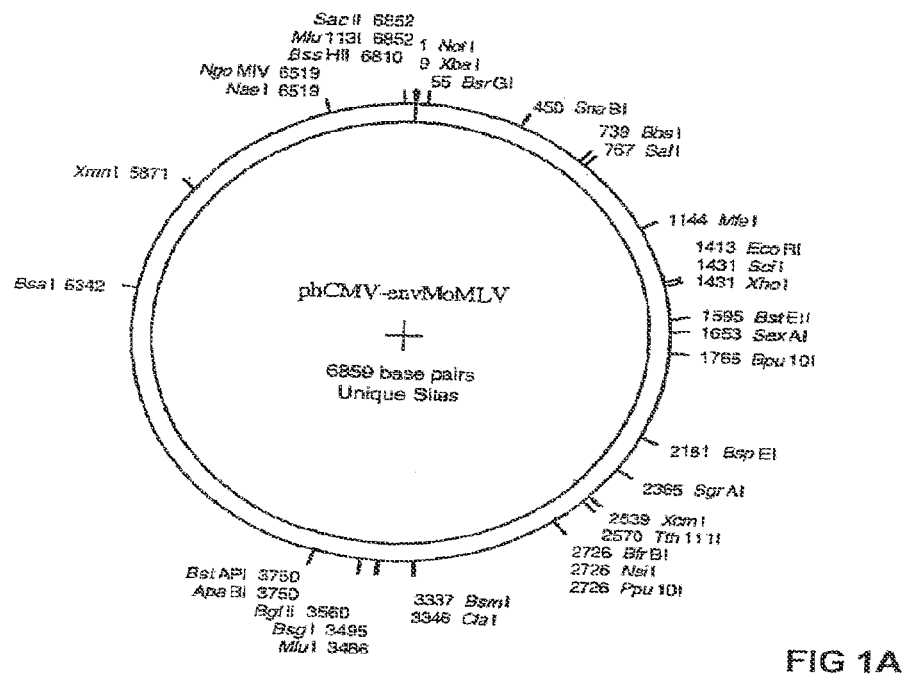
FIG. 1A represents the phCMV-envMOMLV vector (SEQ ID NO: 158 & 159 are disclosed respectively in order of appearance).
Figure 2A:
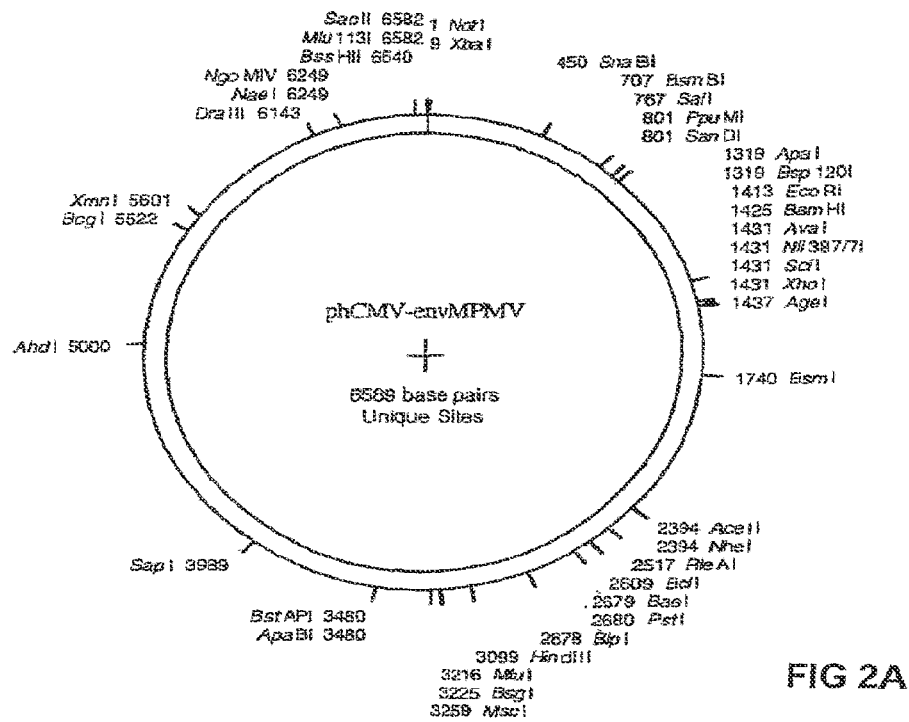
FIG. 2A represents the phCMV-envMPMV vector (SEQ ID NO: 162 & 163 are disclosed respectively in order of appearance).
Figure 2B:
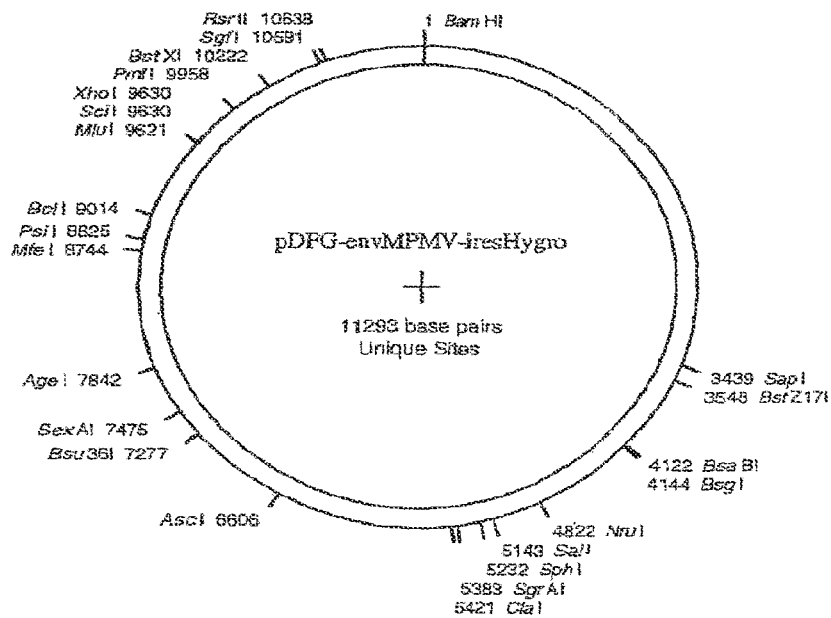
FIG. 2B represents the pDFG-envMPMV-iresHygro vector (SEQ ID NO: 164 & 165 are disclosed respectively in order of appearance).
Figure 4:
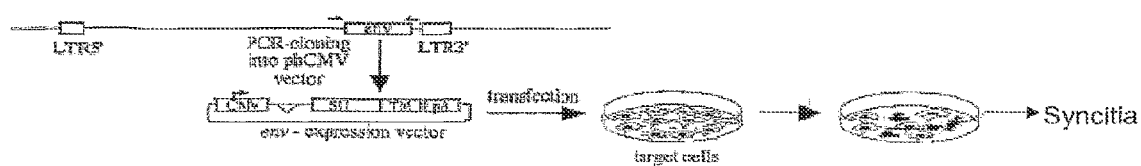
FIG. 4: Schematic representation of the cell-cell fusion assay.
The vector used comprises the nucleic acid encoding an envelope protein of interest (SU and TM subunits), a CMV promoter and a poly A nucleotide element (pA).

The envelope gene of MPMV was retrieved from the pTMO vector (Brody et al., 1994) by PCR using the following primers:
Atacatctcgagaccggtccaactagaaccatgaacttcaattatcatttcatctgga (SEQ ID NO: 55) and
Atacatacgcgtctatgttaaggtcaaatatgagccacc (SEQ ID NO: 56) digested with XhoI and MluI (underlined), and cloned into phCMV-envT digested with the same enzymes. The phCMV-envMPMV expression vector containing and expressing the envelope gene of MPMV was obtained (FIG. 2A). These vectors are used in the cell-cell fusion assay and for the production of p glycoproteins was measured 24 h after transfection with the corresponding expression vectors (FIGS. 1A, 2A and 3A). To visualize syncytia, cells were fixed in methanol and stained by adding May-Grünwald and Giemsa solutions (Sigma) according to the manufacturer's instructions. The fusion index, which represents the percentage of fusion events in a cell population is defined as [(N−S)/7]×100, where N is the number of nuclei in the syncytia, S is the number of syncytia, and T is the total number of nuclei counted (FIG. 4). A phCMV vector not expressing envelope protein was used as a negative control.

Infectious Property: the Infectivity Assay.

$7.5 \times 10^5$ 293T cells were cotransfected with 1.75 µg of CMV-gag-pol-MoMLV, 1.75 µg MFG-nls-lacZ and 0.55 µg phCMV vector (FIGS. 1A, 2A and 3A) expressing the envelope glycoproteins (wild-type or mutated) using the phosphate calcium method. MFG-nls-lacZ vector comprises the MoMLV LTRs, the psi sequence, a NLS (nuclear localisation signal) and the LacZ gene. Supernatants containing the pseudotypes (viral body of MoMLV with envelope protein from another virus strain) were recovered 2 days later, filtered, serially diluted in culture medium and used for infection of $4 \times 10^3$ HeLa cells in 96-well culture plates in the presence of 4 µg/mL polybrene. Plates were fixed 2 days later, X-gal coloured for 1 hour, and foci of β-galactosidase-expressing infected cells were counted to determine pseudotype titers (number of infectious particles by ml of supernatant). A phCMV vector not expressing envelope protein was used as a negative control.

Immunosuppressive Properties: the Establishment of Envelope-Expressing Tumor Cells and In Vivo Assay.

pDFG retroviral expression vectors (1.75 µg) were packaged by transient cotransfection into $7.5 \times 10^5$ 293T cells with 1.75 µg of CMV-gag-pol-MoMLV and 0.55 µg CMV-envAmpho, using the calcium phosphate method. Supernatants were recovered 2 days later, filtered and used for infection of $5 \times 10^5$ MCA205 tumor cells in the presence of 4 µg/mL polybrene, as described in Mangeney & Heidmann, 1998. Cells were maintained in selective medium (400 units/mL hygromycin) for 2 weeks. For in vivo assays, tumor cells were trypsinized, centrifuged and resuspended in PBS at a concentration of $1 \times 10^7$ cells/mL. 100 µL of each suspension were injected s.c. in the shaved right flank of 3 C57/BL6 and 8 to 10 BALB/c mice. Tumor establishment was determined by palpation and tumor area (mm²) was determined by measuring perpendicular tumor diameters (FIG. 5). Immunosuppression index is defined as $i=(S_{env}-S_{none})/S_{none}$, wherein $S_{env}$ is the maximum area reached by a tumour expressing an envelop protein and $S_{none}$ is the maximum area reached by a tumour not expressing envelop protein (negative control).

Results

1—Determination of the Infectious Properties of Various Wild-Type Envelope Proteins The infectiosity of envelope proteins was tested in NIH 3T3 cells (MoMLV) or HeLa cells (HERV-W and MPMV). FIG. 6 shows that the three wild-type envelope proteins (lines 1, 5 and 9) were able to sustain an infection.

2—Determination of the Immunosuppressive Effects of Various Wild-Type Envelope Proteins The immunosuppressive effect of MPMV retrovirus and HERV-W was tested in MCA205 cells, injected in allogenic balb/c or syngenic C57Bl/6 mice. FIG. 7 shows that tumour expressing MPMV (black bars) were large comparing to tumours expressing HERV-W (white bars). Whereas inventors confirmed the immunosuppressive effect of MPMV envelope, they showed that HERV-W was not able to immunosuppress an allogenic host.

In conclusion, the envelope proteins of MPMV and HERV-W have the same properties in term of fusogenicity and infectiosity, but differ for their immunosuppressive properties.

3—Strategy for the Identification of Envelope Protein with Altered Immunosuppressive Properties Based on the different properties of HERV-W and MPMV, inventors attempted to identify domains in the amino acid sequence, which could be involved in the modulation of immunosuppression.

A putative 17 amino acid immunosuppressive domain (ISU) was previously characterized in several publications between amino acid 30 and amino acid 47 of the cristallized subdomain, the TM domain, respectively two leucines (L) in the MoMLV (Blaise et al. 2001 J Virol. 82, 1597-1600).

A two-step strategy was applied; the first step was to modify an envelope protein that in such a way that the derived protein (i.e., the modified protein) retains the fusion and infectious properties of the corresponding none modified protein. Once such a modified envelope protein has been identified, its immunosuppressive effect was tested and compared to that of the none modified protein.

4—Study of Modified HERV-W

One difficulty lays in the fact that previous attempts to modify the amino acid composition of the TM subunit have lead to the loss of association of SU-TM and have altered the infectivity. A deletion from Leucine 30 to Threonine 40 of the MPMV immunosuppressive domain for instance completely abrogates the infectivity of the envelope proteins (Brody et al. 1992 J Virol 66, 3466-3475; Brody et al. 1994 Virology 202, 673-683).

Despite these unsuccessful attempts, the inventors studied the amino acid composition of the ISU domain, and their possible impact on the structure of the domain and achieve a novel definition of said ISU domain involved in immunosuppressive properties observed in vivo. They further determined that some positions in the amino acid sequence of proteins together with the nature of the amino acid residues at these positions were critical for the immuno suppressive effect.

The inventors especially designed some modifications in the amino acid sequence of a non-immunosuppressive envelope protein, i.e., HERV-WEnv protein, to render it immunosuppressive, using for instance substitution of determined residues by the corresponding residues of MPMV.

a. Infectious Properties

The A36G and T47I substitutions of the HERV-W envelope do not modify the infectiosity, the fusogenicity and the immunosuppressive effect of the envelope protein (Table 1). These two amino acids appear not to be determinant for these functions. To the contrary, the R44Q or F50A substitutions strongly altered both the infectious and fusion properties of the envelope protein (Table 1, and FIG. 6, lines 2 and 3).

A double mutant comprising both the R44Q and F50A substitutions was constructed. Surprisingly, the double mutant retained fusion and infectious properties similar to those of the wild type polypeptide (Table 1 and FIG. 6, line 4).

This result and the design of this modified envelope protein using some homologous positions found in the envelope of MoMLV (FIG. 8) suggest that these two amino acids could interact together because of both their respective location in the structure of the TM unit of the envelope protein, and their nature. This possible interaction may explain the compensatory behaviour of this pair of mutations. This was unexpected, because of the previous attempts that fail to identify such amino acids.

b. Immunosuppressive Properties

Another result, as surprising as the above-mentioned, arises from the study of the immunosuppressive effect. Indeed, whereas the wild-type HERV-W envelope protein was not immunosuppressive in view of the size of the tumours, the HERV-W double mutant was more immunosuppressive than the wild-type MPMV envelope proteins (Table 1 and FIG. 7, white bars).

Moreover, inventors identified two amino acids positions in the sequence, one of which was previously not reported as forming part of the ISU domain (position 50), which, taken together, revealed to be involved in the modulation of the immunosuppressive effect of the HERV-W envelope proteins.

TABLE 1

Results obtained for fusion, infectious and immunosuppression properties of HERV-W modified envelope proteins.

| Mutant | Fusion | Infection | Immunosuppression |
|---|---|---|---|
| Wild Type | 55.0 ± 3.7% | 800 ± 200 | −0.30 ± 0.06 |
| R44Q | 32.5 ± 1.3% | <10 | −0.12 ± 0.30 |
| F50A | 5.6 ± 3.0% | <10 | −0.16 ± 0.14 |
| R44Q + F50A | 53.0 ± 2.8% | 947 ± 542 | 0.61 ± 0.10 |
| A36G | 54.5 ± 4.5% | 3950 ± 2250 | −0.02 ± 0.01 |
| T47I | 50.5 ± 1.2% | 300 ± 80 | −0.25 ± 0.04 |
| Negative control | 3.2 ± 1.2% | <10 | 0.00 ± 0.00 |

5—Study of Modified Retrovirus Envelope Proteins

To confirm the fact that these amino acids residues belong to a determinant of immunosuppression, other retroviruses comprising similar amino acid at positions 44 (E or Q) and 50 (F) were screened. Several of these retroviruses have been identified and are disclosed in FIG. 9: Moloney Murine Leukaemia virus (MoMLV), Friend virus, Feline Leukaemia virus (FeLV), Human T-cell lymphotropic virus type-1 (HTLV-1) and simian T-cell lymphotropic virus type-1 (STLV-1).

In two of them, MPMV and MoMLV viruses, amino acid residues 44 and 50 were substituted by the corresponding amino acids found in HERV-W. The following constructs were made: E44R, A50F and E44R/A50F (MoMLV) and, Q44R, A50F and Q44R/A50F (MPMV).

a. Infectious Property

Interestingly, in MoMLV, the simple mutant loses its infectivity properties (Table 2 and FIG. 6, lines 6 and 7), whereas the double mutant has the same properties as the wild-type protein (Table 2 and FIG. 6, line 8).

In MPMV, slight differences were observed between mutants and wild-type, but only the double mutant presents properties strictly identical to the wild-type proteins (Table 3 and FIG. 6, lines 10 to 12).

b. Immunosuppressive Properties

In MoMLV, both a protein with the E44R substitution or a double mutant (E44R+A50F) have their immunosuppressive properties reduced in vivo (Table 2).

In MPMV, both a protein with the Q44R substitution or a double mutant (Q44R+A50F) have their immunosuppressive properties reduced in vivo (Table 3).

TABLE 2

Results obtained for infectious and immunosuppression properties of MoMLV modified envelope proteins (MoMLV is not fusiogenic).

| Mutant | Infection | Immunosuppression |
|---|---|---|
| wt | $4.59 ± 1.97 · 10^5$ | 0.60 ± 0.20 |
| E44R | $6.97 ± 3.98 · 10^4$ | 0.03 ± 0.01 |
| A50F | $<10^1$ | n/d |
| E44R + A50F | $4.34 ± 2.11 · 10^5$ | 0.00 ± 0.01 |
| Negative control | $<10^1$ | −0.00 ± 0.00 | n/d: not determined

TABLE 3

Results obtained for fusion, infectious and immunosuppression properties of MPMV modified envelope proteins.

| Mutant | Fusion | Infection | Immunosuppression |
|---|---|---|---|
| wt | 47.8 ± 3.0% | $3.3 ± 0.4\, 10^4$ | 0.45 ± 0.09 |
| Q44R | 29.8 ± 6.4% | $3.6 ± 0.5\, 10^3$ | −0.32 ± 0.12 |
| A50F | 37.2 ± 5.9% | $8.9 ± 2.7\, 10^3$ | 0.01 ± 0.01 |
| Q44R + A50F | 52.6 ± 3.4% | $2.8 ± 1.0\, 10^4$ | −0.27 ± 0.06 |
| Negative control | 5.1 ± 2.2% | $<10^1$ | 0.00 ± 0.00 |

Taken together, all these results allow to draw the following conclusions:

Firstly, a single mutation seems sufficient to modify the immunosuppressive properties of a retroviral immunosuppressive envelope protein. Indeed, the substitution of the glutamine or glutamic acid in position 44 with an arginine reduced the immunosuppressive behaviour of the mutants. However, the fusion and infectious properties, even if not abolished, are strongly reduced (MPMV).

Secondly, double mutants (at positions 44 and 50) have reduced immunosuppressive properties when compared to the corresponding wild-type envelope protein. Interestingly, MPMV double mutants have fusion properties as efficient as those of wild-type protein, and high infectious properties. The interest of such a protein in the production of viral particles and live vaccine is promising.

Example 2

Methods

Mice and Cell Lines:
Swiss mice (FV permissive), 10 weeks old, were obtained from Janvier (Laval, France). The cell lines 293T (ATCC CRL11268), HeLa (ATCC CCL2), NIH/3T3 (ATCC CRL-1658) and MCA205 (REF) were cultured in DMEM supplemented with 10% fetal calf serum, streptomycin (100 μg/ml) and penicillin (100 units/ml).

Constructions:
Plasmids p57 (Oliff et al. *J Virol* 33, 475-86 (1980)) and pET28(+)b (Novagen) were used.

phCMV-envFV was constructed as phCMV-envMPMV (Example 1), using p57 as PCR template and primers 16 and 17. Mutant derivatives were constructed by inserting into the ClaI/AvrII opened vector two PCR products, the first digested with ClaI, the second with AvrII. These fragments were generated with phosphorylated primer pairs 1-2 and 3-4 for E14R mutation (which corresponds to the E561R mutation of the full length ENV), 1-5 and 3-6 for A20F mutation (which corresponds to the A567F mutation of the full length ENV), and 1-2 and 4-6 for E14R+A20F mutation. pDFG-envFV and its mutant derivative were constructed by inserting the AgeI/

MluI fragments of phCMV-envFV into pDFG-MoTMTag digested with the same enzymes. The double mutant p57 was constructed by inserting the BstZ11I/BsmI fragment of the double mutant phCMV-envFV into p57 digested with the same enzymes.

The bacterial expression vector for the SU subunit of the FV envelope protein was constructed by inserting a PCR fragment generated with phCMV-envFV as a template and primer pair 7-8, and digested with NcoI and XhoI, into pET28 (+)b digested with the same enzymes.

The bacterial expression vectors for the SU and the TM subunits of the FV envelope protein were constructed by inserting a PCR fragment generated with wild-type or double-mutant phCMV-envFV as a template and primer pair 7-8 or 9-10, and digested with NcoI and XhoI, into pET28 (+)b digested with the same enzymes.

Recombinant Proteins:
Recombinant proteins were produced in BL21(DE3) *E. coli* cells (Stratagene) using pET28(+)b (Novagen) as an expression vector. The SU subunit was produced as inclusion bodies, and the wild-type and mutant TM subunits as soluble material. They were purified on HiTrap Chelating HP columns (Amersham) according to the manufacturer's instructions. The TM subunits were further purified on a Superdex 75 HR10/30 column (Amersham) to isolate the major trimeric form, their LPS contents were quantitated using the LAL QCL-1000 kit (Cambrex) and adjusted to 5 µg/mg of protein by addition of *E. coli* LPS (strain 0111:B4, Sigma).

Mice Immunization:
Mice were injected thrice at one week interval with either 100 µg of recombinant TM subunits or $1.5 \times 10^{10}$ RNA copies of an intact or UV-inactivated FV viral particles. 100 µg of

| | SEQUENCE | SEQ ID |
|---|---|---|
| 1 | CAACCTTACCAACCCTGATAAAACTCAAGA | SEQ ID NO: 131 |
| 2 | CAGTCCTCCTCTTTTTAGGAACAACAGGTCTAGGC | SEQ ID NO: 132 |
| 3 | TGTGCTGCCCTAAAAGAAGAATGTTGTT | SEQ ID NO: 133 |
| 4 | GGACTAAAGCCTGGACTACTGAGATCCTG | SEQ ID NO: 134 |
| 5 | CAGTCCTCCTTCTTTTAGGAACAACAGGT | SEQ ID NO: 135 |
| 6 | TGTGCTTTCCTAAAAGAAGAATGTTGTTTCTAT | SEQ ID NO: 136 |
| 7 | ATACATCCATGGCGTGTTCAACGCTCCCAAAATCCCCTA | SEQ ID NO: 137 |
| 8 | ATACATCTCGAGTTCTCTTTTATGTCTATAGGATTTTTCAAAC | SEQ ID NO: 138 |
| 9 | ATACATCCATGGCTGCCGTACAAGATGATCTCA | SEQ ID NO: 140 |
| 10 | ATACATCTCGAGATCTCTTACTAGGCCTGTATGGTCAGC | SEQ ID NO: 141 |

Virus Production, Quantitation and Inactivation:
$7.5 \times 10^5$ 293T cells were transfected with 4 µg of p57 DNA using a calcium phosphate transfection kit (Invitrogen). 48 h later, cell supernatants were used to infect $5 \times 10^5$ NIH/3T3 cells in the presence of 4 µg/mL polybrene and infected cells were cultured for 4 additional days. Viral particles were collected from cell supernatants, concentrated by ultracentrifugation, resuspended in PBS, and frozen. Inactivation was performed by exposing a viral suspension in PBS to UV light at 0.5 mW/cm² during 30 minutes.

Immunosuppression Assay:
MCA205 cells were transduced with either an envelope gene expression vector or an empty vector, and engrafted into allogenic mice where they established transient tumors, as described in example 1. The immunosuppression index was calculated as $(A_{env}-A_{none})/A_{none}$, where $A_{env}$ and $A_{none}$ are the mean tumor areas obtained with cells expressing the envelope gene and the empty cassette, respectively.

Cell-cell fusion and infectivity assays were performed as described in Example 1, with phCMV-envFV and their mutant derivatives as envelope expression vectors.

Viral Load Assay:
RNA from 2 µl of concentrated virus or 20 µl of cell supernatant or serum was extracted using the RNAeasy microkit (QIAgen), reverse-transcribed using the MoMuLV reverse transcription kit (Applied) and random hexamers as primers, and cDNA was quantitated by real-time PCR using the Platinum SYBR Green qPCR kit (Invitrogen) and primers CTCAGGGAGCAGCGGGA (SEQ ID NO: 142) and TAGCTTAAGTCTGTTCCAGGCAGTG (SEQ ID NO: 143).

CpG (phosphorothioate oligonucleotide TCCATGACGTTC-CTGACGTT (SEQ ID NO: 144)) was systematically added as an adjuvant. Sera were collected 4 days after the last immunization. Inactivated viral particles-immunized mice were challenged with $10^6$ RNA copies of the wild-type FV, and post-challenge sera were collected 5 days later.

Immunological FV Detection:
Recombinant SU subunit was produced as inclusion bodies in BL21(DE3) *E. coli* cells (Stratagene) using pET28(+)b (Novagen) as an expression vector, purified on a HiTrap Chelating HP column (Amersham) according to the manufacturer's instructions, and used to coat MaxiSorp microplates (Nunc) at a concentration of 2 µg/ml. IgG levels in serially diluted sera were quantitated using an anti-mouse IgG antibody conjugated to HRP (Amersham) and OPD as a chromogenic reagent (Sigma).

Results

1. Loss of Envelope Protein-Induced Immunosuppression Leads to Complete Immune Rejection of an Infectious Retrovirus:

The genetic, double-mutation-generated disjunction between immunosuppression and infectivity evidenced in Example 1 opens the possibility to generate an entire retrovirus devoid of the immunosuppressive activity of its envelope protein, but still replicative and infectious.

The Friend Murine Leukemia Virus (FV) was chosen as a model, because the mouse genome does not contain a related endogenous retrovirus that could impair its in vivo detection.

The key residues of the FV envelope were replaced by those of Syncytin-1 (HERV-W ENV), and it was checked, as for the MPMV envelope, that the double mutation E14R+ A20F (which corresponds to the E561R+A567F mutation of the full length ENV) reversed immunosuppression without altering infectivity (FIGS. 11A and 11B). The wild-type envelope gene was replaced by its non-immunosuppressive mutant in the FV molecular clone 57, and each type of retroviral particles was produced in vitro. The virus yields were similar as measured by a quantitative RT-PCR assay of the viral RNA in the cell supernatants.

As expected, both virus types display the same propagation kinetics in an in vitro infection assay in NIH/3T3 cells (FIG. 11C), and similarly when injected in vivo in 5-Gray irradiated, immunocompromised mice (FIG. 12A)

In normal mice, the wild-type FV first established high viremia in all mice during the primo-infection phase (at day 7 after virus injection, FIGS. 12A-12B). This phase was followed by the establishment of persistent infections, the mice being able to control viral replication to various extents, as expected with non-congenic, outbred mice. After 4 months, 80% of the infected mice disclosed an erythroleukemia syndrome, with a hematocrit level below 35%.

In contrast the mutated non-immunosuppressive FV was undetectable as early as 14 days after injection of even very high doses of viral copies ($10^6$ RNA copies, $10^2$ $ID_{50}$) with no evidence for any pathology. Noteworthily, IgG directed against the FV envelope protein were detected persistently in mice infected with wild-type FV, but only transiently in mice infected with the double-mutant FV (FIG. 13), indicating complete clearance of the mutated virus.

In conclusion, the present experiments demonstrate that envelope-driven immunosuppression is essential for FV infection, as its absence leads to thorough immune rejection of the incoming virus.

2. Increased Immunogenicity of Immunosuppression-Negative Recombinant Envelope Proteins and Inactivated Viral Particles:

As the key element for viral entry into the target cell, retroviral envelope proteins are systematically included in every vaccinal formulation, either as recombinant proteins, as fragments thereof, or as genes carried by a defective viral vector. One could suspect that envelope protein-mediated immunosuppression could inhibit the response mounted against an immunogen containing the ISU, thus lowering its vaccinal efficiency.

To test this hypothesis, two kinds of ISU-containing immunogens were generated: 1) recombinant proteins corresponding to the ectodomains of the TM subunit of the wild-type or mutant FV envelope protein, produced in *E. coli* as soluble— thus correctly folded—and trimeric forms displaying identical behavior upon purification; 2) wild-type and mutant FV particles that were intact or inactivated by exposure to UV light, in order to preserve the native structure of their envelope proteins. These immunogens were injected thrice in Swiss mice to generate a strong secondary humoral response.

As illustrated in FIG. 14A, only the mutant non-immunosuppressive envelope protein raises such a response, with high IgG levels. In every cases, the signals obtained with plates coated with the wild-type or the mutant TM subunits were quantitatively the same, indicating that the anti-TM antibodies in the mice sera are not preferentially directed against the ISU itself but rather against other epitopes within the TM subunits.

Thus, the double mutation introduced in FV envelope protein does not convert its ISU into a highly efficient epitope. In addition, IgM levels raised by the wild-type envelope protein are much higher than those raised by its non-immunosuppressive mutant counterpart. These results suggest that the immunosuppressive domain of FV envelope protein directly inhibits the immune system, and that this effect does not require viral entry and replication in the target cell nor even any other viral component than the TM subunit alone.

FIG. 14B confirms these results with MoMLV ENV and HERV-W ENV. Almost no IgG response is elicited against the wild type recombinant TM subunit of MoMLV ENV, whereas the non immunosuppressive double mutant (see Example 1) shows a strong IgG response. Furthermore, as expected, an IgG response is seen against the TM subunit HERV-W ENV, which is naturally deprived of immunosuppressive activity, whereas the immunosuppressive double mutant (see Example 1) elicits only a slight IgG response.

3. Loss of Envelope Protein-Induced Immunosuppression Improves the Vaccinal Efficiency of Inactivated Viral Particles:

One could suspect that this antigenicity-inhibiting effect of the ISU might lower the efficiency of any vaccine formulation containing an immunosuppressive envelope protein, and thus, that the specific, double mutation-induced disruption of this effect might improve vaccinal efficiency.

To test this hypothesis, mice immunized with either wild type and double mutant inactivated viral particles or with intact double mutant viral particles were challenged with the intact wild-type FV. Serum viral loads were then assayed at peak viremia, five days after challenge (FIG. 15).

The virus was detectable in all mice immunized with the wild-type inactivated FV, yet with a geometric mean viral load 50-fold lower than that of control mice immunized with the adjuvant only, indicating a significant but incomplete protection conferred by immunization with wild-type particles. In contrast, the viral loads of 6 of the 14 mice immunized with the non-immunosuppressive inactivated double mutant FV were below the detection threshold of the assay, and the geometric mean viral load was reduced 7500-fold as compared to mice immunized with adjuvant only. Furthermore, the viral loads of 12 out of 14 mice immunized with the intact non-immunosuppressive double mutant FV were below the detection threshold and the geometrical mean viral load was also below the detection threshold.

These results show that disrupting immunosuppression by mutations that preserve the canonical function—thus the structure—of an envelope protein improves the efficiency of vaccinal formulation based on such proteins.

Example 3

Methods

Mice and Cell Lines:

C57BL/6 and SCID mice, 8-12 weeks old, were obtained from Janvier (France). B16 (murine melanoma cell line of C57BL/6 origin, EACC 94042254) and 293T (human embryonic kidney cells, ATCC CRL11268) were maintained in DMEM supplemented with 10% heat-inactivated foetal calf serum and antibiotics.

Figure 1B:
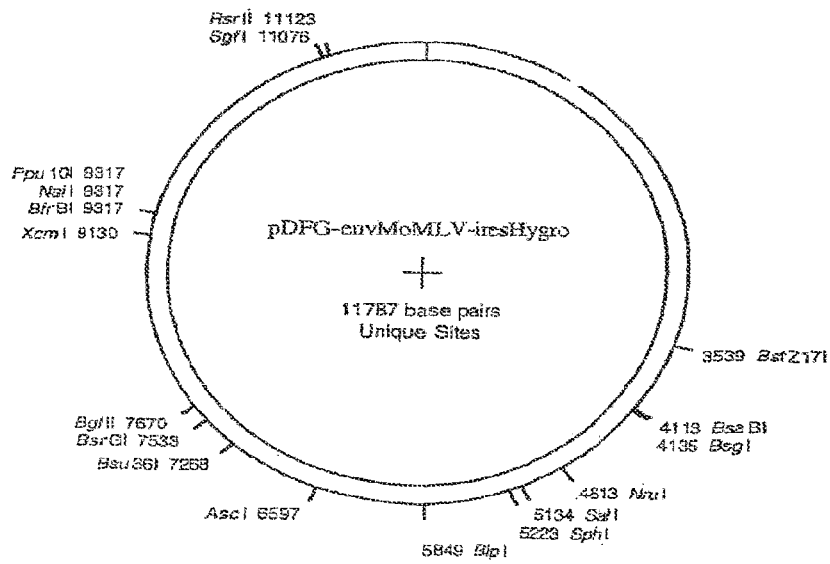
FIG. 1B represents the pDFG-envMoMLV-iresHygro vector (SEQ ID NO: 160 & 161 are disclosed respectively in order of appearance).

Constructions:

a plncxH1 expression vectors derived from the plncx (Miller and Rosman Biotechniques 1989; 7: 989-90) and the pSUPER (Brummelkamp et al. Science 2002; 296: 550-3) vectors was constructed to generate short transcripts directed against MelARV (targeted to the genomic transcript within the gag sequence; nt positions 1220-1238 from the start codon), or against the green fluorescent protein transcript (nt position 215-233 from the start codon) as a control. They were obtained by first inserting annealed 64-mer oligonucleotides (sequences in FIG. 1B) into pSUPER opened at the Bg/II and HindIII sites, followed by introduction of the BamHI-HindIII fragment from these constructs into plncx opened at the corresponding sites. The expression vector for the MelARV envelope (pDFG MelARVenv) and the control (pDFG none) were constructed by introducing (or not) a RT-PCR product, generated from the MelARV viral RNA using an AgeI-containing primer at the envelope 5'-end and a XhoI-containing primer at the envelope 3'-end, into a hygromycin-containing pDFG vector (Mangeney and Heidmann Proc Natl Acad Sci USA 1998; 95: 14920-14925) opened at the same sites.

Establishment of ERV$^{KD}$ B16 Tumor Cells:

$7.5 \times 10^5$ 293T cells were cotransfected with the plncxH1 vector (1.75 µg) and expression vectors for the MLV proteins (0.55 µg for the amphotropic MLV envelope vector and 1.75 µg for the MLV gag and pol vector, see Blaise et al. J Virol 2004; 78: 1050-1054). Thirty six hours post-transfection, viral supernatants were collected for infection of the B16 tumor cells (2.5 ml of supernatant for $5 \times 10^5$ cells, with 8 µg/ml polybrene). Cells were maintained in selective medium (1 mg/ml neomycin) for three weeks. In some experiments, the pDFG MelARVenv expression vector (or control pDFG none) was additionally introduced into the cells using the same protocol and infected cells were selected with 300 units/ml hygromycin.

Expression of MelARV Proteins:

Analysis of MelARV expression was performed by Western blot analyses. The supernatants of $10^7$ cells were collected, centrifuged for 10 min at 100 xg, filtered and concentrated by ultra-centrifugation in a SW41 Beckman rotor (150,000 xg, 1 hour, 4° C.). Pellets were resuspended in lysis buffer, submitted to SDS-PAGE, blotted and revealed with an anti-Env mAb (Ciancolo et al. J Exp Med 1984; 159:964-969) and an anti-Gag goat serum (Viromed Biosafety Labs).

In Vitro Transformation Assay:

Both control- and ERV$^{KD}$-B16 cells were plated in soft agar to determine the efficiency of anchorage-independent growth. Cells ($2 \times 10^3$ or $2 \times 10^4$) were plated in 5 ml of 0.33% agar in DMEM with 10% foetal bovine serum overlaid onto a solid layer of 0.5% agar in DMEM supplemented with 10% foetal bovine serum. The culture was maintained for 4 weeks, the colonies were stained with INT solution (Sigma-Aldrich) and then counted.

Tumor Progression In Vivo:

For in vivo assays, tumor cells were washed three times with PBS, scrapped without trypsination, and subcutaneously inoculated in the shaved area of the right flank of the mice. Tumor establishment was determined by palpation and tumor area was determined by measuring perpendicular tumor diameters.

CD4$^+$CD25$^+$ T Cell Purification and Adoptive Transfer in Syngenic C57BL/6 Mice:

CD4$^+$CD25$^+$ cells were freshly isolated from spleens of C57BL/6 mice engrafted with $2 \times 10^5$ B16 cells 17 days before. Cells were purified by a two step procedure of negative and positive selections, using MACS magnetic beads (mouse regulatory T cell isolation kit, Miltenyi Biotech), according to the manufacturer's instructions. Fifty thousands purified lymphocytes were transferred intravenously into naive C57BL/6 mice. Recipient mice were challenged the same day with $2 \times 10^5$ control- or ERV$^{KD}$-B16 cells in the right flank.

Results

1. Knocking down ERV does not Modify the Transformed Phenotype of B16 Melanoma Cells.

An RNA interference approach was used based on stable vectors producing short double-stranded RNA (dsRNA) directed against the viral genome of the MelARV element and the irrelevant gfp gene as a control. The rationale of the procedure and the structure of the plasmids used are illustrated in FIGS. 16A-16B. FIG. 16C clearly shows that the ERV-specific dsRNA vector almost completely abolished ERV expression in the transduced B16 cells (ERV$^{KD}$ B16 cells), with a>10-fold reduction in the amount of both the Env and Gag viral proteins as compared to the control transduced cells (control B16 cells). As a next step, the transformed phenotype of the ERV$^{KD}$ and control B16 cells was assayed both in vitro and in vivo. In vitro, the anchorage-independent growth rate was measured after plating in semi-solid media (soft agar assay). As illustrated in FIG. 17A, the ERV$^{KD}$ B16 cell line gave rise to a similar number of colonies as the control B16 cells. In vivo, the growth rate of the two cell populations was analyzed after engrafting into X-irradiated or SCID mice. As illustrated in FIG. 17B, both cell populations have a transformed phenotype, with similar growth rates. Altogether, these results show that knocking down the MelARV endogenous retrovirus has no effect on the transformed state of the melanoma cells.

2. Knocking Down ERV Inhibits B16 Tumor Cell Growth In Vivo and Increases Survival of Immunocompetent Hosts.

To investigate whether tumor cells may overwhelm the antitumor response in vivo through an ERV-dependent mechanism, the Inventors explored the impact of the knocking down of MelARV on tumor progression by injecting C57BL/6 immunocompetent mice with the control and the ERV$^{KD}$ B16 cells. As illustrated in FIG. 18A, growth of control B16 cells, as expected, led to large tumors in most of the animals, whereas the ERV$^{KD}$ B16 cells yielded tumors of a limited size and in only a small number of engrafted mice. The difference in tumor cell growth is also clearly substantiated by the extent of animal survival (FIG. 18B): as soon as day 70, 90% of the mice engrafted with the control B16 cells had been killed by their tumor, whereas 80% of mice engrafted with ERV$^{KD}$ B16 cells were alive and tumor-free (and still so at day 130). In an attempt to identify the MelARV genes involved in the observed effects, an expression vector (lacking the dsRNA-targeted sequence) for the sole MelARV env gene was introduced back into the ERV$^{KD}$ B16 cells. The resulting double-transduced ERV$^{KD}$+env (or control) B16 cells were then engrafted into C57BL/6 mice. As illustrated in FIG. 18C, this resulted in partial reversion of the knockdown effect, with already 50% of the mice engrafted with the Env-expressing cells dead by day 70. This reversion indicates that the env gene is—at least in part—responsible for tumor immune escape. The partial effect of the reversion is most likely explained by the lower expression (FIG. 19) of the Env protein when expressed by the exogenous vector.

Along this line, it is of interest that a first series of experiments using synthetic siRNA targeted to MelARV, and injected intraperitoneously 12 days after engraftment of B16 cells into immunocompetent mice, actually resulted in a ⅓ inhibition of tumor growth as compared to mice injected with control siRNA (FIG. 20A) and, as illustrated in the supplementary FIG. 20B, in a reproducible increase in survival delay.

The present data demonstrate that tumors are able to overwhelm the immune system by expressing the envelope of an ERV and that blocking ERV expression resulted in enhanced tumor rejection.

It is noteworthy that in humans the expression of ERV env genes, mainly restricted to placenta and testis in normal tissues, can be observed in several tumor types such as seminomas and melanomas. Such HERV ENV proteins have been shown to be immunosuppressive. Therefore, inhibiting the expression or the activity of these ENV proteins is a promising approach to enhance immune response against ENV-expressing tumors. Such an inhibition of the activity of the tumoral ENV proteins could be performed, for instance, by an immune response elicited by a prophylactic or a therapeutic vaccination with mutated ENV proteins depleted of their immunosuppressive activity according to the invention or by compounds directly binding to tumoral ENV proteins.

The invention claimed is:

1. An isolated mutated ENV protein resulting from mutation of a transmembrane subunit of a wild type viral ENV protein, the transmembrane subunit of said wild type viral ENV protein comprising an immunosuppressive domain comprising the following amino acid sequence:

$$NY_1Y_2Y_3LY_4Y_5LY_6Y_7Y_8X_1Y_9Y_{10}Y_{11}CY_{12}X_2 \quad \text{(SEQ ID NO: 156)}$$

wherein,
$Y_1$ is C or R,
$Y_2$ is R, M, L or Q,
$Y_3$ is C, G or A,
$Y_4$ is D,
$Y_5$ is L, M, Y or I,
$Y_6$ is F, T, L or M,
$Y_7$ is W, L or A,
$Y_8$ is E, K, Q, A or S,
$Y_9$ is G or E,
$Y_{10}$ is G,
$Y_{11}$ is L, I or V,
$Y_{12}$ is K, A, V, L, G, M or I,
$X_1$ is E, K or Q, and
$X_2$ is A, V, L, I, K or M, or
an isolated fragment of said mutated ENV protein, provided that said fragment comprises SEQ ID NO: 156, wherein,
in the mutated ENV protein or fragment thereof, amino acid $X_1$ is substituted by R or H,
there is no substitution other than that of amino acid $X_1$, and optionally also $X_2$, and
said mutated ENV protein or fragment thereof has decreased immunosuppressive activity with respect to the wild type viral ENV protein.

2. The isolated mutated ENV protein or fragment thereof according to claim 1, wherein the transmembrane subunit of said wild type viral ENV protein comprises an immunosuppressive domain comprising the following amino acid sequence:

$$NY_1Y_2Y_3LY_4Y_5LY_6Y_7Y_8X_1Y_9Y_{10}Y_{11}CY_{12}X_2 \quad \text{(SEQ ID NO: 156)}$$

wherein,
$Y_1$ is C or R,
$Y_2$ is R,
$Y_3$ is C or G,
$Y_4$ is D,
$Y_5$ is L or M,
$Y_6$ is F or T,
$Y_7$ is W, L or A,
$Y_8$ is E, K, Q, A or S,
$Y_9$ is G,
$Y_{10}$ is G,
$Y_{11}$ is L or I,
$Y_{12}$ is K, A, V or L,
$X_1$ is E, K or Q, and
$X_2$ is A.

3. The isolated mutated ENV protein or fragment thereof according to claim 1, wherein amino acid $X_1$ is substituted by R or H and amino acid $X_2$ is substituted by F, M, Y or W.

4. The isolated mutated ENV protein or fragment thereof according to claim 1, wherein the wild type viral ENV protein is:
a HERV ENV selected from the group consisting of:
   HERV-FRD ENV as set forth in SEQ ID NO: 82,
   HERV-T ENV as set forth in SEQ ID NO: 84,
   HERV-R ENV as set forth in SEQ ID NO: 86,
   HERV-V ENV as set forth in SEQ ID NO: 88, and
   HERV-R(b) ENV as set forth in SEQ ID NO: 90, or
an ENV selected from the group consisting of:
   HTLV-1 ENV as set forth in SEQ ID NO: 92,
   HTLV-2 ENV as set forth in SEQ ID NO: 94,
   PERV ENV as set forth in SEQ ID NO: 98,
   STLV-1 ENV as set forth in SEQ ID NO: 100,
   MoMLV ENV as set forth in SEQ ID NO: 70,
   MPMV ENV as set forth in SEQ ID NO: 72, and
   FV ENV as set forth in SEQ ID NO: 102.

5. The isolated mutated ENV protein or fragment thereof according to claim 1, wherein the transmembrane subunit of said wild type viral ENV protein comprises an immunosuppressive domain comprising one of SEQ ID NO: 33, SEQ ID NO: 34, SEQ ID NO: 35, SEQ ID NO: 36, SEQ ID NO: 38 or SEQ ID NO: 39.

6. The isolated mutated ENV protein or fragment thereof according to claim 1, wherein the transmembrane subunit of said mutated viral ENV protein comprises a mutated immunosuppressive domain comprising one of SEQ ID NO: 48, SEQ ID NO: 49, SEQ ID NO: 50, SEQ ID NO: 53 or SEQ ID NO: 54.

7. The isolated mutated ENV protein or fragment thereof according to claim 1, wherein the amino acid sequence of the mutated ENV protein is selected from the group consisting of: SEQ ID NO: 120, SEQ ID NO: 124, SEQ ID NO: 128, SEQ ID NO: 146, SEQ ID NO: 108, SEQ ID NO: 112, and SEQ ID NO: 150.

8. The isolated mutated ENV protein or fragment thereof according to claim 3, wherein the amino acid sequence of the mutated ENV protein is selected from the group consisting of: SEQ ID NO: 122, SEQ ID NO: 126, SEQ ID NO: 130, SEQ ID NO: 148, SEQ ID NO: 110, SEQ ID NO: 114, and SEQ ID NO: 152.

9. A pharmaceutical composition, comprising as active substance the mutated ENV protein as defined in claim 1, in association with a pharmaceutically acceptable carrier.

10. An isolated mutated ENV protein resulting from mutation of a transmembrane subunit of a wild type viral ENV protein, or an isolated fragment of said mutated ENV protein, said mutated ENV protein or fragment having a decreased immunosuppressive activity with respect to the wild type viral ENV protein, the transmembrane subunit of said mutated ENV protein or isolated fragment thereof having a mutated immunosuppressive domain comprising SEQ ID NO: 43.

11. A pharmaceutical composition comprising as active substance the mutated ENV protein as defined in claim 10, in association with a pharmaceutically acceptable carrier.

12. The isolated mutated ENV protein or fragment thereof according to claim 3, wherein amino acid $X_1$ is substituted by R and amino acid $X_2$ is substituted by F.

13. An isolated protein, comprising the following amino acid sequence:

$$NY_1Y_2Y_3LY_4Y_5LY_6Y_7Y_8X_1Y_9Y_{10}Y_{11}CY_{12}X_2 \quad \text{(SEQ ID NO: 156)}$$

wherein,
$Y_1$ is C or R,
$Y_2$ is R, M, L or Q,
$Y_3$ is C, G or A,
$Y_4$ is D,
$Y_5$ is L, M, Y or I,
$Y_6$ is F, T, L or M,
$Y_7$ is W, L or A,
$Y_8$ is E, K, Q, A or S,
$Y_9$ is G or E,
$Y_{10}$ is G,
$Y_{11}$ is L, I or V,
$Y_{12}$ is K, A, V, L, G, M or I,
$X_1$ is R or H, and
$X_2$ is A, V, L, I, K, F, M, Y or W.

14. The isolated protein according to claim 13, wherein:
$Y_1$ is C or R,
$Y_2$ is R,
$Y_3$ is C or G,
$Y_4$ is D,
$Y_5$ is L or M,
$Y_6$ is F or T,
$Y_7$ is W, L or A,
$Y_8$ is E, K, Q, A or S,
$Y_9$ is G,
$Y_{10}$ is G,
$Y_{11}$ is L or I,
$Y_{12}$ is K, A, V or L,
$X_1$ is R or H, and
$X_2$ is A, F, M, Y or W.

15. The isolated protein according to claim 14, wherein $X_2$ is F, M, Y or W.

16. The isolated protein according to claim 14, wherein $X_1$ is R and $X_2$ is F.

17. A pharmaceutical composition, comprising as active substance the protein as defined in claim 14, in association with a pharmaceutically acceptable carrier.

\* \* \* \* \*

SEQUENCE LISTING

```
<160> NUMBER OF SEQ ID NOS: 171

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Gly Leu Cys Ala Phe
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Gly Gly Leu Cys Lys Phe
  1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Gly Gly Leu Cys Leu Phe
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gly Gly Leu Cys Met Phe
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Gly Leu Cys Val Phe
  1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Gly Leu Cys Ile Phe
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Gly Thr Cys Ala Phe
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gly Gly Thr Cys Lys Phe
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Gly Thr Cys Met Phe
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Gly Gly Thr Cys Ile Phe
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Arg Gly Gly Ile Cys Ala Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gly Gly Ile Cys Lys Phe
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gly Gly Ile Cys Leu Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gly Gly Ile Cys Met Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Gly Ile Cys Val Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Gly Gly Ile Cys Ile Phe
1               5

<210> SEQ ID NO 17
<211> LENGTH: 7
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 17

Gln Gly Gly Leu Cys Lys Ala
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gly Gly Leu Cys Ala Ala
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gly Gly Leu Cys Leu Ala
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gly Gly Ile Cys Leu Ala
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Gly Gly Leu Cys Ala Ala
  1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Gly Gly Leu Cys Val Ala
  1               5

<210> SEQ ID NO 23
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Gly Gly Thr Cys Leu Phe
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Gly Gly Thr Cys Met Phe
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Gly Arg Thr Cys Leu Phe
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Gly Gly Leu Cys Ile Phe
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Gly Gly Leu Cys Lys Phe
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Gly Gly Leu Cys Ala Phe
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Gly Gly Leu Cys Leu Phe
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Gly Gly Ile Cys Leu Phe
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Gly Gly Leu Cys Val Phe
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Gly Gly Thr Cys Val Phe
 1               5

<210> SEQ ID NO 33
<211> LENGTH: 20
<212> TYPE: PRT
<213> ORGANISM: Human T-cell leukaemia virus type 1

<400> SEQUENCE: 33

Ala Gln Asn Arg Arg Gly Leu Asp Leu Leu Phe Trp Glu Gln Gly Gly
 1               5                  10                  15

Leu Cys Lys Ala
            20

<210> SEQ ID NO 34
<211> LENGTH: 20
<212> TYPE: PRT
<213> ORGANISM: Human endogenous retrovirus T

<400> SEQUENCE: 34

```
Leu Gln Asn Cys Arg Cys Leu Asp Leu Leu Phe Leu Ser Gln Gly Gly
1               5                   10                  15

Leu Cys Ala Ala
            20
```

<210> SEQ ID NO 35
<211> LENGTH: 20
<212> TYPE: PRT
<213> ORGANISM: Human endogenous retrovirus FRD

<400> SEQUENCE: 35

```
Leu Gln Asn Arg Arg Gly Leu Asp Met Leu Thr Ala Ala Gln Gly Gly
1               5                   10                  15

Leu Cys Leu Ala
            20
```

<210> SEQ ID NO 36
<211> LENGTH: 20
<212> TYPE: PRT
<213> ORGANISM: Mason-Pfizer monkey virus

<400> SEQUENCE: 36

```
Leu Gln Asn Arg Arg Gly Leu Asp Leu Leu Thr Ala Glu Gln Gly Gly
1               5                   10                  15

Ile Cys Leu Ala
            20
```

<210> SEQ ID NO 37
<211> LENGTH: 20
<212> TYPE: PRT
<213> ORGANISM: Feline leukemia virus

<400> SEQUENCE: 37

```
Leu Gln Asn Arg Arg Gly Leu Asp Ile Leu Phe Leu Gln Glu Gly Gly
1               5                   10                  15

Leu Cys Ala Ala
            20
```

<210> SEQ ID NO 38
<211> LENGTH: 20
<212> TYPE: PRT
<213> ORGANISM: Moloney murine leukaemia virus

<400> SEQUENCE: 38

```
Leu Gln Asn Arg Arg Gly Leu Asp Leu Leu Phe Leu Lys Glu Gly Gly
1               5                   10                  15

Leu Cys Ala Ala
            20
```

<210> SEQ ID NO 39
<211> LENGTH: 20
<212> TYPE: PRT
<213> ORGANISM: Porcine endogenous retrovirus

<400> SEQUENCE: 39

```
Leu Gln Asn Arg Arg Gly Leu Asp Leu Leu Phe Leu Lys Glu Gly Gly
1               5                   10                  15

Leu Cys Val Ala
            20
```

<210> SEQ ID NO 40
<211> LENGTH: 20
<212> TYPE: PRT

-continued

<213> ORGANISM: Human endogenous retrovirus W

<400> SEQUENCE: 40

Leu Gln Asn Arg Arg Ala Leu Asp Leu Leu Thr Ala Glu Arg Gly Gly
1               5                   10                  15

Thr Cys Leu Phe
            20

<210> SEQ ID NO 41
<211> LENGTH: 20
<212> TYPE: PRT
<213> ORGANISM: Human endogenous retrovirus W

<400> SEQUENCE: 41

Leu Gln Asn Trp Arg Ala Leu Asp Leu Leu Thr Ala Lys Arg Gly Gly
1               5                   10                  15

Thr Cys Leu Phe
            20

<210> SEQ ID NO 42
<211> LENGTH: 20
<212> TYPE: PRT
<213> ORGANISM: Human endogenous retrovirus W

<400> SEQUENCE: 42

Leu Gln Asn Trp Arg Ala Leu Asp Leu Leu Ile Ala Lys Arg Gly Gly
1               5                   10                  15

Thr Cys Val Phe
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Gln Asn Arg Arg Gly Leu Asp Leu Leu Thr Ala Glu Arg Gly Gly
1               5                   10                  15

Thr Cys Leu Phe
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Gln Asn Arg Arg Ala Leu Asp Leu Leu Thr Ala Glu Arg Gly Gly
1               5                   10                  15

Ile Cys Leu Phe
            20

<210> SEQ ID NO 45
<211> LENGTH: 20
<212> TYPE: PRT
<213> ORGANISM: Human endogenous retrovirus H1

<400> SEQUENCE: 45

Leu Gln Asn Arg Arg Gly Leu Asp Leu Leu Thr Ala Glu Lys Gly Gly
1               5                   10                  15

Leu Cys Ile Phe
            20

<210> SEQ ID NO 46
<211> LENGTH: 20
<212> TYPE: PRT
<213> ORGANISM: Human endogenous retrovirus Fc(1)

<400> SEQUENCE: 46

Met Gln Asn Arg Arg Ala Leu Asp Leu Leu Thr Ala Asp Lys Gly Gly
1               5                   10                  15

Thr Cys Met Phe
            20

<210> SEQ ID NO 47
<211> LENGTH: 20
<212> TYPE: PRT
<213> ORGANISM: Human endogenous retrovirus Fc(2)

<400> SEQUENCE: 47

Ala Gln Asn Arg Gln Ala Leu Asp Leu Leu Met Ala Glu Lys Gly Arg
1               5                   10                  15

Thr Cys Leu Phe
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Gln Asn Arg Arg Gly Leu Asp Leu Leu Phe Trp Glu Arg Gly Gly
1               5                   10                  15

Leu Cys Lys Phe
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Gln Asn Cys Arg Cys Leu Asp Leu Leu Phe Leu Ser Arg Gly Gly
1               5                   10                  15

Leu Cys Ala Phe
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Gln Asn Arg Arg Gly Leu Asp Met Leu Thr Ala Ala Arg Gly Gly

Leu Cys Leu Phe
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Gln Asn Arg Arg Gly Leu Asp Leu Leu Thr Ala Glu Arg Gly Gly
  1               5                  10                  15

Ile Cys Leu Phe
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Asn Arg Arg Gly Leu Asp Ile Leu Phe Leu Gln Arg Gly Gly
  1               5                  10                  15

Leu Cys Ala Phe
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Gln Asn Arg Arg Gly Leu Asp Leu Leu Phe Leu Lys Arg Gly Gly
  1               5                  10                  15

Leu Cys Ala Phe
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Gln Asn Arg Arg Gly Leu Asp Leu Leu Phe Leu Lys Arg Gly Gly
  1               5                  10                  15

Leu Cys Val Phe
            20

<210> SEQ ID NO 55
<211> LENGTH: 58
<212> TYPE: DNA
<213> ORGANISM: Artificial Sequence
<220> FEATURE:
<223> OTHER INFORMATION: Description of Artificial Sequence:

-continued oligonucleotide

<400> SEQUENCE: 55
atacatctcg agaccggtcc aactagaacc atgaacttca attatcattt catctgga        58

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
atacatacgc gtctatgtta aggtcaaata tgagccacc                             39

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
tagtccttca aatcgccgcg gtttagactt gctaa                                 35

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58 acaaggggt acctgtttat ttttagggga aga                                    33

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
ccgctgaaag aggggcata tgtttatttt taggga                                 37

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 60
aaccgctgaa agaggggta cctgtttagc tttagggaa ga                           42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 61
aaccgctgaa caaggggta cctgtttagc tttaggggaa ga                          42

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cttcggcgtc tctcgagaga cgccgaag                                        28

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
caaaacagaa gaggattaga tctacttaca gc                                   32

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tacttacagc agagagagga ggtatctgct tag                                  33

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gggaggtatc tgcttatttt tacaggaaaa atgtt                                35

<210> SEQ ID NO 66
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acttacagca gagagaggag gtatctgctt atttttacag gaaaaatg                  48

<210> SEQ ID NO 67
<211> LENGTH: 20
<212> TYPE: PRT
<213> ORGANISM: Ebola virus

<400> SEQUENCE: 67

Ile Leu Asn Arg Lys Ala Ile Asp Phe Leu Leu Gln Arg Trp Gly Gly
 1               5                  10                  15
```

<210> SEQ ID NO 68
<211> LENGTH: 20
<212> TYPE: PRT
<213> ORGANISM: Marburg virus

<400> SEQUENCE: 68

```
Leu Ile Asn Arg His Ala Ile Asp Phe Leu Leu Thr Arg Trp Gly Gly
 1               5                  10                  15

Thr Cys Lys Val
            20
```

<210> SEQ ID NO 69
<211> LENGTH: 1998
<212> TYPE: DNA
<213> ORGANISM: Moloney murine leukaemia virus
<220> FEATURE:
<221> NAME/KEY: CDS
<222> LOCATION: (1)..(1998)
<223> OTHER INFORMATION: coding sequence of envelope protein

<400> SEQUENCE: 69

```
atg gcg cgt tca acg ctc tca aaa ccc ctt aaa aat aag gtt aac ccg      48
Met Ala Arg Ser Thr Leu Ser Lys Pro Leu Lys Asn Lys Val Asn Pro
 1               5                  10                  15 cga ggc ccc cta atc ccc tta att ctt ctg atg ctc aga ggg gtc agt      96
Arg Gly Pro Leu Ile Pro Leu Ile Leu Leu Met Leu Arg Gly Val Ser
                20                  25                  30 act gct tcg ccc ggc tcc agt cct cat caa gtc tat aat atc acc tgg     144
Thr Ala Ser Pro Gly Ser Ser Pro His Gln Val Tyr Asn Ile Thr Trp
             35                  40                  45 gag gta acc aat gga gat cgg gag acg gta tgg gca act tct ggc aac     192
Glu Val Thr Asn Gly Asp Arg Glu Thr Val Trp Ala Thr Ser Gly Asn
         50                  55                  60 cac cct ctg tgg acc tgg tgg cct gac ctt acc cca gat tta tgt atg     240
His Pro Leu Trp Thr Trp Trp Pro Asp Leu Thr Pro Asp Leu Cys Met
 65                  70                  75                  80 tta gcc cac cat gga cca tct tat tgg ggg cta gaa tat caa tcc cct     288
Leu Ala His His Gly Pro Ser Tyr Trp Gly Leu Glu Tyr Gln Ser Pro
                 85                  90                  95 ttt tct tct ccc ccg ggg ccc cct tgt tgc tca ggg ggc agc agc cca     336
Phe Ser Ser Pro Pro Gly Pro Pro Cys Cys Ser Gly Gly Ser Ser Pro
                100                 105                 110 ggc tgt tcc aga gac tgc gaa gaa cct tta acc tcc ctc acc cct cgg     384
Gly Cys Ser Arg Asp Cys Glu Glu Pro Leu Thr Ser Leu Thr Pro Arg
            115                 120                 125 tgc aac act gcc tgg aac aga ctc aag cta gac cag aca act cat aaa     432
Cys Asn Thr Ala Trp Asn Arg Leu Lys Leu Asp Gln Thr Thr His Lys
        130                 135                 140 tca aat gag gga ttt tat gtt tgc ccc ggg ccc cac cgc ccc gaa        480
Ser Asn Glu Gly Phe Tyr Val Cys Pro Gly Pro His Arg Pro Arg Glu
145                 150                 155                 160 tcc aag tca tgt ggg ggt cca gac tcc ttc tac tgt gcc tat tgg ggc     528
Ser Lys Ser Cys Gly Gly Pro Asp Ser Phe Tyr Cys Ala Tyr Trp Gly
                165                 170                 175 tgt gag aca acc ggt aga gct tac tgg aag ccc tca tca tgg gat        576
Cys Glu Thr Thr Gly Arg Ala Tyr Trp Lys Pro Ser Ser Ser Trp Asp
                180                 185                 190 ttc atc aca gta aac aac aat ctc acc tct gac cag gct gtc cag gta     624
Phe Ile Thr Val Asn Asn Asn Leu Thr Ser Asp Gln Ala Val Gln Val
            195                 200                 205
```

| | |
|---|---|
| tgc aaa gat aat aag tgg tgc aac ccc tta gtt att cgg ttt aca gac<br>Cys Lys Asp Asn Lys Trp Cys Asn Pro Leu Val Ile Arg Phe Thr Asp<br>210                       215                     220 | 672 |
| gcc ggg aga cgg gtt act tcc tgg acc aca gga cat tac tgg ggc tta<br>Ala Gly Arg Arg Val Thr Ser Trp Thr Thr Gly His Tyr Trp Gly Leu<br>225                       230                     235                     240 | 720 |
| cgt ttg tat gtc tcc gga caa gat cca ggg ctt aca ttt ggg atc cga<br>Arg Leu Tyr Val Ser Gly Gln Asp Pro Gly Leu Thr Phe Gly Ile Arg<br>                       245                     250                     255 | 768 |
| ctc aga tac caa aat cta gga ccc cgc gtc cca ata ggg cca aac ccc<br>Leu Arg Tyr Gln Asn Leu Gly Pro Arg Val Pro Ile Gly Pro Asn Pro<br>             260                     265                     270 | 816 |
| gtt ctg gca gac caa cag cca ctc tcc aag ccc aaa cct gtt aag tcg<br>Val Leu Ala Asp Gln Gln Pro Leu Ser Lys Pro Lys Pro Val Lys Ser<br>             275                     280                     285 | 864 |
| cct tca gtc acc aaa cca ccc agt ggg act cct ctc tcc cct acc caa<br>Pro Ser Val Thr Lys Pro Pro Ser Gly Thr Pro Leu Ser Pro Thr Gln<br>290                       295                     300 | 912 |
| ctt cca ccg gcg gga acg gaa aat agg ctg cta aac tta gta gac gga<br>Leu Pro Pro Ala Gly Thr Glu Asn Arg Leu Leu Asn Leu Val Asp Gly<br>305                       310                     315                     320 | 960 |
| gcc tac caa gcc ctc aac ctc acc agt cct gac aaa acc caa gag tgc<br>Ala Tyr Gln Ala Leu Asn Leu Thr Ser Pro Asp Lys Thr Gln Glu Cys<br>             325                     330                     335 | 1008 |
| tgg ttg tgt cta gta gcg gga ccc ccc tac tac gaa ggg gtt gcc gtc<br>Trp Leu Cys Leu Val Ala Gly Pro Pro Tyr Tyr Glu Gly Val Ala Val<br>             340                     345                     350 | 1056 |
| ctg ggt acc tac tcc aac cat acc tct gct cca gcc aac tgc tcc gtg<br>Leu Gly Thr Tyr Ser Asn His Thr Ser Ala Pro Ala Asn Cys Ser Val<br>             355                     360                     365 | 1104 |
| gcc tcc caa cac aag ttg acc ctg tcc gaa gtg acc gga cag gga ctc<br>Ala Ser Gln His Lys Leu Thr Leu Ser Glu Val Thr Gly Gln Gly Leu<br>             370                     375                     380 | 1152 |
| tgc ata gga gca gtt ccc aaa aca cat cag gcc cta tgt aat acc acc<br>Cys Ile Gly Ala Val Pro Lys Thr His Gln Ala Leu Cys Asn Thr Thr<br>385                       390                     395                     400 | 1200 |
| cag aca agc agt cga ggg tcc tat tat cta gtt gcc cct aca ggt acc<br>Gln Thr Ser Ser Arg Gly Ser Tyr Tyr Leu Val Ala Pro Thr Gly Thr<br>                       405                     410                     415 | 1248 |
| atg tgg gct tgt agt acc ggg ctt act cca tgc atc tcc acc acc ata<br>Met Trp Ala Cys Ser Thr Gly Leu Thr Pro Cys Ile Ser Thr Thr Ile<br>             420                     425                     430 | 1296 |
| ctg aac ctt acc act gat tat tgt gtt ctt gtc gaa ctc tgg cca aga<br>Leu Asn Leu Thr Thr Asp Tyr Cys Val Leu Val Glu Leu Trp Pro Arg<br>             435                     440                     445 | 1344 |
| gtc acc tat cat tcc ccc agc tat gtt tac ggc ctg ttt gag aga tcc<br>Val Thr Tyr His Ser Pro Ser Tyr Val Tyr Gly Leu Phe Glu Arg Ser<br>450                       455                     460 | 1392 |
| aac cga cac aaa aga gaa ccg gtg tcg tta acc ctg gcc cta tta ttg<br>Asn Arg His Lys Arg Glu Pro Val Ser Leu Thr Leu Ala Leu Leu Leu<br>465                       470                     475                     480 | 1440 |
| ggt gga cta acc atg ggg gga att gcc gct gga ata gga aca ggg act<br>Gly Gly Leu Thr Met Gly Gly Ile Ala Ala Gly Ile Gly Thr Gly Thr<br>                       485                     490                     495 | 1488 |
| act gct cta atg gcc act cag caa ttc cag cag ctc caa gcc gca gta<br>Thr Ala Leu Met Ala Thr Gln Gln Phe Gln Gln Leu Gln Ala Ala Val<br>             500                     505                     510 | 1536 |
| cag gat gat ctc agg gag gtt gaa aaa tca atc tct aac cta gaa aag<br>Gln Asp Asp Leu Arg Glu Val Glu Lys Ser Ile Ser Asn Leu Glu Lys<br>515                       520                     525 | 1584 |

-continued

```
tct ctc act tcc ctg tct gaa gtt gtc cta cag aat cga agg ggc cta      1632
Ser Leu Thr Ser Leu Ser Glu Val Val Leu Gln Asn Arg Arg Gly Leu
        530                 535                 540 gac ttg tta ttt cta aaa gaa gga ggg ctg tgt gct gct cta aaa gaa      1680
Asp Leu Leu Phe Leu Lys Glu Gly Gly Leu Cys Ala Ala Leu Lys Glu
545                 550                 555                 560 gaa tgt tgc ttc tat gcg gac cac aca gga cta gtg aga gac agc atg      1728
Glu Cys Cys Phe Tyr Ala Asp His Thr Gly Leu Val Arg Asp Ser Met
                565                 570                 575 gcc aaa ttg aga gag agg ctt aat cag aga cag aaa ctg ttt gag tca      1776
Ala Lys Leu Arg Glu Arg Leu Asn Gln Arg Gln Lys Leu Phe Glu Ser
            580                 585                 590 act caa gga tgg ttt gag gga ctg ttt aac aga tcc cct tgg ttt acc      1824
Thr Gln Gly Trp Phe Glu Gly Leu Phe Asn Arg Ser Pro Trp Phe Thr
        595                 600                 605 acc ttg ata tct acc att atg gga ccc ctc att gta ctc cta atg att      1872
Thr Leu Ile Ser Thr Ile Met Gly Pro Leu Ile Val Leu Leu Met Ile
610                 615                 620 ttg ctc ttc gga ccc tgc att ctt aat cga tta gtc caa ttt gtt aaa      1920
Leu Leu Phe Gly Pro Cys Ile Leu Asn Arg Leu Val Gln Phe Val Lys
625                 630                 635                 640 gac agg ata tca gtg gtc cag gct cta gtt ttg act caa caa tat cac      1968
Asp Arg Ile Ser Val Val Gln Ala Leu Val Leu Thr Gln Gln Tyr His
                645                 650                 655 cag ctg aag cct ata gag tac gag cca tag                              1998
Gln Leu Lys Pro Ile Glu Tyr Glu Pro
            660                 665

<210> SEQ ID NO 70
<211> LENGTH: 665
<212> TYPE: PRT
<213> ORGANISM: Moloney murine leukaemia virus

<400> SEQUENCE: 70

Met Ala Arg Ser Thr Leu Ser Lys Pro Leu Lys Asn Lys Val Asn Pro
 1               5                  10                  15

Arg Gly Pro Leu Ile Pro Leu Ile Leu Leu Met Leu Arg Gly Val Ser
            20                  25                  30

Thr Ala Ser Pro Gly Ser Ser Pro His Gln Val Tyr Asn Ile Thr Trp
        35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190
```

```
Phe Ile Thr Val Asn Asn Asn Leu Thr Ser Asp Gln Ala Val Gln Val
            195                 200                 205
Cys Lys Asp Asn Lys Trp Cys Asn Pro Leu Val Ile Arg Phe Thr Asp
            210                 215                 220
Ala Gly Arg Arg Val Thr Ser Trp Thr Thr Gly His Tyr Trp Gly Leu
225                 230                 235                 240
Arg Leu Tyr Val Ser Gly Gln Asp Pro Gly Leu Thr Phe Gly Ile Arg
            245                 250                 255
Leu Arg Tyr Gln Asn Leu Gly Pro Arg Val Pro Ile Gly Pro Asn Pro
            260                 265                 270
Val Leu Ala Asp Gln Gln Pro Leu Ser Lys Pro Lys Pro Val Lys Ser
            275                 280                 285
Pro Ser Val Thr Lys Pro Ser Gly Thr Pro Leu Ser Pro Thr Gln
            290                 295                 300
Leu Pro Pro Ala Gly Thr Glu Asn Arg Leu Leu Asn Leu Val Asp Gly
305                 310                 315                 320
Ala Tyr Gln Ala Leu Asn Leu Thr Ser Pro Asp Lys Thr Gln Glu Cys
            325                 330                 335
Trp Leu Cys Leu Val Ala Gly Pro Pro Tyr Tyr Glu Gly Val Ala Val
            340                 345                 350
Leu Gly Thr Tyr Ser Asn His Thr Ser Ala Pro Ala Asn Cys Ser Val
            355                 360                 365
Ala Ser Gln His Lys Leu Thr Leu Ser Glu Val Thr Gly Gln Gly Leu
            370                 375                 380
Cys Ile Gly Ala Val Pro Lys Thr His Gln Ala Leu Cys Asn Thr Thr
385                 390                 395                 400
Gln Thr Ser Ser Arg Gly Ser Tyr Tyr Leu Val Ala Pro Thr Gly Thr
            405                 410                 415
Met Trp Ala Cys Ser Thr Gly Leu Thr Pro Cys Ile Ser Thr Thr Ile
            420                 425                 430
Leu Asn Leu Thr Thr Asp Tyr Cys Val Leu Val Glu Leu Trp Pro Arg
            435                 440                 445
Val Thr Tyr His Ser Pro Ser Tyr Val Tyr Gly Leu Phe Glu Arg Ser
            450                 455                 460
Asn Arg His Lys Arg Glu Pro Val Ser Leu Thr Leu Ala Leu Leu Leu
465                 470                 475                 480
Gly Gly Leu Thr Met Gly Gly Ile Ala Ala Gly Ile Gly Thr Gly Thr
            485                 490                 495
Thr Ala Leu Met Ala Thr Gln Gln Phe Gln Gln Leu Gln Ala Ala Val
            500                 505                 510
Gln Asp Asp Leu Arg Glu Val Glu Lys Ser Ile Ser Asn Leu Glu Lys
            515                 520                 525
Ser Leu Thr Ser Leu Ser Glu Val Val Leu Gln Asn Arg Arg Gly Leu
            530                 535                 540
Asp Leu Leu Phe Leu Lys Glu Gly Gly Leu Cys Ala Ala Leu Lys Glu
545                 550                 555                 560
Glu Cys Cys Phe Tyr Ala Asp His Thr Gly Leu Val Arg Asp Ser Met
            565                 570                 575
Ala Lys Leu Arg Glu Arg Leu Asn Gln Arg Gln Lys Leu Phe Glu Ser
            580                 585                 590
Thr Gln Gly Trp Phe Glu Gly Leu Phe Asn Arg Ser Pro Trp Phe Thr
            595                 600                 605
Thr Leu Ile Ser Thr Ile Met Gly Pro Leu Ile Val Leu Leu Met Ile
```

```
                    610                 615                 620
Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                    645                 650                 655

Gln Leu Lys Pro Ile Glu Tyr Glu Pro
                660                 665

<210> SEQ ID NO 71
<211> LENGTH: 1761
<212> TYPE: DNA
<213> ORGANISM: Mason-Pfizer monkey virus
<220> FEATURE:
<221> NAME/KEY: CDS
<222> LOCATION: (1)..(1761)
<223> OTHER INFORMATION: coding sequence of envelope protein

<400> SEQUENCE: 71 atg aac ttc aat tat cat ttc atc tgg agc tta gtg ata cta tct caa    48
Met Asn Phe Asn Tyr His Phe Ile Trp Ser Leu Val Ile Leu Ser Gln
1               5                   10                  15 ata tct caa gtt caa gcc ggt ttt gga gat ccg cgt gaa gcc ctg gca    96
Ile Ser Gln Val Gln Ala Gly Phe Gly Asp Pro Arg Glu Ala Leu Ala
            20                  25                  30 gaa ata caa ca

```
Thr Leu Asp Leu Leu Ala Thr Val His Ser Leu Leu Asn Ala Ser Gln
225                 230                 235                 240 ccc agt tta gcc gaa gat tgc tgg ctg tgc tta cag tca gga gat ccc      768
Pro Ser Leu Ala Glu Asp Cys Trp Leu Cys Leu Gln Ser Gly Asp Pro
                245                 250                 255 gtt cct ctt gcc ctg ccc tat aat gat aca ctc tgc tct aac ttt gcc      816
Val Pro Leu Ala Leu Pro Tyr Asn Asp Thr Leu Cys Ser Asn Phe Ala
            260                 265                 270 tgt tta tct aat cac tcc tgc cct tta acc ccc cct ttt tta gta cag      864
Cys Leu Ser Asn His Ser Cys Pro Leu Thr Pro Pro Phe Leu Val Gln
        275                 280                 285 ccc ttt aac ttc act gat tcc aat tgc ctt tac gct cat tat caa aac      912
Pro Phe Asn Phe Thr Asp Ser Asn Cys Leu Tyr Ala His Tyr Gln Asn
    290                 295                 300 aac tca ttt gac ata gat gta ggt cta gct agc ttt act aat tgc tct      960
Asn Ser Phe Asp Ile Asp Val Gly Leu Ala Ser Phe Thr Asn Cys Ser
305                 310                 315                 320 agc tat tat aac gtt tct aca gcc tcc aaa ccc tct aat tcc cta tgc     1008
Ser Tyr Tyr Asn Val Ser Thr Ala Ser Lys Pro Ser Asn Ser Leu Cys
                325                 330                 335 gcc cca aac agc tcg gtt ttt gta tgc ggt aac aat aag gca tac act     1056
Ala Pro Asn Ser Ser Val Phe Val Cys Gly Asn Asn Lys Ala Tyr Thr
            340                 345                 350 tat cta ccc aca aat tgg acg gga agt tgt gta ctt gct act ctt ttg     1104
Tyr Leu Pro Thr Asn Trp Thr Gly Ser Cys Val Leu Ala Thr Leu Leu
        355                 360                 365 ccc gat ata gac atc att cca ggt agt gag cct gtc ccc att cca gct     1152
Pro Asp Ile Asp Ile Ile Pro Gly Ser Glu Pro Val Pro Ile Pro Ala
    370                 375                 380 att gat cat ttt tta ggc aaa gcc aaa aga gca atc caa ctt atc ccc     1200
Ile Asp His Phe Leu Gly Lys Ala Lys Arg Ala Ile Gln Leu Ile Pro
385                 390                 395                 400 ctg ttc gta ggg tta ggt ata act act gca gta tct act ggg gct gct     1248
Leu Phe Val Gly Leu Gly Ile Thr Thr Ala Val Ser Thr Gly Ala Ala
                405                 410                 415 ggt cta ggg gtt tcc atc act caa tat aca aaa tta tct cat caa cta     1296
Gly Leu Gly Val Ser Ile Thr Gln Tyr Thr Lys Leu Ser His Gln Leu
            420                 425                 430 ata tca gat gtt caa gct att tct agc act ata caa gat ctc caa gat     1344
Ile Ser Asp Val Gln Ala Ile Ser Ser Thr Ile Gln Asp Leu Gln Asp
        435                 440                 445 cag gta gac tct cta gca gaa gta gta ctg caa aac aga aga gga tta     1392
Gln Val Asp Ser Leu Ala Glu Val Val Leu Gln Asn Arg Arg Gly Leu
    450                 455                 460 gat cta ctt aca gca gag cag gga ggt atc tgc tta gcc tta cag gaa     1440
Asp Leu Leu Thr Ala Glu Gln Gly Gly Ile Cys Leu Ala Leu Gln Glu
465                 470                 475                 480 aaa tgt tgt ttc tac gcc aat aaa tct gga atc gtc aga gac aag att     1488
Lys Cys Cys Phe Tyr Ala Asn Lys Ser Gly Ile Val Arg Asp Lys Ile
                485                 490                 495 aaa aac cta caa gac gac tta gaa aga cgc cga aga caa ctg atc gac     1536
Lys Asn Leu Gln Asp Asp Leu Glu Arg Arg Arg Arg Gln Leu Ile Asp
            500                 505                 510 aac cca ttt tgg acc agt ttt cat gga ttc ctc cct tat gtt atg ccc     1584
Asn Pro Phe Trp Thr Ser Phe His Gly Phe Leu Pro Tyr Val Met Pro
        515                 520                 525 cta tta ggc cct ttg ctt tgc tta ttg ctt gtg tta tct ttc ggt cca     1632
Leu Leu Gly Pro Leu Leu Cys Leu Leu Leu Val Leu Ser Phe Gly Pro
    530                 535                 540 att att ttc aac aag ctt atg acc ttt att aaa cat caa att gag agc     1680
```

```
Ile Ile Phe Asn Lys Leu Met Thr Phe Ile Lys His Gln Ile Glu Ser
545                 550                 555                 560 atc cag gcc aaa cct ata caa gtc cat tat cat cgc ctt gaa caa gaa      1728
Ile Gln Ala Lys Pro Ile Gln Val His Tyr His Arg Leu Glu Gln Glu
                565                 570                 575 gac agt ggt ggc tca tat ttg acc tta aca tag                          1761
Asp Ser Gly Gly Ser Tyr Leu Thr Leu Thr
                580                 585

<210> SEQ ID NO 72
<211> LENGTH: 586
<212> TYPE: PRT
<213> ORGANISM: Mason-Pfizer monkey virus

<400> SEQUENCE: 72

Met Asn Phe Asn Tyr His Phe Ile Trp Ser Leu Val Ile Leu Ser Gln
1               5                   10                  15

Ile Ser Gln Val Gln Ala Gly Phe Gly Asp Pro Arg Glu Ala Leu Ala
                20                  25                  30

Glu Ile Gln Gln Lys His Gly Lys Pro Cys Asp Cys Ala Gly Gly Tyr
            35                  40                  45

Val Ser Ser Pro Pro Ile Asn Ser Leu Thr Thr Val Ser Cys Ser Thr
        50                  55                  60

His Thr Ala Tyr Ser Val Thr Asn Ser Leu Lys Trp Gln Cys Val Ser
65                  70                  75                  80

Thr Pro Thr Thr Pro Ser Asn Thr His Ile Gly Ser Cys Pro Gly Glu
                85                  90                  95

Cys Asn Thr Ile Ser Tyr Asp Ser Val His Ala Ser Cys Tyr Asn His
            100                 105                 110

Tyr Gln Gln Cys Asn Ile Gly Asn Lys Thr Tyr Leu Thr Ala Thr Ile
        115                 120                 125

Thr Gly Asp Arg Thr Pro Ala Ile Gly Asp Gly Asn Val Pro Thr Val
    130                 135                 140

Leu Gly Thr Ser His Asn Leu Ile Thr Ala Gly Cys Pro Asn Gly Lys
145                 150                 155                 160

Lys Gly Gln Val Val Cys Trp Asn Ser Arg Pro Ser Val His Ile Ser
                165                 170                 175

Asp Gly Gly Gly Pro Gln Asp Lys Ala Arg Asp Ile Ile Val Asn Lys
            180                 185                 190

Lys Phe Glu Glu Leu His Arg Ser Leu Phe Pro Glu Leu Ser Tyr His
        195                 200                 205

Pro Leu Ala Leu Pro Glu Ala Arg Gly Lys Glu Lys Ile Asp Ala His
    210                 215                 220

Thr Leu Asp Leu Leu Ala Thr Val His Ser Leu Leu Asn Ala Ser Gln
225                 230                 235                 240

Pro Ser Leu Ala Glu Asp Cys Trp Leu Cys Leu Gln Ser Gly Asp Pro
                245                 250                 255

Val Pro Leu Ala Leu Pro Tyr Asn Asp Thr Leu Cys Ser Asn Phe Ala
            260                 265                 270

Cys Leu Ser Asn His Ser Cys Pro Leu Thr Pro Pro Phe Leu Val Gln
        275                 280                 285

Pro Phe Asn Phe Thr Asp Ser Asn Cys Leu Tyr Ala His Tyr Gln Asn
    290                 295                 300

Asn Ser Phe Asp Ile Asp Val Gly Leu Ala Ser Phe Thr Asn Cys Ser
305                 310                 315                 320

Ser Tyr Tyr Asn Val Ser Thr Ala Ser Lys Pro Ser Asn Ser Leu Cys
```

```
                    325                 330                 335
Ala Pro Asn Ser Ser Val Phe Val Cys Gly Asn Asn Lys Ala Tyr Thr
                340                 345                 350

Tyr Leu Pro Thr Asn Trp Thr Gly Ser Cys Val Leu Ala Thr Leu Leu
            355                 360                 365

Pro Asp Ile Asp Ile Ile Pro Gly Ser Glu Pro Val Pro Ile Pro Ala
        370                 375                 380

Ile Asp His Phe Leu Gly Lys Ala Lys Arg Ala Ile Gln Leu Ile Pro
385                 390                 395                 400

Leu Phe Val Gly Leu Gly Ile Thr Thr Ala Val Ser Thr Gly Ala Ala
                405                 410                 415

Gly Leu Gly Val Ser Ile Thr Gln Tyr Thr Lys Leu Ser His Gln Leu
            420                 425                 430

Ile Ser Asp Val Gln Ala Ile Ser Ser Thr Ile Gln Asp Leu Gln Asp
        435                 440                 445

Gln Val Asp Ser Leu Ala Glu Val Val Leu Gln Asn Arg Arg Gly Leu
    450                 455                 460

Asp Leu Leu Thr Ala Glu Gln Gly Gly Ile Cys Leu Ala Leu Gln Glu
465                 470                 475                 480

Lys Cys Cys Phe Tyr Ala Asn Lys Ser Gly Ile Val Arg Asp Lys Ile
                485                 490                 495

Lys Asn Leu Gln Asp Asp Leu Glu Arg Arg Arg Gln Leu Ile Asp
            500                 505                 510

Asn Pro Phe Trp Thr Ser Phe His Gly Phe Leu Pro Tyr Val Met Pro
        515                 520                 525

Leu Leu Gly Pro Leu Leu Cys Leu Leu Val Leu Ser Phe Gly Pro
    530                 535                 540

Ile Ile Phe Asn Lys Leu Met Thr Phe Ile Lys His Gln Ile Glu Ser
545                 550                 555                 560

Ile Gln Ala Lys Pro Ile Gln Val His Tyr His Arg Leu Glu Gln Glu
                565                 570                 575

Asp Ser Gly Gly Ser Tyr Leu Thr Leu Thr
            580                 585

<210> SEQ ID NO 73
<211> LENGTH: 1617
<212> TYPE: DNA
<213> ORGANISM: Human endogenous retrovirus W
<220> FEATURE:
<221> NAME/KEY: CDS
<222> LOCATION: (1)..(1617)
<223> OTHER INFORMATION: coding sequence of envelope protein

<400> SEQUENCE: 73 atg gcc ctc cct tat cat att ttt ctc ttt act gtt ctt tta ccc tct        48
Met Ala Leu Pro Tyr His Ile Phe Leu Phe Thr Val Leu Leu Pro Ser
1               5                   10                  15 ttc act ctc act gca ccc cct cca tgc cgc tgt atg acc agt agc tcc        96
Phe Thr Leu Thr Ala Pro Pro Pro Cys Arg Cys Met Thr Ser Ser Ser
                20                  25                  30 cct tac caa gag ttt cta tgg aga atg cag cgt ccc gga aat att gat       144
Pro Tyr Gln Glu Phe Leu Trp Arg Met Gln Arg Pro Gly Asn Ile Asp
            35                  40                  45 gcc cca tcg tat agg agt ctt tct aag gga acc ccc acc ttc act gcc       192
Ala Pro Ser Tyr Arg Ser Leu Ser Lys Gly Thr Pro Thr Phe Thr Ala
        50                  55                  60 cac acc cat atg ccc cgc aac tgc tat cac tct gcc act ctt tgc atg       240
His Thr His Met Pro Arg Asn Cys Tyr His Ser Ala Thr Leu Cys Met
    65                  70                  75                  80
```

|  |  |  |  |  |  |  |  |  |  |  |  |  |  |  |  |
|---|---|---|---|---|---|---|---|---|---|---|---|---|---|---|---|
| | 65 | | | | | 70 | | | | | 75 | | | | 80 |

```
cat gca aat act cat tat tgg aca gga aaa atg att aat cct agt tgt      288
His Ala Asn Thr His Tyr Trp Thr Gly Lys Met Ile Asn Pro Ser Cys
                    85                  90                  95 cct gga gga ctt gga gtc act gtc tgt tgg act tac ttc acc caa act      336
Pro Gly Gly Leu Gly Val Thr Val Cys Trp Thr Tyr Phe Thr Gln Thr
                100                 105                 110 ggt atg tct gat ggg ggt gga gtt caa gat cag gca aga gaa aaa cat      384
Gly Met Ser Asp Gly Gly Gly Val Gln Asp Gln Ala Arg Glu Lys His
                115                 120                 125 gta aaa gaa gta atc tcc caa ctc acc cgg gta cat ggc acc tct agc      432
Val Lys Glu Val Ile Ser Gln Leu Thr Arg Val His Gly Thr Ser Ser
            130                 135                 140 ccc tac aaa gga cta gat ctc tca aaa cta cat gaa acc ctc cgt acc      480
Pro Tyr Lys Gly Leu Asp Leu Ser Lys Leu His Glu Thr Leu Arg Thr
145                 150                 155                 160 cat act cgc ctg gta agc cta ttt aat acc acc ctc act ggg ctc cat      528
His Thr Arg Leu Val Ser Leu Phe Asn Thr Thr Leu Thr Gly Leu His
                    165                 170                 175 gag gtc tcg gcc caa aac cct act aac tgt tgg ata tgc ctc ccc ctg      576
Glu Val Ser Ala Gln Asn Pro Thr Asn Cys Trp Ile Cys Leu Pro Leu
                180                 185                 190 aac ttc agg cca tat gtt tca atc cct gta cct gaa caa tgg aac aac      624
Asn Phe Arg Pro Tyr Val Ser Ile Pro Val Pro Glu Gln Trp Asn Asn
                195                 200                 205 ttc agc aca gaa ata aac acc act tcc gtt tta gta gga cct ctt gtt      672
Phe Ser Thr Glu Ile Asn Thr Thr Ser Val Leu Val Gly Pro Leu Val
                210                 215                 220 tcc aat ctg gaa ata acc cat acc tca aac ctc acc tgt gta aaa ttt      720
Ser Asn Leu Glu Ile Thr His Thr Ser Asn Leu Thr Cys Val Lys Phe
225                 230                 235                 240 agc aat act aca tac aca acc aac tcc caa tgc atc agg tgg gta act      768
Ser Asn Thr Thr Tyr Thr Thr Asn Ser Gln Cys Ile Arg Trp Val Thr
                    245                 250                 255 cct ccc aca caa ata gtc tgc cta ccc tca gga ata ttt ttt gtc tgt      816
Pro Pro Thr Gln Ile Val Cys Leu Pro Ser Gly Ile Phe Phe Val Cys
                260                 265                 270 ggt acc tca gcc tat cgt tgt ttg aat ggc tct tca gaa tct atg tgc      864
Gly Thr Ser Ala Tyr Arg Cys Leu Asn Gly Ser Ser Glu Ser Met Cys
                275                 280                 285 ttc ctc tca ttc tta gtg ccc cct atg acc atc tac act gaa caa gat      912
Phe Leu Ser Phe Leu Val Pro Pro Met Thr Ile Tyr Thr Glu Gln Asp
                290                 295                 300 tta tac agt tat gtc ata tct aag ccc cgc aac aaa aga gta ccc att      960
Leu Tyr Ser Tyr Val Ile Ser Lys Pro Arg Asn Lys Arg Val Pro Ile
305                 310                 315                 320 ctt cct ttt gtt ata gga gca gga gtg cta ggt gca cta ggt act ggc     1008
Leu Pro Phe Val Ile Gly Ala Gly Val Leu Gly Ala Leu Gly Thr Gly
                    325                 330                 335 att ggc ggt atc aca acc tct act cag ttc tac tac aaa cta tct caa     1056
Ile Gly Gly Ile Thr Thr Ser Thr Gln Phe Tyr Tyr Lys Leu Ser Gln
                340                 345                 350 gaa cta aat ggg gac atg gaa cgg gtc gcc gac tcc ctg gtc acc ttg     1104
Glu Leu Asn Gly Asp Met Glu Arg Val Ala Asp Ser Leu Val Thr Leu
                355                 360                 365 caa gat caa ctt aac tcc cta gca gca gta gtc ctt caa aat cga aga     1152
Gln Asp Gln Leu Asn Ser Leu Ala Ala Val Val Leu Gln Asn Arg Arg
                370                 375                 380 gct tta gac ttg cta acc gct gaa aga ggg gga acc tgt tta ttt tta     1200
Ala Leu Asp Leu Leu Thr Ala Glu Arg Gly Gly Thr Cys Leu Phe Leu
```

```
                385              390              395              400
ggg gaa gaa tgc tgt tat tat gtt aat caa tcc gga atc gtc act gag      1248
Gly Glu Glu Cys Cys Tyr Tyr Val Asn Gln Ser Gly Ile Val Thr Glu
                405              410              415 aaa gtt aaa gaa att cga gat cga ata caa cgt aga gca gag gag ctt      1296
Lys Val Lys Glu Ile Arg Asp Arg Ile Gln Arg Arg Ala Glu Glu Leu
                420              425              430 cga aac act gga ccc tgg ggc ctc ctc agc caa tgg atg ccc tgg att      1344
Arg Asn Thr Gly Pro Trp Gly Leu Leu Ser Gln Trp Met Pro Trp Ile
                435              440              445 ctc ccc ttc tta gga cct cta gca gct ata ata ttg cta ctc ctc ttt      1392
Leu Pro Phe Leu Gly Pro Leu Ala Ala Ile Ile Leu Leu Leu Leu Phe
                450              455              460 gga ccc tgt atc ttt aac ctc ctt gtt aac ttt gtc tct tcc aga atc      1440
Gly Pro Cys Ile Phe Asn Leu Leu Val Asn Phe Val Ser Ser Arg Ile
465              470              475              480 gaa gct gta aaa cta caa atg gag ccc aag atg cag tcc aag act aag      1488
Glu Ala Val Lys Leu Gln Met Glu Pro Lys Met Gln Ser Lys Thr Lys
                485              490              495 atc tac cgc aga ccc ctg gac cgg cct gct agc cca cga tct gat gtt      1536
Ile Tyr Arg Arg Pro Leu Asp Arg Pro Ala Ser Pro Arg Ser Asp Val
                500              505              510 aat gac atc aaa ggc acc cct cct gag gaa atc tca gct gca caa cct      1584
Asn Asp Ile Lys Gly Thr Pro Pro Glu Glu Ile Ser Ala Ala Gln Pro
                515              520              525 cta cta cgc ccc aat tca gca gga agc agt tag                          1617
Leu Leu Arg Pro Asn Ser Ala Gly Ser Ser
                530              535

<210> SEQ ID NO 74
<211> LENGTH: 538
<212> TYPE: PRT
<213> ORGANISM: Human endogenous retrovirus W

<400> SEQUENCE: 74

Met Ala Leu Pro Tyr His Ile Phe Leu Phe Thr Val Leu Leu Pro Ser
 1               5                  10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
```

```
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240
Ser Asn Thr Thr Tyr Thr Thr Asn Ser Gln Cys Ile Arg Trp Val Thr
                245                 250                 255
Pro Pro Thr Gln Ile Val Cys Leu Pro Ser Gly Ile Phe Phe Val Cys
            260                 265                 270
Gly Thr Ser Ala Tyr Arg Cys Leu Asn Gly Ser Ser Glu Ser Met Cys
        275                 280                 285
Phe Leu Ser Phe Leu Val Pro Pro Met Thr Ile Tyr Thr Glu Gln Asp
    290                 295                 300
Leu Tyr Ser Tyr Val Ile Ser Lys Pro Arg Asn Lys Arg Val Pro Ile
305                 310                 315                 320
Leu Pro Phe Val Ile Gly Ala Gly Val Leu Gly Ala Leu Gly Thr Gly
                325                 330                 335
Ile Gly Gly Ile Thr Thr Ser Thr Gln Phe Tyr Tyr Lys Leu Ser Gln
            340                 345                 350
Glu Leu Asn Gly Asp Met Glu Arg Val Ala Asp Ser Leu Val Thr Leu
        355                 360                 365
Gln Asp Gln Leu Asn Ser Leu Ala Ala Val Val Leu Gln Asn Arg Arg
    370                 375                 380
Ala Leu Asp Leu Leu Thr Ala Glu Arg Gly Gly Thr Cys Leu Phe Leu
385                 390                 395                 400
Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430
Arg Asn Thr Gly Pro Trp Gly Leu Leu Ser Gln Trp Met Pro Trp Ile
        435                 440                 445
Leu Pro Phe Leu Gly Pro Leu Ala Ala Ile Ile Leu Leu Leu Leu Phe
    450                 455                 460
Gly Pro Cys Ile Phe Asn Leu Leu Val Asn Phe Val Ser Ser Arg Ile
465                 470                 475                 480
Glu Ala Val Lys Leu Gln Met Glu Pro Lys Met Gln Ser Lys Thr Lys
                485                 490                 495
Ile Tyr Arg Arg Pro Leu Asp Arg Pro Ala Ser Pro Arg Ser Asp Val
            500                 505                 510
Asn Asp Ile Lys Gly Thr Pro Pro Glu Glu Ile Ser Ala Ala Gln Pro
        515                 520                 525
Leu Leu Arg Pro Asn Ser Ala Gly Ser Ser
    530                 535

<210> SEQ ID NO 75
<211> LENGTH: 20
<212> TYPE: PRT
<213> ORGANISM: Fowlpox virus

<400> SEQUENCE: 75

Leu Gln Asn Arg Arg Gly Leu Asp Leu Leu Thr Ala Glu Gln Gly Gly
  1               5                  10                  15

Ile Cys Leu Ala

-continued

```
                        20

<210> SEQ ID NO 76
<211> LENGTH: 20
<212> TYPE: PRT
<213> ORGANISM: Simian sarcoma-associated virus

<400> SEQUENCE: 76

Leu Gln Asn Arg Arg Gly Leu Asp Leu Leu Phe Leu Lys Glu Gly Gly
 1               5                  10                  15

Leu Cys Ala Ala
            20

<210> SEQ ID NO 77
<211> LENGTH: 20
<212> TYPE: PRT
<213> ORGANISM: Friend virus

<400> SEQUENCE: 77

Leu Gln Asn Arg Arg Gly Leu Asp Leu Leu Phe Leu Lys Glu Gly Gly
 1               5                  10                  15

Leu Cys Ala Ala
            20

<210> SEQ ID NO 78
<211> LENGTH: 20
<212> TYPE: PRT
<213> ORGANISM: Python endogenous retrovirus

<400> SEQUENCE: 78

Leu Gln Asn Arg Arg Gly Leu Asp Leu Leu Phe Leu Lys Glu Gly Gly
 1               5                  10                  15

Leu Cys Val Ala
            20

<210> SEQ ID NO 79
<211> LENGTH: 20
<212> TYPE: PRT
<213> ORGANISM: Gibbon leukemia virus X

<400> SEQUENCE: 79

Leu Gln Asn Arg Arg Gly Leu Asp Leu Leu Phe Leu Lys Glu Gly Gly
 1               5                  10                  15

Leu Cys Ala Ala
            20

<210> SEQ ID NO 80
<211> LENGTH: 20
<212> TYPE: PRT
<213> ORGANISM: Simian T-cell leukaemia virus type 1

<400> SEQUENCE: 80

Ala Gln Asn Arg Arg Gly Leu Asp Leu Leu Phe Trp Glu Gln Gly Gly
 1               5                  10                  15

Leu Cys Lys Ala
            20

<210> SEQ ID NO 81
<211> LENGTH: 1615
<212> TYPE: DNA
<213> ORGANISM: Human endogenous retrovirus FRD

<400> SEQUENCE: 81
```

```
atgggcctgc tcctgctggt tctcattctc acgccttcac tagcagccta ccgccatcct    60
gatttcccgt tattggaaaa agctcagcaa ctgctccaaa gtacaggatc cccttactcc   120
accaattgct ggttatgtac tagctcttcc actgaaacac cagggacagc ttatccagcc   180
tcgcccagag aatggacaag catagaggcg aattacata tttcctatcg atgggaccct   240
aatctgaaag gactgatgag gcctgcaaat agtcttcttt caacagtaaa gcaagatttc   300
cctgatatcc gccagaaacc tcccattttc ggacccatct ttactaatat caacctaatg   360
ggaatagccc ctatttgtgt tatggccaaa aggaaaaatg aacaaatgt aggcactctt   420
ccaagtacag tctgtaatgt tactttcact gtagattcta accaacagac ttaccaaaca   480
tacacccaca accaattccg ccatcaacca agattcccca aacctccaaa tattactttt   540
cctcagggaa ctttgctaga taaatccagc cggttttgcc agggacgccc aagctcatgc   600
agtactcgaa acttctggtt ccggcctgct gattataacc aatgtctgca aatttccaac   660
ctcagctcta cagcggaatg ggttctattg gaccaaactc gaaattctct tttttgggaa   720
aataaaacca agggagctaa ccagagccaa acaccctgcg tccaagtctt agcaggcatg   780
actatagcca ccagctacct gggcatatca gcagtctcag aattttttgg aacctccctc   840
accccttat ttcatttcca tatctctaca tgccttaaaa ctcaaggagc cttttatatt   900
tgtggccagt cgattcacca atgcctcccc agtaactgga ctggaacttg taccataggc   960
tatgtaaccc cagacatctt catagcccct ggcaatctct ctcttccaat accaatctat  1020
gggaattccc cgttgcccag ggtgaggagg gcaatccatt tcattcccct ctcgcgggga  1080
ctcggcattc tagctggtac gggaaccgga attgctggaa tcacaaaagc ttccctcacc  1140
tatagccagc tctcaaagga aatagccaac aacattgaca ccatggctaa gccttaacg  1200
accatgcaag aacaaatcga ctctttagca gccgtagtcc ttcaaaatcg tcgaggacta  1260
gacatgttaa cggcagcaca gggaggaatt tgtttggcct tagatgaaaa atgttgcttt  1320
tgggtaaatc aatcaggaaa agtacaagac aacatcagac aactcctaaa tcaagcctcc  1380
agtttacggg aacgagccac tcagggttgg ttaaattggg aaggaacttg gaaatggttc  1440
tctgggttc ttccccttac aggcccactt gttagtctcc tacttttgct ccttttggt   1500
ccatgtctcc taaatctaat aacccaattt gtctcctctc gccttcaggc cataaagctc  1560
cagacgaatc tcagtgcagg acgccatcct cgcaatattc aagagtcacc cttct       1615
```

<210> SEQ ID NO 82
<211> LENGTH: 538
<212> TYPE: PRT
<213> ORGANISM: Human endogenous retrovirus FRD

<400> SEQUENCE: 82

```
Met Gly Leu Leu Leu Leu Val Leu Ile Leu Thr Pro Ser Leu Ala Ala
 1               5                  10                  15

Tyr Arg His Pro Asp Phe Pro Leu Leu Glu Lys Ala Gln Gln Leu Leu
                20                  25                  30

Gln Ser Thr Gly Ser Pro Tyr Ser Thr Asn Cys Trp Leu Cys Thr Ser
            35                  40                  45

Ser Ser Thr Glu Thr Pro Gly Thr Ala Tyr Pro Ala Ser Pro Arg Glu
        50                  55                  60

Trp Thr Ser Ile Glu Ala Glu Leu His Ile Ser Tyr Arg Trp Asp Pro
    65                  70                  75                  80

Asn Leu Lys Gly Leu Met Arg Pro Ala Asn Ser Leu Leu Ser Thr Val
                85                  90                  95
```

-continued

```
Lys Gln Asp Phe Pro Asp Ile Arg Gln Lys Pro Pro Ile Phe Gly Pro
                100                 105                 110
Ile Phe Thr Asn Ile Asn Leu Met Gly Ile Ala Pro Ile Cys Val Met
            115                 120                 125
Ala Lys Arg Lys Asn Gly Thr Asn Val Gly Thr Leu Pro Ser Thr Val
130                 135                 140
Cys Asn Val Thr Phe Thr Val Asp Ser Asn Gln Gln Thr Tyr Gln Thr
145                 150                 155                 160
Tyr Thr His Asn Gln Phe Arg His Gln Pro Arg Phe Pro Lys Pro Pro
                165                 170                 175
Asn Ile Thr Phe Pro Gln Gly Thr Leu Leu Asp Lys Ser Ser Arg Phe
            180                 185                 190
Cys Gln Gly Arg Pro Ser Ser Cys Ser Thr Arg Asn Phe Trp Phe Arg
        195                 200                 205
Pro Ala Asp Tyr Asn Gln Cys Leu Gln Ile Ser Asn Leu Ser Ser Thr
        210                 215                 220
Ala Glu Trp Val Leu Leu Asp Gln Thr Arg Asn Ser Leu Phe Trp Glu
225                 230                 235                 240
Asn Lys Thr Lys Gly Ala Asn Gln Ser Gln Thr Pro Cys Val Gln Val
                245                 250                 255
Leu Ala Gly Met Thr Ile Ala Thr Ser Tyr Leu Gly Ile Ser Ala Val
            260                 265                 270
Ser Glu Phe Phe Gly Thr Ser Leu Thr Pro Leu Phe His Phe His Ile
        275                 280                 285
Ser Thr Cys Leu Lys Thr Gln Gly Ala Phe Tyr Ile Cys Gly Gln Ser
        290                 295                 300
Ile His Gln Cys Leu Pro Ser Asn Trp Thr Gly Thr Cys Thr Ile Gly
305                 310                 315                 320
Tyr Val Thr Pro Asp Ile Phe Ile Ala Pro Gly Asn Leu Ser Leu Pro
                325                 330                 335
Ile Pro Ile Tyr Gly Asn Ser Pro Leu Pro Arg Val Arg Arg Ala Ile
            340                 345                 350
His Phe Ile Pro Leu Leu Ala Gly Leu Gly Ile Leu Ala Gly Thr Gly
        355                 360                 365
Thr Gly Ile Ala Gly Ile Thr Lys Ala Ser Leu Thr Tyr Ser Gln Leu
        370                 375                 380
Ser Lys Glu Ile Ala Asn Asn Ile Asp Thr Met Ala Lys Ala Leu Thr
385                 390                 395                 400
Thr Met Gln Glu Gln Ile Asp Ser Leu Ala Ala Val Val Leu Gln Asn
                405                 410                 415
Arg Arg Gly Leu Asp Met Leu Thr Ala Ala Gln Gly Gly Ile Cys Leu
            420                 425                 430
Ala Leu Asp Glu Lys Cys Cys Phe Trp Val Asn Gln Ser Gly Lys Val
        435                 440                 445
Gln Asp Asn Ile Arg Gln Leu Leu Asn Gln Ala Ser Ser Leu Arg Glu
        450                 455                 460
Arg Ala Thr Gln Gly Trp Leu Asn Trp Glu Gly Thr Trp Lys Trp Phe
465                 470                 475                 480
Ser Trp Val Leu Pro Leu Thr Gly Pro Leu Val Ser Leu Leu Leu Leu
                485                 490                 495
Leu Leu Phe Gly Pro Cys Leu Leu Asn Leu Ile Thr Gln Phe Val Ser
            500                 505                 510
Ser Arg Leu Gln Ala Ile Lys Leu Gln Thr Asn Leu Ser Ala Gly Arg
        515                 520                 525
```

His Pro Arg Asn Ile Gln Glu Ser Pro Phe
    530                 535

<210> SEQ ID NO 83
<211> LENGTH: 1878
<212> TYPE: DNA
<213> ORGANISM: Human endogenous retrovirus T

<400> SEQUENCE: 83

```
atgggtcccg aagcctgggt caggcccctt aaaactgcgc ctaagccggg tgaagccatt      60
agattaattc ttttattta cctctcttgt ttcttttgc ctgttatgtc ctctgagcct       120
tcctactcct ttctcctcac ctctttcaca acaggacgtg tattcgcaaa cactacttgg     180
agggccggta cctccaagga agtctccttt gcagttgatt tatgtgtact gttcccagag     240
ccagctcgta cccatgaaga gcaacataat ttgccggtca taggagcagg aagtgtcgac     300
cttgcagcag gatttggaca ctctgggagc caaactggat gtggaagctc caaaggtgca     360
gaaaaagggc tccaaaatgt tgactttttac ctctgtcctg aaatcacccc tgacgctagc   420
tgtagagata cttaccagtt tttctgccct gattggacat gtgtaacttt agccacctac    480
tctgggggat caactagatc ttcaactctt tccataagtc gtgttcctca tcctaaatta    540
tgtactagaa aaaattgtaa tcctcttact ataactgtcc atgaccctaa tgcagctcaa    600
tggtattatg gcatgtcatg gggattaaga ctttatatcc caggatttga tgttgggact    660
atgttcacca tccaaaagaa aatcttggtc tcatggagct cccccaagcc aatcgggcct    720
ttaactgatc taggtgaccc tatattccag aaacacctg acaaagttga tttaactgtt    780
cctctgccat tcttagttcc tagaccccag ctacaacaac aacatcttca acccagccta    840
atgtctatac taggtggagt acaccatctc cttaacctca cccagcctaa actagcccaa   900
gattgttggc tatgtttaaa agcaaaaccc ccttattatg taggattagg agtagaagcc    960
acacttaaac gtggccctct atcttgtcat acacgacccc gtgctctcac aataggagat  1020
gtgtctggaa atgcttcctg tctgattagt accgggtata acttatctgc ttctcctttt  1080
caggctactt gtaatcagtc cctgcttact tccataagca cctcagtctc ttaccaagca  1140
cccaacaata cctggttggc ctgcacctca ggtctcactc gctgcattaa tggaactgaa  1200
ccaggaccctc tcctgtgcgt gttagttcat gtacttcccc aggtatatgt gtacagtgga  1260
ccagaaggac gacaactcat cgctcccccct gagttacatc ccaggttgca ccaagctgtc  1320
ccacttctgg ttcccctatt ggctggtctt agcatagctg atcagcagc cattggtacg   1380
gctgccctgg ttcaaggaga aactggacta atatccctgt ctcaacaggt ggatgctgat  1440
tttagtaacc tccagtctgc catagatata ctacattccc aggtagagtc tctggctgaa  1500
gtagttcttc aaaactgccg atgcttagat ctgctattcc tctctcaagg aggtttatgt  1560
gcagctctag gagaaagttg ttgcttctat gccaatcaat ctggagtcat aaaaggtaca  1620
gtaaaaaaag ttcgagaaaa tctagatagg caccaacaag aacgagaaaa taacatcccc  1680
tggtatcaaa gcatgtttaa ctggaaccca tggctaacta ctttaatcac tgggttagct  1740
ggacctctcc tcatcctact attaagtta atttttgggc cttgtatatt aaattcgttt   1800
cttaatttta taaacaacg catagcttct gtcaaactta cgtatcttaa gactcaatat  1860
gacacccttg ttaataac                                                 1878
```

<210> SEQ ID NO 84
<211> LENGTH: 626
<212> TYPE: PRT

<213> ORGANISM: Human endogenous retrovirus T

<400> SEQUENCE: 84

```
Met Gly Pro Glu Ala Trp Val Arg Pro Leu Lys Thr Ala Pro Lys Pro
  1               5                  10                  15

Gly Glu Ala Ile Arg Leu Ile Leu Phe Ile Tyr Leu Ser Cys Phe Phe
             20                  25                  30

Leu Pro Val Met Ser Ser Glu Pro Ser Tyr Ser Phe Leu Leu Thr Ser
         35                  40                  45

Phe Thr Thr Gly Arg Val Phe Ala Asn Thr Thr Trp Arg Ala Gly Thr
 50                  55                  60

Ser Lys Glu Val Ser Phe Ala Val Asp Leu Cys Val Leu Phe Pro Glu
 65                  70                  75                  80

Pro Ala Arg Thr His Glu Glu Gln His Asn Leu Pro Val Ile Gly Ala
                 85                  90                  95

Gly Ser Val Asp Leu Ala Ala Gly Phe Gly His Ser Gly Ser Gln Thr
            100                 105                 110

Gly Cys Gly Ser Ser Lys Gly Ala Glu Lys Gly Leu Gln Asn Val Asp
            115                 120                 125

Phe Tyr Leu Cys Pro Gly Asn His Pro Asp Ala Ser Cys Arg Asp Thr
130                 135                 140

Tyr Gln Phe Phe Cys Pro Asp Trp Thr Cys Val Thr Leu Ala Thr Tyr
145                 150                 155                 160

Ser Gly Gly Ser Thr Arg Ser Ser Thr Leu Ser Ile Ser Arg Val Pro
                165                 170                 175

His Pro Lys Leu Cys Thr Arg Lys Asn Cys Asn Pro Leu Thr Ile Thr
            180                 185                 190

Val His Asp Pro Asn Ala Ala Gln Trp Tyr Tyr Gly Met Ser Trp Gly
            195                 200                 205

Leu Arg Leu Tyr Ile Pro Gly Phe Asp Val Gly Thr Met Phe Thr Ile
210                 215                 220

Gln Lys Lys Ile Leu Val Ser Trp Ser Ser Pro Lys Pro Ile Gly Pro
225                 230                 235                 240

Leu Thr Asp Leu Gly Asp Pro Ile Phe Gln Lys His Pro Asp Lys Val
                245                 250                 255

Asp Leu Thr Val Pro Leu Pro Phe Leu Val Pro Arg Pro Gln Leu Gln
            260                 265                 270

Gln Gln His Leu Gln Pro Ser Leu Met Ser Ile Leu Gly Gly Val His
            275                 280                 285

His Leu Leu Asn Leu Thr Gln Pro Lys Leu Ala Gln Asp Cys Trp Leu
290                 295                 300

Cys Leu Lys Ala Lys Pro Pro Tyr Tyr Val Gly Leu Gly Val Glu Ala
305                 310                 315                 320

Thr Leu Lys Arg Gly Pro Leu Ser Cys His Thr Arg Pro Arg Ala Leu
                325                 330                 335

Thr Ile Gly Asp Val Ser Gly Asn Ala Ser Cys Leu Ile Ser Thr Gly
            340                 345                 350

Tyr Asn Leu Ser Ala Ser Pro Phe Gln Ala Thr Cys Asn Gln Ser Leu
            355                 360                 365

Leu Thr Ser Ile Ser Thr Ser Val Ser Tyr Gln Ala Pro Asn Asn Thr
            370                 375                 380

Trp Leu Ala Cys Thr Ser Gly Leu Thr Arg Cys Ile Asn Gly Thr Glu
385                 390                 395                 400

Pro Gly Pro Leu Leu Cys Val Leu Val His Val Leu Pro Gln Val Tyr
```

| | | | | | | | | | | | |
|---|---|---|---|---|---|---|---|---|---|---|---|
| | | | 405 | | | 410 | | | 415 | | |
| Val | Tyr | Ser | Gly | Pro | Glu | Gly | Arg | Gln | Leu | Ile | Ala | Pro | Pro | Glu | Leu |
| | | | 420 | | | | 425 | | | | 430 | | | | |
| His | Pro | Arg | Leu | His | Gln | Ala | Val | Pro | Leu | Leu | Val | Pro | Leu | Leu | Ala |
| | | 435 | | | | 440 | | | | 445 | | | | | |
| Gly | Leu | Ser | Ile | Ala | Gly | Ser | Ala | Ala | Ile | Gly | Thr | Ala | Ala | Leu | Val |
| | 450 | | | | 455 | | | | 460 | | | | | | |
| Gln | Gly | Glu | Thr | Gly | Leu | Ile | Ser | Leu | Ser | Gln | Val | Asp | Ala | Asp |
| 465 | | | | 470 | | | | 475 | | | | 480 | | |
| Phe | Ser | Asn | Leu | Gln | Ser | Ala | Ile | Asp | Ile | Leu | His | Ser | Gln | Val | Glu |
| | | | 485 | | | | 490 | | | | 495 | | | | |
| Ser | Leu | Ala | Glu | Val | Val | Leu | Gln | Asn | Cys | Arg | Cys | Leu | Asp | Leu | Leu |
| | | | 500 | | | | 505 | | | | 510 | | | | |
| Phe | Leu | Ser | Gln | Gly | Gly | Leu | Cys | Ala | Ala | Leu | Gly | Glu | Ser | Cys | Cys |
| | | 515 | | | | 520 | | | | 525 | | | | | |
| Phe | Tyr | Ala | Asn | Gln | Ser | Gly | Val | Ile | Lys | Gly | Thr | Val | Lys | Lys | Val |
| | | 530 | | | | 535 | | | | 540 | | | | | |
| Arg | Glu | Asn | Leu | Asp | Arg | His | Gln | Gln | Glu | Arg | Glu | Asn | Asn | Ile | Pro |
| 545 | | | | 550 | | | | 555 | | | | 560 | | | |
| Trp | Tyr | Gln | Ser | Met | Phe | Asn | Trp | Asn | Pro | Trp | Leu | Thr | Thr | Leu | Ile |
| | | | 565 | | | | 570 | | | | 575 | | | | |
| Thr | Gly | Leu | Ala | Gly | Pro | Leu | Leu | Leu | Leu | Leu | Ser | Leu | Ile | Phe |
| | | 580 | | | | 585 | | | | 590 | | | | | |
| Gly | Pro | Cys | Ile | Leu | Asn | Ser | Phe | Leu | Asn | Phe | Ile | Lys | Gln | Arg | Ile |
| | | 595 | | | | 600 | | | | 605 | | | | | |
| Ala | Ser | Val | Lys | Leu | Thr | Tyr | Leu | Lys | Thr | Gln | Tyr | Asp | Thr | Leu | Val |
| | 610 | | | | 615 | | | | 620 | | | | | | |
| Asn | Asn |
| 625 | |

```
<210> SEQ ID NO 85
<211> LENGTH: 1812
<212> TYPE: DNA
<213> ORGANISM: Human endogenous retrovirus R

<400> SEQUENCE: 85
```

| | |
|---|---|
| atgctgggta tgaacatgct actcatcact ttgttcttgc tactcccctt atccatgtta | 60 |
| aaaggagaac cctgggaggg atgcctccac tgcacccaca ctacgtggtc ggggaacatc | 120 |
| atgactaaaa ccctgttgta tcacacttat tatgagtgtg ctgggacctg cctaggaact | 180 |
| tgtactcaca accagacaac ctactcagtc tgtgacccag aaggggcca gccttatgtg | 240 |
| tgttatgacc ctaagtcttc acctgggatc tggtttgaaa ttcatgtcgg gtcaaaggaa | 300 |
| ggggatcttc taaaccaaac caaggtattt ccctctggca aggatgtcgt atccttatac | 360 |
| tttgatgttt gccagatagt atccatgggc tcactctttc ccgtaatctt cagttccatg | 420 |
| gagtactata gtagctgcca taaaaatagg tatgcacacc ctgcttgttc caccgattcc | 480 |
| ccagtaacaa cttgctggga ctgcacaacg tggtccacta accaacaatc actagggcca | 540 |
| attatgctta ccaaaatacc attagaacca gattgtaaaa caagcacttg caattctgta | 600 |
| aatcttacca tcttagagcc agatcagccc atatggacaa caggtttaaa agcaccgcta | 660 |
| ggggcacgag tcagcggtga agaaattggc ccaggagcct atgtctatct atatatcata | 720 |
| aagaaaactc ggacccgctc aacccaacag ttccgagttt ttgagtcatt ctatgagcat | 780 |
| gttaaccaga aattgcctga gccccctccc ttggccagta atttattcgc ccaactggct | 840 |

```
gaaaacatag ccagcagcct gcacgttgct tcatgttatg tctgtggggg aatgaacatg    900
ggagaccaat ggccatggga agcaagggaa ctaatgcccc aagataattt cacactaacc    960
gcctcttccc tcgaacctgc accatcaagt cagagcatct ggttcttaaa acctccatt   1020 attggaaaat tctgtattgc tcgctgggga aaggccttta cagacccagt aggagagtta   1080
acttgcctag acaacaata ttacaacgag acactaggaa agactttatg gaggggcaaa    1140
agcaataatt ctgaatcacc acacccaagc ccattctctc gtttcccatc tttaaaccat   1200
tcttggtacc aacttgaagc tccaaatacc tggcaggcac cctctggcct ctactggatc   1260
tgtgggccac aagcatatcg acaactgcca gctaaatggt caggggcctg tgtactgggg   1320
acaattaggc cgtccttctt cctaatgccc ctaaacagg gagaagcctt aggatacccc     1380
atctatgatg aaactaaaag gaaaagcaaa agaggcataa ctataggaga ttggaaggac   1440
agtgaatggc ctcctgaaag aataattcaa tattatggcc cagccacctg ggcagaagat   1500
ggaatgtggg gataccgcac cccagtttac atgcttaacc gcattataag attgcaggca   1560
gtactagaaa tcattaccaa tgaaactgca ggggccttga atctgcttgc ccagcaagcc   1620
acaaaaatga aaatgtcat ttatcaaaat agactggcct tagactacct cctagcccag    1680
gaagagggag tatgcggaaa gttcagcctt actaactgct gcctggaact tgatgacgaa   1740
ggaaaggtta tcaaagaaat aactgctaaa atccaaaagt tagctcacat cccagttcag   1800
acttggaaag ga                                                       1812
```

<210> SEQ ID NO 86
<211> LENGTH: 604
<212> TYPE: PRT
<213> ORGANISM: Human endogenous retrovirus R

<400> SEQUENCE: 86

```
Met Leu Gly Met Asn Met Leu Leu Ile Thr Leu Phe Leu Leu Leu Pro
  1               5                  10                  15

Leu Ser Met Leu Lys Gly Glu Pro Trp Glu Gly Cys Leu His Cys Thr
             20                  25                  30

His Thr Thr Trp Ser Gly Asn Ile Met Thr Lys Thr Leu Leu Tyr His
         35                  40                  45

Thr Tyr Tyr Glu Cys Ala Gly Thr Cys Leu Gly Thr Cys Thr His Asn
     50                  55                  60

Gln Thr Thr Tyr Ser Val Cys Asp Pro Gly Arg Gly Gln Pro Tyr Val
 65                  70                  75                  80

Cys Tyr Asp Pro Lys Ser Ser Pro Gly Ile Trp Phe Glu Ile His Val
                 85                  90                  95

Gly Ser Lys Glu Gly Asp Leu Leu Asn Gln Thr Lys Val Phe Pro Ser
            100                 105                 110

Gly Lys Asp Val Val Ser Leu Tyr Phe Asp Val Cys Gln Ile Val Ser
        115                 120                 125

Met Gly Ser Leu Phe Pro Val Ile Phe Ser Ser Met Glu Tyr Tyr Ser
    130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205
```

Gln Pro Ile Trp Thr Thr Gly Leu Lys Ala Pro Leu Gly Ala Arg Val
210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
            245                 250                 255

Phe Tyr Glu His Val Asn Gln Lys Leu Pro Glu Pro Pro Leu Ala
            260                 265                 270

Ser Asn Leu Phe Ala Gln Leu Ala Glu Asn Ile Ala Ser Ser Leu His
            275                 280                 285

Val Ala Ser Cys Tyr Val Cys Gly Gly Met Asn Met Gly Asp Gln Trp
290                 295                 300

Pro Trp Glu Ala Arg Glu Leu Met Pro Gln Asp Asn Phe Thr Leu Thr
305                 310                 315                 320

Ala Ser Ser Leu Glu Pro Ala Pro Ser Ser Gln Ser Ile Trp Phe Leu
            325                 330                 335

Lys Thr Ser Ile Ile Gly Lys Phe Cys Ile Ala Arg Trp Gly Lys Ala
            340                 345                 350

Phe Thr Asp Pro Val Gly Glu Leu Thr Cys Leu Gly Gln Gln Tyr Tyr
            355                 360                 365

Asn Glu Thr Leu Gly Lys Thr Leu Trp Arg Gly Lys Ser Asn Asn Ser
370                 375                 380

Glu Ser Pro His Pro Ser Pro Phe Ser Arg Phe Pro Ser Leu Asn His
385                 390                 395                 400

Ser Trp Tyr Gln Leu Glu Ala Pro Asn Thr Trp Gln Ala Pro Ser Gly
            405                 410                 415

Leu Tyr Trp Ile Cys Gly Pro Gln Ala Tyr Arg Gln Leu Pro Ala Lys
            420                 425                 430

Trp Ser Gly Ala Cys Val Leu Gly Thr Ile Arg Pro Ser Phe Phe Leu
            435                 440                 445

Met Pro Leu Lys Gln Gly Glu Ala Leu Gly Tyr Pro Ile Tyr Asp Glu
450                 455                 460

Thr Lys Arg Lys Ser Lys Arg Gly Ile Thr Ile Gly Asp Trp Lys Asp
465                 470                 475                 480

Ser Glu Trp Pro Pro Glu Arg Ile Ile Gln Tyr Tyr Gly Pro Ala Thr
            485                 490                 495

Trp Ala Glu Asp Gly Met Trp Gly Tyr Arg Thr Pro Val Tyr Met Leu
            500                 505                 510

Asn Arg Ile Ile Arg Leu Gln Ala Val Leu Glu Ile Thr Asn Glu
            515                 520                 525

Thr Ala Gly Ala Leu Asn Leu Leu Ala Gln Gln Ala Thr Lys Met Arg
530                 535                 540

Asn Val Ile Tyr Gln Asn Arg Leu Ala Leu Asp Tyr Leu Leu Ala Gln
545                 550                 555                 560

Glu Glu Gly Val Cys Gly Lys Phe Ser Leu Thr Asn Cys Cys Leu Glu
            565                 570                 575

Leu Asp Asp Glu Gly Lys Val Ile Lys Glu Ile Thr Ala Lys Ile Gln
            580                 585                 590

Lys Leu Ala His Ile Pro Val Gln Thr Trp Lys Gly
            595                 600

<210> SEQ ID NO 87
<211> LENGTH: 1563
<212> TYPE: DNA

<213> ORGANISM: Human endogenous retrovirus V

<400> SEQUENCE: 87

```
atgcccctac tctcacaggc acagtggaat gaaaattccc ttgtcagttt ttccaaaata      60
attgcttcgg gaaaccatct aagcaactgt tggatctgcc acaacttcat caccaggtcc     120
tcatcttacc aatatatttt ggtaagaaat ttttctttaa acctaacatt tggttcagga     180
atccctgaag ccaacataa atctgttccg ctccaggttt cgcttgctaa ctcagcgcac      240
caagtcccct gcctggatct cactccacct ttcaatcaaa gctctaaaac ttctttctat     300
ttctacaact gctcttctct aaaccaaacc tgttgtccat gccctgaagg acactgtgac     360
aggaagaaca cctctgagga gggattcccc agtcccacca tccatcccat gagcttctcc     420
ccagcaggct gccaccctaa cttgactcac tggtgtccag ctaaacaaat gaacgattat     480
cgagacaagt caccccaaaa ccgctgtgca gcttgggaag aaaagagct aatcacatgg      540
agggttctat attcgcttcc caaggcacac actgtcccca catggccaaa atctactgtt     600
cccctgggag ggcctctatc ccctgcatgc aatcaaacta ttccagcagg gtggaaatcg     660
cagttacaca gtggttcga cagccacatc ccccggtggg cctgtacccc tcctggctat      720
gtatttttat gtgggccaca aaaaaataaa ctgcccttg atggaagtcc taagataacc      780
tattcaaccc ccctgtggc aaacctctac acttgcatta taacatcca acatacggga       840
gaatgtctg tgggactttt gggaccacgg gggataggtg tgaccattta taacaccacc       900
caacccagac agaaaagagc tctgggtcta atactggcag gatgggtgc ggccatagga       960
atgatcgccc catggggagg gttcacttat catgatgtca ccctcagaaa tctctccaga    1020
caaatagaca acatagctaa gagtaccaga gatagcatct ctaaactcaa ggcctccata    1080
gattctctag caaatgtagt catggacaac agattggcct tagattacct cttagcagag    1140
cagggtggag tctgtgcagt gatcaataaa tcctgttgcg tttatgtcaa taacagtggg    1200
gcgatagagg aggatataaa aaagatctat gatgaggcta cgtggctcca tgactttgga    1260
aaaggaggtg cttcagcaag ggccatctgg gaggctgtga agtctgccct cccctccctc    1320
aactggtttg tcccttttact gggaccagca acagttatac tcttactttt cctctttggc    1380
ccttgtttct ttaatttact gattaagtgt gtctcttcta ggataaagca atttcacatg    1440
aagtcccccc aaatggaaag atatcagcta tctgtcattg gaggcccag cacctataag     1500
cacatctccc ccttggatgc cagtgggcaa agattccggg aaactatgga ggaattttct    1560
ctc                                                                  1563
```

<210> SEQ ID NO 88
<211> LENGTH: 521
<212> TYPE: PRT
<213> ORGANISM: Human endogneous retrovirus V

<400> SEQUENCE: 88

```
Met Pro Leu Leu Ser Gln Ala Gln Trp Asn Glu Asn Ser Leu Val Ser
 1               5                  10                  15

Phe Ser Lys Ile Ile Ala Ser Gly Asn His Leu Ser Asn Cys Trp Ile
            20                  25                  30

Cys His Asn Phe Ile Thr Arg Ser Ser Ser Tyr Gln Tyr Ile Leu Val
        35                  40                  45

Arg Asn Phe Ser Leu Asn Leu Thr Phe Gly Ser Gly Ile Pro Glu Gly
    50                  55                  60

Gln His Lys Ser Val Pro Leu Gln Val Ser Leu Ala Asn Ser Ala His
65                  70                  75                  80
```

```
Gln Val Pro Cys Leu Asp Leu Thr Pro Pro Phe Asn Gln Ser Ser Lys
                85                  90                  95

Thr Ser Phe Tyr Phe Tyr Asn Cys Ser Ser Leu Asn Gln Thr Cys Cys
            100                 105                 110

Pro Cys Pro Glu Gly His Cys Asp Arg Lys Asn Thr Ser Glu Glu Gly
            115                 120                 125

Phe Pro Ser Pro Thr Ile His Pro Met Ser Phe Ser Pro Ala Gly Cys
        130                 135                 140

His Pro Asn Leu Thr His Trp Cys Pro Ala Lys Gln Met Asn Asp Tyr
145                 150                 155                 160

Arg Asp Lys Ser Pro Gln Asn Arg Cys Ala Ala Trp Glu Gly Lys Glu
                165                 170                 175

Leu Ile Thr Trp Arg Val Leu Tyr Ser Leu Pro Lys Ala His Thr Val
            180                 185                 190

Pro Thr Trp Pro Lys Ser Thr Val Pro Leu Gly Gly Pro Leu Ser Pro
        195                 200                 205

Ala Cys Asn Gln Thr Ile Pro Ala Gly Trp Lys Ser Gln Leu His Lys
    210                 215                 220

Trp Phe Asp Ser His Ile Pro Arg Trp Ala Cys Thr Pro Pro Gly Tyr
225                 230                 235                 240

Val Phe Leu Cys Gly Pro Gln Lys Asn Lys Leu Pro Phe Asp Gly Ser
                245                 250                 255

Pro Lys Ile Thr Tyr Ser Thr Pro Pro Val Ala Asn Leu Tyr Thr Cys
            260                 265                 270

Ile Asn Asn Ile Gln His Thr Gly Glu Cys Ala Val Gly Leu Leu Gly
        275                 280                 285

Pro Arg Gly Ile Gly Val Thr Ile Tyr Asn Thr Thr Gln Pro Arg Gln
    290                 295                 300

Lys Arg Ala Leu Gly Leu Ile Leu Ala Gly Met Gly Ala Ala Ile Gly
305                 310                 315                 320

Met Ile Ala Pro Trp Gly Gly Phe Thr Tyr His Asp Val Thr Leu Arg
                325                 330                 335

Asn Leu Ser Arg Gln Ile Asp Asn Ile Ala Lys Ser Thr Arg Asp Ser
            340                 345                 350

Ile Ser Lys Leu Lys Ala Ser Ile Asp Ser Leu Ala Asn Val Val Met
        355                 360                 365

Asp Asn Arg Leu Ala Leu Asp Tyr Leu Leu Ala Glu Gln Gly Gly Val
    370                 375                 380

Cys Ala Val Ile Asn Lys Ser Cys Cys Val Tyr Val Asn Asn Ser Gly
385                 390                 395                 400

Ala Ile Glu Glu Asp Ile Lys Lys Ile Tyr Asp Glu Ala Thr Trp Leu
                405                 410                 415

His Asp Phe Gly Lys Gly Gly Ala Ser Ala Arg Ala Ile Trp Glu Ala
            420                 425                 430

Val Lys Ser Ala Leu Pro Ser Leu Asn Trp Phe Val Pro Leu Leu Gly
        435                 440                 445

Pro Ala Thr Val Ile Leu Leu Leu Phe Leu Phe Gly Pro Cys Phe Phe
    450                 455                 460

Asn Leu Leu Ile Lys Cys Val Ser Ser Arg Ile Lys Gln Phe His Met
465                 470                 475                 480

Lys Ser Pro Gln Met Glu Arg Tyr Gln Leu Ser Val Ile Gly Gly Pro
                485                 490                 495

Ser Thr Tyr Lys His Ile Ser Pro Leu Asp Ala Ser Gly Gln Arg Phe
```

```
                500              505              510
Arg Glu Thr Met Glu Glu Phe Ser Leu
            515              520
```

<210> SEQ ID NO 89
<211> LENGTH: 1542
<212> TYPE: DNA
<213> ORGANISM: Human endogenous retrovirus R(b)

<400> SEQUENCE: 89

```
atggatccac tacacacgat tgaaaaagtt cctgcaagaa gaaacatcca cgacagagga      60
caccaaggcc accgaatggg agatggaacc cctggaaggc ctaagatttc tgttcaacaa     120
atgacaagat tttcccttat aatattttc ctttctgctc cttttgttgt taatgcctct     180
acctctaacg ttttcctaca atgggcacac agttatgcag atggcttaca acaaggagac     240
ccttgctggg tctgtggttc gttacccgtc actaacacca tggagctacc ttggtgggtc     300
tccccgctac aagggaaaga ctgggttttt tttcaaagct ttataggga tcttaaacaa     360
tggacagggg cacagatgac tggggtaact agaaaaaaca tttcagaatg gcctataaat     420
aaaactttaa atgagccagg gcatgataaa ccattctcag taatgagac aagggataaa     480
gtaatagcct ttgccatccc cttgttggat accaaggtgt tgtccagac ttccagacct     540
cagaacactc aatatagaaa tgggtttctc cagatatggg acgggttcat ttggctgaca     600
gccactaagg gacacttaag ccagatagct cccttatgct gggagcaaag aaatcactcc     660
cttgataact ggccaaacac aactcgtgtt atgggatgga ttccacctgg acagtgccga     720
catactatac tgttacaaca gagggaccta tttgccacag actggtctca gcaacctggc     780
ttgaattggt atgctcccaa cggaacccag tggctctgca gcccaaactt atggccttgg     840
cttccctcag gttggttagg atgctgcact ctaggtattc cctgggcaca aggacgctgg     900
gtaaaaacca tggaagtcta tccttatctt ccacatgtgg ttaaccaagg gactagggcc     960
attgttcaca ggaatgatca cctacccaca atctttatgc cctcagtagg tttaggaact    1020
gtaatacagc acatagaggc tctagccaat tttacccaac gggccctaaa tgacagcctc    1080
caaagtattt ctctcatgaa tgctgaagtg tattatatgc acgaggacat cttacaaaac    1140
cgaatggccc tagatatttt aactgcggct gaaggaggaa cctgtgccct catcaaaact    1200
gaatgttgtg tgtatattcc caataactct agaaacattt ccttggcctt agaggataca    1260
tgtcggcaaa tccaagtcat ctccagctct gcactgtcac tccatgactg gatagcatct    1320
cagtttagtg gaagaccttc ctggtggcag aaaatcctca ttgtccttgc caccctctgg    1380
agcgtaggca tagcactgtg ttgtggactg tattttgtc gcatgttttc ccaacacatt    1440
ccccaaactc attcgattat atttcaacag gaacttccct tgagcccccc aagtcaggag    1500
cattaccaga gccaaagaga catcttccac tctaacgccc cc                       1542
```

<210> SEQ ID NO 90
<211> LENGTH: 514
<212> TYPE: PRT
<213> ORGANISM: Human endogenous retrovirus R(b)

<400> SEQUENCE: 90

```
Met Asp Pro Leu His Thr Ile Glu Lys Val Pro Ala Arg Arg Asn Ile
  1               5                  10                  15

His Asp Arg Gly His Gln Gly His Arg Met Gly Asp Gly Thr Pro Gly
             20                  25                  30

Arg Pro Lys Ile Ser Val Gln Gln Met Thr Arg Phe Ser Leu Ile Ile
```

-continued

```
                35                  40                  45
Phe Phe Leu Ser Ala Pro Phe Val Val Asn Ala Ser Thr Ser Asn Val
         50                  55                  60
Phe Leu Gln Trp Ala His Ser Tyr Ala Asp Gly Leu Gln Gln Gly Asp
 65                  70                  75                  80
Pro Cys Trp Val Cys Gly Ser Leu Pro Val Thr Asn Thr Met Glu Leu
                 85                  90                  95
Pro Trp Trp Val Ser Pro Leu Gln Gly Lys Asp Trp Val Phe Phe Gln
                100                 105                 110
Ser Phe Ile Gly Asp Leu Lys Gln Trp Thr Gly Ala Gln Met Thr Gly
            115                 120                 125
Val Thr Arg Lys Asn Ile Ser Glu Trp Pro Ile Asn Lys Thr Leu Asn
        130                 135                 140
Glu Pro Gly His Asp Lys Pro Phe Ser Val Asn Glu Thr Arg Asp Lys
145                 150                 155                 160
Val Ile Ala Phe Ala Ile Pro Leu Leu Asp Thr Lys Val Phe Val Gln
                165                 170                 175
Thr Ser Arg Pro Gln Asn Thr Gln Tyr Arg Asn Gly Phe Leu Gln Ile
                180                 185                 190
Trp Asp Gly Phe Ile Trp Leu Thr Ala Thr Lys Gly His Leu Ser Gln
            195                 200                 205
Ile Ala Pro Leu Cys Trp Glu Gln Arg Asn His Ser Leu Asp Asn Trp
        210                 215                 220
Pro Asn Thr Thr Arg Val Met Gly Trp Ile Pro Pro Gly Gln Cys Arg
225                 230                 235                 240
His Thr Ile Leu Leu Gln Gln Arg Asp Leu Phe Ala Thr Asp Trp Ser
                245                 250                 255
Gln Gln Pro Gly Leu Asn Trp Tyr Ala Pro Asn Gly Thr Gln Trp Leu
            260                 265                 270
Cys Ser Pro Asn Leu Trp Pro Trp Leu Pro Ser Gly Trp Leu Gly Cys
        275                 280                 285
Cys Thr Leu Gly Ile Pro Trp Ala Gln Gly Arg Trp Val Lys Thr Met
290                 295                 300
Glu Val Tyr Pro Tyr Leu Pro His Val Val Asn Gln Gly Thr Arg Ala
305                 310                 315                 320
Ile Val His Arg Asn Asp His Leu Pro Thr Ile Phe Met Pro Ser Val
                325                 330                 335
Gly Leu Gly Thr Val Ile Gln His Ile Glu Ala Leu Ala Asn Phe Thr
            340                 345                 350
Gln Arg Ala Leu Asn Asp Ser Leu Gln Ser Ile Ser Leu Met Asn Ala
        355                 360                 365
Glu Val Tyr Tyr Met His Glu Asp Ile Leu Gln Asn Arg Met Ala Leu
370                 375                 380
Asp Ile Leu Thr Ala Ala Glu Gly Gly Thr Cys Ala Leu Ile Lys Thr
385                 390                 395                 400
Glu Cys Cys Val Tyr Ile Pro Asn Asn Ser Arg Asn Ile Ser Leu Ala
                405                 410                 415
Leu Glu Asp Thr Cys Arg Gln Ile Gln Val Ile Ser Ser Ala Leu
            420                 425                 430
Ser Leu His Asp Trp Ile Ala Ser Gln Phe Ser Gly Arg Pro Ser Trp
        435                 440                 445
Trp Gln Lys Ile Leu Ile Val Leu Ala Thr Leu Trp Ser Val Gly Ile
        450                 455                 460
```

```
Ala Leu Cys Cys Gly Leu Tyr Phe Cys Arg Met Phe Ser Gln His Ile
465                 470                 475                 480

Pro Gln Thr His Ser Ile Ile Phe Gln Gln Glu Leu Pro Leu Ser Pro
                485                 490                 495

Pro Ser Gln Glu His Tyr Gln Ser Gln Arg Asp Ile Phe His Ser Asn
                500                 505                 510

Ala Pro

<210> SEQ ID NO 91
<211> LENGTH: 1464
<212> TYPE: DNA
<213> ORGANISM: Human T-cell lymphotropic virus type 1

<400> SEQUENCE: 91
atgggtaagt tctcgccac tttgattta ttcttccagt tctgccccct catcttcggt        60
gattacagcc ccagctgctg tactctcaca attggagtct cctcatacca ctctaaaccc       120
tgcaatcctg cccagccagt tgttcgtgg accctcgacc tgctggccct ttcagcagat       180
caggccctac agccccctg ccctaaccta gtaagttact ccagctacca tgccacctat        240
tccctatatc tattccctca ttggactaag aagccaaacc gaaatggcgg aggctattat       300
tcagcctctt attcagaccc ttgttcctta agtgcccat acctgggtg ccaatcatgg         360 acctgccccct atacaggagc cgtctccagc ccctactgga agtttcaaca cgatgtcaat      420
tttactcaag aagtttcacg cctcaatatt aatctccatt tttcaaaatg cggttttccc       480
ttctcccttc agtcgacgc tccaggatat gaccccatct ggttcctta accgaaccc          540 agccaactgc ctcccaccgc ccctcctcta ctcccccact ctaacctaga ccacatcctc       600
gagccctcta ccatggaa tcaaaaactc ctgaccccttg tccagttaac cctacaaagc        660
actaattata cttgcattgt ctgtatcgat cgtgccagcc tctccacttg gcacgtccta       720
tactctccca acgtctctgt tccatcctct tcttctaccc cctcctttta cccatcgtta      780
gcgcttccag ccccccaccct gacgttacca tttaactgga cccactgctt tgaccccag      840 attcaagcta tgtctcctc ccctgtcat aactccctca tcctgcccccc ctttttccttg       900 tcacctgttc ccaccctagg atcccgctcc cgccgagcgg taccggtggc ggtctggctt       960
gtctccgccc tggccatggg agccggagtg gctggcggga ttaccggctc catgtccctc      1020
gcctcaggaa agagcctcct acatgaggtg gacaaagata tttcccagtt aactcaagca     1080
atagtcaaaa accacaaaaa tctactcaaa attgcgcagt atgctgccca gaacagacga     1140
ggccttgatc tcctgttctg ggagcaagga ggattatgca aagcattaca agaacagtgc    1200
cgttttccga atattaccaa ttcccatgtc caatactac aagaaagacc ccccttgag    1260 aatcgagtcc tgactggctg gggccttaac tgggaccttg gcctctcaca gtgggctcga    1320
gaggccttac aaactggaat caccttgtt gcgctactcc ttcttgttat ccttgcagga    1380
ccatgcatcc tccgtcagct acgacacctc ccctcgcgcg tcagatacc ccattactct    1440 cttataaacc ctgagtcatc cctg                                           1464

<210> SEQ ID NO 92
<211> LENGTH: 488
<212> TYPE: PRT
<213> ORGANISM: Human T-cell lymphotropic virus type 1

<400> SEQUENCE: 92

Met Gly Lys Phe Leu Ala Thr Leu Ile Leu Phe Phe Gln Phe Cys Pro
1               5                   10                  15
```

```
Leu Ile Phe Gly Asp Tyr Ser Pro Ser Cys Cys Thr Leu Thr Ile Gly
                20                  25                  30
Val Ser Ser Tyr His Ser Lys Pro Cys Asn Pro Ala Gln Pro Val Cys
            35                  40                  45
Ser Trp Thr Leu Asp Leu Leu Ala Leu Ser Ala Asp Gln Ala Leu Gln
        50                  55                  60
Pro Pro Cys Pro Asn Leu Val Ser Tyr Ser Ser Tyr His Ala Thr Tyr
65                  70                  75                  80
Ser Leu Tyr Leu Phe Pro His Trp Thr Lys Lys Pro Asn Arg Asn Gly
                85                  90                  95
Gly Gly Tyr Tyr Ser Ala Ser Tyr Ser Asp Pro Cys Ser Leu Lys Cys
            100                 105                 110
Pro Tyr Leu Gly Cys Gln Ser Trp Thr Cys Pro Tyr Thr Gly Ala Val
        115                 120                 125
Ser Ser Pro Tyr Trp Lys Phe Gln His Asp Val Asn Phe Thr Gln Glu
130                 135                 140
Val Ser Arg Leu Asn Ile Asn Leu His Phe Ser Lys Cys Gly Phe Pro
145                 150                 155                 160
Phe Ser Leu Leu Val Asp Ala Pro Gly Tyr Asp Pro Ile Trp Phe Leu
                165                 170                 175
Asn Thr Glu Pro Ser Gln Leu Pro Pro Thr Ala Pro Pro Leu Leu Pro
            180                 185                 190
His Ser Asn Leu Asp His Ile Leu Glu Pro Ser Ile Pro Trp Lys Ser
        195                 200                 205
Lys Leu Leu Thr Leu Val Gln Leu Thr Leu Gln Ser Thr Asn Tyr Thr
        210                 215                 220
Cys Ile Val Cys Ile Asp Arg Ala Ser Leu Ser Thr Trp His Val Leu
225                 230                 235                 240
Tyr Ser Pro Asn Val Ser Val Pro Ser Ser Ser Thr Pro Leu Leu
                245                 250                 255
Tyr Pro Ser Leu Ala Leu Pro Ala Pro His Leu Thr Leu Pro Phe Asn
            260                 265                 270
Trp Thr His Cys Phe Asp Pro Gln Ile Gln Ala Ile Val Ser Ser Pro
        275                 280                 285
Cys His Asn Ser Leu Ile Leu Pro Pro Phe Ser Leu Ser Pro Val Pro
290                 295                 300
Thr Leu Gly Ser Arg Ser Arg Arg Ala Val Pro Val Ala Val Trp Leu
305                 310                 315                 320
Val Ser Ala Leu Ala Met Gly Ala Gly Val Ala Gly Gly Ile Thr Gly
                325                 330                 335
Ser Met Ser Leu Ala Ser Gly Lys Ser Leu Leu His Glu Val Asp Lys
            340                 345                 350
Asp Ile Ser Gln Leu Thr Gln Ala Ile Val Lys Asn His Lys Asn Leu
        355                 360                 365
Leu Lys Ile Ala Gln Tyr Ala Ala Gln Asn Arg Arg Gly Leu Asp Leu
        370                 375                 380
Leu Phe Trp Glu Gln Gly Gly Leu Cys Lys Ala Leu Gln Glu Gln Cys
385                 390                 395                 400
Arg Phe Pro Asn Ile Thr Asn Ser His Val Pro Ile Leu Gln Glu Arg
                405                 410                 415
Pro Pro Leu Glu Asn Arg Val Leu Thr Gly Trp Gly Leu Asn Trp Asp
            420                 425                 430
Leu Gly Leu Ser Gln Trp Ala Arg Glu Ala Leu Gln Thr Gly Ile Thr
        435                 440                 445
```

Leu Val Ala Leu Leu Leu Val Ile Leu Ala Gly Pro Cys Ile Leu
        450                 455                 460

Arg Gln Leu Arg His Leu Pro Ser Arg Val Tyr Pro His Tyr Ser
465                 470                 475                 480

Leu Ile Asn Pro Glu Ser Ser Leu
                485

<210> SEQ ID NO 93
<211> LENGTH: 1458
<212> TYPE: DNA
<213> ORGANISM: Human T-cell lymphotropic virus type 2

<400> SEQUENCE: 93

```
atgggtaatg ttttcttcct acttttattc agtctcacac attttccact agcccagcag      60
agccgatgca cactcacgat tggtatctcc tcctaccact ccagcccctg tagcccaacc     120
caacccgtct gcacgtggaa cctcgacctt aattccctaa caacggacca acgactacac     180
cccccctgcc ctaacctaat tacttactct ggcttccata agacttattc cttatactta     240
ttcccacatt ggataaaaaa gccaaacaga cagggcctag ggtactactc gccttcctac     300
aatgacccctt gctcgctaca atgcccctac ttgggctgcc aagcatggac atccgcatac     360
acggccccg tctccagtcc atcctggaag tttcattcag atgtaaattt cacccaggaa     420
gtcagccaag tgtcccttcg actacacttc tctaagtgcg gctcctccat gaccctccta     480
gtagatgccc ctggatatga tcctttatgg ttcatcacct cagaacccac tcagcctcca     540
ccaacttctc ccccattggt ccatgactcc gaccttgaac atgtcctaac ccctccacg     600
tcctggacga ccaaaatact caaatttatc cagctgacct tacagagcac caattactcc     660
tgcatggttt gcgtggatag atccagcctc tcatcctggc atgtactcta caccccccaac     720
atctccattc ccaacaaac ctcctcccga accatcctct ttccttccct tgccctgccc     780
gctcctccat cccaaccctt cccttggacc cattgctacc aacctcgcct acaggcgata     840
acaacagata actgcaacaa ctccattatc ctccccccctt tttccctcgc tcccgtacct     900
cctccggcga aagacgccg ccgtgccgtt caatagcag tgtggcttgt ctccgcccta     960
gcggccggaa caggtatcgc tggtggagta acaggctccc tatctctggc ttccagtaaa    1020
agccttctcc tcgaggttga caaagacatc tcccacctta cccaggccat agtcaaaat    1080
catcaaaaca tcctccgggt tgcacagtat gcagcccaaa atagacgagg attagacctc    1140
ctattctggg aacaagggg tttgtgcaag gccatacagg agcaatgttg cttcctcaac    1200
atcagtaaca ctcatgtatc cgtcctccag gaacggcccc ctcttgaaaa acgtgtcatc    1260
accggctggg gactaaactg ggatcttgga ctgtcccaat gggcacgaga agccctccag    1320
acaggcataa ccattctcgc tctactcctc ctcgtcatat tgtttggccc ctgtatcctc    1380
cgccaaatcc aggcccttcc acagcggtta caaaaccgac ataaccagta ttcccttatc    1440
aacccagaaa ccatgcta                                                  1458
```

<210> SEQ ID NO 94
<211> LENGTH: 486
<212> TYPE: PRT
<213> ORGANISM: Human T-cell lymphotropic virus type 2

<400> SEQUENCE: 94

Met Gly Asn Val Phe Phe Leu Leu Leu Phe Ser Leu Thr His Phe Pro
1               5                   10                  15

Leu Ala Gln Gln Ser Arg Cys Thr Leu Thr Ile Gly Ile Ser Ser Tyr

```
                    20                  25                  30
His Ser Ser Pro Cys Ser Pro Thr Gln Pro Val Cys Thr Trp Asn Leu
            35                  40                  45

Asp Leu Asn Ser Leu Thr Thr Asp Gln Arg Leu His Pro Pro Cys Pro
    50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ala Trp Thr Ser Ala Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205

Phe Ile Gln Leu Thr Leu Gln Ser Thr Asn Tyr Ser Cys Met Val Cys
    210                 215                 220

Val Asp Arg Ser Ser Leu Ser Ser Trp His Val Leu Tyr Thr Pro Asn
225                 230                 235                 240

Ile Ser Ile Pro Gln Gln Thr Ser Ser Arg Thr Ile Leu Phe Pro Ser
                245                 250                 255

Leu Ala Leu Pro Ala Pro Pro Ser Gln Pro Phe Pro Trp Thr His Cys
            260                 265                 270

Tyr Gln Pro Arg Leu Gln Ala Ile Thr Thr Asp Asn Cys Asn Asn Ser
        275                 280                 285

Ile Ile Leu Pro Pro Phe Ser Leu Ala Pro Val Pro Pro Pro Ala Thr
    290                 295                 300

Arg Arg Arg Arg Ala Val Pro Ile Ala Val Trp Leu Val Ser Ala Leu
305                 310                 315                 320

Ala Ala Gly Thr Gly Ile Ala Gly Gly Val Thr Gly Ser Leu Ser Leu
                325                 330                 335

Ala Ser Ser Lys Ser Leu Leu Leu Glu Val Asp Lys Asp Ile Ser His
            340                 345                 350

Leu Thr Gln Ala Ile Val Lys Asn His Gln Asn Ile Leu Arg Val Ala
        355                 360                 365

Gln Tyr Ala Ala Gln Asn Arg Arg Gly Leu Asp Leu Leu Phe Trp Glu
    370                 375                 380

Gln Gly Gly Leu Cys Lys Ala Ile Gln Glu Gln Cys Cys Phe Leu Asn
385                 390                 395                 400

Ile Ser Asn Thr His Val Ser Val Leu Gln Glu Arg Pro Pro Leu Glu
                405                 410                 415

Lys Arg Val Ile Thr Gly Trp Gly Leu Asn Trp Asp Leu Gly Leu Ser
            420                 425                 430

Gln Trp Ala Arg Glu Ala Leu Gln Thr Gly Ile Thr Ile Leu Ala Leu
        435                 440                 445
```

Leu Leu Leu Val Ile Leu Phe Gly Pro Cys Ile Leu Arg Gln Ile Gln
    450                 455                 460

Ala Leu Pro Gln Arg Leu Gln Asn Arg His Asn Gln Tyr Ser Leu Ile
465                 470                 475                 480

Asn Pro Glu Thr Met Leu
            485

<210> SEQ ID NO 95
<211> LENGTH: 1926
<212> TYPE: DNA
<213> ORGANISM: Feline leukemia virus

<400> SEQUENCE: 95

| | | | | | |
|---|---|---|---|---|---|
| atggaaagtc | caacgcaccc | aaaaccctct | aaagataaga | ctctctcgtg | gaacttagtg | 60 |
| tttctggtgg | ggatcttatt | cacaatagac | ataggaatgg | ccaatcctag | tccacaccaa | 120 |
| atatataatg | taacttgggt | aataaccaat | gtacaaacta | cacccaagc | taatgccacc | 180 |
| tctatgttag | gaaccttaac | cgatgtctac | cctaccctac | atgttgactt | atgtgaccta | 240 |
| gtgggagaca | cctgggaacc | tatagtccta | agcccaacca | atgtaaaaca | cggggcacgt | 300 |
| tacccttcct | caaatatgg | atgtaaaact | acagataga | aaaaacagca | acagacatac | 360 |
| cccttttacg | tctgccccgg | acatgccccc | tcgctggggc | caagggaac | acattgtgga | 420 |
| ggggcacaag | atgggttttg | tgccgcatgg | ggatgtgaaa | ccaccggaga | agcttggtgg | 480 |
| aagccctcct | cctcatggga | ctatatcaca | gtaaaaagag | ggagtagtca | ggacaataac | 540 |
| tgtgagggaa | aatgcaaccc | cctgattttg | cagttcaccc | agaaggggaa | acaagcctct | 600 |
| tgggacggac | ctaagatgtg | gggattgcga | ctataccgta | caggatatga | ccctatcgcc | 660 |
| ttattcacgg | tatcccggca | ggtgtcaacc | attacgccgc | tcaggcaat | gggaccaaac | 720 |
| ctagtcttac | ctgatcaaaa | accccatcc | cgacaatctc | aaacagggtc | caaagtggcg | 780 |
| acccagaggc | cccaaacgaa | tgaaagcgcc | ccaaggtctg | ttgccccac | accgtgggt | 840 |
| cccaaacgga | ttgggaccgg | agataggtta | ataaatttag | tacaagggac | atacctagcc | 900 |
| ttaaatgcca | ccgaccccaa | caaaactaaa | gactgttggc | tctgcctggt | ttctcgacca | 960 |
| ccctattacg | aagggattgc | aatcttaggt | aactacagca | ccaaacaaa | ccctcccca | 1020 |
| tcctgcctat | ctattccgca | acacaagctg | accatatctg | aagtatcagg | gcaaggactg | 1080 |
| tgcataggga | ctgttcctaa | gacccaccag | gctttgtgca | ataagacgca | acagggacat | 1140 |
| acaggggcgc | actatctagc | cgccccaat | ggcacctatt | gggcctgtaa | cactggactc | 1200 |
| accccatgca | tttccatggc | ggtgctcaat | tggacctctg | attttgtgt | cttaatcgaa | 1260 |
| ttatggccca | gagtgactta | ccatcaaccc | gaatatgtgt | acacacattt | tgccaaagct | 1320 |
| gtcaggttcc | gaagagaacc | aatatcacta | actgttgccc | tcatgttggg | aggactcact | 1380 |
| gtaggggca | tagccgcggg | ggtcggaaca | gggactaaag | ccctccttga | acagcccag | 1440 |
| ttcagacaac | tacaaatggc | catgcacaca | gacatccagg | ccctagaaga | gtcaattagt | 1500 |
| gccttagaaa | agtccctgac | ctcccttttct | gaagtagtct | tacaaaacag | acggggccta | 1560 |
| gatattctat | tcctacaaga | gggagggctc | tgtgccgcat | taaagaaga | atgttgcttc | 1620 |
| tatgcggatc | acaccggact | cgtccgagac | aatatggcta | aattaagaga | aagactaaaa | 1680 |
| cagcggcaac | aactgtttga | ctcccaacag | ggatggtttg | aaggatggtt | caacaggtcc | 1740 |
| ccctggttta | caaccctaat | ttcctccatt | atgggcccct | tactaatcct | actcctaatt | 1800 |
| ctcctcttcg | gccatgcat | ccttaacaga | ttagtacaat | tcgtaaaaga | cagaatatct | 1860 |
| gtggtacaag | ccttaatttt | aacccaacag | taccaacaga | taaagcaata | cgatccggac | 1920 | cgacca                                                            1926

<210> SEQ ID NO 96
<211> LENGTH: 642
<212> TYPE: PRT
<213> ORGANISM: Feline leukemia virus

<400> SEQUENCE: 96

Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Ile Val Leu Ser Pro Thr Asn Val Lys
                85                  90                  95

His Gly Ala Arg Tyr Pro Ser Ser Lys Tyr Gly Cys Lys Thr Thr Asp
            100                 105                 110

Arg Lys Lys Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175

Gln Asp Asn Asn Cys Glu Gly Lys Cys Asn Pro Leu Ile Leu Gln Phe
            180                 185                 190

Thr Gln Lys Gly Lys Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Ile Pro Gln His Lys Leu Thr Ile
            340                 345                 350

Ser Glu Val Ser Gly Gln Gly Leu Cys Ile Gly Thr Val Pro Lys Thr
        355                 360                 365

-continued

```
His Gln Ala Leu Cys Asn Lys Thr Gln Gln Gly His Thr Gly Ala His
        370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
            405                 410                 415

Val Leu Ile Glu Leu Trp Pro Arg Val Thr Tyr His Gln Pro Glu Tyr
                420                 425                 430

Val Tyr Thr His Phe Ala Lys Ala Val Arg Phe Arg Glu Pro Ile
            435                 440                 445

Ser Leu Thr Val Ala Leu Met Leu Gly Gly Leu Thr Val Gly Gly Ile
450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro
```

<210> SEQ ID NO 97
<211> LENGTH: 1977
<212> TYPE: DNA
<213> ORGANISM: Porcine endogenous retrovirus

<400> SEQUENCE: 97

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc agggccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg ccatgggag atggaaagat     540 tggcaacagc gggtacaaaa agatgtacga aataagcaaa taagctgtca ttcgttagac     600
```

```
ctagattact taaaaataag tttcactgaa aaaggaaaac aagaaaatat tcaaaagtgg    660
gtaaatggta tgtcttgggg aatagtgtac tatagaggct ctgggagaaa gaaaggatct    720
gttctgacta ttcgcctcag aatagaaact cagatggaac ctccggttgc ataggacca    780
aataagggtt tggccgaaca aggacctcca atccaagaac agaggccatc tcctaacccc    840
tctgattaca atacaacctc tggatcagtc cccactgagc ctaacatcac tattaaaaca    900
ggggcgaaac ttttaacct catccaggga gcttttcaag ctcttaactc cacgactcca    960
gaggctacct cttcttgttg ctttgctta gcttcgggcc caccttacta tgagggaatg   1020
gctagaggag ggaaattcaa tgtgacaaag gaacatagag accaatgtac atggggatcc   1080
caaaataagc ttacccttac tgaggtttct ggaaaaggca cctgcatagg gatggttccc   1140
ccatcccacc aacacctttg taaccacact gaagcctta atcgaacctc tgagagtcag   1200
tatctggtac ctggttatga caggtggtgg gcatgtaata ctggattaac cccttgtgtt   1260
tccaccttgg ttttcaacca aactaaagac ttttgcgtta tggtccaaat tgtccccgg   1320
gtgtactact atcccgaaaa agcagtcctt gatgaatatg actatagata taatcggcca   1380
aaaagagagc ccatatccct gacactagct gtaatgctcg gattgggagt ggctgcaggc   1440
gtgggaacag aacggctgc cctaatcaca ggaccgcaac agctggagaa aggacttagt   1500
aacctacatc gaattgtaac ggaaaatctc caagccctag aaaaatctgt cagtaacctg   1560
gaggaatccc taacctcctt atctgaagtg gttctacaga acagaagggg gttagatctg   1620
ttatttctaa aagaaggagg gttatgtgta gccttaaaag aggaatgctg cttctatgta   1680
gatcactcag gagccatcag agactccatg agcaagctta gagaaaggtt agagaggcgt   1740
cgaagggaaa gagaggctga ccaggggtgg tttgaaggat ggttcaacag gtctccttgg   1800
atggctaccc tactttctgc tttaacagga cccttaatag tcctcctcct gttactcaca   1860
gttgggccat gtattattaa caagttaatt gccttcatta gaacgaat aagtgcagtc   1920
cagatcatgg tacttagaca acagtaccaa agcccgtcta gcagagaagc tggccgc     1977
```

<210> SEQ ID NO 98
<211> LENGTH: 659
<212> TYPE: PRT
<213> ORGANISM: Porcine endogenous retrovirus

<400> SEQUENCE: 98

```
Met His Pro Thr Leu Ser Arg Arg His Leu Pro Ile Arg Gly Gly Lys
  1               5                  10                  15

Pro Lys Arg Leu Lys Ile Pro Leu Ser Phe Ala Ser Ile Ala Trp Phe
             20                  25                  30

Leu Thr Leu Ser Ile Thr Pro Gln Val Asn Gly Lys Arg Leu Val Asp
         35                  40                  45

Ser Pro Asn Ser His Lys Pro Leu Ser Leu Thr Trp Leu Leu Thr Asp
     50                  55                  60

Ser Gly Thr Gly Ile Asn Ile Asn Ser Thr Gln Gly Glu Ala Pro Leu
 65                  70                  75                  80

Gly Thr Trp Trp Pro Glu Leu Tyr Val Cys Leu Arg Ser Val Ile Pro
                 85                  90                  95

Gly Leu Asn Asp Gln Ala Thr Pro Pro Asp Val Leu Arg Ala Tyr Gly
            100                 105                 110

Phe Tyr Val Cys Pro Gly Pro Pro Asn Asn Glu Glu Tyr Cys Gly Asn
        115                 120                 125

Pro Gln Asp Phe Phe Cys Lys Gln Trp Ser Cys Val Thr Ser Asn Asp
```

-continued

```
            130                 135                 140
Gly Asn Trp Lys Trp Pro Val Ser Gln Gln Asp Arg Val Ser Tyr Ser
145                 150                 155                 160

Phe Val Asn Asn Pro Thr Ser Tyr Asn Gln Phe Asn Tyr Gly His Gly
                    165                 170                 175

Arg Trp Lys Asp Trp Gln Gln Arg Val Gln Lys Asp Val Arg Asn Lys
                    180                 185                 190

Gln Ile Ser Cys His Ser Leu Asp Leu Asp Tyr Leu Lys Ile Ser Phe
                    195                 200                 205

Thr Glu Lys Gly Lys Gln Glu Asn Ile Gln Lys Trp Val Asn Gly Met
            210                 215                 220

Ser Trp Gly Ile Val Tyr Tyr Arg Gly Ser Gly Arg Lys Lys Gly Ser
225                 230                 235                 240

Val Leu Thr Ile Arg Leu Arg Ile Glu Thr Gln Met Glu Pro Pro Val
                    245                 250                 255

Ala Ile Gly Pro Asn Lys Gly Leu Ala Glu Gln Gly Pro Pro Ile Gln
                    260                 265                 270

Glu Gln Arg Pro Ser Pro Asn Pro Ser Asp Tyr Asn Thr Thr Ser Gly
            275                 280                 285

Ser Val Pro Thr Glu Pro Asn Ile Thr Ile Lys Thr Gly Ala Lys Leu
290                 295                 300

Phe Asn Leu Ile Gln Gly Ala Phe Gln Ala Leu Asn Ser Thr Thr Pro
305                 310                 315                 320

Glu Ala Thr Ser Ser Cys Trp Leu Cys Leu Ala Ser Gly Pro Pro Tyr
                    325                 330                 335

Tyr Glu Gly Met Ala Arg Gly Gly Lys Phe Asn Val Thr Lys Glu His
                    340                 345                 350

Arg Asp Gln Cys Thr Trp Gly Ser Gln Asn Lys Leu Thr Leu Thr Glu
            355                 360                 365

Val Ser Gly Lys Gly Thr Cys Ile Gly Met Val Pro Pro Ser His Gln
370                 375                 380

His Leu Cys Asn His Thr Glu Ala Phe Asn Arg Thr Ser Glu Ser Gln
385                 390                 395                 400

Tyr Leu Val Pro Gly Tyr Asp Arg Trp Trp Ala Cys Asn Thr Gly Leu
                    405                 410                 415

Thr Pro Cys Val Ser Thr Leu Val Phe Asn Gln Thr Lys Asp Phe Cys
                    420                 425                 430

Val Met Val Gln Ile Val Pro Arg Val Tyr Tyr Pro Glu Lys Ala
                    435                 440                 445

Val Leu Asp Glu Tyr Asp Tyr Arg Tyr Asn Arg Pro Lys Arg Glu Pro
            450                 455                 460

Ile Ser Leu Thr Leu Ala Val Met Leu Gly Leu Gly Val Ala Ala Gly
465                 470                 475                 480

Val Gly Thr Gly Thr Ala Ala Leu Ile Thr Gly Pro Gln Gln Leu Glu
                    485                 490                 495

Lys Gly Leu Ser Asn Leu His Arg Ile Val Thr Glu Asn Leu Gln Ala
                    500                 505                 510

Leu Glu Lys Ser Val Ser Asn Leu Glu Glu Ser Leu Thr Ser Leu Ser
            515                 520                 525

Glu Val Val Leu Gln Asn Arg Arg Gly Leu Asp Leu Leu Phe Leu Lys
            530                 535                 540

Glu Gly Gly Leu Cys Val Ala Leu Lys Glu Glu Cys Cys Phe Tyr Val
545                 550                 555                 560
```

| | | | | | | | | | | | |
|---|---|---|---|---|---|---|---|---|---|---|---|
| Asp | His | Ser | Gly | Ala | Ile | Arg | Asp | Ser | Met | Ser | Lys | Leu | Arg | Glu | Arg |
| | | | 565 | | | | 570 | | | | 575 | | | | |

Leu Glu Arg Arg Arg Glu Arg Glu Ala Asp Gln Gly Trp Phe Glu
            580             585             590

Gly Trp Phe Asn Arg Ser Pro Trp Met Ala Thr Leu Leu Ser Ala Leu
        595             600             605

Thr Gly Pro Leu Ile Val Leu Leu Leu Leu Thr Val Gly Pro Cys
    610             615             620

Ile Ile Asn Lys Leu Ile Ala Phe Ile Arg Glu Arg Ile Ser Ala Val
625             630             635             640

Gln Ile Met Val Leu Arg Gln Gln Tyr Gln Ser Pro Ser Arg Glu
            645             650             655

Ala Gly Arg

```
<210> SEQ ID NO 99
<211> LENGTH: 1464
<212> TYPE: DNA
<213> ORGANISM: Simian T-cell lymphotropic virus type 1

<400> SEQUENCE: 99
atgggtaagt tcttgcctc tttgacttta ttcttccagt tctgccccct cattctcggt        60
gattacagcc ccagctgctg tactctcacc attggagtct cctcatacca ttctaaaccc       120
tgcaatcctg cccagccggt tgttcatgg actctcgacc tactggccct ttcagcagat       180
caagccctac agcccccctg ccctaatcta ataggttact ccagctacca tgccacctat       240
tccctatatc tatttcctca ttggattaaa aagccaaacc gaaacggtgg aggctactat       300
tcagcatctt attcagaccc ttgttcccta aagtgcccat acctagggtg ccaatcatgg       360
acctgccctt ataccaggagc cgtctccagc ccctactgga atttcaaca agatgtcaat       420 tttactcaag aagtctcacg cctcaatctt aatctccatt tttcaaaatg cggtttctcc       480
ttctcccttc tagttgacgc cccaggatat gaccccatct ggttccttaa caccgaaccc       540
aaccaactgc ctcccaccgc ccctcctcta ctccccccact ctaacctaga ccacatcctc       600
gagccctcta ccatggaa atcaaaactt ctgactcttg tccaactaac cctacagagc       660
actaactata cttgcattgt ctgtgtagat cgtgccagcc tatccacttg gcacgtcctg       720
tactctccca cgcctctgt tccatcctct tcttctaccc ccctccttta cccatcgtta       780
gcgcttccag cccccacct gacgttacca tttaactgga cccactgctt tgaccccag       840 attcaagcta tagtcctcc cccctgtctt aactccctca tcctgccccc cttttccttg       900
tcacctgttc ccaccctagg atcccgttcc cgccgagcgg taccggtggc ggtctggctt       960
gtctccgccc tggccatggg agccgggatg gctggcggga ttaccggctc catgtccctt      1020
gcctcaggaa ggagcctcct acatgaggtg gacaaggata tttcccaatt aactcaagca      1080
atagtcaaaa accacaaaaa tctactcaaa attgcgcagt atgctgccca gaacagacga      1140
ggccttgatc tcctgttctg ggagcaagga ggattatgca aagcactaca agaacagtgc      1200 tgtttttctaa atattaccaa ttcccatgtc tcaatactac aagaacgacc cccccttgag      1260
aatcgagtcc tcaccggctg gggccttaac tgggaccttg gcctctcaca gtgggctcga      1320
gaggccttac aaactggaat caccttgtt gcactactcc ttcttgttat ccttgcagga      1380
ccatgcatcc tccgtcaact acgacacctc ccctcgcgcg tcagataccc ccattattct      1440
cttataaacc ctgagtcatc cctg                                             1464

<210> SEQ ID NO 100
```

```
<211> LENGTH: 488
<212> TYPE: PRT
<213> ORGANISM: Simian T-cell lymphotropic virus type 1

<400> SEQUENCE: 100
```

| | | | | | | | | | | | | | | |
|---|---|---|---|---|---|---|---|---|---|---|---|---|---|---|
| Met | Gly | Lys | Phe | Leu | Ala | Ser | Leu | Thr | Leu | Phe | Phe | Gln | Phe | Cys | Pro |
| 1 | | | | 5 | | | | | 10 | | | | | 15 | |

| Leu | Ile | Leu | Gly | Asp | Tyr | Ser | Pro | Ser | Cys | Cys | Thr | Leu | Thr | Ile | Gly |
|---|---|---|---|---|---|---|---|---|---|---|---|---|---|---|---|
| | | | 20 | | | | | 25 | | | | | 30 | | |

| Val | Ser | Ser | Tyr | His | Ser | Lys | Pro | Cys | Asn | Pro | Ala | Gln | Pro | Val | Cys |
|---|---|---|---|---|---|---|---|---|---|---|---|---|---|---|---|
| | | 35 | | | | | 40 | | | | | 45 | | | |

| Ser | Trp | Thr | Leu | Asp | Leu | Leu | Ala | Leu | Ser | Ala | Asp | Gln | Ala | Leu | Gln |
|---|---|---|---|---|---|---|---|---|---|---|---|---|---|---|---|
| | 50 | | | | | 55 | | | | | 60 | | | | |

| Pro | Pro | Cys | Pro | Asn | Leu | Ile | Gly | Tyr | Ser | Ser | Tyr | His | Ala | Thr | Tyr |
|---|---|---|---|---|---|---|---|---|---|---|---|---|---|---|---|
| 65 | | | | | 70 | | | | | 75 | | | | | 80 |

| Ser | Leu | Tyr | Leu | Phe | Pro | His | Trp | Ile | Lys | Lys | Pro | Asn | Arg | Asn | Gly |
|---|---|---|---|---|---|---|---|---|---|---|---|---|---|---|---|
| | | | | 85 | | | | | 90 | | | | | 95 | |

| Gly | Gly | Tyr | Tyr | Ser | Ala | Ser | Tyr | Ser | Asp | Pro | Cys | Ser | Leu | Lys | Cys |
|---|---|---|---|---|---|---|---|---|---|---|---|---|---|---|---|
| | | | 100 | | | | | 105 | | | | | 110 | | |

| Pro | Tyr | Leu | Gly | Cys | Gln | Ser | Trp | Thr | Cys | Pro | Tyr | Thr | Gly | Ala | Val |
|---|---|---|---|---|---|---|---|---|---|---|---|---|---|---|---|
| | | 115 | | | | | 120 | | | | | 125 | | | |

| Ser | Ser | Pro | Tyr | Trp | Lys | Phe | Gln | Gln | Asp | Val | Asn | Phe | Thr | Gln | Glu |
|---|---|---|---|---|---|---|---|---|---|---|---|---|---|---|---|
| | 130 | | | | | 135 | | | | | 140 | | | | |

| Val | Ser | Arg | Leu | Asn | Leu | Asn | Leu | His | Phe | Ser | Lys | Cys | Gly | Phe | Ser |
|---|---|---|---|---|---|---|---|---|---|---|---|---|---|---|---|
| 145 | | | | | 150 | | | | | 155 | | | | | 160 |

| Phe | Ser | Leu | Leu | Val | Asp | Ala | Pro | Gly | Tyr | Asp | Pro | Ile | Trp | Phe | Leu |
|---|---|---|---|---|---|---|---|---|---|---|---|---|---|---|---|
| | | | | 165 | | | | | 170 | | | | | 175 | |

| Asn | Thr | Glu | Pro | Asn | Gln | Leu | Pro | Pro | Thr | Ala | Pro | Pro | Leu | Leu | Pro |
|---|---|---|---|---|---|---|---|---|---|---|---|---|---|---|---|
| | | | 180 | | | | | 185 | | | | | 190 | | |

| His | Ser | Asn | Leu | Asp | His | Ile | Leu | Glu | Pro | Ser | Ile | Pro | Trp | Lys | Ser |
|---|---|---|---|---|---|---|---|---|---|---|---|---|---|---|---|
| | | 195 | | | | | 200 | | | | | 205 | | | |

| Lys | Leu | Leu | Thr | Leu | Val | Gln | Leu | Thr | Leu | Gln | Ser | Thr | Asn | Tyr | Thr |
|---|---|---|---|---|---|---|---|---|---|---|---|---|---|---|---|
| | 210 | | | | | 215 | | | | | 220 | | | | |

| Cys | Ile | Val | Cys | Val | Asp | Arg | Ala | Ser | Leu | Ser | Thr | Trp | His | Val | Leu |
|---|---|---|---|---|---|---|---|---|---|---|---|---|---|---|---|
| 225 | | | | | 230 | | | | | 235 | | | | | 240 |

| Tyr | Ser | Pro | Asn | Ala | Ser | Val | Pro | Ser | Ser | Ser | Thr | Pro | Leu | Leu |
|---|---|---|---|---|---|---|---|---|---|---|---|---|---|---|
| | | | | 245 | | | | | 250 | | | | | 255 |

| Tyr | Pro | Ser | Leu | Ala | Leu | Pro | Ala | Pro | His | Leu | Thr | Leu | Pro | Phe | Asn |
|---|---|---|---|---|---|---|---|---|---|---|---|---|---|---|---|
| | | | 260 | | | | | 265 | | | | | 270 | | |

| Trp | Thr | His | Cys | Phe | Asp | Pro | Gln | Ile | Gln | Ala | Ile | Val | Ser | Ser | Pro |
|---|---|---|---|---|---|---|---|---|---|---|---|---|---|---|---|
| | | 275 | | | | | 280 | | | | | 285 | | | |

| Cys | Leu | Asn | Ser | Leu | Ile | Leu | Pro | Pro | Phe | Ser | Leu | Ser | Pro | Val | Pro |
|---|---|---|---|---|---|---|---|---|---|---|---|---|---|---|---|
| | 290 | | | | | 295 | | | | | 300 | | | | |

| Thr | Leu | Gly | Ser | Arg | Ser | Arg | Arg | Ala | Val | Pro | Val | Ala | Val | Trp | Leu |
|---|---|---|---|---|---|---|---|---|---|---|---|---|---|---|---|
| 305 | | | | | 310 | | | | | 315 | | | | | 320 |

| Val | Ser | Ala | Leu | Ala | Met | Gly | Ala | Gly | Met | Ala | Gly | Ile | Thr | Gly |
|---|---|---|---|---|---|---|---|---|---|---|---|---|---|---|
| | | | | 325 | | | | | 330 | | | | | 335 |

| Ser | Met | Ser | Leu | Ala | Ser | Gly | Arg | Ser | Leu | Leu | His | Glu | Val | Asp | Lys |
|---|---|---|---|---|---|---|---|---|---|---|---|---|---|---|---|
| | | | 340 | | | | | 345 | | | | | 350 | | |

| Asp | Ile | Ser | Gln | Leu | Thr | Gln | Ala | Ile | Val | Lys | Asn | His | Lys | Asn | Leu |
|---|---|---|---|---|---|---|---|---|---|---|---|---|---|---|---|
| | | 355 | | | | | 360 | | | | | 365 | | | |

| Leu | Lys | Ile | Ala | Gln | Tyr | Ala | Ala | Gln | Asn | Arg | Arg | Gly | Leu | Asp | Leu |
|---|---|---|---|---|---|---|---|---|---|---|---|---|---|---|---|
| | 370 | | | | | 375 | | | | | 380 | | | | |

| Leu | Phe | Trp | Glu | Gln | Gly | Gly | Leu | Cys | Lys | Ala | Leu | Gln | Glu | Gln | Cys |
|---|---|---|---|---|---|---|---|---|---|---|---|---|---|---|---|
| 385 | | | | | 390 | | | | | 395 | | | | | 400 |

```
Cys Phe Leu Asn Ile Thr Asn Ser His Val Ser Ile Leu Gln Glu Arg
            405                 410                 415

Pro Pro Leu Glu Asn Arg Val Leu Thr Gly Trp Gly Leu Asn Trp Asp
            420                 425                 430

Leu Gly Leu Ser Gln Trp Ala Arg Glu Ala Leu Gln Thr Gly Ile Thr
            435                 440                 445

Leu Val Ala Leu Leu Leu Val Ile Leu Ala Gly Pro Cys Ile Leu
            450                 455                 460

Arg Gln Leu Arg His Leu Pro Ser Arg Val Arg Tyr Pro His Tyr Ser
465                 470                 475                 480

Leu Ile Asn Pro Glu Ser Ser Leu
            485

<210> SEQ ID NO 101
<211> LENGTH: 2025
<212> TYPE: DNA
<213> ORGANISM: Friend virus

<400> SEQUENCE: 101
atggcgtgtt caacgctccc aaaatcccct aaagataaga ttgacccgcg ggacctccta      60
atccccttaa ttctcttcct gtctctcaaa ggggccagat ccgcagcacc cggctccagc     120
cctcaccagg tctacaacat tacctgggaa gtgaccaatg gggatcggga gacagtatgg     180
gcaatatcag gcaaccaccc tctgtggact tggtggccag tcctcacccc agatttgtgt     240
atgttagctc tcagtgggcc gccccactgg gggctagagt atcaggcccc ctattcctcg     300 ccccggggc cccttgttg ctcagggagc agcgggagca gtgcaggctg ttccagagac     360
tgcgacgagc ccttgacctc cctcacccct cggtgcaaca ctgcctggaa cagacttaag     420
ctagaccagg taactcataa atcaagtgag ggatttttatg tctgccccgg gtcacatcgc     480
ccccgggaag ccaagtcctg tggaggtcca gactccttct actgtgcctc ttggggctgc     540
gagacaaccg gtagagtata ctggaagccc tcctcctctt gggactacat cacagtggac     600
aacaatctca ccactagcca ggctgtccag gtatgcaaag acaataagtg gtgcaatccc     660
ttggctatcc agtttacaaa cgccgggaaa caggtcacct catggacaac tggacactat     720
tggggtctac gtctttatgt ctctggggcgg gacccggggc ttactttcgg gatccgactc     780
agatatcaaa atctaggacc tcgggtcccg ataggaccga accccgtcct ggcagaccaa     840
ctttcgctcc cgcgacctaa tccctaccc aaacctgcca gtctccccc cgcctctaat     900 tcgactccca cattgatttc cccgtccccc actccactc agccccgcc agcaggaacg     960 ggagacaggt tactaaatct agtacaggga gcttaccagg cactcaacct taccaaccct    1020
gataaaactc aagagtgctg ttatgccta gtgtctggac ccccctatta cgaaggggtt    1080
gccgtcctag gtacttattc aaccatacc tctgccccag ctaactgctc cgtggcctcc    1140
caacacaagt tgaccctgtc cgaagtgact ggacgggac tctgcatagg aacagtccca    1200
aaaactcacc aggccctgtg caacactacc cttaagatag acaaaggc ttactatcta    1260 gttgccccca caggaactac gtgggcatgt aacactggac tcactccatg cctatctgcc    1320
accgtgctta tcgcaccac tgactattgc gttctcgtag agttatggcc cagggtcacc    1380
taccatcctc ccagttacgt ctatagccag tttgaaaaat cctatagaca taaaagagaa    1440
ccagtgtcct taaccttggc cctattatta ggtgggctaa ctatgggtgg catcgccgcg    1500
ggagtaggga caggaactac cgccctggtc gccacccagc agttccagca gctccatgct    1560
gccgtacaag atgatctcaa agaagtcgaa aagtcaatta ctaacctaga aaagtctctt    1620
```

-continued

```
acttcgttgt ctgaggttgt gctgcagaat cgacgaggcc tagacctgtt gttcctaaaa    1680
gaaggaggac tgtgtgctgc cctaaaagaa gaatgttgtt tctatgctga ccatacaggc    1740
ctagtaagag atagtatggc caaattaaga gagagactca ctcagagaca aaaactattt    1800
gagtcgagcc aaggatggtt cgaaggattg tttaacagat ccccctggtt taccacgtta    1860
atatccacca tcatggggcc tctcattata ctcctactaa ttctgctttt tggaccctgc    1920
attcttaatc gattagttca atttgttaaa gacaggatct cagtagtcca ggctttagtc    1980
ctgactcaac aataccacca gctaaaacca ctagaatacg agcca                    2025
```

<210> SEQ ID NO 102
<211> LENGTH: 675
<212> TYPE: PRT
<213> ORGANISM: Friend virus

<400> SEQUENCE: 102

```
Met Ala Cys Ser Thr Leu Pro Lys Ser Pro Lys Asp Lys Ile Asp Pro
 1               5                  10                  15

Arg Asp Leu Leu Ile Pro Leu Ile Leu Phe Leu Ser Leu Lys Gly Ala
                20                  25                  30

Arg Ser Ala Ala Pro Gly Ser Ser Pro His Gln Val Tyr Asn Ile Thr
            35                  40                  45

Trp Glu Val Thr Asn Gly Asp Arg Glu Thr Val Trp Ala Ile Ser Gly
        50                  55                  60

Asn His Pro Leu Trp Thr Trp Trp Pro Val Leu Thr Pro Asp Leu Cys
 65                  70                  75                  80

Met Leu Ala Leu Ser Gly Pro Pro His Trp Gly Leu Glu Tyr Gln Ala
                85                  90                  95

Pro Tyr Ser Ser Pro Pro Gly Pro Pro Cys Cys Ser Gly Ser Ser Gly
               100                 105                 110

Ser Ser Ala Gly Cys Ser Arg Asp Cys Asp Glu Pro Leu Thr Ser Leu
           115                 120                 125

Thr Pro Arg Cys Asn Thr Ala Trp Asn Arg Leu Lys Leu Asp Gln Val
       130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
               165                 170                 175

Ser Trp Gly Cys Glu Thr Thr Gly Arg Val Tyr Trp Lys Pro Ser Ser
           180                 185                 190

Ser Trp Asp Tyr Ile Thr Val Asp Asn Asn Leu Thr Thr Ser Gln Ala
       195                 200                 205

Val Gln Val Cys Lys Asp Asn Lys Trp Cys Asn Pro Leu Ala Ile Gln
   210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
               245                 250                 255

Gly Ile Arg Leu Arg Tyr Gln Asn Leu Gly Pro Arg Val Pro Ile Gly
           260                 265                 270

Pro Asn Pro Val Leu Ala Asp Gln Leu Ser Leu Pro Arg Pro Asn Pro
       275                 280                 285

Leu Pro Lys Pro Ala Lys Ser Pro Pro Ala Ser Asn Ser Thr Pro Thr
   290                 295                 300
```

```
Leu Ile Ser Pro Ser Pro Thr Pro Thr Gln Pro Pro Ala Gly Thr
305                 310                 315                 320

Gly Asp Arg Leu Leu Asn Leu Val Gln Gly Ala Tyr Gln Ala Leu Asn
            325                 330                 335

Leu Thr Asn Pro Asp Lys Thr Gln Glu Cys Trp Leu Cys Leu Val Ser
        340                 345                 350

Gly Pro Pro Tyr Tyr Glu Gly Val Ala Val Leu Gly Thr Tyr Ser Asn
    355                 360                 365

His Thr Ser Ala Pro Ala Asn Cys Ser Val Ala Ser Gln His Lys Leu
370                 375                 380

Thr Leu Ser Glu Val Thr Gly Arg Gly Leu Cys Ile Gly Thr Val Pro
385                 390                 395                 400

Lys Thr His Gln Ala Leu Cys Asn Thr Thr Leu Lys Ile Asp Lys Gly
                405                 410                 415

Ser Tyr Tyr Leu Val Ala Pro Thr Gly Thr Thr Trp Ala Cys Asn Thr
            420                 425                 430

Gly Leu Thr Pro Cys Leu Ser Ala Thr Val Leu Asn Arg Thr Thr Asp
        435                 440                 445

Tyr Cys Val Leu Val Glu Leu Trp Pro Arg Val Thr Tyr His Pro Pro
    450                 455                 460

Ser Tyr Val Tyr Ser Gln Phe Glu Lys Ser Tyr Arg His Lys Arg Glu
465                 470                 475                 480

Pro Val Ser Leu Thr Leu Ala Leu Leu Leu Gly Gly Leu Thr Met Gly
                485                 490                 495

Gly Ile Ala Ala Gly Val Gly Thr Gly Thr Thr Ala Leu Val Ala Thr
            500                 505                 510

Gln Gln Phe Gln Gln Leu His Ala Ala Val Gln Asp Asp Leu Lys Glu
        515                 520                 525

Val Glu Lys Ser Ile Thr Asn Leu Glu Lys Ser Leu Thr Ser Leu Ser
    530                 535                 540

Glu Val Val Leu Gln Asn Arg Arg Gly Leu Asp Leu Leu Phe Leu Lys
545                 550                 555                 560

Glu Gly Gly Leu Cys Ala Ala Leu Lys Glu Glu Cys Cys Phe Tyr Ala
                565                 570                 575

Asp His Thr Gly Leu Val Arg Asp Ser Met Ala Lys Leu Arg Glu Arg
            580                 585                 590

Leu Thr Gln Arg Gln Lys Leu Phe Glu Ser Ser Gln Gly Trp Phe Glu
        595                 600                 605

Gly Leu Phe Asn Arg Ser Pro Trp Phe Thr Thr Leu Ile Ser Thr Ile
    610                 615                 620

Met Gly Pro Leu Ile Ile Leu Leu Leu Ile Leu Leu Phe Gly Pro Cys
625                 630                 635                 640

Ile Leu Asn Arg Leu Val Gln Phe Val Lys Asp Arg Ile Ser Val Val
                645                 650                 655

Gln Ala Leu Val Leu Thr Gln Gln Tyr His Gln Leu Lys Pro Leu Glu
            660                 665                 670

Tyr Glu Pro
        675

<210> SEQ ID NO 103
<211> LENGTH: 1926
<212> TYPE: DNA
<213> ORGANISM: Artificial sequence
<220> FEATURE:
<223> OTHER INFORMATION: Description of Artificial Sequence: Synthetic
      Mutated FeLV ENV
```

<220> FEATURE:
<221> NAME/KEY: modified_base
<222> LOCATION: (1579)..(1581)
<223> OTHER INFORMATION: cgt, cgc, cga, cgg, aga or agg

<400> SEQUENCE: 103

| | | | | | | |
|---|---|---|---|---|---|---|
| atggaaagtc | caacgcaccc | aaaaccctct | aaagataaga | ctctctcgtg | gaacttagtg | 60 |
| tttctggtgg | ggatcttatt | cacaatagac | ataggaatgg | ccaatcctag | tccacaccaa | 120 |
| atatataatg | taacttgggt | aataaccaat | gtacaaacta | acacccaagc | taatgccacc | 180 |
| tctatgttag | gaaccttaac | cgatgtctac | cctaccctac | atgttgactt | atgtgaccta | 240 |
| gtgggagaca | cctgggaacc | tatagtccta | agcccaacca | atgtaaaaca | cggggcacgt | 300 |
| taccccttcct | caaaatatgg | atgtaaaact | acagatagaa | aaaaacagca | acagacatac | 360 |
| cccttttacg | tctgccccgg | acatgccccc | tcgctggggc | caaagggaac | acattgtgga | 420 |
| ggggcacaag | atgggttttg | tgccgcatgg | ggatgtgaaa | ccaccggaga | agcttggtgg | 480 |
| aagccctcct | cctcatggga | ctatatcaca | gtaaaaagag | ggagtagtca | ggacaataac | 540 |
| tgtgagggaa | aatgcaaccc | cctgattttg | cagttcaccc | agaaggggaa | acaagcctct | 600 |
| tgggacggac | ctaagatgtg | gggattgcga | ctataccgta | caggatatga | ccctatcgcc | 660 |
| ttattcacgg | tatcccggca | ggtgtcaacc | attacgccgc | ctcaggcaat | gggaccaaac | 720 |
| ctagtcttac | ctgatcaaaa | accccccatcc | cgacaatctc | aaacagggtc | caaagtggcg | 780 |
| acccagaggc | cccaaacgaa | tgaaagcgcc | ccaaggtctg | ttgcccccac | caccgtgggt | 840 |
| cccaaacgga | ttgggaccgg | agataggtta | ataaatttag | tacaagggac | atacctagcc | 900 |
| ttaaatgcca | ccgaccccaa | caaaactaaa | gactgttggc | tctgcctggt | ttctcgacca | 960 |
| ccctattacg | aagggattgc | aatcttaggt | aactacagca | accaaacaaa | ccctccccca | 1020 |
| tcctgcctat | ctattccgca | acacaagctg | accatatctg | aagtatcagg | gcaaggactg | 1080 |
| tgcatagggc | ctgttcctaa | gacccaccag | gctttgtgca | ataagacgca | acagggacat | 1140 |
| acagggggcgc | actatctagc | cgcccccaat | ggcacctatt | gggcctgtaa | cactggactc | 1200 |
| accccatgca | tttccatggc | ggtgctcaat | tggacctctg | attttttgtgt | cttaatcgaa | 1260 |
| ttatggccca | gagtgactta | ccatcaaccc | gaatatgtgt | acacacattt | tgccaaagct | 1320 |
| gtcaggttcc | gaagagaacc | aatatcacta | actgttgccc | tcatgttggg | aggactcact | 1380 |
| gtaggggggca | tagccgcggg | ggtcggaaca | gggactaaag | ccctccttga | aacagcccag | 1440 |
| ttcagacaac | tacaaatggc | catgcacaca | gacatccagg | ccctagaaga | gtcaattagt | 1500 |
| gccttagaaa | agtccctgac | ctcccttct | gaagtagtct | tacaaaacag | acggggccta | 1560 |
| gatattctat | tcctacaann | nggagggctc | tgtgccgcat | taaaagaaga | atgttgcttc | 1620 |
| tatgcggatc | acaccggact | cgtccgagac | aatatggcta | aattaagaga | aagactaaaa | 1680 |
| cagcggcaac | aactgtttga | ctcccaacag | ggatggtttg | aaggatggtt | caacaggtcc | 1740 |
| ccctggttta | caaccctaat | ttcctccatt | atgggcccct | tactaatcct | actcctaatt | 1800 |
| ctcctcttcg | gcccatgcat | ccttaacaga | ttagtacaat | tcgtaaaaga | cagaatatct | 1860 |
| gtggtacaag | ccttaatttt | aacccaacag | taccaacaga | taaagcaata | cgatccggac | 1920 |
| cgacca | | | | | | 1926 |

<210> SEQ ID NO 104
<211> LENGTH: 642
<212> TYPE: PRT
<213> ORGANISM: Artificial sequence
<220> FEATURE:
<223> OTHER INFORMATION: Description of Artificial Sequence: Synthetic Mutated FeLV ENV

<400> SEQUENCE: 104

```
Met Glu Ser Pro Thr His Pro Lys Pro Ser Lys Asp Lys Thr Leu Ser
 1               5                  10                  15

Trp Asn Leu Val Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Ile Val Leu Ser Pro Thr Asn Val Lys
                85                  90                  95

His Gly Ala Arg Tyr Pro Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175

Gln Asp Asn Asn Cys Glu Gly Lys Cys Asn Pro Leu Ile Leu Gln Phe
            180                 185                 190

Thr Gln Lys Gly Lys Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Ile Pro Gln His Lys Leu Thr Ile
            340                 345                 350

Ser Glu Val Ser Gly Gln Gly Leu Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
```

```
                        405                 410                 415
Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Arg Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 105
<211> LENGTH: 1926
<212> TYPE: DNA
<213> ORGANISM: Artificial sequence
<220> FEATURE:
<223> OTHER INFORMATION: Description of Artificial Sequence: Synthetic
      Mutated FeLV ENV
<220> FEATURE:
<221> NAME/KEY: modified_base
<222> LOCATION: (1579)..(1581)
<223> OTHER INFORMATION: cgt, cgc, cga, cgg, aga or agg
<220> FEATURE:
<221> NAME/KEY: modified_base
<222> LOCATION: (1597)..(1599)
<223> OTHER INFORMATION: ttt or ttc

<400> SEQUENCE: 105
atggaaagtc aacgcaccc aaaaccctct aaagataaga ctctctcgtg gaacttagtg      60
tttctggtgg ggatcttatt cacaatagac ataggaatgg ccaatcctag tccacaccaa     120 atataataatg taacttgggt aataaccaat gtacaaacta cacccaagc taatgccacc    180 tctatgttag gaaccttaac cgatgtctac cctaccctac atgttgactt atgtgaccta    240
gtgggagaca cctgggaacc tatagtccta agcccaacca atgtaaaaca cggggcacgt    300 taccccttcct caaatatgg atgtaaaact acagatagaa aaaacagca acagacatac    360 ccctttacg tctgccccgg acatgccccc tcgctgggc aaagggaac acattgtgga    420 gggcacaag atgggttttg tgccgcatgg ggatgtgaaa ccaccggaga agcttggtgg    480
```

```
aagccctcct cctcatggga ctatatcaca gtaaaaagag ggagtagtca ggacaataac      540
tgtgagggaa aatgcaaccc cctgattttg cagttcaccc agaaggggaa acaagcctct      600
tgggacggac ctaagatgtg gggattgcga ctataccgta caggatatga ccctatcgcc      660
ttattcacgg tatcccggca ggtgtcaacc attacgccgc ctcaggcaat gggaccaaac      720
ctagtcttac ctgatcaaaa acccccatcc cgacaatctc aaacagggtc caaagtggcg      780
acccagaggc cccaaacgaa tgaaagcgcc ccaaggtctg ttgcccccac caccgtgggt      840
cccaaacgga ttgggaccgg agataggtta ataaatttag tacaagggac atacctagcc      900
ttaaatgcca ccgaccccaa caaaactaaa gactgttggc tctgcctggt ttctcgacca      960
ccctattacg aagggattgc aatcttaggt aactacagca accaaacaaa ccctccccca     1020
tcctgcctat ctattccgca acacaagctg accatatctg aagtatcagg gcaaggactg     1080
tgcataggga ctgttcctaa gacccaccag gctttgtgca ataagacgca acagggacat     1140 acagggcgc actatctagc cgcccccaat ggcacctatt gggcctgtaa cactggactc     1200
accccatgca tttccatggc ggtgctcaat tggacctctg attttgtgt cttaatcgaa     1260 ttatggccca gagtgactta ccatcaaccc gaatatgtgt acacacattt tgccaaagct     1320
gtcaggttcc gaagagaacc aatatcacta actgttgccc tcatgttggg aggactcact     1380 gtaggggca tagccgcggg ggtcggaaca gggactaaag ccctccttga acagcccag     1440 ttcagacaac tacaaatggc catgcacaca gacatccagg ccctagaaga gtcaattagt     1500
gccttagaaa agtccctgac ctccctttct gaagtagtct tacaaaacag acggggccta     1560
gatattctat tcctacaann nggagggctc tgtgccnnnt taaaagaaga atgttgcttc     1620
tatgcggatc acaccggact cgtccgagac aatatggcta aattaagaga aagactaaaa     1680
cagcggcaac aactgtttga ctcccaacag ggatggtttg aaggatggtt caacaggtcc     1740 ccctggtttta caaccctaat ttcctccatt atgggcccct tactaatcct actcctaatt     1800
ctcctcttcg gcccatgcat ccttaacaga ttagtacaat tcgtaaaaga cagaatatct     1860
gtggtacaag ccttaatttt aacccaacag taccaacaga taaagcaata cgatccggac     1920
cgacca                                                               1926
```

<210> SEQ ID NO 106
<211> LENGTH: 642
<212> TYPE: PRT
<213> ORGANISM: Artificial sequence
<220> FEATURE:
<223> OTHER INFORMATION: Description of Artificial Sequence: Synthetic Mutated FeLV ENV

<400> SEQUENCE: 106

```
Met Glu Ser Pro Thr His Pro Lys Pro Ser Lys Asp Lys Thr Leu Ser
  1               5                  10                  15

Trp Asn Leu Val Phe Leu Val Gly Ile Le

```
His Gly Ala Arg Tyr Pro Ser Ser Lys Tyr Gly Cys Lys Thr Thr Asp
                100                 105                 110

Arg Lys Lys Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175

Gln Asp Asn Asn Cys Glu Gly Lys Cys Asn Pro Leu Ile Leu Gln Phe
                180                 185                 190

Thr Gln Lys Gly Lys Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
        210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
                260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
        290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Ile Pro Gln His Lys Leu Thr Ile
                340                 345                 350

Ser Glu Val Ser Gly Gln Gly Leu Cys Ile Gly Thr Val Pro Lys Thr
        355                 360                 365

His Gln Ala Leu Cys Asn Lys Thr Gln Gln Gly His Thr Gly Ala His
        370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
                420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
        450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
                500                 505                 510

Val Leu Gln Asn Arg Arg Gly Leu Asp Ile Leu Phe Leu Gln Arg Gly
        515                 520                 525
```

```
Gly Leu Cys Ala Phe Leu Lys Glu Glu Cys Cys Phe Tyr Ala Asp His
    530                 535                 540
Thr Gly Leu Val Arg Asp Asn Met Ala Lys Leu Arg Glu Arg Leu Lys
545                 550                 555                 560
Gln Arg Gln Gln Leu Phe Asp Ser Gln Gln Gly Trp Phe Glu Gly Trp
                565                 570                 575
Phe Asn Arg Ser Pro Trp Phe Thr Thr Leu Ile Ser Ser Ile Met Gly
            580                 585                 590
Pro Leu Leu Ile Leu Leu Leu Ile Leu Leu Phe Gly Pro Cys Ile Leu
        595                 600                 605
Asn Arg Leu Val Gln Phe Val Lys Asp Arg Ile Ser Val Val Gln Ala
    610                 615                 620
Leu Ile Leu Thr Gln Gln Tyr Gln Gln Ile Lys Gln Tyr Asp Pro Asp
625                 630                 635                 640
Arg Pro

<210> SEQ ID NO 107
<211> LENGTH: 1464
<212> TYPE: DNA
<213> ORGANISM: Artificial sequence
<220> FEATURE:
<223> OTHER INFORMATION: Description of Artificial Sequence: Synthetic
      Mutated HTLV-1 ENV
<220> FEATURE:
<221> NAME/KEY: modified_base
<222> LOCATION: (1165)..(1167)
<223> OTHER INFORMATION: cgt, cgc, cga, cgg, aga or agg

<400> SEQUENCE: 107
atgggtaagt tctctcgccac tttgatttta ttcttccagt tctgccccct catcttcggt      60
gattacagcc ccagctgctg tactctcaca attggagtct cctcatacca ctctaaaccc     120
tgcaatcctg cccagccagt tgttcgtgg acctcgacc tgctggccct ttcagcagat      180
caggccctac agccccctg ccctaaccta gtaagttact ccagctacca tgccacctat     240
tccctatatc tattccctca ttggactaag aagccaaacc gaaatggcgg aggctattat     300
tcagcctctt attcagaccc ttgttcctta aagtgcccat acctggggtg ccaatcatgg     360 acctgccct atacaggagc cgtctccagc ccctactgga gtttcaaca cgatgtcaat     420 tttactcaag aagtttcacg cctcaatatt aatctccatt tttcaaaatg cggtttttcc     480
ttctcccttc tagtcgacgc tccaggatat gaccccatct ggttccttaa taccgaaccc     540
agccaactgc ctcccaccgc ccctcctcta ctccccccact ctaacctaga ccacatcctc     600
gagccctcta taccatggaa atcaaaactc ctgaccctg tccagttaac cctacaaagc     660
actaattata cttgcattgt ctgtatcgat cgtgccagcc tctccactg gcacgtccta     720 tactctcccca cgtctctgt tccatcctct tcttctaccc ccctccttta cccatcgtta     780
gcgcttccag ccccccacct gacgttacca tttaactgga cccactgctt tgaccccaag     840
attcaagcta tagtctcctc ccctgtcat aactccctca tcctgcccccc ctttctcttg     900 tcacctgttc ccaccctagg atcccgctcc cgccgagcgg taccggtggc ggtctggctt     960
gtctccgccc tggccatggg agccggagtg gctggcggga ttaccggctc catgtccctc    1020
gcctcaggaa agagcctcct acatgaggtg gacaaagata ttccccagtt aactcaagca    1080
atagtcaaaa accacaaaaa tctactcaaa attgcgcagt atgctgccca gaacagacga    1140
ggccttgatc tcctgttctg ggagnnngga ggattatgca aagcattaca agaacagtgc    1200
cgttttccga atattaccaa ttccccatgtc ccaatactac aagaaaagacc cccccttgag    1260
```

```
aatcgagtcc tgactggctg gggccttaac tgggacctty gcctctcaca gtgggctcga    1320
gaggccttac aaactggaat caccctttgtt gcgctactcc ttcttgttat ccttgcagga   1380
ccatgcatcc tccgtcagct acgacacctc ccctcgcgcg tcagataccc ccattactct   1440
cttataaacc ctgagtcatc cctg                                          1464
```

<210> SEQ ID NO 108
<211> LENGTH: 488
<212> TYPE: PRT
<213> ORGANISM: Artificial sequence
<220> FEATURE:
<223> OTHER INFORMATION: Description of Artificial Sequence: Synthetic Mutated HTLV-1 ENV

<400> SEQUENCE: 108

```
Met Gly Lys Phe Leu Ala Thr Leu Ile Leu Phe Phe Gln Phe Cys Pro
  1               5                  10                  15

Leu Ile Phe Gly Asp Tyr Ser Pro Ser Cys Cys Thr Leu Thr Ile Gly
             20                  25                  30

Val Ser Ser Tyr His Ser Lys Pro Cys Asn Pro Ala Gln Pro Val Cys
         35                  40                  45

Ser Trp Thr Leu Asp Leu Leu Ala Leu Ser Ala Asp Gln Ala Leu Gln
     50                  55                  60

Pro Pro Cys Pro Asn Leu Val Ser Tyr Ser Tyr His Ala Thr Tyr
 65                  70                  75                  80

Ser Leu Tyr Leu Phe Pro His Trp Thr Lys Lys Pro Asn Arg Asn Gly
                 85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser Arg Ser Arg Arg Ala Val Pro Val Ala Val Trp Leu
305                 310                 315                 320
```

```
Val Ser Ala Leu Ala Met Gly Ala Gly Val Ala Gly Gly Ile Thr Gly
            325                 330                 335

Ser Met Ser Leu Ala Ser Gly Lys Ser Leu Leu His Glu Val Asp Lys
        340                 345                 350

Asp Ile Ser Gln Leu Thr Gln Ala Ile Val Lys Asn His Lys Asn Leu
        355                 360                 365

Leu Lys Ile Ala Gln Tyr Ala Ala Gln Asn Arg Arg Gly Leu Asp Leu
        370                 375                 380

Leu Phe Trp Glu Arg Gly Gly Leu Cys Lys Ala Leu Gln Glu Gln Cys
385                 390                 395                 400

Arg Phe Pro Asn Ile Thr Asn Ser His Val Pro Ile Leu Gln Glu Arg
                405                 410                 415

Pro Pro Leu Glu Asn Arg Val Leu Thr Gly Trp Gly Leu Asn Trp Asp
            420                 425                 430

Leu Gly Leu Ser Gln Trp Ala Arg Glu Ala Leu Gln Thr Gly Ile Thr
            435                 440                 445

Leu Val Ala Leu Leu Leu Val Ile Leu Ala Gly Pro Cys Ile Leu
        450                 455                 460

Arg Gln Leu Arg His Leu Pro Ser Arg Val Arg Tyr Pro His Tyr Ser
465                 470                 475                 480

Leu Ile Asn Pro Glu Ser Ser Leu
                485

<210> SEQ ID NO 109
<211> LENGTH: 1464
<212> TYPE: DNA
<213> ORGANISM: Artificial sequence
<220> FEATURE:
<223> OTHER INFORMATION: Description of Artificial Sequence: Synthetic
      Mutated HTLV-1 ENV
<220> FEATURE:
<221> NAME/KEY: modified_base
<222> LOCATION: (1165)..(1167)
<223> OTHER INFORMATION: cgt, cgc, cga, cgg, aga or agg
<220> FEATURE:
<221> NAME/KEY: modified_base
<222> LOCATION: (1183)..(1185)
<223> OTHER INFORMATION: ttt or ttc

<400> SEQUENCE: 109
atgggtaagt tctctcgccac tttgatttta ttcttccagt tctgccccct catcttcggt      60
gattacagcc ccagctgctg tactctcaca attggagtct cctcatacca ctctaaaccc     120
tgcaatcctg cccagccagt tgttcgtgg accctcgacc tgctggccct ttcagcagat      180
caggccctac agcccccctg ccctaaccta gtaagttact ccagctacca tgccacctat     240
tccctatatc tattccctca ttggactaag aagccaaacc gaaatggcgg aggctattat     300
tcagcctctt attcagaccc ttgttcctta aagtgcccat acctggggtg ccaatcatgg     360
acctgcccct atacaggagc cgtctccagc ccctactgga gtttcaaca cgatgtcaat     420 tttactcaag aagtttcacg cctcaatatt aatctccatt tttcaaaatg cggttttccc     480
ttctcccttc tagtcgacgc tccaggatat gaccccatct ggttccttaa taccgaaccc     540
agccaactgc ctcccaccgc ccctcctcta ctcccccact ctaacctaga ccacatcctc     600
gagccctcta ccatggaa tcaaaaactc ctgaccccttg tccagttaac ctacaaagc      660 actaattata cttgcattgt ctgtatcgat cgtgccagcc tctccacttg gcacgtccta     720
tactctccca acgtctctgt tccatcctct tcttctaccc cctcctttta cccatcgtta     780
gcgcttccag ccccccacct gacgttacca tttaactgga cccactgctt tgaccccag     840
```

```
attcaagcta tagtctcctc ccctgtcat aactccctca tcctgcccc c

-continued

```
Tyr Pro Ser Leu Ala Leu Pro Ala Pro His Leu Thr Leu Pro Phe Asn
260 265 270

Trp Thr His Cys Phe Asp Pro Gln Ile Gln Ala Ile Val Ser Ser Pro
275 280 285

Cys His Asn Ser Leu Ile Leu Pro Pro Phe Ser Leu Ser Pro Val Pro
290 295 300

Thr Leu Gly Ser Arg Ser Arg Arg Ala Val Pro Val Ala Val Trp Leu
305 310 315 320

Val Ser Ala Leu Ala Met Gly Ala Gly Val Ala Gly Gly Ile Thr Gly
325 330 335

Ser Met Ser Leu Ala Ser Gly Lys Ser Leu Leu His Glu Val Asp Lys
340 345 350

Asp Ile Ser Gln Leu Thr Gln Ala Ile Val Lys Asn His Lys Asn Leu
355 360 365

Leu Lys Ile Ala Gln Tyr Ala Ala Gln Asn Arg Arg Gly Leu Asp Leu
370 375 380

Leu Phe Trp Glu Arg Gly Gly Leu Cys Lys Phe Leu Gln Glu Gln Cys
385 390 395 400

Arg Phe Pro Asn Ile Thr Asn Ser His Val Pro Ile Leu Gln Glu Arg
405 410 415

Pro Pro Leu Glu Asn Arg Val Leu Thr Gly Trp Gly Leu Asn Trp Asp
420 425 430

Leu Gly Leu Ser Gln Trp Ala Arg Glu Ala Leu Gln Thr Gly Ile Thr
435 440 445

Leu Val Ala Leu Leu Leu Leu Val Ile Leu Ala Gly Pro Cys Ile Leu
450 455 460

Arg Gln Leu Arg His Leu Pro Ser Arg Val Arg Tyr Pro His Tyr Ser
465 470 475 480

Leu Ile Asn Pro Glu Ser Ser Leu
485

<210> SEQ ID NO 111
<211> LENGTH: 1458
<212> TYPE: DNA
<213> ORGANISM: Artificial sequence
<220> FEATURE:
<223> OTHER INFORMATION: Description of Artificial Sequence: Synthetic
Mutated HTLV-2 ENV
<220> FEATURE:
<221> NAME/KEY: modified_base
<222> LOCATION: (1153)..(1155)
<223> OTHER INFORMATION: cgt, cgc, cga, cgg, aga or agg
<400> SEQUENCE: 111
atgggtaatg ttttcttcct acttttattc agtctcacac attttccact agcccagcag 60
agccgatgca cactcacgat tggtatctcc tcctaccact ccagcccctg tagcccaacc 120
caacccgtct gcacgtggaa cctcgacctt aattccctaa caacggacca acgactacac 180
ccccccctgcc ctaacctaat tacttactct ggcttccata agacttattc cttatactta 240
ttcccacatt ggataaaaaa gccaaacaga cagggcctag ggtactactc gccttcctac 300
aatgaccctt gctcgctaca atgcccctac ttgggctgcc aagcatggac atccgcatac 360
acgggccccg tctccagtcc atcctggaag tttcattcag atgtaaattt cacccaggaa 420
gtcagccaag tgtcccttcg actacacttc tctaagtgcg gctcctccat gaccctccta 480
gtagatgccc ctggatatga tcctttatgg ttcatcacct cagaacccac tcagcctcca 540
ccaacttctc ccccattggt ccatgactcc gaccttgaac atgtcctaac cccctccacg 600

```
tcctggacga ccaaaatact caaatttatc cagctgacct tacagagcac caattactcc      660
tgcatggttt gcgtggatag atccagcctc tcatcctggc atgtactcta cacccccaac      720
atctccattc cccaacaaac ctcctcccga accatcctct tccttcccct tgccctgccc      780
gctcctccat cccaacccct tcccttggacc cattgctacc aacctcgcct acaggcgata      840
acaacagata actgcaacaa ctccattatc ctcccccctt tttccctcgc tcccgtacct      900
cctccggcga caagacgccg ccgtgccgtt ccaatagcag tgtggcttgt ctccgccta      960 gcggccggaa caggtatcgc tggtggagta acaggctccc tatctctggc ttccagtaaa    1020
agccttctcc tcgaggttga caaagacatc tcccaccttta cccaggccat agtcaaaaat    1080
catcaaaaca tcctccgggt tgcacagtat gcagcccaaa atagacgagg attagacctc    1140
ctattctggg aannnggggg tttgtgcaag gccatacagg agcaatgttg cttcctcaac    1200
atcagtaaca ctcatgtatc cgtcctccag gaacggcccc ctcttgaaaa acgtgtcatc    1260
accggctggg gactaaactg ggatcttgga ctgtcccaat gggcacgaga agccctccag    1320
acaggcataa ccattctcgc tctactcctc ctcgtcatat tgtttggccc ctgtatcctc    1380
cgccaaatcc aggcccttcc acagcggtta caaaaccgac ataaccagta ttcccttatc    1440
aacccagaaa ccatgcta                                                   1458
```

<210> SEQ ID NO 112
<211> LENGTH: 486
<212> TYPE: PRT
<213> ORGANISM: Artificial sequence
<220> FEATURE:
<223> OTHER INFORMATION: Description of Artificial Sequence: Synthetic
      Mutated HTLV-2 ENV

<400> SEQUENCE: 112

```
Met Gly Asn Val Phe Phe Leu Leu Leu Phe Ser Leu Thr His Phe Pro
  1               5                  10                  15

Leu Ala Gln Gln Ser Arg Cys Thr Leu Thr Ile Gly Ile Ser Ser Tyr
             20                  25                  30

His Ser Ser Pro Cys Ser Pro Thr Gln Pro Val Cys Thr Trp Asn Leu
         35                  40                  45

Asp Leu Asn Ser Leu Thr Thr Asp Gln Arg Leu His Pro Pro Cys Pro
     50                  55                  60

Asn Leu Ile Thr Tyr Ser Gly Phe His Lys Thr Tyr Ser Leu Tyr Leu
 65                  70                  75                  80

Phe Pro His Trp Ile Lys Lys Pro Asn Arg Gln Gly Leu Gly Tyr Tyr
                 85                  90                  95

Ser Pro Ser Tyr Asn Asp Pro Cys Ser Leu Gln Cys Pro Tyr Leu Gly
            100                 105                 110

Cys Gln Ala Trp Thr Ser Ala Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205
```

-continued

Phe Ile Gln Leu Thr Leu Gln Ser Thr Asn Tyr Ser Cys Met Val Cys
    210                 215                 220

Val Asp Arg Ser Ser Leu Ser Ser Trp His Val Leu Tyr Thr Pro Asn
225                 230                 235                 240

Ile Ser Ile Pro Gln Gln Thr Ser Ser Arg Thr Ile Leu Phe Pro Ser
                245                 250                 255

Leu Ala Leu Pro Ala Pro Pro Ser Gln Pro Phe Pro Trp Thr His Cys
            260                 265                 270

Tyr Gln Pro Arg Leu Gln Ala Ile Thr Thr Asp Asn Cys Asn Asn Ser
        275                 280                 285

Ile Ile Leu Pro Pro Phe Ser Leu Ala Pro Val Pro Pro Pro Ala Thr
    290                 295                 300

Arg Arg Arg Arg Ala Val Pro Ile Ala Val Trp Leu Val Ser Ala Leu
305                 310                 315                 320

Ala Ala Gly Thr Gly Ile Ala Gly Gly Val Thr Gly Ser Leu Ser Leu
                325                 330                 335

Ala Ser Ser Lys Ser Leu Leu Leu Glu Val Asp Lys Asp Ile Ser His
            340                 345                 350

Leu Thr Gln Ala Ile Val Lys Asn His Gln Asn Ile Leu Arg Val Ala
        355                 360                 365

Gln Tyr Ala Ala Gln Asn Arg Arg Gly Leu Asp Leu Leu Phe Trp Glu
    370                 375                 380

Arg Gly Gly Leu Cys Lys Ala Ile Gln Glu Gln Cys Cys Phe Leu Asn
385                 390                 395                 400

Ile Ser Asn Thr His Val Ser Val Leu Gln Glu Arg Pro Pro Leu Glu
                405                 410                 415

Lys Arg Val Ile Thr Gly Trp Gly Leu Asn Trp Asp Leu Gly Leu Ser
            420                 425                 430

Gln Trp Ala Arg Glu Ala Leu Gln Thr Gly Ile Thr Ile Leu Ala Leu
        435                 440                 445

Leu Leu Leu Val Ile Leu Phe Gly Pro Cys Ile Leu Arg Gln Ile Gln
    450                 455                 460

Ala Leu Pro Gln Arg Leu Gln Asn Arg His Asn Gln Tyr Ser Leu Ile
465                 470                 475                 480

Asn Pro Glu Thr Met Leu
                485

<210> SEQ ID NO 113
<211> LENGTH: 1458
<212> TYPE: DNA
<213> ORGANISM: Artificial sequence
<220> FEATURE:
<223> OTHER INFORMATION: Description of Artificial Sequence: Synthetic
      Mutated HTLV-2 ENV
<220> FEATURE:
<221> NAME/KEY: modified_base
<222> LOCATION: (1153)..(1155)
<223> OTHER INFORMATION: cgt, cgc, cga, cgg, aga or agg
<220> FEATURE:
<221> NAME/KEY: modified_base
<222> LOCATION: (1171)..(1173)
<223> OTHER INFORMATION: ttt or ttc

<400> SEQUENCE: 113
atgggtaatg ttttcttcct acttttattc agtctcacac attttccact agcccagcag 60
agccgatgca cactcacgat tggtatctcc tcctaccact ccagcccctg tagcccaacc 120
caacccgtct gcacgtggaa cctcgacctt aattccctaa caacggacca acgactacac 180

```
cccccctgcc ctaacctaat tacttactct ggcttccata agacttattc cttatactta    240
ttcccacatt ggataaaaaa gccaaacaga cagggcctag ggtactactc gccttcctac    300
aatgacccct gctcgctaca atgcccctac ttgggctgcc aagcatggac atccgcatac    360
acgggccccg tctccagtcc atcctggaag tttcattcag atgtaaattt cacccaggaa    420
gtcagccaag tgtcccttcg actacacttc tctaagtgcg gctcctccat gaccctccta    480
gtagatgccc ctggatatga tcctttatgg ttcatcacct cagaacccac tcagcctcca    540
ccaacttctc ccccattggt ccatgactcc gaccttgaac atgtcctaac ccctccacg     600 tcctggacga ccaaaatact caaatttatc cagctgacct tacagagcac caattactcc    660
tgcatggttt gcgtggatag atccagcctc tcatcctggc atgtactcta cacccccaac    720
atctccattc cccaacaaac ctcctcccga accatcctct ttccttccct tgccctgccc    780
gctcctccat cccaaccctt cccttggacc cattgctacc aacctcgcct acaggcgata    840
acaacagata actgcaacaa ctccattatc ctcccccctt tttccctcgc tcccgtacct    900
cctccggcga caagacgccg ccgtgccgtt ccaatagcag tgtggcttgt ctccgcccta    960
gcggccggaa caggtatcgc tggtggagta acaggctccc tatctctggc ttccagtaaa    1020
agccttctcc tcgaggttga caaagacatc tcccaccta cccaggccat agtcaaaaat    1080
catcaaaaca tcctccgggt tgcacagtat gcagcccaaa atagacgagg attagacctc    1140
ctattctggg aannnggggg tttgtgcaag nnnatacagg agcaatgttg cttcctcaac    1200
atcagtaaca ctcatgtatc cgtcctccag gaacggcccc ctcttgaaaa acgtgtcatc    1260
accggctggg gactaaactg ggatcttgga ctgtcccaat gggcacgaga agccctccag    1320
acaggcataa ccattctcgc tctactcctc ctcgtcatat tgtttggccc ctgtatcctc    1380
cgccaaatcc aggcccttcc acagcggtta caaaaccgac ataaccagta ttcccttatc    1440
aacccagaaa ccatgcta                                                  1458

<210> SEQ ID NO 114
<211> LENGTH: 486
<212> TYPE: PRT
<213> ORGANISM: Artificial sequence
<220> FEATURE:
<223> OTHER INFORMATION: Description of Artificial Sequence: Synthetic
      Mutated HTLV-2 ENV

<400> SEQUENCE: 114

Met Gly Asn Val Phe Phe Leu Leu Leu Phe Ser Leu Thr His Phe Pro
  1               5                  10                  15

Leu Ala Gln Gln Ser Arg Cys Thr Leu Thr Ile Gly Ile Ser Ser Tyr
             20                  25                  30

His Ser Ser Pro Cys Ser Pro Thr Gln Pro Val Cys Thr Trp Asn Leu
         35                  40                  45

Asp Leu Asn Ser Leu Thr Thr Asp Gln Arg Leu His Pro Pro Cys Pro
     50                  55                  60

Asn Leu Ile Thr Tyr Ser Gly Phe His Lys Thr Tyr Ser Leu Tyr Leu
 65                  70                  75                  80

Phe Pro His Trp Ile Lys Lys Pro Asn Arg Gln Gly Leu Gly Tyr Tyr
                 85                  90                  95

Ser Pro Ser Tyr Asn Asp Pro Cys Ser Leu Gln Cys Pro Tyr Leu Gly
            100                 105                 110

Cys Gln Ala Trp Thr Ser Ala Tyr Thr Gly Pro Val Ser Ser Pro Ser
        115                 120                 125

Trp Lys Phe His Ser Asp Val Asn Phe Thr Gln Glu Val Ser Gln Val
```

|  |  |  |  |  |  |  |  |  |  |  |  |
|---|---|---|---|---|---|---|---|---|---|---|---|
|  |  | 130 |  |  | 135 |  |  | 140 |  |  |  |
| Ser | Leu | Arg | Leu | His | Phe | Ser | Lys | Cys | Gly | Ser | Ser | Met | Thr | Leu | Leu |
| 145 |  |  |  |  | 150 |  |  |  |  | 155 |  |  |  |  | 160 |
| Val | Asp | Ala | Pro | Gly | Tyr | Asp | Pro | Leu | Trp | Phe | Ile | Thr | Ser | Glu | Pro |
|  |  |  |  | 165 |  |  |  |  | 170 |  |  |  |  | 175 |  |
| Thr | Gln | Pro | Pro | Pro | Thr | Ser | Pro | Pro | Leu | Val | His | Asp | Ser | Asp | Leu |
|  |  |  | 180 |  |  |  |  | 185 |  |  |  |  | 190 |  |  |
| Glu | His | Val | Leu | Thr | Pro | Ser | Thr | Ser | Trp | Thr | Lys | Ile | Leu | Lys |
|  |  |  | 195 |  |  |  |  | 200 |  |  |  |  | 205 |  |
| Phe | Ile | Gln | Leu | Thr | Leu | Gln | Ser | Thr | Asn | Tyr | Ser | Cys | Met | Val | Cys |
| 210 |  |  |  |  | 215 |  |  |  |  | 220 |  |  |  |  |  |
| Val | Asp | Arg | Ser | Ser | Leu | Ser | Ser | Trp | His | Val | Leu | Tyr | Thr | Pro | Asn |
| 225 |  |  |  |  | 230 |  |  |  |  | 235 |  |  |  |  | 240 |
| Ile | Ser | Ile | Pro | Gln | Gln | Thr | Ser | Ser | Arg | Thr | Ile | Leu | Phe | Pro | Ser |
|  |  |  |  | 245 |  |  |  |  | 250 |  |  |  |  | 255 |  |
| Leu | Ala | Leu | Pro | Ala | Pro | Pro | Ser | Gln | Pro | Phe | Pro | Trp | Thr | His | Cys |
|  |  |  | 260 |  |  |  |  | 265 |  |  |  |  | 270 |  |  |
| Tyr | Gln | Pro | Arg | Leu | Gln | Ala | Ile | Thr | Thr | Asp | Asn | Cys | Asn | Asn | Ser |
|  |  | 275 |  |  |  |  | 280 |  |  |  |  | 285 |  |  |  |
| Ile | Ile | Leu | Pro | Pro | Phe | Ser | Leu | Ala | Pro | Val | Pro | Pro | Ala | Thr |
|  | 290 |  |  |  |  | 295 |  |  |  |  | 300 |  |  |  |  |
| Arg | Arg | Arg | Arg | Ala | Val | Pro | Ile | Ala | Val | Trp | Leu | Val | Ser | Ala | Leu |
| 305 |  |  |  |  | 310 |  |  |  |  | 315 |  |  |  |  | 320 |
| Ala | Ala | Gly | Thr | Gly | Ile | Ala | Gly | Gly | Val | Thr | Gly | Ser | Leu | Ser | Leu |
|  |  |  | 325 |  |  |  |  | 330 |  |  |  |  | 335 |  |  |
| Ala | Ser | Ser | Lys | Ser | Leu | Leu | Leu | Glu | Val | Asp | Lys | Asp | Ile | Ser | His |
|  |  | 340 |  |  |  |  | 345 |  |  |  |  | 350 |  |  |  |
| Leu | Thr | Gln | Ala | Ile | Val | Lys | Asn | His | Gln | Asn | Ile | Leu | Arg | Val | Ala |
|  | 355 |  |  |  |  | 360 |  |  |  |  | 365 |  |  |  |  |
| Gln | Tyr | Ala | Ala | Gln | Asn | Arg | Arg | Gly | Leu | Asp | Leu | Leu | Phe | Trp | Glu |
|  | 370 |  |  |  |  | 375 |  |  |  |  | 380 |  |  |  |  |
| Arg | Gly | Gly | Leu | Cys | Lys | Phe | Ile | Gln | Glu | Gln | Cys | Cys | Phe | Leu | Asn |
| 385 |  |  |  |  | 390 |  |  |  |  | 395 |  |  |  |  | 400 |
| Ile | Ser | Asn | Thr | His | Val | Ser | Val | Leu | Gln | Glu | Arg | Pro | Pro | Leu | Glu |
|  |  |  | 405 |  |  |  |  | 410 |  |  |  |  | 415 |  |  |
| Lys | Arg | Val | Ile | Thr | Gly | Trp | Gly | Leu | Asn | Trp | Asp | Leu | Gly | Leu | Ser |
|  |  |  | 420 |  |  |  |  | 425 |  |  |  |  | 430 |  |  |
| Gln | Trp | Ala | Arg | Glu | Ala | Leu | Gln | Thr | Gly | Ile | Thr | Ile | Leu | Ala | Leu |
|  |  | 435 |  |  |  |  | 440 |  |  |  |  | 445 |  |  |  |
| Leu | Leu | Leu | Val | Ile | Leu | Phe | Gly | Pro | Cys | Ile | Leu | Arg | Gln | Ile | Gln |
| 450 |  |  |  |  | 455 |  |  |  |  | 460 |  |  |  |  |  |
| Ala | Leu | Pro | Gln | Arg | Leu | Gln | Asn | Arg | His | Asn | Gln | Tyr | Ser | Leu | Ile |
| 465 |  |  |  |  | 470 |  |  |  |  | 475 |  |  |  |  | 480 |
| Asn | Pro | Glu | Thr | Met | Leu |
|  |  |  |  | 485 |  |

```
<210> SEQ ID NO 115
<211> LENGTH: 1614
<212> TYPE: DNA
<213> ORGANISM: Artificial sequence
<220> FEATURE:
<223> OTHER INFORMATION: Description of Artificial Sequence: Synthetic
      Mutated HERV-W ENV
<220> FEATURE:
<221> NAME/KEY: modified_base
<222> LOCATION: (1177)..(1179)
<223> OTHER INFORMATION: gaa, gag, caa or cag
```

-continued

<400> SEQUENCE: 115

```
atggccctcc cttatcatat ttttctcttt actgttcttt taccctcttt cactctcact        60
gcaccccctc catgccgctg tatgaccagt agctcccctt accaagagtt tctatggaga       120
atgcagcgtc ccggaaatat tgatgcccca tcgtatagga gtctttctaa gggaacccCC       180
accttcactg cccacaccca tatgccccgc aactgctatc actctgccac tctttgcatg       240
catgcaaata ctcattattg acaggaaaa atgattaatc ctagttgtcc tggaggactt       300
ggagtcactg tctgttggac ttacttcacc caaactggta tgtctgatgg gggtggagtt       360
caagatcagg caagagaaaa acatgtaaaa gaagtaatct cccaactcac ccgggtacat       420
ggcacctcta gccctacaa aggactagat ctctcaaaac tacatgaaac cctccgtacc        480
catactcgcc tggtaagcct atttaatacc accctcactg ggctccatga ggtctcggcc       540
caaaaccta ctaactgttg gatatgcctc ccctgaact tcaggccata tgtttcaatc        600
cctgtacctg aacaatggaa caacttcagc acagaaataa acaccacttc cgttttagta       660
ggacctcttg tttccaatct ggaaataacc catacctcaa acctcacctg tgtaaaattt       720
agcaatacta catacacaac caactcccaa tgcatcaggt gggtaactcc tcccacacaa       780
atagtctgcc taccctcagg aatatttttt gtctgtggta cctcagccta tcgttgttg        840
aatggctctt cagaatctat gtgcttcctc tcattcttag tgccccctat gaccatctac       900
actgaacaag atttatacag ttatgtcata tctaagcccc gcaacaaaag agtacccatt       960
cttccttttg ttataggagc aggagtgcta ggtgcactag gtactggcat ggcggtatc       1020
acaacctcta ctcagttcta ctacaaacta tctcaagaac taaatgggga catggaacgg      1080
gtcgccgact ccctggtcac cttgcaagat caacttaact ccctagcagc agtagtcctt       1140
caaaatcgaa gagctttaga cttgctaacc gctgaannng ggggaacctg tttattttta      1200
ggggaagaat gctgttatta tgttaatcaa tccggaatcg tcactgagaa agttaaagaa      1260
attcgagatc gaatacaacg tagagcagag gagcttcgaa acactggacc ctggggcctc      1320
ctcagccaat ggatgccctg gattctcccc ttcttaggac tctagcagc tataatattg       1380
ctactcctct ttggaccctg tatctttaac ctccttgtta actttgtctc ttccagaatc      1440
gaagctgtaa aactacaaat ggagcccaag atgcagtcca agactaagat ctaccgcaga      1500
cccCCтggacc ggcctgctag cccacgatct gatgttaatg acatcaaagg cacccCtcct      1560
gaggaaatct cagctgcaca acctctacta cgccccaatt cagcaggaag cagt            1614
```

<210> SEQ ID NO 116
<211> LENGTH: 538
<212> TYPE: PRT
<213> ORGANISM: Artificial sequence
<220> FEATURE:
<223> OTHER INFORMATION: Description of Artificial Sequence: Synthetic Mutated HERV-W ENV
<220> FEATURE:
<221> NAME/KEY: MOD_RES
<222> LOCATION: (393)..(393)
<223> OTHER INFORMATION: Glu or Gln

<400> SEQUENCE: 116

```
Met Ala Leu Pro Tyr His Ile Phe Leu Phe Thr Val Leu Leu Pro Ser
 1               5                  10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45
```

```
Ala Pro Ser Tyr Arg Ser Leu Ser Lys Gly Thr Pro Thr Phe Thr Ala
        50                  55                  60
His Thr His Met Pro Arg Asn Cys Tyr His Ser Ala Thr Leu Cys Met
 65                  70                  75                  80
His Ala Asn Thr His Tyr Trp Thr Gly Lys Met Ile Asn Pro Ser Cys
                85                  90                  95
Pro Gly Gly Leu Gly Val Thr Val Cys Trp Thr Tyr Phe Thr Gln Thr
            100                 105                 110
Gly Met Ser Asp Gly Gly Val Gln Asp Gln Ala Arg Glu Lys His
        115                 120                 125
Val Lys Glu Val Ile Ser Gln Leu Thr Arg Val His Gly Thr Ser Ser
130                 135                 140
Pro Tyr Lys Gly Leu Asp Leu Ser Lys Leu His Glu Thr Leu Arg Thr
145                 150                 155                 160
His Thr Arg Leu Val Ser Leu Phe Asn Thr Thr Leu Thr Gly Leu His
                165                 170                 175
Glu Val Ser Ala Gln Asn Pro Thr Asn Cys Trp Ile Cys Leu Pro Leu
                180                 185                 190
Asn Phe Arg Pro Tyr Val Ser Ile Pro Val Pro Glu Gln Trp Asn Asn
            195                 200                 205
Phe Ser Thr Glu Ile Asn Thr Thr Ser Val Leu Val Gly Pro Leu Val
210                 215                 220
Ser Asn Leu Glu Ile Thr His Thr Ser Asn Leu Thr Cys Val Lys Phe
225                 230                 235                 240
Ser Asn Thr Thr Tyr Thr Thr Asn Ser Gln Cys Ile Arg Trp Val Thr
                245                 250                 255
Pro Pro Thr Gln Ile Val Cys Leu Pro Ser Gly Ile Phe Phe Val Cys
            260                 265                 270
Gly Thr Ser Ala Tyr Arg Cys Leu Asn Gly Ser Ser Glu Ser Met Cys
        275                 280                 285
Phe Leu Ser Phe Leu Val Pro Pro Met Thr Ile Tyr Thr Glu Gln Asp
290                 295                 300
Leu Tyr Ser Tyr Val Ile Ser Lys Pro Arg Asn Lys Arg Val Pro Ile
305                 310                 315                 320
Leu Pro Phe Val Ile Gly Ala Gly Val Leu Gly Ala Leu Gly Thr Gly
                325                 330                 335
Ile Gly Gly Ile Thr Thr Ser Thr Gln Phe Tyr Tyr Lys Leu Ser Gln
                340                 345                 350
Glu Leu Asn Gly Asp Met Glu Arg Val Ala Asp Ser Leu Val Thr Leu
            355                 360                 365
Gln Asp Gln Leu Asn Ser Leu Ala Ala Val Val Leu Gln Asn Arg Arg
        370                 375                 380
Ala Leu Asp Leu Leu Thr Ala Glu Xaa Gly Gly Thr Cys Leu Phe Leu
385                 390                 395                 400
Gly Glu Glu Cys Cys Tyr Tyr Val Asn Gln Ser Gly Ile Val Thr Glu
                405                 410                 415
Lys Val Lys Glu Ile Arg Asp Arg Ile Gln Arg Arg Ala Glu Glu Leu
                420                 425                 430
Arg Asn Thr Gly Pro Trp Gly Leu Leu Ser Gln Trp Met Pro Trp Ile
            435                 440                 445
Leu Pro Phe Leu Gly Pro Leu Ala Ala Ile Ile Leu Leu Leu Leu Phe
450                 455                 460
Gly Pro Cys Ile Phe Asn Leu Leu Val Asn Phe Val Ser Ser Arg Ile
```

```
                465                 470                 475                 480
Glu Ala Val Lys Leu Gln Met Glu Pro Lys Met Gln Ser Lys Thr Lys
                    485                 490                 495

Ile Tyr Arg Arg Pro Leu Asp Arg Pro Ala Ser Pro Arg Ser Asp Val
                500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
        530                 535

<210> SEQ ID NO 117
<211> LENGTH: 1614
<212> TYPE: DNA
<213> ORGANISM: Artificial sequence
<220> FEATURE:
<223> OTHER INFORMATION: Description of Artificial Sequence: Synthetic
      Mutated HERV-W ENV
<220> FEATURE:
<221> NAME/KEY: modified_base
<222> LOCATION: (1177)..(1179)
<223> OTHER INFORMATION: gaa, gag, caa or cag
<220> FEATURE:
<221> NAME/KEY: modified_base
<222> LOCATION: (1195)..(1197)
<223> OTHER INFORMATION: gct, gcc, gca or gcg

<400> SEQUENCE: 117
atggccctcc cttatcatat ttttctcttt actgttcttt taccctcttt cactctcact     60 gcacccctc catgccgctg tatgaccagt agctccccttt accaagagtt tctatggaga    120
```

```
atgcagcgtc ccggaaatat tgatgcccca tcgtatagga gtctttctaa gggaaccccc    180
accttcactg cccacaccca tatgccccgc aactgctatc actctgccac tctttgcatg    240
catgcaaata ctcattattg gacaggaaaa atgattaatc ctagttgtcc tggaggactt    300
ggagtcactg tctgttggac ttacttcacc caaactggta tgtctgatgg gggtggagtt    360
caagatcagg caagagaaaa acatgtaaaa gaagtaatct cccaactcac ccgggtacat    420
ggcacctcta gccctacaa aggactagat ctctcaaaac tacatgaaac cctccgtacc    480
catactcgcc tggtaagcct atttaatacc accctcactg ggctccatga ggtctcggcc    540 caaacccta ctaactgttg gatatgcctc cccctgaact tcaggccata tgtttcaatc    600
cctgtacctg aacaatggaa caacttcagc acagaaataa acaccacttc cgttttagta    660
ggacctcttg tttccaatct ggaaataacc catacctcaa acctcacctg tgtaaaattt    720
agcaatacta catacacaac caactcccaa tgcatcaggt gggtaactcc tcccacacaa    780
atagtctgcc taccctcagg aatatttttt gtctgtggta cctcagccta tcgttgtttg    840
aatggctctt cagaatctat gtgcttcctc tcattcttag tgccccctat gaccatctac    900
actgaacaag atttatacag ttatgtcata tctaagcccc gcaacaaaag agtacccatt    960 cttcctttttg ttataggagc aggagtgcta ggtgcactag gtactggcat ggcggtatc    1020 acaacctcta ctcagttcta ctacaaacta tctcaagaac taatggggga catggaacgg    1080
gtcgccgact ccctggtcac cttgcaagat caacttaact ccctagcagc agtagtcctt    1140
caaaatcgaa gagctttaga cttgctaacc gctgaannng ggggaacctg tttannntta    1200
ggggaagaat gctgttatta tgttaatcaa tccggaatcg tcactgagaa agttaaagaa    1260
attcgagatc gaatacaacg tagagcagag gagcttcgaa acactggacc ctggggcctc    1320
ctcagccaat ggatgccctg gattctcccc ttcttaggac tctagcagc tataatattg    1380 ctactcctct ttggaccctg tatctttaac ctccttgtta actttgtctc ttccagaatc    1440
```

```
gaagctgtaa aactacaaat ggagcccaag atgcagtcca agactaagat ctaccgcaga      1500
cccctggacc ggcctgctag cccacgatct gatgttaatg acatcaaagg caccccctcct     1560 gaggaaatct cagctgcaca acctctacta cgccccaatt cagcaggaag cagt            1614
```

<210> SEQ ID NO 118
<211> LENGTH: 538
<212> TYPE: PRT
<213> ORGANISM: Artificial sequence
<220> FEATURE:
<223> OTHER INFORMATION: Description of Artificial Sequence: Synthetic
      Mutated HERV-W ENV
<220> FEATURE:
<221> NAME/KEY: MOD_RES
<222> LOCATION: (393)..(393)
<223> OTHER INFORMATION: Glu or Gln

<400> SEQUENCE: 118

```
Met Ala Leu Pro Tyr His Ile Phe Leu Phe Thr Val Leu Leu Pro Ser
  1               5                  10                  15

Phe Thr Leu Thr Ala Pro Pro Cys Arg Cys Met Thr Ser Ser Ser
             20                  25                  30

Pro Tyr Gln Glu Phe Leu Trp Arg Met Gln Arg Pro Gly Asn Ile Asp
         35                  40                  45

Ala Pro Ser Tyr Arg Ser Leu Ser Lys Gly Thr Pro Thr Phe Thr Ala
     50                  55                  60

His Thr His Met Pro Arg Asn Cys Tyr His Ser Ala Thr Leu Cys Met
 65                  70                  75                  80

His Ala Asn Thr His Tyr Trp Thr Gly Lys Met Ile Asn Pro Ser Cys
                 85                  90                  95

Pro Gly Gly Leu Gly Val Thr Val Cys Trp Thr Tyr Phe Thr Gln Thr
            100                 105                 110

Gly Met Ser Asp Gly Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
```

```
                305                 310                 315                 320
Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
                340                 345                 350

Glu Leu Asn Gly Asp Met Glu Arg Val Ala Asp Ser Leu Val Thr Leu
                355                 360                 365

Gln Asp Gln Leu Asn Ser Leu Ala Ala Val Val Leu Gln Asn Arg Arg
            370                 375                 380

Ala Leu Asp Leu Leu Thr Ala Glu Xaa Gly Gly Thr Cys Leu Ala Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
                420                 425                 430

Arg Asn Thr Gly Pro Trp Gly Leu Leu Ser Gln Trp Met Pro Trp Ile
                435                 440                 445

Leu Pro Phe Leu Gly Pro Leu Ala Ala Ile Ile Leu Leu Leu Leu Phe
            450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
                500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
            530                 535

<210> SEQ ID NO 119
<211> LENGTH: 1615
<212> TYPE: DNA
<213> ORGANISM: Artificial sequence
<220> FEATURE:
<223> OTHER INFORMATION: Description of Artificial Sequence: Synthetic
      Mutated HERV-FRD ENV
<220> FEATURE:
<221> NAME/KEY: modified_base
<222> LOCATION: (1279)..(1281)
<223> OTHER INFORMATION: cgt, cgc, cga, cgg, aga or agg

<400> SEQUENCE: 119
atgggcctgc tcctgctggt tctcattctc acgccttcac tagcagccta ccgccatcct    60
gatttcccgt tattggaaaa agctcagcaa ctgctccaaa gtacaggatc cccttactcc   120
accaattgct ggttatgtac tagctcttcc actgaaacac agggacagc ttatccagcc    180 tcgcccagag aatggacaag catagaggcg gaattacata tttcctatcg atgggaccct   240
aatctgaaag gactgatgag gcctgcaaat agtcttcttt caacagtaaa gcaagatttc   300
cctgatatcc gccagaaacc tcccattttc ggacccatct ttactaatat caacctaatg   360
ggaatagccc ctatttgtgt tatggccaaa aggaaaaatg aacaaatgt aggcactctt    420 ccaagtacag tctgtaatgt tactttcact gtagattcta accaacagac ttaccaaaca   480
tacacccaca accaattccg ccatcaacca agattcccca aacctccaaa tattactttt   540 cctcaggaa ctttgctaga taaatccagc cggttttgcc agggacgccc aagctcatgc   600
agtactcgaa acttctggtt ccggcctgct gattataacc aatgtctgca aatttccaac   660
```

-continued

```
ctcagctcta cagcggaatg ggttctattg gaccaaactc gaaattctct tttttgggaa    720
aataaaacca agggagctaa ccagagccaa acaccctgcg tccaagtctt agcaggcatg    780
actatagcca ccagctacct gggcatatca gcagtctcag aattttttgg aacctccctc    840 accccttat ttcatttcca tatctctaca tgccttaaaa ctcaaggagc cttttatatt     900
tgtggccagt cgattcacca atgcctcccc agtaactgga ctggaacttg taccataggc    960
tatgtaaccc cagacatctt catagcccct ggcaatctct ctcttccaat accaatctat   1020
gggaattccc cgttgcccag ggtgaggagg gcaatccatt tcattcccct tctcgcggga   1080
ctcggcattc tagctggtac gggaaccgga attgctggaa tcacaaaagc ttccctcacc   1140
tatagccagc tctcaaagga aatagccaac aacattgaca ccatggctaa agccttaacg   1200
accatgcaag aacaaatcga ctctttagca gccgtagtcc ttcaaaatcg tcgaggacta   1260
gacatgttaa cggcagcann nggaggaatt tgtttggcct tagatgaaaa atgttgcttt   1320
tgggtaaatc aatcaggaaa agtacaagac aacatcagac aactcctaaa tcaagcctcc   1380
agtttacggg aacgagccac tcagggttgg ttaaattggg aaggaacttg gaaatggttc   1440
tcttgggttc ttccccttac aggcccactt gttagtctcc tacttttgct ccttttggt    1500 ccatgtctcc taaatctaat aacccaattt gtctcctctc gccttcaggc cataaagctc   1560
cagacgaatc tcagtgcagg acgccatcct cgcaatattc aagagtcacc cttct        1615
```

<210> SEQ ID NO 120
<211> LENGTH: 538
<212> TYPE: PRT
<213> ORGANISM: Artificial sequence
<220> FEATURE:
<223> OTHER INFORMATION: Description of Artificial Sequence: Synthetic
      Mutated HERV-FRD ENV

<400> SEQUENCE: 120

```
Met Gly Leu Leu Leu Val Leu Ile Leu Thr Pro Ser Leu Ala Ala
  1               5                  10                  15

Tyr Arg His Pro Asp Phe Pro Leu Leu Glu Lys Ala Gln Gln Leu Leu
             20                  25                  30

Gln Ser Thr Gly Ser Pro Tyr Ser Thr Asn Cys Trp Leu Cys Thr Ser
         35                  40                  45

Ser Ser Thr Glu Thr Pro Gly Thr Ala Tyr Pro Ala Ser Pro Arg Glu
     50                  55                  60

Trp Thr Ser Ile Glu Ala Glu Leu His Ile Ser Tyr Arg Trp Asp Pro
 65                  70                  75                  80

Asn Leu Lys Gly Leu Met Arg Pro Ala Asn Ser Leu Leu Ser Thr Val
                 85                  90                  95

Lys Gln Asp Phe Pro Asp Ile Arg Gln Lys Pro Pro Ile Phe Gly Pro
            100                 105                 110

Ile Phe Thr Asn Ile Asn Leu Met Gly Ile Ala Pro Ile Cys Val Met
        115                 120                 125

Ala Lys Arg Lys Asn Gly Thr Asn Val Gly Thr Leu Pro Ser Thr Val
    130                 135                 140

Cys Asn Val Thr Phe Thr Val Asp Ser Asn Gln Gln Thr Tyr Gln Thr
145                 150                 155                 160

Tyr Thr His Asn Gln Phe Arg His Gln Pro Arg Phe Pro Lys Pro Pro
                165                 170                 175

Asn Ile Thr Phe Pro Gln Gly Thr Leu Leu Asp Lys Ser Ser Arg Phe
            180                 185                 190
```

```
Cys Gln Gly Arg Pro Ser Ser Cys Ser Thr Arg Asn Phe Trp Phe Arg
            195                 200                 205

Pro Ala Asp Tyr Asn Gln Cys Leu Gln Ile Ser Asn Leu Ser Ser Thr
    210                 215                 220

Ala Glu Trp Val Leu Leu Asp Gln Thr Arg Asn Ser Leu Phe Trp Glu
225                 230                 235                 240

Asn Lys Thr Lys Gly Ala Asn Gln Ser Gln Thr Pro Cys Val Gln Val
                245                 250                 255

Leu Ala Gly Met Thr Ile Ala Thr Ser Tyr Leu Gly Ile Ser Ala Val
            260                 265                 270

Ser Glu Phe Phe Gly Thr Ser Leu Thr Pro Leu Phe His Phe His Ile
        275                 280                 285

Ser Thr Cys Leu Lys Thr Gln Gly Ala Phe Tyr Ile Cys Gly Gln Ser
    290                 295                 300

Ile His Gln Cys Leu Pro Ser Asn Trp Thr Gly Thr Cys Thr Ile Gly
305                 310                 315                 320

Tyr Val Thr Pro Asp Ile Phe Ile Ala Pro Gly Asn Leu Ser Leu Pro
                325                 330                 335

Ile Pro Ile Tyr Gly Asn Ser Pro Leu Pro Arg Val Arg Arg Ala Ile
            340                 345                 350

His Phe Ile Pro Leu Leu Ala Gly Leu Gly Ile Leu Ala Gly Thr Gly
        355                 360                 365

Thr Gly Ile Ala Gly Ile Thr Lys Ala Ser Leu Thr Tyr Ser Gln Leu
    370                 375                 380

Ser Lys Glu Ile Ala Asn Asn Ile Asp Thr Met Ala Lys Ala Leu Thr
385                 390                 395                 400

Thr Met Gln Glu Gln Ile Asp Ser Leu Ala Ala Val Val Leu Gln Asn
                405                 410                 415

Arg Arg Gly Leu Asp Met Leu Thr Ala Ala Arg Gly Gly Ile Cys Leu
            420                 425                 430

Ala Leu Asp Glu Lys Cys Cys Phe Trp Val Asn Gln Ser Gly Lys Val
        435                 440                 445

Gln Asp Asn Ile Arg Gln Leu Leu Asn Gln Ala Ser Ser Leu Arg Glu
    450                 455                 460

Arg Ala Thr Gln Gly Trp Leu Asn Trp Glu Gly Thr Trp Lys Trp Phe
465                 470                 475                 480

Ser Trp Val Leu Pro Leu Thr Gly Pro Leu Val Ser Leu Leu Leu Leu
                485                 490                 495

Leu Leu Phe Gly Pro Cys Leu Leu Asn Leu Ile Thr Gln Phe Val Ser
            500                 505                 510

Ser Arg Leu Gln Ala Ile Lys Leu Gln Thr Asn Leu Ser Ala Gly Arg
        515                 520                 525

His Pro Arg Asn Ile Gln Glu Ser Pro Phe
    530                 535

<210> SEQ ID NO 121
<211> LENGTH: 1615
<212> TYPE: DNA
<213> ORGANISM: Artificial sequence
<220> FEATURE:
<223> OTHER INFORMATION: Description of Artificial Sequence: Synthetic
      Mutated HERV-FRD ENV
<220> FEATURE:
<221> NAME/KEY: modified_base
<222> LOCATION: (1279)..(1281)
<223> OTHER INFORMATION: cgt, cgc, cga, cgg, aga or agg
<220> FEATURE:
<221> NAME/KEY: modified_base
```

<222> LOCATION: (1297)..(1299)
<223> OTHER INFORMATION: ttt or ttc

<400> SEQUENCE: 121

```
atgggcctgc tcctgctggt tctcattctc acgccttcac tagcagccta ccgccatcct      60
gatttcccgt tattggaaaa agctcagcaa ctgctccaaa gtacaggatc cccttactcc     120
accaattgct ggttatgtac tagctcttcc actgaaacac cagggacagc ttatccagcc     180
tcgcccagag aatggacaag catagaggcg gaattacata tttcctatcg atgggaccct     240
aatctgaaag gactgatgag gcctgcaaat agtcttcttt caacagtaaa gcaagatttc     300
cctgatatcc gccagaaacc tcccattttc ggacccatct ttactaatat caacctaatg     360
ggaatagccc ctatttgtgt tatggccaaa aggaaaaatg aacaaatgt aggcactctt      420
ccaagtacag tctgtaatgt tactttcact gtagattcta accaacagac ttaccaaaca     480
tacacccaca accaattccg ccatcaacca agattcccca aacctccaaa tattactttt     540
cctcagggaa ctttgctaga taaatccagc cggttttgcc agggacgccc aagctcatgc     600
agtactcgaa acttctggtt ccggcctgct gattataacc aatgtctgca aatttccaac     660
ctcagctcta cagcggaatg ggttctattg gaccaaactc gaaattctct tttttgggaa     720
aataaaacca agggagctaa ccagagccaa acaccctgcg tccaagtctt agcaggcatg     780
actatagcca ccagctacct gggcatatca gcagtctcag aattttttgg aacctccctc     840
accccttat ttcatttcca tatctctaca tgccttaaaa ctcaaggagc cttttatatt      900
tgtggccagt cgattcacca atgcctcccc agtaactgga ctggaacttg taccataggc     960
tatgtaaccc cagacatctt catagcccct ggcaatctct ctcttccaat accaatctat    1020
gggaattccc cgttgcccag ggtgaggagg gcaatccatt tcattcccct ctcgcggga    1080
ctcggcattc tagctggtac gggaaccgga attgctggaa tcacaaaagc ttccctcacc    1140
tatagccagc tctcaaagga aatagccaac aacattgaca ccatggctaa gccttaacg    1200
accatgcaag aacaaatcga ctctttagca gccgtagtcc ttcaaaatcg tcgaggacta    1260
gacatgttaa cggcagcann nggaggaatt tgtttgnnnt tagatgaaaa atgttgcttt    1320
tgggtaaatc aatcaggaaa agtacaagac aacatcagac aactcctaaa tcaagcctcc    1380
agtttacggg aacgagccac tcagggttgg ttaaattggg aaggaacttg gaaatggttc    1440
tcttgggttc ttccccttac aggcccactt gttagtctcc tacttttgct cctttttggt    1500
ccatgtctcc taaatctaat aacccaattt gtctcctctc gccttcaggc cataaagctc    1560
cagacgaatc tcagtgcagg acgccatcct cgcaatattc aagagtcacc cttct         1615
```

<210> SEQ ID NO 122
<211> LENGTH: 538
<212> TYPE: PRT
<213> ORGANISM: Artificial sequence
<220> FEATURE:
<223> OTHER INFORMATION: Description of Artificial Sequence: Synthetic Mutated HERV-FRD ENV

<400> SEQUENCE: 122

```
Met Gly Leu Leu Leu Leu Val Leu Ile Leu Thr Pro Ser Leu Ala Ala
  1               5                  10                  15

Tyr Arg His Pro Asp Phe Pro Leu Leu Glu Lys Ala Gln Gln Leu Leu
                 20                  25                  30

Gln Ser Thr Gly Ser Pro Tyr Ser Thr Asn Cys Trp Leu Cys Thr Ser
             35                  40                  45

Ser Ser Thr Glu Thr Pro Gly Thr Ala Tyr Pro Ala Ser Pro Arg Glu
```

-continued

```
            50                  55                  60
Trp Thr Ser Ile Glu Ala Glu Leu His Ile Ser Tyr Arg Trp Asp Pro
 65                  70                  75                  80

Asn Leu Lys Gly Leu Met Arg Pro Ala Asn Ser Leu Leu Ser Thr Val
                 85                  90                  95

Lys Gln Asp Phe Pro Asp Ile Arg Gln Lys Pro Pro Ile Phe Gly Pro
                100                 105                 110

Ile Phe Thr Asn Ile Asn Leu Met Gly Ile Ala Pro Ile Cys Val Met
                115                 120                 125

Ala Lys Arg Lys Asn Gly Thr Asn Val Gly Thr Leu Pro Ser Thr Val
130                 135                 140

Cys Asn Val Thr Phe Thr Val Asp Ser Asn Gln Gln Thr Tyr Gln Thr
145                 150                 155                 160

Tyr Thr His Asn Gln Phe Arg His Gln Pro Arg Phe Pro Lys Pro Pro
                165                 170                 175

Asn Ile Thr Phe Pro Gln Gly Thr Leu Leu Asp Lys Ser Ser Arg Phe
                180                 185                 190

Cys Gln Gly Arg Pro Ser Ser Cys Ser Thr Arg Asn Phe Trp Phe Arg
                195                 200                 205

Pro Ala Asp Tyr Asn Gln Cys Leu Gln Ile Ser Asn Leu Ser Ser Thr
210                 215                 220

Ala Glu Trp Val Leu Leu Asp Gln Thr Arg Asn Ser Leu Phe Trp Glu
225                 230                 235                 240

Asn Lys Thr Lys Gly Ala Asn Gln Ser Gln Thr Pro Cys Val Gln Val
                245                 250                 255

Leu Ala Gly Met Thr Ile Ala Thr Ser Tyr Leu Gly Ile Ser Ala Val
                260                 265                 270

Ser Glu Phe Phe Gly Thr Ser Leu Thr Pro Leu Phe His Phe His Ile
                275                 280                 285

Ser Thr Cys Leu Lys Thr Gln Gly Ala Phe Tyr Ile Cys Gly Gln Ser
                290                 295                 300

Ile His Gln Cys Leu Pro Ser Asn Trp Thr Gly Thr Cys Thr Ile Gly
305                 310                 315                 320

Tyr Val Thr Pro Asp Ile Phe Ile Ala Pro Gly Asn Leu Ser Leu Pro
                325                 330                 335

Ile Pro Ile Tyr Gly Asn Ser Pro Leu Pro Arg Val Arg Arg Ala Ile
                340                 345                 350

His Phe Ile Pro Leu Leu Ala Gly Leu Gly Ile Leu Ala Gly Thr Gly
                355                 360                 365

Thr Gly Ile Ala Gly Ile Thr Lys Ala Ser Leu Thr Tyr Ser Gln Leu
                370                 375                 380

Ser Lys Glu Ile Ala Asn Asn Ile Asp Thr Met Ala Lys Ala Leu Thr
385                 390                 395                 400

Thr Met Gln Glu Gln Ile Asp Ser Leu Ala Ala Val Val Leu Gln Asn
                405                 410                 415

Arg Arg Gly Leu Asp Met Leu Thr Ala Ala Arg Gly Gly Ile Cys Leu
                420                 425                 430

Phe Leu Asp Glu Lys Cys Cys Phe Trp Val Asn Gln Ser Gly Lys Val
                435                 440                 445

Gln Asp Asn Ile Arg Gln Leu Leu Asn Gln Ala Ser Ser Leu Arg Glu
                450                 455                 460

Arg Ala Thr Gln Gly Trp Leu Asn Trp Glu Gly Thr Trp Lys Trp Phe
465                 470                 475                 480
```

```
Ser Trp Val Leu Pro Leu Thr Gly Pro Leu Val Ser Leu Leu Leu Leu
                485                 490                 495
Leu Leu Phe Gly Pro Cys Leu Leu Asn Leu Ile Thr Gln Phe Val Ser
            500                 505                 510
Ser Arg Leu Gln Ala Ile Lys Leu Gln Thr Asn Leu Ser Ala Gly Arg
        515                 520                 525
His Pro Arg Asn Ile Gln Glu Ser Pro Phe
        530                 535
```

<210> SEQ ID NO 123
<211> LENGTH: 1563
<212> TYPE: DNA
<213> ORGANISM: Artificial sequence
<220> FEATURE:
<223> OTHER INFORMATION: Description of Artificial Sequence: Synthetic
      Mutated HERV-V ENV
<220> FEATURE:
<221> NAME/KEY: modified_base
<222> LOCATION: (1141)..(1143)
<223> OTHER INFORMATION: cgt, cgc, cga, cgg, aga or agg

<400> SEQUENCE: 123

```
atgcccctac tctcacaggc acagtggaat gaaaattccc ttgtcagttt ttccaaaata    60
attgcttcgg gaaaccatct aagcaactgt tggatctgcc acaacttcat caccaggtcc   120
tcatcttacc aatatatttt ggtaagaaat ttttctttaa acctaacatt tggttcagga   180
atccctgaag gccaacataa atctgttccg ctccaggttt cgcttgctaa ctcagcgcac   240
caagtcccct gcctggatct cactccacct ttcaatcaaa gctctaaaac ttcttttctat   300
ttctacaact gctcttctct aaaccaaacc tgttgtccat gccctgaagg acactgtgac   360
aggaagaaca cctctgagga gggattcccc agtcccacca tccatcccat gagcttctcc   420
ccagcaggct gccaccctaa cttgactcac tggtgtccag ctaaacaaat gaacgattat   480
cgagacaagt caccccaaaa ccgctgtgca gcttgggaag aaaagagct aatcacatgg    540
agggttctat attcgcttcc caaggcacac actgtcccca catggccaaa atctactgtt   600
cccctgggag gcctctatc ccctgcatgc aatcaaacta ttccagcagg gtggaaatcg   660
cagttacaca agtggttcga cagccacatc ccccgtgggg cctgtacccc tcctggctat   720
gtatttttat gtgggccaca aaaaaataaa ctgcccttttg atggaagtcc taagataacc   780
tattcaaccc cccctgtggc aaacctctac acttgcatta ataacatcca acatacggga   840
gaatgtgctg tgggactttt gggaccacgg gggataggtg tgaccattta taacaccacc   900
caacccagac agaaaagagc tctgggtcta atactggcag ggatgggtgc ggccatagga   960
atgatcgccc catggggagg gttcacttat catgatgtca ccctcagaaa tctctccaga  1020
caaatagaca acatagctaa gagtaccaga gatagcatct ctaaactcaa ggcctccata  1080
gattctctag caaatgtagt catggacaac agattggcct tagattacct cttagcagag  1140
nnnggtggag tctgtgcagt gatcaataaa tcctgttgcg tttatgtcaa taacagtggg  1200
gcgatagagg aggatataaa aaagatctat gatgaggcta cgtggctcca tgactttgga  1260
aaaggaggtg cttcagcaag ggccatctgg gaggctgtga agtctgccct ccctcccctc  1320
aactggtttg tccctttact gggaccagca acagttatac tcttactttt cctctttggc  1380
ccttgtttct ttaatttact gattaagtgt gtctcttcta ggataaagca attccacatg  1440
aagtccccc aaatggaaag atatcagcta tctgtcattg gagccccag cacctataag   1500
cacatctccc ccttggatgc cagtgggcaa agattccggg aaactatgga ggaattttct  1560
ctc                                                                1563
```

<210> SEQ ID NO 124
<211> LENGTH: 521
<212> TYPE: PRT
<213> ORGANISM: Artificial sequence
<220> FEATURE:
<223> OTHER INFORMATION: Description of Artificial Sequence: Synthetic Mutated HERV-V ENV

<400> SEQUENCE: 124

```
Met Pro Leu Leu Ser Gln Ala Gln Trp Asn Glu Asn Ser Leu Val Ser
 1               5                  10                  15

Phe Ser Lys Ile Ile Ala Ser Gly Asn His Leu Ser Asn Cys Trp Ile
             20                  25                  30

Cys His Asn Phe Ile Thr Arg Ser Ser Ser Tyr Gln Tyr Ile Leu Val
         35                  40                  45

Arg Asn Phe Ser Leu Asn Leu Thr Phe Gly Ser Gly Ile Pro Glu Gly
     50                  55                  60

Gln His Lys Ser Val Pro Leu Gln Val Ser Leu Ala Asn Ser Ala His
 65                  70                  75                  80

Gln Val Pro Cys Leu Asp Leu Thr Pro Pro Phe Asn Gln Ser Ser Lys
                 85                  90                  95

Thr Ser Phe Tyr Phe Tyr Asn Cys Ser Ser Leu Asn Gln Thr Cys Cys
            100                 105                 110

Pro Cys Pro Glu Gly His Cys Asp Arg Lys Asn Thr Ser Glu Glu Gly
        115                 120                 125

Phe Pro Ser Pro Thr Ile His Pro Met Ser Phe Ser Pro Ala Gly Cys
    130                 135                 140

His Pro Asn Leu Thr His Trp Cys Pro Ala Lys Gln Met Asn Asp Tyr
145                 150                 155                 160

Arg Asp Lys Ser Pro Gln Asn Arg Cys Ala Ala Trp Glu Gly Lys Glu
                165                 170                 175

Leu Ile Thr Trp Arg Val Leu Tyr Ser Leu Pro Lys Ala His Thr Val
            180                 185                 190

Pro Thr Trp Pro Lys Ser Thr Val Pro Leu Gly Gly Pro Leu Ser Pro
        195                 200                 205

Ala Cys Asn Gln Thr Ile Pro Ala Gly Trp Lys Ser Gln Leu His Lys
    210                 215                 220

Trp Phe Asp Ser His Ile Pro Arg Trp Ala Cys Thr Pro Pro Gly Tyr
225                 230                 235                 240

Val Phe Leu Cys Gly Pro Gln Lys Asn Lys Leu Pro Phe Asp Gly Ser
                245                 250                 255

Pro Lys Ile Thr Tyr Ser Thr Pro Pro Val Ala Asn Leu Tyr Thr Cys
            260                 265                 270

Ile Asn Asn Ile Gln His Thr Gly Glu Cys Ala Val Gly Leu Leu Gly
        275                 280                 285

Pro Arg Gly Ile Gly Val Thr Ile Tyr Asn Thr Thr Gln Pro Arg Gln
    290                 295                 300

Lys Arg Ala Leu Gly Leu Ile Leu Ala Gly Met Gly Ala Ala Ile Gly
305                 310                 315                 320

Met Ile Ala Pro Trp Gly Gly Phe Thr Tyr His Asp Val Thr Leu Arg
                325                 330                 335

Asn Leu Ser Arg Gln Ile Asp Asn Ile Ala Lys Ser Thr Arg Asp Ser
            340                 345                 350

Ile Ser Lys Leu Lys Ala Ser Ile Asp Ser Leu Ala Asn Val Val Met
        355                 360                 365
```

Asp Asn Arg Leu Ala Leu Asp Tyr Leu Leu Ala Glu Arg Gly Gly Val
        370             375             380

Cys Ala Val Ile Asn Lys Ser Cys Cys Val Tyr Val Asn Asn Ser Gly
385             390             395             400

Ala Ile Glu Glu Asp Ile Lys Lys Ile Tyr Asp Glu Ala Thr Trp Leu
            405             410             415

His Asp Phe Gly Lys Gly Gly Ala Ser Ala Arg Ala Ile Trp Glu Ala
        420             425             430

Val Lys Ser Ala Leu Pro Ser Leu Asn Trp Phe Val Pro Leu Leu Gly
        435             440             445

Pro Ala Thr Val Ile Leu Leu Leu Phe Leu Phe Gly Pro Cys Phe Phe
450             455             460

Asn Leu Leu Ile Lys Cys Val Ser Ser Arg Ile Lys Gln Phe His Met
465             470             475             480

Lys Ser Pro Gln Met Glu Arg Tyr Gln Leu Ser Val Ile Gly Gly Pro
            485             490             495

Ser Thr Tyr Lys His Ile Ser Pro Leu Asp Ala Ser Gly Gln Arg Phe
        500             505             510

Arg Glu Thr Met Glu Glu Phe Ser Leu
        515             520

<210> SEQ ID NO 125
<211> LENGTH: 1563
<212> TYPE: DNA
<213> ORGANISM: Artificial sequence
<220> FEATURE:
<223> OTHER INFORMATION: Description of Artificial Sequence: Synthetic
      Mutated HERV-V ENV
<220> FEATURE:
<221> NAME/KEY: modified_base
<222> LOCATION: (1141)..(1143)
<223> OTHER INFORMATION: cgt, cgc, cga, cgg, aga or agg
<220> FEATURE:
<221> NAME/KEY: modified_base
<222> LOCATION: (1159)..(1161)
<223> OTHER INFORMATION: ttt or ttc

<400> SEQUENCE: 125
atgcccctac tctcacaggc acagtggaat gaaaattccc ttgtcagttt ttccaaaata      60
attgcttcgg gaaaccatct aagcaactgt tggatctgcc acaacttcat caccaggtcc     120
tcatcttacc aatatatttt ggtaagaaat ttttctttaa acctaacatt tggttcagga     180
atccctgaag ccaacataa atctgttccg ctccaggttt cgcttgctaa ctcagcgcac     240
caagtcccct gcctggatct cactccacct ttcaatcaaa gctctaaaac ttctttctat     300
ttctacaact gctcttctct aaaccaaacc tgttgtccat gccctgaagg acactgtgac     360
aggaagaaca cctctgagga gggattcccc agtcccacca tccatcccat gagcttctcc     420
ccagcaggct gccaccctaa cttgactcac tggtgtccag ctaaacaaat gaacgattat     480
cgagacaagt caccccaaaa ccgctgtgca gcttgggaag aaaagagct aatcacatgg      540 agggttctat attcgcttcc caaggcacac actgtcccca catggccaaa atctactgtt     600
cccctgggag ggcctctatc ccctgcatgc aatcaaacta ttccagcagg gtggaaatcg     660
cagttacaca gtggttcga cagccacatc ccccggtggg cctgtacccc tcctggctat     720
gtatttttat gtgggccaca aaaaaataaa ctgcccttg atggaagtcc taagataacc     780
tattcaaccc cccctgtggc aaacctctac acttgcatta taacatcca acatacggga     840 gaatgtgctg tgggactttt gggaccacgg gggataggtg tgaccattta taacaccacc     900

-continued

```
caacccagac agaaaagagc tctgggtcta atactggcag ggatgggtgc ggccatagga    960
atgatcgccc catggggagg gttcacttat catgatgtca ccctcagaaa tctctccaga   1020
caaatagaca acatagctaa gagtaccaga gatagcatct ctaaactcaa ggcctccata   1080
gattctctag caaatgtagt catggacaac agattggcct tagattacct cttagcagag   1140
nnnggtggag tctgtgcann natcaataaa tcctgttgcg tttatgtcaa taacagtggg   1200
gcgatagagc aggatataaa aaagatctat gatgaggcta cgtggctcca tgactttgga   1260
aaaggaggtg cttcagcaag ggccatctgg gaggctgtga agtctgccct ccctccctc    1320 aactggtttg tccctttact gggaccagca acagttatac tcttactttt cctctttggc   1380
ccttgtttct ttaatttact gattaagtgt gtctcttcta ggataaagca atttcacatg   1440 aagtccccc aaatggaaag atatcagcta tctgtcattg gaggcccag cacctataag    1500 cacatctccc ccttggatgc cagtgggcaa agattccggg aaactatgga ggaattttct   1560
ctc                                                                 1563
```

<210> SEQ ID NO 126
<211> LENGTH: 521
<212> TYPE: PRT
<213> ORGANISM: Artificial sequence
<220> FEATURE:
<223> OTHER INFORMATION: Description of Artificial Sequence: Synthetic Mutated HERV-V ENV

<400> SEQUENCE: 126

```
Met Pro Leu Leu Ser Gln Ala Gln Trp Asn Glu Asn Ser Leu Val Ser
 1               5                  10                  15

Phe Ser Lys Ile Ile Ala Ser Gly Asn His Leu Ser Asn Cys Trp Ile
             20                  25                  30

Cys His Asn Phe Ile Thr Arg Ser Ser Ser Tyr Gln Tyr Ile Leu Val
         35                  40                  45

Arg Asn Phe Ser Leu Asn Leu Thr Phe Gly Ser Gly Ile Pro Glu Gly
     50                  55                  60

Gln His Lys Ser Val Pro Leu Gln Val Ser Leu Ala Asn Ser Ala His
 65                  70                  75                  80

Gln Val Pro Cys Leu Asp Leu Thr Pro Pro Phe Asn Gln Ser Ser Lys
                 85                  90                  95

Thr Ser Phe Tyr Phe Tyr Asn Cys Ser Ser Leu Asn Gln Thr Cys Cys
            100                 105                 110

Pro Cys Pro Glu Gly His Cys Asp Arg Lys Asn Thr Ser Glu Glu Gly
        115                 120                 125

Phe Pro Ser Pro Thr Ile His Pro Met Ser Phe Ser Pro Ala Gly Cys
    130                 135                 140

His Pro Asn Leu Thr His Trp Cys Pro Ala Lys Gln Met Asn Asp Tyr
145                 150                 155                 160

Arg Asp Lys Ser Pro Gln Asn Arg Cys Ala Ala Trp Glu Gly Lys Glu
                165                 170                 175

Leu Ile Thr Trp Arg Val Leu Tyr Ser Leu Pro Lys Ala His Thr Val
            180                 185                 190

Pro Thr Trp Pro Lys Ser Thr Val Pro Leu Gly Gly Pro Leu Ser Pro
        195                 200                 205

Ala Cys Asn Gln Thr Ile Pro Ala Gly Trp Lys Ser Gln Leu His Lys
    210                 215                 220

Trp Phe Asp Ser His Ile Pro Arg Trp Ala Cys Thr Pro Pro Gly Tyr
225                 230                 235                 240
```

```
Val Phe Leu Cys Gly Pro Gln Lys Asn Lys Leu Pro Phe Asp Gly Ser
                245                 250                 255

Pro Lys Ile Thr Tyr Ser Thr Pro Val Ala Asn Leu Tyr Thr Cys
        260                 265                 270

Ile Asn Asn Ile Gln His Thr Gly Glu Cys Ala Val Gly Leu Leu Gly
                275                 280                 285

Pro Arg Gly Ile Gly Val Thr Ile Tyr Asn Thr Thr Gln Pro Arg Gln
290                 295                 300

Lys Arg Ala Leu Gly Leu Ile Leu Ala Gly Met Gly Ala Ala Ile Gly
305                 310                 315                 320

Met Ile Ala Pro Trp Gly Gly Phe Thr Tyr His Asp Val Thr Leu Arg
                325                 330                 335

Asn Leu Ser Arg Gln Ile Asp Asn Ile Ala Lys Ser Thr Arg Asp Ser
            340                 345                 350

Ile Ser Lys Leu Lys Ala Ser Ile Asp Ser Leu Ala Asn Val Val Met
        355                 360                 365

Asp Asn Arg Leu Ala Leu Asp Tyr Leu Leu Ala Glu Arg Gly Gly Val
            370                 375                 380

Cys Ala Phe Ile Asn Lys Ser Cys Cys Val Tyr Val Asn Asn Ser Gly
385                 390                 395                 400

Ala Ile Glu Glu Asp Ile Lys Lys Ile Tyr Asp Glu Ala Thr Trp Leu
                405                 410                 415

His Asp Phe Gly Lys Gly Gly Ala Ser Ala Arg Ala Ile Trp Glu Ala
            420                 425                 430

Val Lys Ser Ala Leu Pro Ser Leu Asn Trp Phe Val Pro Leu Leu Gly
        435                 440                 445

Pro Ala Thr Val Ile Leu Leu Leu Phe Leu Phe Gly Pro Cys Phe Phe
450                 455                 460

Asn Leu Leu Ile Lys Cys Val Ser Ser Arg Ile Lys Gln Phe His Met
465                 470                 475                 480

Lys Ser Pro Gln Met Glu Arg Tyr Gln Leu Ser Val Ile Gly Gly Pro
                485                 490                 495

Ser Thr Tyr Lys His Ile Ser Pro Leu Asp Ala Ser Gly Gln Arg Phe
            500                 505                 510

Arg Glu Thr Met Glu Glu Phe Ser Leu
            515                 520

<210> SEQ ID NO 127
<211> LENGTH: 1878
<212> TYPE: DNA
<213> ORGANISM: Artificial sequence
<220> FEATURE:
<223> OTHER INFORMATION: Description of Artificial Sequence: Synthetic
      Mutated HERV-T ENV
<220> FEATURE:
<221> NAME/KEY: modified_base
<222> LOCATION: (1546)..(1548)
<223> OTHER INFORMATION: cgt, cgc, cga, cgg, aga or agg

<400> SEQUENCE: 127
atgggtcccg aagcctgggt caggccccctt aaaactgcgc ctaagccggg tgaagccatt      60
agattaattc tttttattta cctctcttgt ttcttttgc ctgttatgtc ctctgagcct     120
tcctactcct ttctcctcac ctctttcaca acaggacgtg tattcgcaaa cactacttgg     180
agggccggta cctccaagga agtctccttt gcagttgatt tatgtgtact gttcccagag     240
ccagctcgta cccatgaaga gcaacataat ttgccggtca taggagcagg aagtgtcgac     300
cttgcagcag gatttggaca ctctgggagc caaactggat gtggaagctc caaaggtgca     360
```

-continued

```
gaaaaagggc tccaaaatgt tgacttttac ctctgtcctg gaaatcaccc tgacgctagc    420
tgtagagata cttaccagtt tttctgccct gattggacat gtgtaacttt agccacctac    480
tctgggggat caactagatc ttcaactctt tccataagtc gtgttcctca tcctaaatta    540
tgtactagaa aaaattgtaa tcctcttact ataactgtcc atgaccctaa tgcagctcaa    600
tggtattatg gcatgtcatg gggattaaga ctttatatcc caggatttga tgttgggact    660
atgttcacca tccaaaagaa aatcttggtc tcatggagct cccccaagcc aatcgggcct    720
ttaactgatc taggtgaccc tatattccag aaacacctg acaaagttga tttaactgtt    780
cctctgccat tcttagttcc tagacccag ctacaacaac aacatcttca acccagccta    840
atgtctatac taggtggagt acaccatctc cttaacctca cccagcctaa actagcccaa    900
gattgttggc tatgtttaaa agcaaaaccc ccttattatg taggattagg agtagaagcc    960
acacttaaac gtggccctct atcttgtcat acacgacccc gtgctctcac aataggagat   1020
gtgtctggaa atgcttcctg tctgattagt accgggtata acttatctgc ttctcctttt   1080
caggctactt gtaatcagtc cctgcttact tccataagca cctcagtctc ttaccaagca   1140
cccaacaata cctggttggc ctgcacctca ggtctcactc gctgcattaa tggaactgaa   1200
ccaggacctc tcctgtgcgt gttagttcat gtacttcccc aggtatatgt gtacagtgga   1260
ccagaaggac gacaactcat cgctccccct gagttacatc ccaggttgca ccaagctgtc   1320
ccacttctgg ttcccctatt ggctggtctt agcatagctg gatcagcagc cattggtacg   1380
gctgccctgg ttcaaggaga aactggacta atatccctgt ctcaacaggt ggatgctgat   1440
tttagtaacc tccagtctgc catagatata ctacattccc aggtagagtc tctggctgaa   1500
gtagttcttc aaaactgccg atgcttagat ctgctattcc tctctnnngg aggtttatgt   1560
gcagctctag gagaaagttg ttgcttctat gccaatcaat ctggagtcat aaaaggtaca   1620
gtaaaaaaag ttcgagaaaa tctagatagg caccaacaag aacgagaaaa taacatcccc   1680
tggtatcaaa gcatgtttaa ctggaaccca tggctaacta ctttaatcac tgggttagct   1740
ggacctctcc tcatcctact attaagttta atttttgggc cttgtatatt aaattcgttt   1800
cttaatttta taaaacaacg catagcttct gtcaaactta cgtatcttaa gactcaatat   1860
gacacccttg ttaataac                                                 1878
```

<210> SEQ ID NO 128
<211> LENGTH: 626
<212> TYPE: PRT
<213> ORGANISM: Artificial sequence
<220> FEATURE:
<223> OTHER INFORMATION: Description of Artificial Sequence: Synthetic Mutated HERV-T ENV

<400> SEQUENCE: 128

```
Met Gly Pro Glu Ala Trp Val Arg Pro Leu Lys Thr Ala Pro Lys Pro
 1               5                  10                  15

Gly Glu Ala Ile Arg Leu Ile Leu Phe Ile Tyr Leu Ser Cys Phe Phe
            20                  25                  30

Leu Pro Val Met Ser Ser Glu Pro Ser Tyr Ser Phe Leu Leu Thr Ser
        35                  40                  45

Phe Thr Thr Gly Arg Val Phe Ala Asn Thr Thr Trp Arg Ala Gly Thr
    50                  55                  60

Ser Lys Glu Val Ser Phe Ala Val Asp Leu Cys Val Leu Phe Pro Glu
65                  70                  75                  80

Pro Ala Arg Thr His Glu Glu Gln His Asn Leu Pro Val Ile Gly Ala
```

```
                    85                  90                  95
Gly Ser Val Asp Leu Ala Ala Gly Phe Gly His Ser Gly Ser Gln Thr
                100                 105                 110
Gly Cys Gly Ser Ser Lys Gly Ala Glu Lys Gly Leu Gln Asn Val Asp
                115                 120                 125
Phe Tyr Leu Cys Pro Gly Asn His Pro Asp Ala Ser Cys Arg Asp Thr
                130                 135                 140
Tyr Gln Phe Phe Cys Pro Asp Trp Thr Cys Val Thr Leu Ala Thr Tyr
145                 150                 155                 160
Ser Gly Gly Ser Thr Arg Ser Ser Thr Leu Ser Ile Ser Arg Val Pro
                165                 170                 175
His Pro Lys Leu Cys Thr Arg Lys Asn Cys Asn Pro Leu Thr Ile Thr
                180                 185                 190
Val His Asp Pro Asn Ala Ala Gln Trp Tyr Tyr Gly Met Ser Trp Gly
                195                 200                 205
Leu Arg Leu Tyr Ile Pro Gly Phe Asp Val Gly Thr Met Phe Thr Ile
                210                 215                 220
Gln Lys Lys Ile Leu Val Ser Trp Ser Ser Pro Lys Pro Ile Gly Pro
225                 230                 235                 240
Leu Thr Asp Leu Gly Asp Pro Ile Phe Gln Lys His Pro Asp Lys Val
                245                 250                 255
Asp Leu Thr Val Pro Leu Pro Phe Leu Val Pro Arg Pro Gln Leu Gln
                260                 265                 270
Gln Gln His Leu Gln Pro Ser Leu Met Ser Ile Leu Gly Gly Val His
                275                 280                 285
His Leu Leu Asn Leu Thr Gln Pro Lys Leu Ala Gln Asp Cys Trp Leu
                290                 295                 300
Cys Leu Lys Ala Lys Pro Pro Tyr Tyr Val Gly Leu Gly Val Glu Ala
305                 310                 315                 320
Thr Leu Lys Arg Gly Pro Leu Ser Cys His Thr Arg Pro Arg Ala Leu
                325                 330                 335
Thr Ile Gly Asp Val Ser Gly Asn Ala Ser Cys Leu Ile Ser Thr Gly
                340                 345                 350
Tyr Asn Leu Ser Ala Ser Pro Phe Gln Ala Thr Cys Asn Gln Ser Leu
                355                 360                 365
Leu Thr Ser Ile Ser Thr Ser Val Ser Tyr Gln Ala Pro Asn Asn Thr
                370                 375                 380
Trp Leu Ala Cys Thr Ser Gly Leu Thr Arg Cys Ile Asn Gly Thr Glu
385                 390                 395                 400
Pro Gly Pro Leu Leu Cys Val Leu Val His Val Leu Pro Gln Val Tyr
                405                 410                 415
Val Tyr Ser Gly Pro Glu Gly Arg Gln Leu Ile Ala Pro Pro Glu Leu
                420                 425                 430
His Pro Arg Leu His Gln Ala Val Pro Leu Leu Val Pro Leu Leu Ala
                435                 440                 445
Gly Leu Ser Ile Ala Gly Ser Ala Ala Ile Gly Thr Ala Ala Leu Val
                450                 455                 460
Gln Gly Glu Thr Gly Leu Ile Ser Leu Ser Gln Gln Val Asp Ala Asp
465                 470                 475                 480
Phe Ser Asn Leu Gln Ser Ala Ile Asp Ile Leu His Ser Gln Val Glu
                485                 490                 495
Ser Leu Ala Glu Val Val Leu Gln Asn Cys Arg Cys Leu Asp Leu Leu
                500                 505                 510
```

```
Phe Leu Ser Arg Gly Gly Leu Cys Ala Ala Leu Gly Glu Ser Cys Cys
        515                 520                 525

Phe Tyr Ala Asn Gln Ser Gly Val Ile Lys Gly Thr Val Lys Lys Val
        530                 535                 540

Arg Glu Asn Leu Asp Arg His Gln Gln Glu Arg Glu Asn Asn Ile Pro
545                 550                 555                 560

Trp Tyr Gln Ser Met Phe Asn Trp Asn Pro Trp Leu Thr Thr Leu Ile
                565                 570                 575

Thr Gly Leu Ala Gly Pro Leu Leu Ile Leu Leu Leu Ser Leu Ile Phe
            580                 585                 590

Gly Pro Cys Ile Leu Asn Ser Phe Leu Asn Phe Ile Lys Gln Arg Ile
        595                 600                 605

Ala Ser Val Lys Leu Thr Tyr Leu Lys Thr Gln Tyr Asp Thr Leu Val
    610                 615                 620

Asn Asn
625

<210> SEQ ID NO 129
<211> LENGTH: 1878
<212> TYPE: DNA
<213> ORGANISM: Artificial sequence
<220> FEATURE:
<223> OTHER INFORMATION: Description of Artificial Sequence: Synthetic
      Mutated HERV-T ENV
<220> FEATURE:
<221> NAME/KEY: modified_base
<222> LOCATION: (1546)..(1548)
<223> OTHER INFORMATION: cgt, cgc, cga, cgg, aga or agg
<220> FEATURE:
<221> NAME/KEY: modified_base
<222> LOCATION: (1564)..(1566)
<223> OTHER INFORMATION: ttt or ttc

<400> SEQUENCE: 129
atgggtcccg aagcctgggt caggccccctt aaaactgcgc ctaagccggg tgaagccatt      60
agattaattc ttttttattta cctctcttgt ttcttttttgc ctgttatgtc ctctgagcct    120
tcctactcct ttctcctcac ctctttcaca acaggacgtg tattcgcaaa cactacttgg     180
agggccggta cctccaagga agtctccttt gcagttgatt tatgtgtact gttcccagag    240
ccagctcgta cccatgaaga gcaacataat ttgccggtca taggagcagg aagtgtcgac    300
cttgcagcag gatttggaca ctctgggagc caaactggat gtggaagctc caaaggtgca    360
gaaaaagggc tccaaaatgt tgacttttac tctctgtcctg gaaatcaccc tgacgctagc    420
tgtagagata cttaccagtt tttctgccct gattggacat gtgtaacttt agccacctac    480
tctgggggat caactagatc ttcaactctt tccataagtc gtgttcctca tcctaaatta    540
tgtactagaa aaaattgtaa tcctcttact ataactgtcc atgaccctaa tgcagctcaa    600
tggtattatg gcatgtcatg gggattaaga ctttatatcc caggatttga tgttgggact    660
atgttcacca tccaaaagaa aatcttggtc tcatggagct ccccaagcc aatcgggcct      720 ttaactgatc taggtgaccc tatattccag aaacaccctg acaaagttga tttaactgtt    780
cctctgccat tcttagttcc tagaccccag ctacaacaac aacatcttca cccagcctaa    840
atgtctatac taggtggagt acaccatctc cttaacctca cccagcctaa actagcccaa    900
gattgttggc tatgtttaaa agcaaaaccc ccttattatg taggattagg agtagaagcc    960
acacttaaac gtggccctct atcttgtcat acacgacccc gtgctctcac aataggagat   1020
gtgtctggaa atgcttcctg tctgattagt accgggtata acttatctgc ttctcctttt   1080
caggctactt gtaatcagtc cctgcttact tccataagca cctcagtctc ttaccaagca   1140
```

```
cccaacaata cctggttggc ctgcacctca ggtctcactc gctgcattaa tggaactgaa    1200
ccaggacctc tcctgtgcgt gttagttcat gtacttcccc aggtatatgt gtacagtgga    1260
ccagaaggac gacaactcat cgctccccct gagttacatc ccaggttgca ccaagctgtc    1320
ccacttctgg ttcccctatt ggctggtctt agcatagctg gatcagcagc cattggtacg    1380
gctgccctgg ttcaaggaga aactggacta atatccctgt ctcaacaggt ggatgctgat    1440
tttagtaacc tccagtctgc catagatata ctacattccc aggtagagtc tctggctgaa    1500
gtagttcttc aaaactgccg atgcttagat ctgctattcc tctctnnngg aggtttatgt    1560
gcannnctag gagaaagttg ttgcttctat gccaatcaat ctggagtcat aaaaggtaca    1620
gtaaaaaaag ttcgagaaaa tctagatagg caccaacaag aacgagaaaa taacatcccc    1680
tggtatcaaa gcatgtttaa ctggaaccca tggctaacta ctttaatcac tgggttagct    1740
ggacctctcc tcatcctact attaagttta attttgggc cttgtatatt aaattcgttt     1800
cttaatttta taaaacaacg catagcttct gtcaaactta cgtatcttaa gactcaatat    1860
gacacccttg ttaataac                                                  1878
```

<210> SEQ ID NO 130
<211> LENGTH: 626
<212> TYPE: PRT
<213> ORGANISM: Artificial sequence
<220> FEATURE:
<223> OTHER INFORMATION: Description of Artificial Sequence: Synthetic
      Mutated HERV-T ENV

<400> SEQUENCE: 130

```
Met Gly Pro Glu Ala Trp Val Arg Pro Leu Lys Thr Ala Pro Lys Pro
 1               5                  10                  15

Gly Glu Ala Ile Arg Leu Ile Leu Phe Ile Tyr Leu Ser Cys Phe Phe
             20                  25                  30

Leu Pro Val Met Ser Ser Glu Pro Ser Tyr Ser Phe Leu Leu Thr Ser
         35                  40                  45

Phe Thr Thr Gly Arg Val Phe Ala Asn Thr Thr Trp Arg Ala Gly Thr
     50                  55                  60

Ser Lys Glu Val Ser Phe Ala Val Asp Leu Cys Val Leu Phe Pro Glu
 65                  70                  75                  80

Pro Ala Arg Thr His Glu Glu Gln His Asn Leu Pro Val Ile Gly Ala
                 85                  90                  95

Gly Ser Val Asp Leu Ala Ala Gly Phe Gly His Ser Gly Ser Gln Thr
            100                 105                 110

Gly Cys Gly Ser Ser Lys Gly Ala Glu Lys Gly Leu Gln Asn Val Asp
        115                 120                 125

Phe Tyr Leu Cys Pro Gly Asn His Pro Asp Ala Ser Cys Arg Asp Thr
    130                 135                 140

Tyr Gln Phe Phe Cys Pro Asp Trp Thr Cys Val Thr Leu Ala Thr Tyr
145                 150                 155                 160

Ser Gly Gly Ser Thr Arg Ser Ser Thr Leu Ser Ile Ser Arg Val Pro
                165                 170                 175

His Pro Lys Leu Cys Thr Arg Lys Asn Cys Asn Pro Leu Thr Ile Thr
            180                 185                 190

Val His Asp Pro Asn Ala Ala Gln Trp Tyr Tyr Gly Met Ser Trp Gly
        195                 200                 205

Leu Arg Leu Tyr Ile Pro Gly Phe Asp Val Gly Thr Met Phe Thr Ile
    210                 215                 220
```

```
Gln Lys Lys Ile Leu Val Ser Trp Ser Ser Pro Lys Pro Ile Gly Pro
225                 230                 235                 240

Leu Thr Asp Leu Gly Asp Pro Ile Phe Gln Lys His Pro Asp Lys Val
            245                 250                 255

Asp Leu Thr Val Pro Leu Pro Phe Leu Val Pro Arg Pro Gln Leu Gln
                260                 265                 270

Gln Gln His Leu Gln Pro Ser Leu Met Ser Ile Leu Gly Gly Val His
            275                 280                 285

His Leu Leu Asn Leu Thr Gln Pro Lys Leu Ala Gln Asp Cys Trp Leu
        290                 295                 300

Cys Leu Lys Ala Lys Pro Pro Tyr Tyr Val Gly Leu Gly Val Glu Ala
305                 310                 315                 320

Thr Leu Lys Arg Gly Pro Leu Ser Cys His Thr Arg Pro Arg Ala Leu
                325                 330                 335

Thr Ile Gly Asp Val Ser Gly Asn Ala Ser Cys Leu Ile Ser Thr Gly
            340                 345                 350

Tyr Asn Leu Ser Ala Ser Pro Phe Gln Ala Thr Cys Asn Gln Ser Leu
        355                 360                 365

Leu Thr Ser Ile Ser Thr Ser Val Ser Tyr Gln Ala Pro Asn Asn Thr
370                 375                 380

Trp Leu Ala Cys Thr Ser Gly Leu Thr Arg Cys Ile Asn Gly Thr Glu
385                 390                 395                 400

Pro Gly Pro Leu Leu Cys Val Leu Val His Val Leu Pro Gln Val Tyr
                405                 410                 415

Val Tyr Ser Gly Pro Glu Gly Arg Gln Leu Ile Ala Pro Pro Glu Leu
            420                 425                 430

His Pro Arg Leu His Gln Ala Val Pro Leu Leu Val Pro Leu Leu Ala
        435                 440                 445

Gly Leu Ser Ile Ala Gly Ser Ala Ile Gly Thr Ala Ala Leu Val
            450                 455                 460

Gln Gly Glu Thr Gly Leu Ile Ser Leu Ser Gln Gln Val Asp Ala Asp
465                 470                 475                 480

Phe Ser Asn Leu Gln Ser Ala Ile Asp Ile Leu His Ser Gln Val Glu
                485                 490                 495

Ser Leu Ala Glu Val Val Leu Gln Asn Cys Arg Cys Leu Asp Leu Leu
            500                 505                 510

Phe Leu Ser Arg Gly Gly Leu Cys Ala Phe Leu Gly Glu Ser Cys Cys
        515                 520                 525

Phe Tyr Ala Asn Gln Ser Gly Val Ile Lys Gly Thr Val Lys Lys Val
530                 535                 540

Arg Glu Asn Leu Asp Arg His Gln Gln Glu Arg Glu Asn Asn Ile Pro
545                 550                 555                 560

Trp Tyr Gln Ser Met Phe Asn Trp Asn Pro Trp Leu Thr Thr Leu Ile
                565                 570                 575

Thr Gly Leu Ala Gly Pro Leu Leu Ile Leu Leu Leu Ser Leu Ile Phe
            580                 585                 590

Gly Pro Cys Ile Leu Asn Ser Phe Leu Asn Phe Ile Lys Gln Arg Ile
        595                 600                 605

Ala Ser Val Lys Leu Thr Tyr Leu Lys Thr Gln Tyr Asp Thr Leu Val
610                 615                 620

Asn Asn
625

<210> SEQ ID NO 131
```

```
<211> LENGTH: 30
<212> TYPE: DNA
<213> ORGANISM: Artificial sequence
<220> FEATURE:
<223> OTHER INFORMATION: Description of Artificial Sequence: Synthetic
      primer

<400> SEQUENCE: 131
caaccttacc aaccctgata aaactcaaga                                        30

<210> SEQ ID NO 132
<211> LENGTH: 35
<212> TYPE: DNA
<213> ORGANISM: Artificial sequence
<220> FEATURE:
<223> OTHER INFORMATION: Description of Artificial Sequence: Synthetic
      primer

<400> SEQUENCE: 132
cagtcctcct cttttagga acaacaggtc taggc                                   35

<210> SEQ ID NO 133
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 133
tgtgctgccc taaaagaaga atgttgtt                                          28

<210> SEQ ID NO 134
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 134
ggactaaagc ctggactact gagatcctg                                         29

<210> SEQ ID NO 135
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 135
cagtcctcct tctttagga acaacaggt                                          29

<210> SEQ ID NO 136
<211> LENGTH: 33
<212> TYPE: DNA
<213> ORGANISM: Artificial sequence
<220> FEATURE:
<223> OTHER INFORMATION: Description of Artificial Sequence: Synthetic
      primer

<400> SEQUENCE: 136
tgtgctttcc taaaagaaga atgttgtttc tat                                    33

<210> SEQ ID NO 137
<211> LENGTH: 39
<212> TYPE: DNA
```

```
<213> ORGANISM: Artificial sequence
<220> FEATURE:
<223> OTHER INFORMATION: Description of Artificial Sequence: Synthetic
      primer

<400> SEQUENCE: 137
atacatccat ggcgtgttca acgctcccaa aatcccta                              39

<210> SEQ ID NO 138
<211> LENGTH: 43
<212> TYPE: DNA
<213> ORGANISM: Artificial sequence
<220> FEATURE:
<223> OTHER INFORMATION: Description of Artificial Sequence: Synthetic
      primer

<400> SEQUENCE: 138
atacatctcg agttctcttt tatgtctata ggatttttca aac                        43

<210> SEQ ID NO 139
<211> LENGTH: 33
<212> TYPE: DNA
<213> ORGANISM: Artificial sequence
<220> FEATURE:
<223> OTHER INFORMATION: Description of Artificial Sequence: Synthetic
      primer

<400> SEQUENCE: 139
atacatccat ggctgccgta caagatgatc tca                                   33

<210> SEQ ID NO 140
<211> LENGTH: 33
<212> TYPE: DNA
<213> ORGANISM: Artificial sequence
<220> FEATURE:
<223> OTHER INFORMATION: Description of Artificial Sequence: Synthetic
      primer

<400> SEQUENCE: 140
atacatccat ggctgccgta caagatgatc tca                                   33

<210> SEQ ID NO 141
<211> LENGTH: 39
<212> TYPE: DNA
<213> ORGANISM: Artificial sequence
<220> FEATURE:
<223> OTHER INFORMATION: Description of Artificial Sequence: Synthetic
      primer

<400> SEQUENCE: 141
atacatctcg agatctctta ctaggcctgt atggtcagc                             39

<210> SEQ ID NO 142
<211> LENGTH: 17
<212> TYPE: DNA
<213> ORGANISM: Artificial sequence
<220> FEATURE:
<223> OTHER INFORMATION: Description of Artificial Sequence: Synthetic
      primer

<400> SEQUENCE: 142
ctcagggagc agcggga                                                     17

<210> SEQ ID NO 143
<211> LENGTH: 25
<212> TYPE: DNA
<213> ORGANISM: Artificial sequence
<220> FEATURE:
```

```
<223> OTHER INFORMATION: Description of Artificial Sequence: Synthetic
      primer

<400> SEQUENCE: 143
tagcttaagt ctgttccagg cagtg                                           25

<210> SEQ ID NO 144
<211> LENGTH: 20
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 144
tccatgacgt tcctgacgtt                                                 20

<210> SEQ ID NO 145
<211> LENGTH: 1812
<212> TYPE: DNA
<213> ORGANISM: Artificial sequence
<220> FEATURE:
<223> OTHER INFORMATION: Description of Artificial Sequence: Synthetic
      Mutated HERV-R ENV
<220> FEATURE:
<221> NAME/KEY: modified_base
<222> LOCATION: (1681)..(1683)
<223> OTHER INFORMATION: cgt, cgc, cga, cgg, aga or agg

<400> SEQUENCE: 145
atgctgggta tgaacatgct actcatcact ttgttcttgc tactcccctt atccatgtta     60
aaaggagaac cctgggaggg atgcctccac tgcacccaca ctacgtggtc ggggaacatc    120
atgactaaaa ccctgttgta tcacacttat tatgagtgtg ctgggacctg cctaggaact    180
tgtactcaca accagacaac ctactcagtc tgtgacccag aaggggccag gccttatgtg    240
tgttatgacc ctaagtcttc acctgggatc tggtttgaaa ttcatgtcgg gtcaaaggaa    300
ggggatcttc taaaccaaac caaggtattt ccctctggca aggatgtcgt atccttatac    360
tttgatgttt gccagatagt atccatgggc tcactctttc ccgtaatctt cagttccatg    420
gagtactata gtagctgcca taaaaatagg tatgcacacc ctgcttgttc caccgattcc    480
ccagtaacaa cttgctggga ctgcacaacg tggtccacta accaacaatc actagggcca    540
attatgctta ccaaaatacc attagaacca gattgtaaaa caagcacttg caattctgta    600
aatcttacca tcttagagcc agatcagccc atatggacaa caggtttaaa agcaccgcta    660
ggggcacgag tcagcggtga agaaattggc ccaggagcct atgtctatct atatatcata    720
aagaaaactc ggacccgctc aacccaacag ttccgagttt ttgagtcatt ctatgagcat    780
gttaaccaga aattgcctga ccccctcccc ttggccagta atttattcgc caactggct   840 gaaaacatag ccagcagcct gcacgttgct tcatgttatg tctgtggggg aatgaacatg    900
ggagaccaat ggccatggga agcaagggaa ctaatgcccc aagataattt cacactaacc    960
gcctcttccc tcgaacctgc accatcaagt cagagcatct ggttcttaaa aacctccatt   1020
attggaaaat tctgtattgc tcgctgggga aaggccttta cagacccagt aggagagtta   1080
acttgcctag acaacaata  ttacaacgag acactaggaa agactttatg gaggggcaaa   1140
agcaataatt ctgaatcacc acacccaagc ccattctctc gtttcccatc tttaaaccat   1200
tcttggtacc aacttgaagc tccaaatacc tggcaggcac cctctggcct ctactggatc   1260
tgtgggccac aagcatatcg acaactgcca gctaaatggt caggggcctg tgtactgggg   1320
acaattaggc cgtccttctt cctaatgccc ctaaaacagg agaagccctt aggatacccc    1380
```

```
atctatgatg aaactaaaag gaaaagcaaa agaggcataa ctataggaga ttggaaggac    1440
agtgaatggc ctcctgaaag aataattcaa tattatggcc cagccacctg ggcagaagat    1500
ggaatgtggg gataccgcac cccagtttac atgcttaacc gcattataag attgcaggca    1560
gtactagaaa tcattaccaa tgaaactgca ggggccttga atctgcttgc ccagcaagcc    1620
acaaaaatga aaatgtcat ttatcaaaat agactggcct tagactacct cctagcccag     1680
nnngagggag tatgcggaaa gttcagcctt actaactgct gcctggaact tgatgacgaa    1740
ggaaaggtta tcaaagaaat aactgctaaa atccaaaagt tagctcacat cccagttcag    1800
acttggaaag ga                                                        1812
```

<210> SEQ ID NO 146
<211> LENGTH: 604
<212> TYPE: PRT
<213> ORGANISM: Artificial sequence
<220> FEATURE:
<223> OTHER INFORMATION: Description of Artificial Sequence: Synthetic
      Mutated HERV-R ENV

<400> SEQUENCE: 146

```
Met Leu Gly Met Asn Met Leu Leu Ile Thr Leu Phe Leu Leu Leu Pro
  1               5                  10                  15

Leu Ser Met Leu Lys Gly Glu Pro Trp Glu Gly Cys Leu His Cys Thr
             20                  25                  30

His Thr Thr Trp Ser Gly Asn Ile Met Thr Lys Thr Leu Leu Tyr His
         35                  40                  45

Thr Tyr Tyr Glu Cys Ala Gly Thr Cys Leu Gly Thr Cys Thr His Asn
     50                  55                  60

Gln Thr Thr Tyr Ser Val Cys Asp Pro Gly Arg Gly Gln Pro Tyr Val
 65                  70                  75                  80

Cys Tyr Asp Pro Lys Ser Ser Pro Gly Ile Trp Phe Glu Ile His Val
                 85                  90                  95

Gly Ser Lys Glu Gly Asp Leu Leu Asn Gln Thr Lys Val Phe Pro Ser
            100                 105                 110

Gly Lys Asp Val Val Ser Leu Tyr Phe Asp Val Cys Gln Ile Val Ser
        115                 120                 125

Met Gly Ser Leu Phe Pro Val Ile Phe Ser Ser Met Glu Tyr Tyr Ser
    130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205

Gln Pro Ile Trp Thr Thr Gly Leu Lys Ala Pro Leu Gly Ala Arg Val
    210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
                245                 250                 255

Phe Tyr Glu His Val Asn Gln Lys Leu Pro Glu Pro Pro Leu Ala
            260                 265                 270

Ser Asn Leu Phe Ala Gln Leu Ala Glu Asn Ile Ala Ser Ser Leu His
```

|     |     |     |     |     | 275 |     |     |     | 280 |     |     |     |     | 285 |
| --- | --- | --- | --- | --- | --- | --- | --- | --- | --- | --- | --- | --- | --- | --- |

Val Ala Ser Cys Tyr Val Cys Gly Gly Met Asn Met Gly Asp Gln Trp
290                 295                 300

Pro Trp Glu Ala Arg Glu Leu Met Pro Gln Asp Asn Phe Thr Leu Thr
305                 310                 315                 320

Ala Ser Ser Leu Glu Pro Ala Pro Ser Ser Gln Ser Ile Trp Phe Leu
            325                 330                 335

Lys Thr Ser Ile Ile Gly Lys Phe Cys Ile Ala Arg Trp Gly Lys Ala
            340                 345                 350

Phe Thr Asp Pro Val Gly Glu Leu Thr Cys Leu Gly Gln Gln Tyr Tyr
        355                 360                 365

Asn Glu Thr Leu Gly Lys Thr Leu Trp Arg Gly Lys Ser Asn Asn Ser
370                 375                 380

Glu Ser Pro His Pro Ser Pro Phe Ser Arg Phe Pro Ser Leu Asn His
385                 390                 395                 400

Ser Trp Tyr Gln Leu Glu Ala Pro Asn Thr Trp Gln Ala Pro Ser Gly
                405                 410                 415

Leu Tyr Trp Ile Cys Gly Pro Gln Ala Tyr Arg Gln Leu Pro Ala Lys
            420                 425                 430

Trp Ser Gly Ala Cys Val Leu Gly Thr Ile Arg Pro Ser Phe Phe Leu
        435                 440                 445

Met Pro Leu Lys Gln Gly Glu Ala Leu Gly Tyr Pro Ile Tyr Asp Glu
    450                 455                 460

Thr Lys Arg Lys Ser Lys Arg Gly Ile Thr Ile Gly Asp Trp Lys Asp
465                 470                 475                 480

Ser Glu Trp Pro Pro Glu Arg Ile Ile Gln Tyr Tyr Gly Pro Ala Thr
                485                 490                 495

Trp Ala Glu Asp Gly Met Trp Gly Tyr Arg Thr Pro Val Tyr Met Leu
            500                 505                 510

Asn Arg Ile Ile Arg Leu Gln Ala Val Leu Gly Ile Ile Thr Asn Glu
        515                 520                 525

Thr Ala Gly Ala Leu Asn Leu Leu Ala Gln Gln Ala Thr Lys Met Arg
    530                 535                 540

Asn Val Ile Tyr Gln Asn Arg Leu Ala Leu Asp Tyr Leu Leu Ala Gln
545                 550                 555                 560

Arg Glu Gly Val Cys Gly Lys Phe Ser Leu Thr Asn Cys Cys Leu Glu
                565                 570                 575

Leu Asp Asp Glu Gly Lys Val Ile Lys Glu Ile Thr Ala Lys Ile Gln
            580                 585                 590

Lys Leu Ala His Ile Pro Val Gln Thr Trp Lys Gly
        595                 600

<210> SEQ ID NO 147
<211> LENGTH: 1812
<212> TYPE: DNA
<213> ORGANISM: Artificial sequence
<220> FEATURE:
<223> OTHER INFORMATION: Description of Artificial Sequence: Synthetic
      Mutated HERV-R ENV
<220> FEATURE:
<221> NAME/KEY: modified_base
<222> LOCATION: (1681)..(1693)
<223> OTHER INFORMATION: cgt, cgc, cga, cgg, aga or agg
<220> FEATURE:
<221> NAME/KEY: modified_base
<222> LOCATION: (1699)..(1701)
<223> OTHER INFORMATION: ttt or ttc

<400> SEQUENCE: 147

```
atgctgggta tgaacatgct actcatcact tgttcttgc tactccctt atccatgtta      60
aaaggagaac cctgggaggg atgcctccac tgcacccaca ctacgtggtc ggggaacatc    120
atgactaaaa ccctgttgta tcacacttat tatgagtgtg ctgggacctg cctaggaact    180
tgtactcaca accagacaac ctactcagtc tgtgacccag aaggggcca gccttatgtg     240
tgttatgacc ctaagtcttc acctgggatc tggtttgaaa ttcatgtcgg gtcaaaggaa    300
ggggatcttc taaaccaaac caaggtattt ccctctggca aggatgtcgt atccttatac    360
tttgatgttt gccagatagt atccatgggc tcactctttc ccgtaatctt cagttccatg    420
gagtactata gtagctgcca taaaaatagg tatgcacacc ctgcttgttc caccgattcc    480
ccagtaacaa cttgctggga ctgcacaacg tggtccacta accaacaatc actagggcca    540
attatgctta ccaaaatacc attagaacca gattgtaaaa caagcacttg caattctgta    600
aatcttacca tcttagagcc agatcagccc atatggacaa caggtttaaa agcaccgcta    660
ggggcacgag tcagcggtga agaaattggc ccaggagcct atgtctatct atatcata     720
aagaaaactc ggacccgctc aacccaacag ttccgagttt tgagtcatt ctatgagcat     780
gttaaccaga aattgcctga gccccctccc ttggccagta atttattcgc ccaactggct    840
gaaaacatag ccagcagcct gcacgttgct tcatgttatg tctgtggggg aatgaacatg    900
ggagaccaat ggccatggga agcaagggaa ctaatgcccc aagataattt cacactaacc    960
gcctcttccc tcgaacctgc accatcaagt cagagcatct ggttcttaaa acctccatt   1020
attggaaaat tctgtattgc tcgctgggga aaggccttta cagacccagt aggagagtta   1080
acttgcctag acaacaata ttacaacgag acactaggaa agactttatg gagggcaaa    1140
agcaataatt ctgaatcacc cacccaagc ccattctctc gtttcccatc tttaaaccat   1200
tcttggtacc aacttgaagc tccaaatacc tggcaggcac cctctggcct ctactggatc   1260
tgtgggccac aagcatatcg acaactgcca gctaaatggt caggggcctg tgtactgggg   1320
acaattaggc cgtccttctt cctaatgccc ctaaacagg gagaagcctt aggatacccc    1380
atctatgatg aaactaaaag gaaaagcaaa agaggcataa ctataggaga ttggaaggac   1440
agtgaatggc ctcctgaaag aataattcaa tattatggcc cagccacctg ggcagaagat   1500
ggaatgtggg gataccgcac cccagtttac atgcttaacc gcattataag attgcaggca   1560
gtactagaaa tcattaccaa tgaaactgca ggggccttga atctgcttgc ccagcaagcc   1620
acaaaaatga gaaatgtcat ttatcaaaat agactggcct tagactacct cctagcccag   1680
nnngagggag tatgcggann nttcagcctt actaactgct gcctggaact tgatgacgaa   1740
ggaaaggtta tcaaagaaat aactgctaaa atccaaaagt tagctcacat cccagttcag   1800
acttggaaag ga                                                       1812
```

<210> SEQ ID NO 148
<211> LENGTH: 604
<212> TYPE: PRT
<213> ORGANISM: Artificial sequence
<220> FEATURE:
<223> OTHER INFORMATION: Description of Artificial Sequence: Synthetic
      Mutated HERV-R ENV

<400> SEQUENCE: 148

```
Met Leu Gly Met Asn Met Leu Leu Ile Thr Leu Phe Leu Leu Leu Pro
 1               5                  10                  15

Leu Ser Met Leu Lys Gly Glu Pro Trp Glu Gly Cys Leu His Cys Thr
            20                  25                  30
```

-continued

```
His Thr Thr Trp Ser Gly Asn Ile Met Thr Lys Thr Leu Leu Tyr His
         35                  40                  45

Thr Tyr Tyr Glu Cys Ala Gly Thr Cys Leu Gly Thr Cys Thr His Asn
 50                  55                  60

Gln Thr Thr Tyr Ser Val Cys Asp Pro Gly Arg Gly Gln Pro Tyr Val
 65                  70                  75                  80

Cys Tyr Asp Pro Lys Ser Ser Pro Gly Ile Trp Phe Glu Ile His Val
                 85                  90                  95

Gly Ser Lys Glu Gly Asp Leu Leu Asn Gln Thr Lys Val Phe Pro Ser
                100                 105                 110

Gly Lys Asp Val Val Ser Leu Tyr Phe Asp Val Cys Gln Ile Val Ser
            115                 120                 125

Met Gly Ser Leu Phe Pro Val Ile Phe Ser Ser Met Glu Tyr Tyr Ser
130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205

Gln Pro Ile Trp Thr Thr Gly Leu Lys Ala Pro Leu Gly Ala Arg Val
210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
                245                 250                 255

Phe Tyr Glu His Val Asn Gln Lys Leu Pro Glu Pro Pro Leu Ala
                260                 265                 270

Ser Asn Leu Phe Ala Gln Leu Ala Glu Asn Ile Ala Ser Ser Leu His
            275                 280                 285

Val Ala Ser Cys Tyr Val Cys Gly Gly Met Asn Met Gly Asp Gln Trp
        290                 295                 300

Pro Trp Glu Ala Arg Glu Leu Met Pro Gln Asp Asn Phe Thr Leu Thr
305                 310                 315                 320

Ala Ser Ser Leu Glu Pro Ala Pro Ser Ser Gln Ser Ile Trp Phe Leu
                325                 330                 335

Lys Thr Ser Ile Ile Gly Lys Phe Cys Ile Ala Arg Trp Gly Lys Ala
            340                 345                 350

Phe Thr Asp Pro Val Gly Glu Leu Thr Cys Leu Gly Gln Gln Tyr Tyr
        355                 360                 365

Asn Glu Thr Leu Gly Lys Thr Leu Trp Arg Gly Lys Ser Asn Asn Ser
370                 375                 380

Glu Ser Pro His Pro Ser Pro Phe Ser Arg Phe Pro Ser Leu Asn His
385                 390                 395                 400

Ser Trp Tyr Gln Leu Glu Ala Pro Asn Thr Trp Gln Ala Pro Ser Gly
                405                 410                 415

Leu Tyr Trp Ile Cys Gly Pro Gln Ala Tyr Arg Gln Leu Pro Ala Lys
            420                 425                 430

Trp Ser Gly Ala Cys Val Leu Gly Thr Ile Arg Pro Ser Phe Phe Leu
        435                 440                 445

Met Pro Leu Lys Gln Gly Glu Ala Leu Gly Tyr Pro Ile Tyr Asp Glu
450                 455                 460
```

```
Thr Lys Arg Lys Ser Lys Arg Gly Ile Thr Ile Gly Asp Trp Lys Asp
465                 470                 475                 480

Ser Glu Trp Pro Pro Glu Arg Ile Ile Gln Tyr Tyr Gly Pro Ala Thr
                485                 490                 495

Trp Ala Glu Asp Gly Met Trp Gly Tyr Arg Thr Pro Val Tyr Met Leu
            500                 505                 510

Asn Arg Ile Ile Arg Leu Gln Ala Val Leu Glu Ile Ile Thr Asn Glu
        515                 520                 525

Thr Ala Gly Ala Leu Asn Leu Leu Ala Gln Gln Ala Thr Lys Met Arg
    530                 535                 540

Asn Val Ile Tyr Gln Asn Arg Leu Ala Leu Asp Tyr Leu Leu Ala Gln
545                 550                 555                 560

Arg Glu Gly Val Cys Gly Phe Phe Ser Leu Thr Asn Cys Cys Leu Glu
                565                 570                 575

Leu Asp Asp Glu Gly Lys Val Ile Lys Glu Ile Thr Ala Lys Ile Gln
            580                 585                 590

Lys Leu Ala His Ile Pro Val Gln Thr Trp Lys Gly
        595                 600
```

<210> SEQ ID NO 149
<211> LENGTH: 1977
<212> TYPE: DNA
<213> ORGANISM: Artificial sequence
<220> FEATURE:
<223> OTHER INFORMATION: Description of Artificial Sequence: Synthetic
      Mutated PERV ENV
<220> FEATURE:
<221> NAME/KEY: modified_base
<222> LOCATION: (1633)..(1635)
<223> OTHER INFORMATION: cgt, cgc, cga, cgg, aga or agg

<400> SEQUENCE: 149

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta acgccttgt ggacagcccg aactcccata acccttatc tctcacctgg      180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc agggcccca      360
aataatgaag atattgtgg aaatcctcag gatttctttt gcaagcaatg gagctgcgta     420
acttctaatg atgggaattg gaatggcca gtctctcagc aagacagagt aagttactct     480
tttgttaaca atcctaccag ttataatcaa tttaattatg ccatgggag atggaaagat     540
tggcaacagc gggtacaaaa agatgtacga aataagcaaa taagctgtca ttcgttagac     600
ctagattact aaaaataag tttcactgaa aaggaaaac aagaaaatat tcaaaagtgg      660
gtaaatggta tgtcttgggg aatagtgtac tatagaggct ctgggagaaa gaaaggatct     720
gttctgacta ttcgcctcag aatagaaact cagatggaac ctccggttgc tataggacca     780
aataagggtt tggccgaaca aggacctcca atccaagaac agaggccatc tcctaacccc     840
tctgattaca atacaacctc tggatcagtc cccactgagc ctaacatcac tattaaaaca     900
ggggcgaaac tttttaacct catccaggga gcttttcaag ctcttaactc cacgactcca     960
gaggctacct cttcttgttg gctttgctta gcttcgggcc caccttacta tgagggaatg    1020
gctagaggag ggaaattcaa tgtgacaaag gaacatagag accaatgtac atggggatcc    1080
caaaataagc ttaccttac tgaggttct ggaaaaggca cctgcatagg gatggttccc    1140
```

-continued

```
ccatcccacc aacacctttg taaccacact gaagccttta atcgaacctc tgagagtcag    1200
tatctggtac ctggttatga caggtggtgg gcatgtaata ctggattaac cccttgtgtt    1260
tccaccttgg ttttcaacca aactaaagac ttttgcgtta tggtccaaat tgtcccccgg    1320
gtgtactact atcccgaaaa agcagtcctt gatgaatatg actatagata taatcggcca    1380
aaaagagagc ccatatccct gacactagct gtaatgctcg gattgggagt ggctgcaggc    1440
gtgggaacag gaacggctgc cctaatcaca ggaccgcaac agctggagaa aggacttagt    1500
aacctacatc gaattgtaac ggaaaaatctc caagccctag aaaaatctgt cagtaacctg    1560
gaggaatccc taacctcctt atctgaagtg gttctacaga acagaagggg gttagatctg    1620
ttatttctaa aannnggagg gttatgtgta gccttaaaag aggaatgctg cttctatgta    1680
gatcactcag gagccatcag agactccatg agcaagctta gagaaaggtt agagaggcgt    1740
cgaagggaaa gagaggctga ccaggggtgg tttgaaggat ggttcaacag gtctccttgg    1800
atggctaccc tactttctgc tttaacagga cccttaatag tcctcctcct gttactcaca    1860
gttgggccat gtattattaa caagttaatt gccttcatta gaacgaat aagtgcagtc    1920 cagatcatgg tacttagaca acagtaccaa agcccgtcta gcagagaagc tggccgc       1977
```

<210> SEQ ID NO 150
<211> LENGTH: 659
<212> TYPE: PRT
<213> ORGANISM: Artificial sequence
<220> FEATURE:
<223> OTHER INFORMATION: Description of Artificial Sequence: Synthetic Mutated PERV ENV

<400> SEQUENCE: 150

```
Met His Pro Thr Leu Ser Arg Arg His Leu Pro Ile Arg Gly Gly Lys
 1               5                  10                  15

Pro Lys Arg Leu Lys Ile Pro Leu Ser Phe Ala Ser Ile Ala Trp Phe
            20                  25                  30

Leu Thr Leu Ser Ile Thr Pro Gln Val Asn Gly L

-continued

```
             210                 215                 220
Ser Trp Gly Ile Val Tyr Tyr Arg Gly Ser Gly Arg Lys Lys Gly Ser
225                 230                 235                 240

Val Leu Thr Ile Arg Leu Arg Ile Glu Thr Gln Met Glu Pro Pro Val
                    245                 250                 255

Ala Ile Gly Pro Asn Lys Gly Leu Ala Glu Gln Gly Pro Pro Ile Gln
                    260                 265                 270

Glu Gln Arg Pro Ser Pro Asn Pro Ser Asp Tyr Asn Thr Thr Ser Gly
                275                 280                 285

Ser Val Pro Thr Glu Pro Asn Ile Thr Ile Lys Thr Gly Ala Lys Leu
            290                 295                 300

Phe Asn Leu Ile Gln Gly Ala Phe Gln Ala Leu Asn Ser Thr Thr Pro
305                 310                 315                 320

Glu Ala Thr Ser Ser Cys Trp Leu Cys Leu Ala Ser Gly Pro Pro Tyr
                    325                 330                 335

Tyr Glu Gly Met Ala Arg Gly Gly Lys Phe Asn Val Thr Lys Glu His
                340                 345                 350

Arg Asp Gln Cys Thr Trp Gly Ser Gln Asn Lys Leu Thr Leu Thr Glu
            355                 360                 365

Val Ser Gly Lys Gly Thr Cys Ile Gly Met Val Pro Pro Ser His Gln
370                 375                 380

His Leu Cys Asn His Thr Glu Ala Phe Asn Arg Thr Ser Glu Ser Gln
385                 390                 395                 400

Tyr Leu Val Pro Gly Tyr Asp Arg Trp Trp Ala Cys Asn Thr Gly Leu
                    405                 410                 415

Thr Pro Cys Val Ser Thr Leu Val Phe Asn Gln Thr Lys Asp Phe Cys
                420                 425                 430

Val Met Val Gln Ile Val Pro Arg Val Tyr Tyr Pro Glu Lys Ala
            435                 440                 445

Val Leu Asp Glu Tyr Asp Tyr Arg Tyr Asn Arg Pro Lys Arg Glu Pro
450                 455                 460

Ile Ser Leu Thr Leu Ala Val Met Leu Gly Leu Gly Val Ala Ala Gly
465                 470                 475                 480

Val Gly Thr Gly Thr Ala Ala Leu Ile Thr Gly Pro Gln Gln Leu Glu
                    485                 490                 495

Lys Gly Leu Ser Asn Leu His Arg Ile Val Thr Glu Asn Leu Gln Ala
                500                 505                 510

Leu Glu Lys Ser Val Ser Asn Leu Glu Glu Ser Leu Thr Ser Leu Ser
            515                 520                 525

Glu Val Val Leu Gln Asn Arg Arg Gly Leu Asp Leu Leu Phe Leu Lys
530                 535                 540

Arg Gly Gly Leu Cys Val Ala Leu Lys Glu Glu Cys Cys Phe Tyr Val
545                 550                 555                 560

Asp His Ser Gly Ala Ile Arg Asp Ser Met Ser Lys Leu Arg Glu Arg
                    565                 570                 575

Leu Glu Arg Arg Arg Arg Glu Arg Glu Ala Asp Gln Gly Trp Phe Glu
                580                 585                 590

Gly Trp Phe Asn Arg Ser Pro Trp Met Ala Thr Leu Leu Ser Ala Leu
            595                 600                 605

Thr Gly Pro Leu Ile Val Leu Leu Leu Leu Thr Val Gly Pro Cys
610                 615                 620

Ile Ile Asn Lys Leu Ile Ala Phe Ile Arg Glu Arg Ile Ser Ala Val
625                 630                 635                 640
```

Gln Ile Met Val Leu Arg Gln Gln Tyr Gln Ser Pro Ser Ser Arg Glu
                645                 650                 655

Ala Gly Arg

<210> SEQ ID NO 151
<211> LENGTH: 1977
<212> TYPE: DNA
<213> ORGANISM: Artificial sequence
<220> FEATURE:
<223> OTHER INFORMATION: Description of Artificial Sequence: Synthetic
      Mutated PERV ENV
<220> FEATURE:
<221> NAME/KEY: modified_base
<222> LOCATION: (1633)..(1635)
<223> OTHER INFORMATION: cgt, cgc, cga, cgt, aga or agg
<220> FEATURE:
<221> NAME/KEY: modified_base
<222> LOCATION: (1651)..(1653)
<223> OTHER INFORMATION: ttt or ttc

<400> SEQUENCE: 151

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta acgccttgt ggacagcccg aactcccata aaccttatc tctcacctgg      180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct acgggttttt acgtttgccc agggccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg ccatgggag atggaaagat     540
tggcaacagc gggtacaaaa agatgtacga aataagcaaa taagctgtca ttcgttagac     600
ctagattact taaaaataag tttcactgaa aaaggaaaac aagaaaatat tcaaaagtgg     660
gtaaatggta tgtcttgggg aatagtgtac tatagaggct ctgggagaaa gaaaggatct     720
gttctgacta ttcgcctcag aatagaaact cagatgaaac tccggttgc ataggacca      780
aataagggtt tggccgaaca aggacctcca atccaagaac agaggccatc tcctaacccc     840
tctgattaca atacaacctc tggatcagtc cccactgagc taacatcac tattaaaaca     900
ggggcgaaac ttttttaacct catccaggga gctttttcaag ctcttaactc cacgactcca     960
gaggctacct cttcttgttg gctttgctta gcttcgggcc cacctactta tgagggaatg    1020
gctagaggag ggaaattcaa tgtgacaaag gaacatagag accaatgtac atggggatcc    1080
caaaataagc ttacccttac tgaggtttct ggaaaaggca cctgcatagg gatggttccc    1140
ccatccccacc aacaccttttg taaccacact gaagccttta tcgaacctc tgagagtcag    1200
tatctggtac ctggttatga caggtggtgg gcatgtaata ctggattaac ccttgtgtt    1260
tccaccttgg ttttcaacca aactaaagac ttttgcgtta tggtccaaat tgtccccgg     1320
gtgtactact atcccgaaaa agcagtcctt gatgaatatg actatagata taatcggcca     1380
aaaagagagc ccatatccct gacactagct gtaatgctcg gattgggagt ggctgcaggc     1440
gtgggaacag gaacggctgc cctaatcaca ggaccgcaac agctggagaa aggacttagt     1500
aacctacatc gaattgtaac ggaaaatctc aagccctag aaaatctgt cagtaacctg     1560
gaggaatccc taacctcctt atctgaagtg gttctacaga acagaagggg ttagatctg    1620
ttatttctaa aannnggagg gttatgtgta nnnttaaaag aggaatgctg cttctatgta    1680
```

```
gatcactcag gagccatcag agactccatg agcaagctta gagaaaggtt agagaggcgt   1740
cgaagggaaa gagaggctga ccaggggtgg tttgaaggat ggttcaacag gtctccttgg   1800
atggctaccc tactttctgc tttaacagga cccttaatag tcctcctcct gttactcaca   1860
gttgggccat gtattattaa caagttaatt gccttcatta gagaacgaat aagtgcagtc   1920
cagatcatgg tactagaca acagtaccaa agcccgtcta gcagagaagc tggccgc       1977
```

<210> SEQ ID NO 152
<211> LENGTH: 659
<212> TYPE: PRT
<213> ORGANISM: Artificial sequence
<220> FEATURE:
<223> OTHER INFORMATION: Description of Artificial Sequence: Synthetic Mutated PERV ENV

<400> SEQUENCE: 152

```
Met His Pro Thr Leu Ser Arg Arg His Leu Pro Ile Arg Gly Gly Lys
 1               5                  10                  15

Pro Lys Arg Leu Lys Ile Pro Leu Ser Phe Ala Ser Ile Ala Trp Phe
            20                  25                  30

Leu Thr Leu Ser Ile Thr Pro Gln Val Asn Gly Lys Arg Leu Val Asp
        35                  40                  45

Ser Pro Asn Ser His Lys Pro Leu Ser Leu Thr Trp Leu Leu Thr Asp
    50                  55                  60

Ser Gly Thr Gly Ile Asn Ile Asn Ser Thr Gln Gly Glu Ala Pro Leu
65                  70                  75                  80

Gly Thr Trp Trp Pro Glu Leu Tyr Val Cys Leu Arg Ser Val Ile Pro
                85                  90                  95

Gly Leu Asn Asp Gln Ala Thr Pro Pro Asp Val Leu Arg Ala Tyr Gly
            100                 105                 110

Phe Tyr Val Cys Pro Gly Pro Pro Asn Asn Glu Glu Tyr Cys Gly Asn
        115                 120                 125

Pro Gln Asp Phe Phe Cys Lys Gln Trp Ser Cys Val Thr Ser Asn Asp
    130                 135                 140

Gly Asn Trp Lys Trp Pro Val Ser Gln Gln Asp Arg Val Ser Tyr Ser
145                 150                 155                 160

Phe Val Asn Asn Pro Thr Ser Tyr Asn Gln Phe Asn Tyr Gly His Gly
                165                 170                 175

Arg Trp Lys Asp Trp Gln Gln Arg Val Gln Lys Asp Val Arg Asn Lys
            180                 185                 190

Gln Ile Ser Cys His Ser Leu Asp Leu Asp Tyr Leu Lys Ile Ser Phe
        195                 200                 205

Thr Glu Lys Gly Lys Gln Glu Asn Ile Gln Lys Trp Val Asn Gly Met
    210                 215                 220

Ser Trp Gly Ile Val Tyr Tyr Arg Gly Ser Gly Arg Lys Lys Gly Ser
225                 230                 235                 240

Val Leu Thr Ile Arg Leu Arg Ile Glu Thr Gln Met Glu Pro Pro Val
                245                 250                 255

Ala Ile Gly Pro Asn Lys Gly Leu Ala Glu Gln Gly Pro Pro Ile Gln
            260                 265                 270

Glu Gln Arg Pro Ser Pro Asn Pro Ser Asp Tyr Asn Thr Thr Ser Gly
        275                 280                 285

Ser Val Pro Thr Glu Pro Asn Ile Thr Ile Lys Thr Gly Ala Lys Leu
    290                 295                 300

Phe Asn Leu Ile Gln Gly Ala Phe Gln Ala Leu Asn Ser Thr Thr Pro
305                 310                 315                 320
```

Glu Ala Thr Ser Ser Cys Trp Leu Cys Leu Ala Ser Gly Pro Pro Tyr
            325                 330                 335

Tyr Glu Gly Met Ala Arg Gly Lys Phe Asn Val Thr Lys Glu His
            340                 345                 350

Arg Asp Gln Cys Thr Trp Gly Ser Gln Asn Lys Leu Thr Leu Thr Glu
            355                 360                 365

Val Ser Gly Lys Gly Thr Cys Ile Gly Met Val Pro Pro Ser His Gln
370                 375                 380

His Leu Cys Asn His Thr Glu Ala Phe Asn Arg Thr Ser Glu Ser Gln
385                 390                 395                 400

Tyr Leu Val Pro Gly Tyr Asp Arg Trp Trp Ala Cys Asn Thr Gly Leu
            405                 410                 415

Thr Pro Cys Val Ser Thr Leu Val Phe Asn Gln Thr Lys Asp Phe Cys
            420                 425                 430

Val Met Val Gln Ile Val Pro Arg Val Tyr Tyr Tyr Pro Glu Lys Ala
            435                 440                 445

Val Leu Asp Glu Tyr Asp Tyr Arg Tyr Asn Arg Pro Lys Arg Glu Pro
450                 455                 460

Ile Ser Leu Thr Leu Ala Val Met Leu Gly Leu Gly Val Ala Ala Gly
465                 470                 475                 480

Val Gly Thr Gly Thr Ala Ala Leu Ile Thr Gly Pro Gln Gln Leu Glu
            485                 490                 495

Lys Gly Leu Ser Asn Leu His Arg Ile Val Thr Glu Asn Leu Gln Ala
            500                 505                 510

Leu Glu Lys Ser Val Ser Asn Leu Glu Glu Ser Leu Thr Ser Leu Ser
            515                 520                 525

Glu Val Val Leu Gln Asn Arg Arg Gly Leu Asp Leu Leu Phe Leu Lys
530                 535                 540

Arg Gly Gly Leu Cys Val Phe Leu Lys Glu Glu Cys Cys Phe Tyr Val
545                 550                 555                 560

Asp His Ser Gly Ala Ile Arg Asp Ser Met Ser Lys Leu Arg Glu Arg
            565                 570                 575

Leu Glu Arg Arg Arg Arg Glu Arg Glu Ala Asp Gln Gly Trp Phe Glu
            580                 585                 590

Gly Trp Phe Asn Arg Ser Pro Trp Met Ala Thr Leu Leu Ser Ala Leu
            595                 600                 605

Thr Gly Pro Leu Ile Val Leu Leu Leu Leu Thr Val Gly Pro Cys
610                 615                 620

Ile Ile Asn Lys Leu Ile Ala Phe Ile Arg Glu Arg Ile Ser Ala Val
625                 630                 635                 640

Gln Ile Met Val Leu Arg Gln Gln Tyr Gln Ser Pro Ser Ser Arg Glu
            645                 650                 655

Ala Gly Arg

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)
<223> OTHER INFORMATION: Glu or Gln
<220> FEATURE:
<221> NAME/KEY: MOD_RES

```
<222> LOCATION: (4)
<223> OTHER INFORMATION: Leu, Thr or Ile
<220> FEATURE:
<221> NAME/KEY: MOD_RES
<222> LOCATION: (6)
<223> OTHER INFORMATION: Ala, Lys, Leu, Met, Val or Ile

<400> SEQUENCE: 153

Xaa Gly Gly Xaa Cys Xaa Ala
 1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Leu, Thr or Ile
<220> FEATURE:
<221> NAME/KEY: MOD_RES
<222> LOCATION: (6)
<223> OTHER INFORMATION: Ala, Lys, Leu, Met, Val or Ile

<400> SEQUENCE: 154

Arg Gly Gly Xaa Cys Xaa Phe
 1               5

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: variable amino acid
<220> FEATURE:
<221> NAME/KEY: MOD_RES
<222> LOCATION: (4)..(6)
<223> OTHER INFORMATION: variable amino acid
<220> FEATURE:
<221> NAME/KEY: MOD_RES
<222> LOCATION: (8)..(9)
<223> OTHER INFORMATION: variable amino acid
<220> FEATURE:
<221> NAME/KEY: MOD_RES
<222> LOCATION: (11)..(17)
<223> OTHER INFORMATION: variable amino acid
<220> FEATURE:
<221> NAME/KEY: MOD_RES
<222> LOCATION: (19)..(20)
<223> OTHER INFORMATION: variable amino acid

<400> SEQUENCE: 155

Xaa Xaa Asn Xaa Xaa Xaa Leu Xaa Xaa Leu Xaa Xaa Xaa Xaa Xaa Xaa
 1               5                  10                  15

Xaa Cys Xaa Xaa
            20

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(4)
<223> OTHER INFORMATION: variable amino acid
<220> FEATURE:
<221> NAME/KEY: MOD_RES
<222> LOCATION: (6)..(7)
<223> OTHER INFORMATION: variable amino acid
<220> FEATURE:
<221> NAME/KEY: MOD_RES
<222> LOCATION: (9)..(15)
<223> OTHER INFORMATION: variable amino acid
<220> FEATURE:
<221> NAME/KEY: MOD_RES
<222> LOCATION: (17)..(18)
<223> OTHER INFORMATION: variable amino acid
<220> FEATURE:
<223> OTHER INFORMATION: see specification as filed for detailed
      description of substitutions and preferred embodiments

<400> SEQUENCE: 156

Asn Xaa Xaa Xaa Leu Xaa Xaa Leu Xaa Xaa Xaa Xaa Xaa Xaa Xaa Cys
 1               5                  10                  15

Xaa Xaa

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: variable amino acid
<220> FEATURE:
<221> NAME/KEY: MOD_RES
<222> LOCATION: (4)..(6)
<223> OTHER INFORMATION: variable amino acid
<220> FEATURE:
<221> NAME/KEY: MOD_RES
<222> LOCATION: (8)..(9)
<223> OTHER INFORMATION: variable amino acid
<220> FEATURE:
<221> NAME/KEY: MOD_RES
<222> LOCATION: (11)..(17)
<223> OTHER INFORMATION: variable amino acid
<220> FEATURE:
<221> NAME/KEY: MOD_RES
<222> LOCATION: (19)..(20)
<223> OTHER INFORMATION: variable amino acid
<220> FEATURE:
<223> OTHER INFORMATION: see specification as filed for detailed
      description of substitutions and preferred embodiments

<400> SEQUENCE: 157

Xaa Xaa Asn Xaa Xaa Xaa Leu Xaa Xaa Leu Xaa Xaa Xaa Xaa Xaa Xaa
 1               5                  10                  15

Xaa Cys Xaa Xaa
            20

<210> SEQ ID NO 158
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gcggccgctc ta                                                            12
```

```
<210> SEQ ID NO 159
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tccaccgcgg tg                                                        12

<210> SEQ ID NO 160
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggattagtcc aa                                                        12

<210> SEQ ID NO 161
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
accggatccg cg                                                        12

<210> SEQ ID NO 162
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gcggccgctc ta                                                        12

<210> SEQ ID NO 163
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tccaccgcgg tg                                                        12

<210> SEQ ID NO 164
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggatccccgg ga                                                        12

<210> SEQ ID NO 165
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggagacaata cc                                                          12

<210> SEQ ID NO 166
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gcggccgctc ta                                                          12

<210> SEQ ID NO 167
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tccaccgcgg tg                                                          12

<210> SEQ ID NO 168
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggatccgcgc ga                                                          12

<210> SEQ ID NO 169
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggagacaata cc                                                          12

<210> SEQ ID NO 170
<211> LENGTH: 49
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
aguuagagcg guuagaagau ucaagagaac uucuaaccgc ucuaactuu                  49

<210> SEQ ID NO 171
```

-continued

```
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ucagccgcua ccccgaccau ucaagagaug gucgggguag cggcugauu         49
```